United States Patent
Yamashita et al.

(10) Patent No.: US 8,835,488 B2
(45) Date of Patent: Sep. 16, 2014

(54) OPIOID RECEPTOR LIGANDS AND METHODS OF USING AND MAKING SAME

(75) Inventors: Dennis Yamashita, Wayne, PA (US);
Dimitar Gotchev, Hatboro, PA (US);
Philip Pitis, North Wales, PA (US);
Xiao-Tao Chen, Furlong, PA (US);
Guodong Liu, Jamison, PA (US);
Catherine C. K. Yuan, King of Prussia, PA (US)

(73) Assignee: Trevena, Inc., King of Prussia, PA (US)

(*) Notice: Subject to any disclaimer, the term of this patent is extended or adjusted under 35 U.S.C. 154(b) by 0 days.

(21) Appl. No.: 13/428,849

(22) Filed: Mar. 23, 2012

(65) Prior Publication Data
US 2012/0245181 A1 Sep. 27, 2012

Related U.S. Application Data

(60) Provisional application No. 61/596,808, filed on Feb. 9, 2012, provisional application No. 61/466,809, filed on Mar. 23, 2011.

(51) Int. Cl.
*A61K 31/4436* (2006.01)
*C07D 405/14* (2006.01)
*A61K 31/444* (2006.01)
*A61K 45/06* (2006.01)
*A61K 31/35* (2006.01)
*C07D 311/96* (2006.01)
*C07D 405/12* (2006.01)
*C07D 409/14* (2006.01)
*A61K 31/4433* (2006.01)
*C07D 405/04* (2006.01)
*C07D 409/12* (2006.01)

(52) U.S. Cl.
CPC .......... *A61K 31/4433* (2013.01); *C07D 405/14* (2013.01); *A61K 31/444* (2013.01); *A61K 45/06* (2013.01); *A61K 31/35* (2013.01); *C07D 311/96* (2013.01); *C07D 405/12* (2013.01); *C07D 409/14* (2013.01); *A61K 31/4436* (2013.01); *C07D 405/04* (2013.01); *C07D 409/12* (2013.01)
USPC .......................................... 514/444; 514/445

(58) Field of Classification Search
CPC .................................................. A61K 31/4436
USPC .................................................. 514/444, 445
See application file for complete search history.

(56) References Cited

U.S. PATENT DOCUMENTS

| 6,136,839 A | 10/2000 | Isakson et al. |
| 2006/0217372 A1 | 9/2006 | Blanco-Pillado et al. |
| 2010/0280058 A1 | 11/2010 | Dolle et al. |

OTHER PUBLICATIONS

Osol (editor), Remington's Pharmaceutical Sciences, 1980, Philadelphia College of Pharmaceutical Science, Chapter 27: Structure-Activity Relationship and Drug Design, pp. 420-435.*
DeWire et al., A G Protein-Biased Ligand at the μ-Opioid Receptor is Potently Analgesic with Reduced Gastrointestinal and Respiratory Dysfunction Compared with Morphine, 2013, J Pharmacol Exp Ther, vol. 344, pp. 708-717.*
Dewire et al., Journal of Pharmacology and Experimental Therapeutics, Published online before print Jan. 8, 2013, doi: 10.1124/jpet.112.201616 Title: A G protein-biased ligand at the μ-opioid receptor is potently analgesic with reduced gastrointestinal and respiratory dysfunction compared to morphine.
Groarke et al., "Visualization of agonist-induced association and trafficking of green fluorescent protein-tagged forms of both beta-arrestin-1 and the thyrotropin-releasing hormone receptor-1", J. Biol. Chem. 1999, 274(33):23263-23269.
Van, F. and Rolan, P.E., "The utility of the cold pain test to measure analgesia from intravenous morphine", Br. J. Clin. Pharmacol, 1996, 42:663-664.
Wotherspoon, H.A. et al., "Analgesic efficacy of controlled-release dihydrocodeine", Anaesthesia, 1991, 46:915-917.
Pogozheva et al., "Homology Modeling of Opioid Receptor-Ligand Complexes Using Experimental Constraints", The AAPS Journal, 2005, 7(2):E434-E448.

* cited by examiner

*Primary Examiner* — James D Anderson
*Assistant Examiner* — Meghan Finn
(74) *Attorney, Agent, or Firm* — Pepper Hamilton LLP

(57) ABSTRACT

This application describes compounds that can act as opioid receptor ligands, which compounds can be used in the treatment of, for example, pain and pain related disorders.

22 Claims, No Drawings

OPIOID RECEPTOR LIGANDS AND METHODS OF USING AND MAKING SAME

CROSS-REFERENCE TO RELATED APPLICATIONS

This application is a U.S. Non-Provisional application, which claims priority to U.S. Provisional Application No. 61/596,808 filed Feb. 9, 2012, and U.S. Provisional Application No. 61/466,809 filed Mar. 23, 2011, each of which is incorporated herein by reference in its entirety.

FIELD

This application relates to a family of compounds acting as opioid receptor ligands. Such compounds may provide therapeutic benefit in the treatment of pain.

BACKGROUND

Opioid receptors (ORs) mediate the actions of morphine and morphine-like opioids, including most clinical analgesics. Three molecularly and pharmacologically distinct opioid receptor types have been described: δ, κ and μ. Furthermore, each type is believed to have sub-types. All three of these opioid receptor types appear to share the same functional mechanisms at a cellular level. For example, activation of the opioid receptors causes inhibition of adenylate cyclase, and recruits β-arrestin.

When therapeutic doses of morphine are given to patients with pain, the patients report that the pain is less intense, less discomforting, or entirely gone. In addition to experiencing relief of distress, some patients experience euphoria. However, when morphine in a selected pain-relieving dose is given to a pain-free individual, the experience is not always pleasant; nausea is common, and vomiting may also occur. Drowsiness, inability to concentrate, difficulty in mentation, apathy, lessened physical activity, reduced visual acuity, and lethargy may ensue.

There is a continuing need for new OR modulators to be used as analgesics. There is a further need for OR agonists as analgesics having reduced side effects. There is a further need for OR agonists as analgesics having reduced side effects for the treatment of pain, immune dysfunction, inflammation, esophageal reflux, neurological and psychiatric conditions, urological and reproductive conditions, medicaments for drug and alcohol abuse, agents for treating gastritis and diarrhea, cardiovascular agents and/or agents for the treatment of respiratory diseases and cough.

SUMMARY

This application describes opioid receptor (OR) ligands. It also describes methods of modulating opioid receptor activity using the compositions described herein. Certain compositions described herein act as opioid receptor agonists. Other compositions described herein act as opioid receptor antagonists.

This application describes compounds having the structure of Formula I:

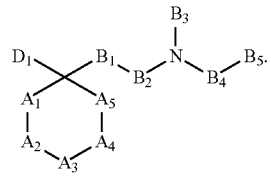

In the structure above, variables $A_1, A_2, A_3, A_4, A_5, B_1, B_2, B_3, B_4, B_5$, and $D_1$ can be selected from the respective groups of chemical moieties later described. OR ligand derivatives and mimetics are also provided. Also provided are processes for preparing these compounds.

This application also describes pharmaceutical compositions comprising one or more compounds as described in this application a pharmaceutically acceptable carrier. Naturally, the compounds described herein can be employed in any form, such as a solid or solution (e.g., aqueous solution) as is described further below. The compounds described herein, for example, can be obtained and employed in a lyophilized form alone or with suitable additives.

Also provided are methods for treating pain and pain-related disorders. Such a method would comprise administering a therapeutically effective amount of one or more compounds described herein to a subjector subject in need thereof.

DETAILED DESCRIPTION

This application describes a family of compounds, OR ligands, with a unique profile. The compounds described herein act as agonists or antagonists of opioid receptor (OR)-mediated signal transduction. The ligands of these receptors can be used to treat pathologies associated with ORs including pain and pain related disorders.

Compounds also comprise Formula I:

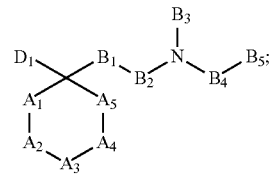

wherein: $A_1$ is null, $CH_2$, $CHR_1$, $CR_1R_2$, $CH$, $CR_1$, $O$, $S$, $SO$, $SO_2$, $NH$ or $NR_1$; $A_2$ is null, $CH_2$, $CHR_5$, $CR_5R_6$, $CH$, $CR_5$, $O$, $S$, $SO$, $SO_2$, $NH$ or $NR_5$; $A_3$ is null, $CH_2$, $CHR_7$, $CR_7R_8$, $O$, $S$, $SO$, $SO_2$, $NH$, $NR_7$, $CH$ or $CR_7$; $A_4$ is null, $CH_2$, cycle of the formula $C(CH_2)_n$, where n=2-5, $CHR_9$, $CR_9R_{10}$, $O$, $S$, $SO$, $SO_2$, $NH$, $NR_9$, $CH$ or $CR_9$; and $A_5$ is null, $CH_2$, $CHR_{11}$, $CR_{11}R_{12}$, $CH_2CH_2$, $CHR_{11}CH_2$, $CH_2CHR_{11}$, $CHR_{11}CHR_{12}$, $O$, $S$, $SO$, $SO_2$, $NH$, $NR_{11}$, $CH$ or $CR_{11}$.

No more than 2 out of 5 $A_a$ (specifically $A_1, A_2, A_3, A_4, A_5$) can be null at the same time. The number of heteroatoms from $A_1$ to $A_5$ cannot exceed 2 at the same time, and O—O, S—O; S—S; S—N fragments in the ring structure are excluded from this composition.

The ring containing $A_1, A_2, A_3, A_4, A_5$ and the carbon connected to $D_1$ can be fused with another ring, such as benzene, pyridine, pyrimidine, furan, thiophene or pyridazine, but not limited to these examples, where the resulting bicycle is chemically stable and synthetically accessible. It is also understood that the above-mentioned fused rings could be multiply substituted with cyano, halogen, alkyl, branched alkyl, halogenated alkyl, hydroxyl, alkyloxy, formyl, acetyl, amino, alkylamino, dialkylamino, mercaptanyl, alkylmercaptanyl, and other small substitution groups. The bonds between $A_1$ and $A_2$, $A_2$ and $A_3$, $A_3$ and $A_4$, $A_4$ and $A_5$ can independently be a single bond or a double bond. The bonds between $A_1$ and $A_2$, $A_2$ and $A_3$, $A_3$ and $A_4$, $A_4$ and $A_5$ cannot be a double bond at the same time.

$A_2$ and $A_4$ can be connected by a carbon bridge. Examples of such a bridge include —$CH_2$—, and —$CH_2CH_2$—.

$B_1$ is $CH_2$, $CHR_{13}$, $CR_{13}R_{14}$, O, S, SO, $SO_2$, NH, $NR_{13}$, $CR_{13}$ or CO. $B_2$ is $CH_2$, $CHR_{15}$, $CR_{15}R_{16}$, $CR_{15}$ or CO. $B_3$ is H, alkyl, branched alkyl, halogenated alkyl, aryl, arylalkyl, alkylcarbonyl, branched alkylcarbonyl, arylcarbonyl, alkoxycarbonyl, or alkylsulfonyl. $B_4$ is null, $C_1$-$C_6$ alkyl, $CH_2$, $CH_2CH_2$, $CHR_{19}$, $CR_{19}R_{20}$ or CO. In some embodiments, when $B_4$ is an alkyl one or more of the hydrogens can be replaced with a deuterium. $B_5$ is alkyl, branched alkyl, halogenated alkyl, carbocycle-substituted alkyl, aryl, carbocycle or arylalkyl.

Aryl, carbocycle (non-aromatic)/heterocycle (non-aromatic with 1-3 heteroatoms, including O, N, S) are either unsubstituted, or substituted with small substitution groups. Small substitution groups can be cyano, halogen, alkyl, branched alkyl, halogenated alkyl, hydroxyl, alkyloxy, amino, alkylamino, dialkylamino, mercaptanyl, alkylmercaptanyl, alkylsulfonyl, aminosulfonyl, alkylaminosulfonyl, alkylcarbonyl, alkoxycarbonyl, aminocarbonyl, alkylaminocarbonyl, dialkylaminocarbonyl, aryl, arylalkyl, carbocycle or carbocycle-alkyl. In some embodiments, the small substitution groups are selected from F, Cl, Br, $CH_3$, $CH_2CH_3$, $CH_2F$, $CHF_2$, $CF_3$, n-Pr, n-Bu, i-Bu, sec-Bu, i-Pr, t-Bu, CN, OH, OMe, OEt, O-iPr, $OCF_3$, $NH_2$, NHMe, $NMe_2$, methoxycarbonyl, methanesulfonyl, Ph, benzyl, $MeSO_2$, formyl, and acetyl.

Carbocycle may contain double bonds, but they should not be aromatic.

$D_1$ is an aryl group or a carbocycle.

An aryl group is either a monocyclic aromatic group or a bicyclic aromatic group, which may contain heteroatoms in the aromatic group (e.g. heteroaryl). The following structures are some examples of representative aryl groups, but the aryl groups are not limited to those examples:

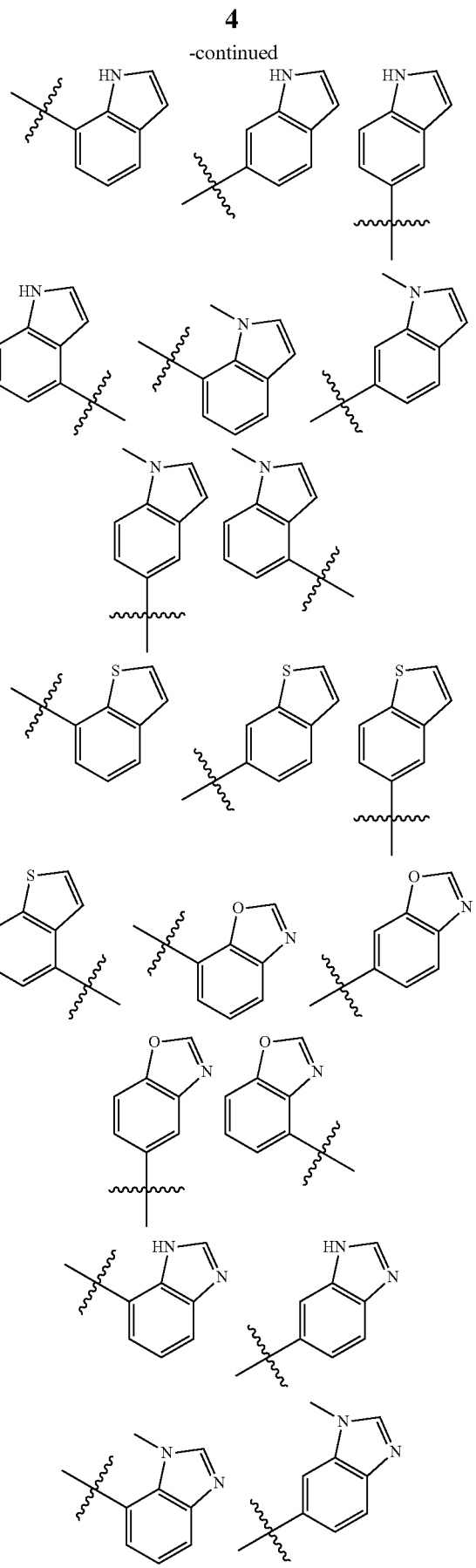

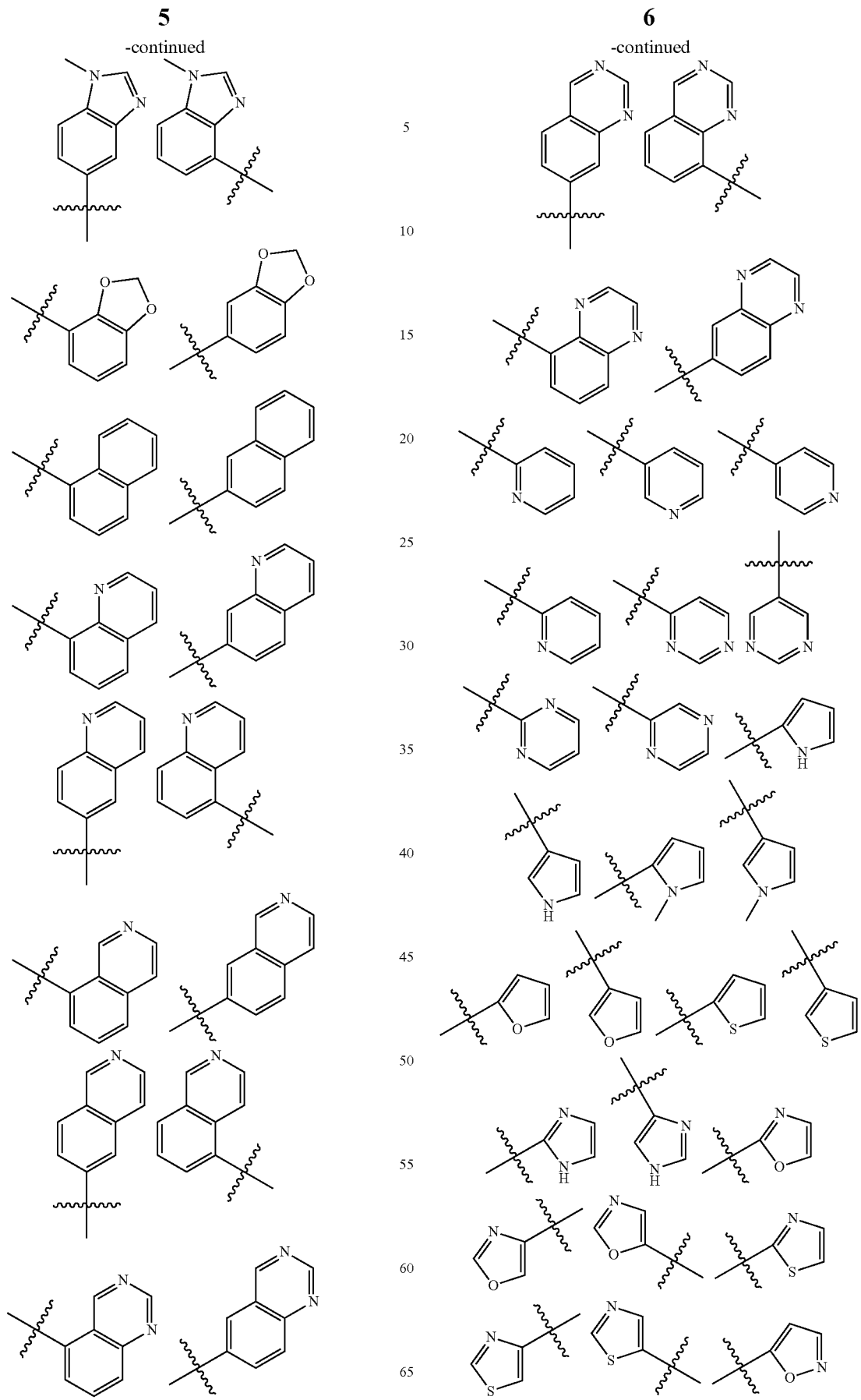

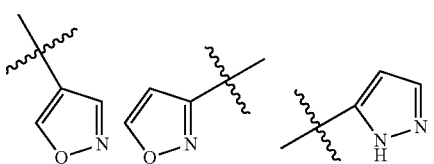
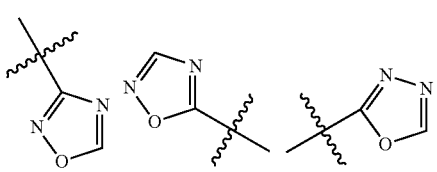
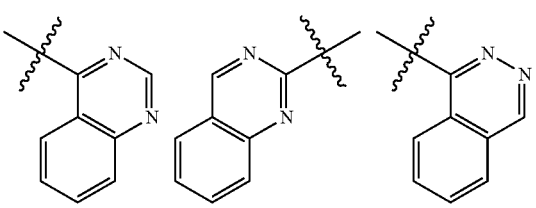
Carbocycle is either a monocyclic or a bicyclic non-aromatic ring system. The following structures are some examples of representative carbocycle, but the carbocycle is not limited to those examples:
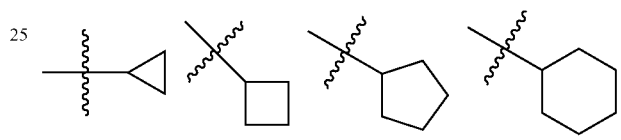
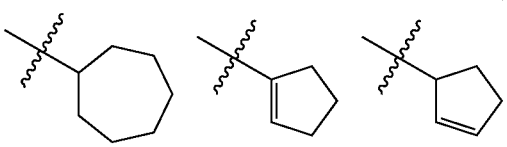
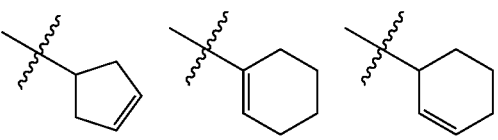
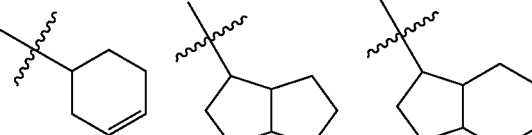
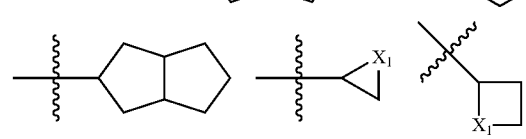
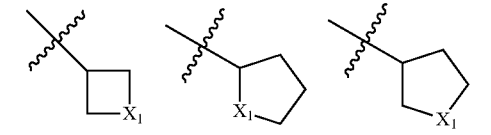
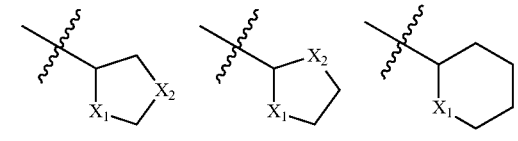
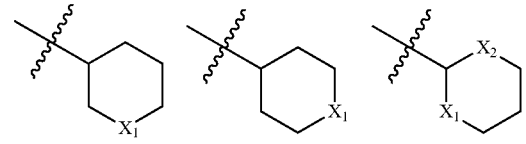

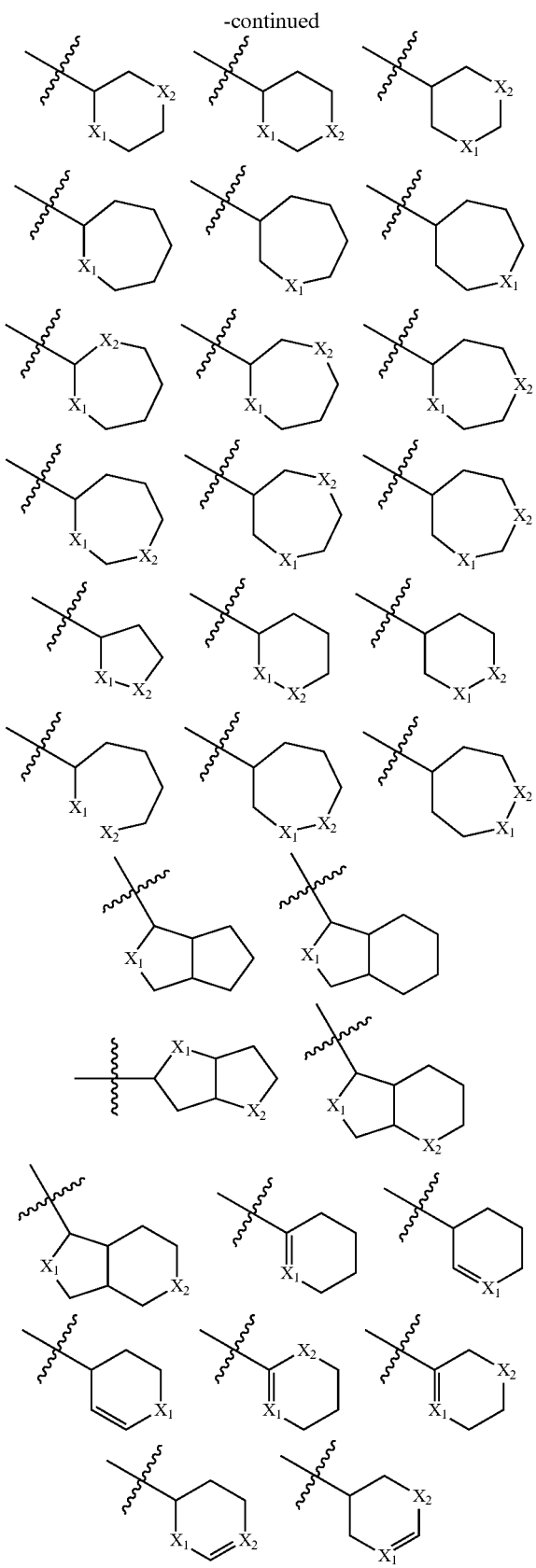

wherein $X_1$, and $X_2$ in the carbocycle examples are independently O, S, N, NH or $NR_{18}$.

The aryl groups can be independently mono or multiply substituted with cyano, halogen, alkyl, branched alkyl, halogenated alkyl, hydroxyl, alkyloxy, amino, alkylamino, dialkylamino, mercaptanyl, alkylmercaptanyl, alkylsulfonyl, aminosulfonyl, alkylaminosulfonyl, alkylcarbonyl, alkoxycarbonyl, aminocarbonyl, alkylaminocarbonyl, dialkylaminocarbonyl, aryl, arylalkyl, carbocycle, carbocycle-alkyl, and/or other small substitution groups. In some embodiments, the small substitution groups are selected from F, Cl, Br, $CH_3$, $CH_2CH_3$, $CH_2F$, $CHF_2$, $CF_3$, n-Pr, n-Bu, i-Bu, sec-Bu, i-Pr, t-Bu, CN, OH, OMe, OEt, O-iPr, $OCF_3$, $NH_2$, NHMe, $NMe_2$, methoxycarbonyl, methanesulfonyl, Ph, benzyl, formyl, and acetyl.

$D_1$ is an aryl, or a carbocycle.

$R_1, R_2, R_5, R_6, R_7, R_8, R_9, R_{10}, R_{11}, R_{12}, R_{13}, R_{14}, R_{15}, R_{16}, R_{18}, R_{19}$, and $R_{20}$ are independently: cyano, halogen, hydroxyl, alkyloxy, alkyl, branched alkyl, halogenated alkyl, branched halogenated alkyl, aryl, arylalkyl, carbocycle, carbocycle-alkyl, alkylcarbonyl, branched alkylcarbonyl, halogenated alkylcarbonyl, branched halogenated alkylcarbonyl, arylcarbonyl or alkoxycarbonyl. In some embodiments, $R_1$, $R_2, R_5, R_6, R_7, R_8, R_9, R_{10}, R_{11}, R_{12}, R_{13}, R_{14}, R_{15}, R_{16}, R_{18}, R_{19}$, and $R_{20}$ are independently F, Cl, Br, $CH_3$, $CH_2CH_3$, $CH_2F$, $CHF_2$, $CF_3$, n-Pr, n-Bu, i-Bu, sec-Bu, i-Pr, t-Bu, CN, OH, OMe, OEt, O-i-Pr, methoxycarbonyl, phenyl, benzyl, formyl or acetyl, whenever the resulting structure is stable.

$R_1$ and $R_2$, $R_5$ and $R_6$, $R_7$ and $R_8$, $R_9$ and $R_{10}$, $R_{11}$ and $R_{12}$, $R_{13}$ and $R_{14}$, $R_{15}$ and $R_{16}$, $R_{19}$ and $R_{20}$, or $R_{15}$ and $R_{19}$ can form a monocycle.

Me is methyl; Et is ethyl; i-Pr is i-propyl; t-Bu is t-butyl; Ph is phenyl.

In some embodiments, the following compounds can be excluded from the genus of compounds:

1) 2-[({2-[2-Ethyl-2-methyl-4-(4-methylphenyl)oxan-4-yl]ethyl}amino)methyl]phenol

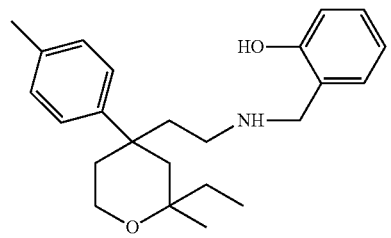 [SMILES: CCC1(C)CC(CCNCc2ccccc2O)(c2ccc(C)cc2)CCO1]

2) 2-[({2-[2-Ethyl-4-(4-fluorophenyl)-2-methyloxan-4-yl]ethyl}amino)methyl]phenol

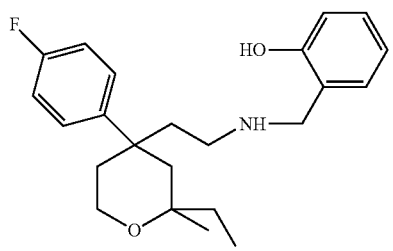 [SMILES: CCC1(C)CC(CCNCc2ccccc2O)(c2ccc(F)cc2)CCO1]

3) {2-[2,2-Dimethyl-4-(4-methylphenyl)oxan-4yl]ethyl}[(4-methoxyphenyl)methyl]amine

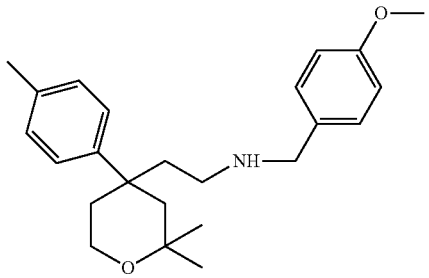

4) {2-[(4S*,4R*)-2,2-dimethyl-4-(4-methylphenyl)oxan-4-yl]ethyl}[(1R)-1-phenylethyl]amine

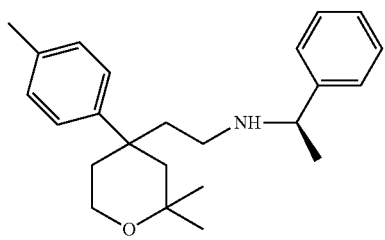 [SMILES: Cc1ccc(C2(CCN[C@H](C)c3ccccc3)CCOC(C)(C)C2)cc1]

5) {2-[(4S*,4R*)-2,2-dimethyl-4-(4-methylphenyl)oxan-4-yl]ethyl}[(1S)-1-phenylethyl]amine

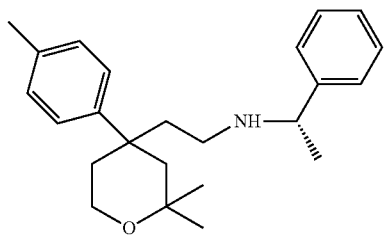 [SMILES: Cc1ccc(C2(CCN[C@@H](C)c3ccccc3)CCOC(C)(C)C2)cc1]

6) Benzyl({2-[2,2-dimethyl-4-(4-methylphenyl)oxan-4-yl]ethyl})amine

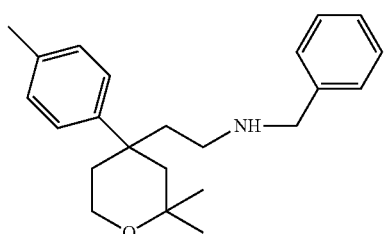

7) 2-[({2-[2-Ethyl-4-(4-fluorophenyl)-2-methyloxan-4-yl]ethyl}amino)methyl]phenol

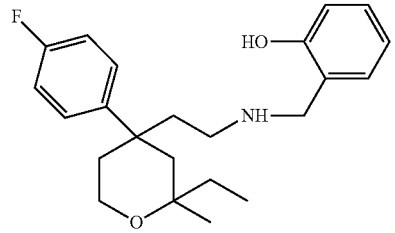 [SMILES: CCC1(C)CC(CCNCc2ccccc2O)(c2ccc(F)cc2)CCO1]

8) Benzyl[2-(2,2-dimethyl-4-phenyloxan-4-yl)ethyl]amine

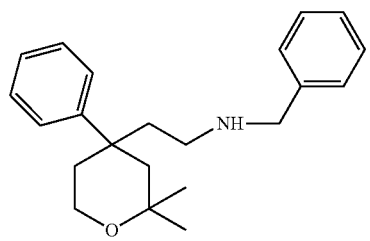 [SMILES: CC1(C)CC(CCNCc2ccccc2)(c2ccccc2)CCO1]

9) {2-[2-Ethyl-4-(4-fluorophenyl)-2-methyloxan-4-yl]ethyl}[(4-methoxyphenyl)methyl]amine

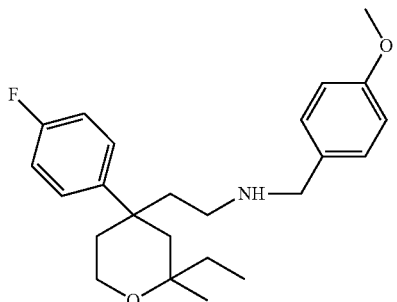

10) [(3,4-Dimethoxyphenyl)methyl]({2-[4-(4-fluorophenyl)-2,2-dimethyloxan-4-yl]ethyl})amine

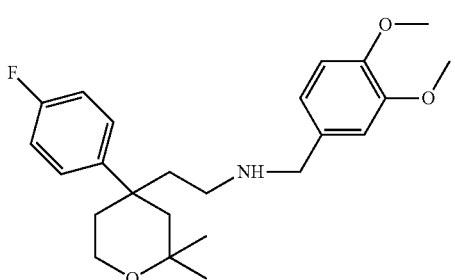

11) {2-[4-(4-Methoxyphenyl)-2,2-dimethyloxan-4-yl]ethyl}(1-phenylethyl)amine

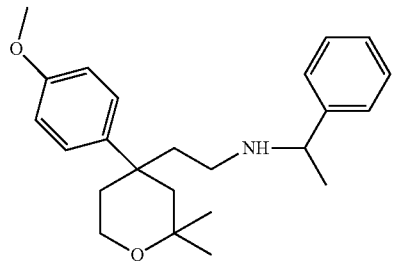 [SMILES: COc1ccc(C2(CCNC(C)c3ccccc3)CCOC(C)(C)C2)cc1]

12) [(4-Chlorophenyl)methyl]({2-[4-(4-methoxyphenyl)-2,2-dimethyloxan-4-yl]ethyl})amine

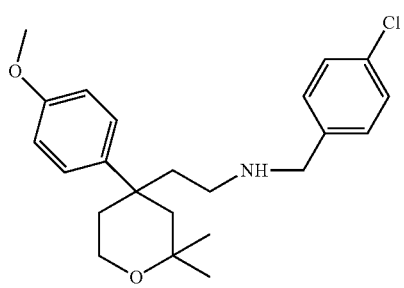 [SMILES: COc1ccc(C2(CCNCc3ccc(Cl)cc3)CCOC(C)(C)C2)cc1]

13) Benzyl({2-[2-ethyl-4-(2-methoxyphenyl)-2-methyloxan-4-yl]ethyl})amine

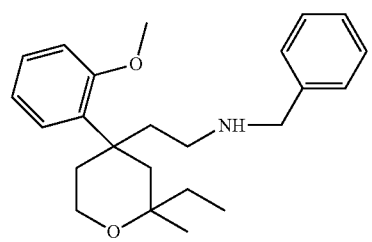 [SMILES: CCC1(C)CC(CCNCc2ccccc2)(c2ccccc2OC)CCO1]

14) [(3,4-dimethoxyphenyl)methyl]({2-[2-ethyl-4-(2-methoxyphenyl)-2-methyloxan-4-yl]ethyl})amine

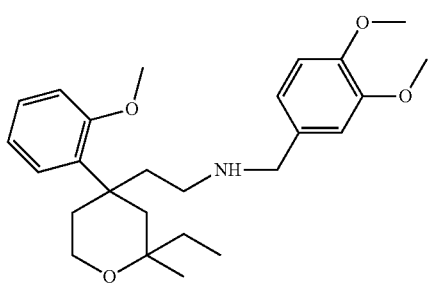 [SMILES: CCC1(C)CC(CCNCc2ccc(OC)c(OC)c2)(c2ccccc2OC)CCO1]

15) 4-[({2-[4-(2-Methoxyphenyl)-2,2-dimethyloxan-4-yl]ethyl}amino)methyl]-N,N-dimethylaniline

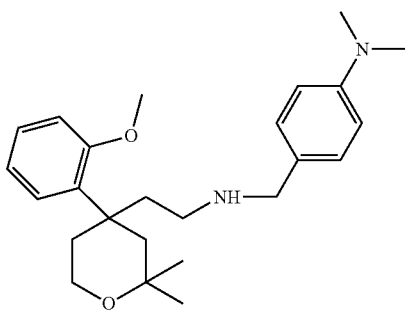 [SMILES: COc1ccccc1C1(CCNCc2ccc(N(C)C)cc2)CCOC(C)(C)C1]

16) Benzyl({2-[4-(4-fluorophenyl)-2,2-dimethyloxan-4-yl]ethyl})amine

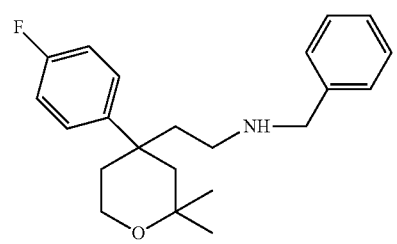 [SMILES: CC1(C)CC(CCNCc2ccccc2)(c2ccc(F)cc2)CCO1]

17) {2-[2,2-dimethyl-4-(4-methylphenyl)oxan-4-yl]ethyl}(1-phenylethyl)amine

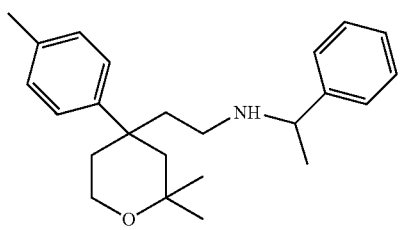 [SMILES: Cc1ccc(C2(CCNC(C)c3ccccc3)CCOC(C)(C)C2)cc1]

18) [2-(2,2-Dimethyl-4-phenyloxan-4-yl)ethyl][(4-methoxyphenyl)methyl]amine

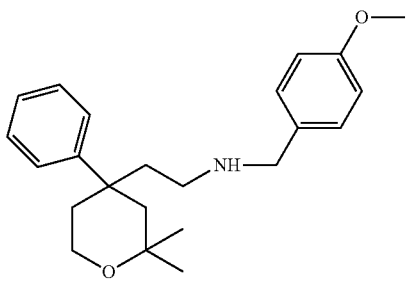 [SMILES: COc1ccc(CNCCC2(c3ccccc3)CCOC(C)(C)C2)cc1]

19) {2-[4-(4-Fluorophenyl)-2,2-dimethyloxan-4-yl]ethyl}[(4-methoxyphenyl)methyl]amine

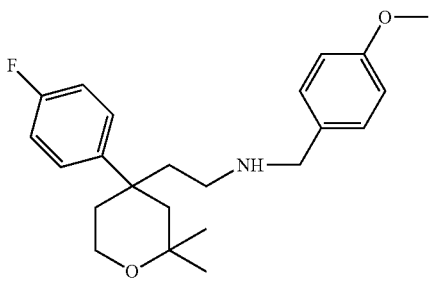 [SMILES: COc1ccc(CNCCC2(c3ccc(F)cc3)CCOC(C)(C)C2)cc1]

20) [(3,4-Dimethoxyphenyl)methyl][2-(2,2-dimethyl-4-phenyloxan-4-yl)ethyl]amine

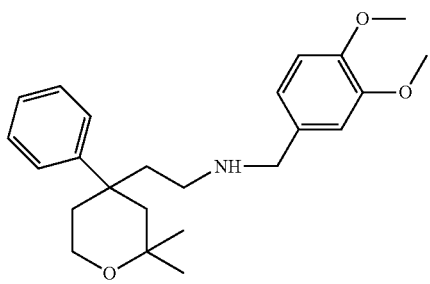 [SMILES: COc1ccc(CNCCC2(c3ccccc3)CCOC(C)(C)C2)cc1OC]

This application also describes compounds having the structure of Formula II-1 and II-2:

II-1

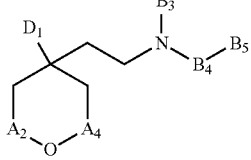

II-2

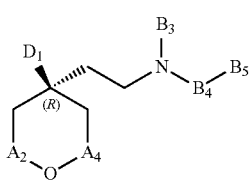

wherein $A_2$ is $CH_2$, $CHR_5$, $CR_5R_6$; $A_4$ is $CH_2$, $CHR_9$, $CR_9R_{10}$ or a cycle of the formula $C(CH_2)_n$, where n=2-5.

Further $R_5$, $R_6$, $R_9$, and $R_{10}$ are independently $CH_3$, $CH_2CH_3$, $CH_2F$, $CHF_2$, $CF_3$, n-Pr, n-Bu, i-Bu, sec-Bu, i-Pr, t-Bu, or phenyl. Further, $R_5$ and $R_6$, or $R_9$ and $R_{10}$ can form a monocyclic carbocycle.

$A_2$ and $A_4$ can be connected by a carbon bridge. This bridge can be —$CH_2$— or —$CH_2CH_2$—.

Further $B_3$ is selected from the following: H, alkyl, branched alkyl, aryl, arylalkyl, alkylcarbonyl, branched alkylcarbonyl, arylcarbonyl, alkoxycarbonyl, and alkylsulfonyl. In some embodiments, $B_3$ is $C_1$-$C_5$ alkyl. In some embodiments, $B_3$ is H.

Further $B_4$ is null, $C_1$-$C_6$ alkyl, $CH_2$, $CH_2CH_2$, $CHR_{19}$, $CR_{19}R_{20}$ or CO. Further, $R_{19}$ and $R_{20}$ can form a monocycle of the formula $(CH_2)_n$, where n=2-4. $B_5$ is alkyl, branched alkyl, carbocycle, carbocycle-substituted alkyl, aryl or arylalkyl.

Further $D_1$ is an aryl. Examples of the aryl groups are shown above.

Each aryl group can be independently mono or multiply substituted with F, Cl, Br, $CH_3$, $CH_2CH_3$, $CH_2F$, $CHF_2$, $CF_3$, n-Pr, n-Bu, i-Bu, sec-Bu, i-Pr, t-Bu, CN, OH, OMe, OEt, O-iPr, $OCF_3$, $NH_2$, NHMe, $NMe_2$, methoxycarbonyl, Ph, benzyl, formyl, or acetyl. That is, each aryl group may be multiply substituted with the same substituent (i.e., 2 chloro groups) or just be multiply substituted, albeit with different groups (e.g. an aryl group with 1 chloro and 1 methyl group would be considered multiply substituted).

This application also describes compounds having the structure of Formula III:

III

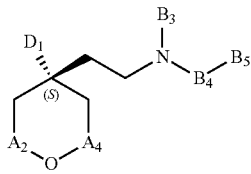

wherein $A_2$ is $CH_2$, $CHR_5$ or $CR_5R_6$; $A_4$ is $CH_2$, $CHR_9$, $CR_9R_{10}$ or a cycle of the formula $C(CH_2)_n$, where n=2-5.

Further $R_5$, $R_6$, $R_9$, and $R_{10}$ are independently $CH_3$, $CH_2CH_3$, $CH_2F$, $CHF_2$, $CF_3$, n-Pr, n-Bu, i-Bu, sec-Bu, i-Pr, t-Bu, or phenyl. $R_5$ and $R_6$, or $R_9$ and $R_{10}$ can form a monocyclic carbocycle.

$A_2$ and $A_4$ can be connected by a carbon bridge. The bridge can be —$CH_2$— or —$CH_2CH_2$—.

Further $B_3$ is selected from H, alkyl, branched alkyl, aryl, arylalkyl, alkylcarbonyl, branched alkylcarbonyl, arylcarbonyl, alkoxycarbonyl or alkylsulfonyl.

Further $B_4$ is null, $C_1$-$C_6$ alkyl, $CH_2$, $CH_2CH_2$, $CHR_{19}$, $CR_{19}R_{20}$ or CO. Further, $R_{19}$ and $R_{20}$ can form a monocycle of the formula $(CH_2)_n$, where n=2-4. $B_5$ is alkyl, branched alkyl, carbocycle, carbocycle-substituted alkyl, aryl or arylalkyl.

Further $D_1$ is an aryl. Examples of the aryl groups are shown above.

The aryl groups can be mono or multiply substituted with F, Cl, Br, $CH_3$, $CH_2CH_3$, $CH_2F$, $CHF_2$, $CF_3$, n-Pr, n-Bu, i-Bu, sec-Bu, i-Pr, t-Bu, CN, OH, OMe, OEt, O-iPr, $OCF_3$, $NH_2$, NHMe, $NMe_2$, methoxycarbonyl, Ph, benzyl, formyl, or acetyl.

This application also describes compounds having the structure of Formula IV-1, IV-2, or IV-3, V, or VI:

IV-1

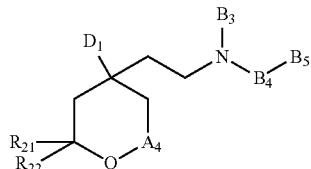

IV-2

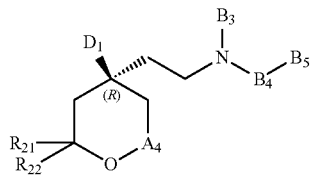

IV-3

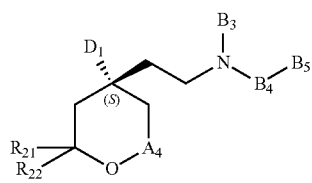

wherein $R_{21}$ and $R_{22}$ are, independently, H or $CH_3$; $A_4$ is $CH_2$, $CR_9R_{10}$ or a cycle of the formula $C(CH_2)_n$, where n=2-5.

Further $R_9$ and $R_{10}$ are independently $CH_3$ or $CH_2CH_3$.

Further $B_3$ is H, $C_1$-$C_6$ alkyl or branched alkyl.

Further $B_4$ is null, $C_1$-$C_6$ alkyl, $CH_2$, $CH_2CH_2$, or —$CHCH_3$.

$B_5$ is —$(CH_2)_nCH_3$, where n=2-3, —$C(CH_3)_3$, cyclohexyl, cyclopentyl, aryl or arylalkyl.

The aryl group can be selected from the list below:

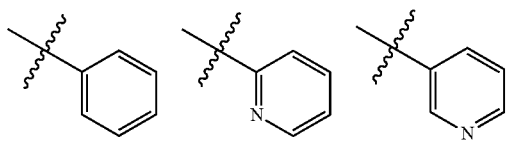

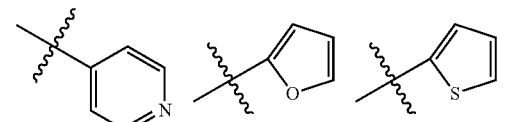

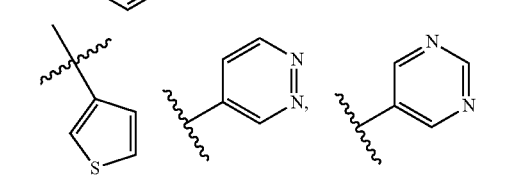

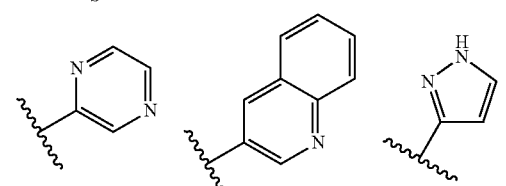

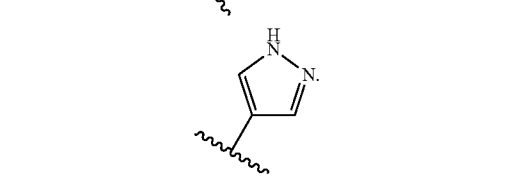

Each aryl groups can be mono or multiply substituted with F, I, Cl, Br, $CH_3$, CN, OH, OMe, OEt, $OCF_3$, $CF_3$, or methanesulfonyl.

Further, in some embodiments, $D_1$ is a phenyl, 2-pyridyl, 3-pyridyl, or 4-pyridyl which can be independently mono or multiply substituted with F, Cl, Br, $OCF_3$, $CF_3$, or $CH_3$.

This application also describes compounds having the structure of Formula V-1, V-2, V-3, VI-1, VI-2, or VI-3:

V-1

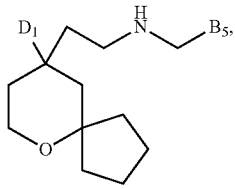

V-2

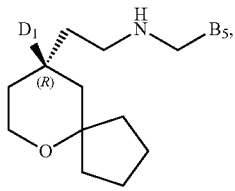

V-3

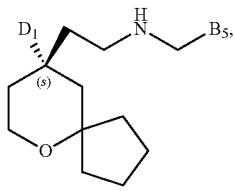

VI-1

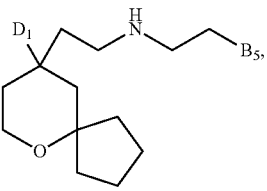

VI-2

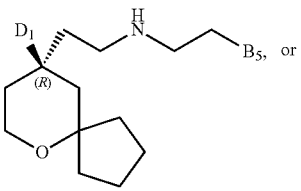

VI-3

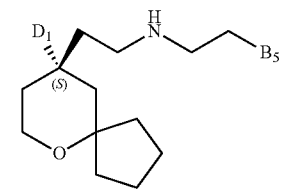

wherein $D_1$ is an aryl; $B_5$ is an aryl or carbocycle.

In some embodiments, each aryl group is independently selected from the list below:

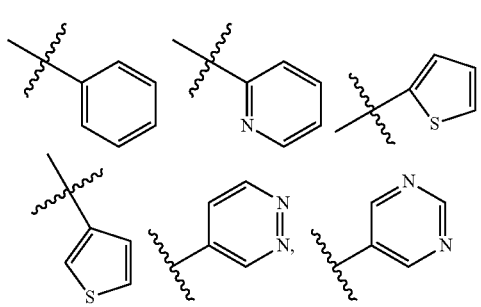

-continued

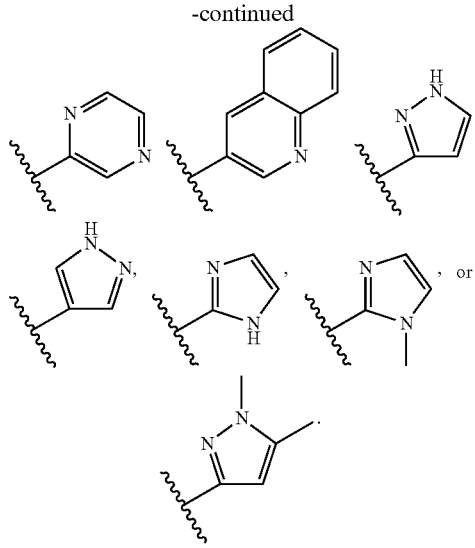

In some embodiments, each aryl group is independently mono or multiply substituted. In some embodiments, each aryl group can be independently mono or multiply substituted with I, F, Cl, Br, CH$_3$, CN, OH, OMe, OEt, OCF$_3$, CF$_3$, or methane sulfonyl. Further, in some embodiments, the carbocycle is cyclohexyl, cyclohexenyl or cyclopentyl.

In some embodiments, D$_1$ is an optionally mono or multiply substituted aryl. In some embodiments, B$_5$ is an optionally mono or multiply substituted aryl or carbocycle. In some embodiments, D$_1$ or B$_5$ is independently selected from the group consisting of:

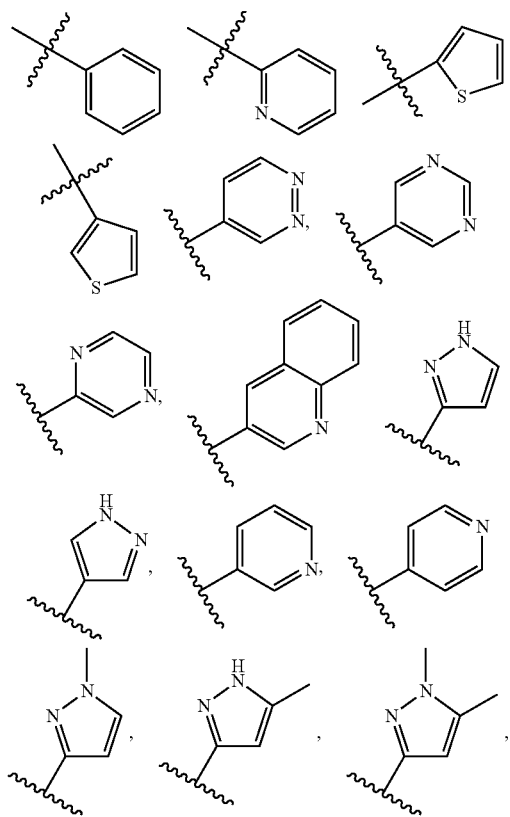

-continued

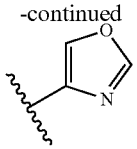

and
wherein the carbocycle is cyclohexyl, cyclohexenyl or cyclopentyl.

In some embodiments, D$_1$ is optionally mono or multiply substituted phenyl, 2-pyridyl, 3-pyridyl, or 4-pyridyl. In some embodiments, D$_1$ is optionally substituted with one or more of F, Cl, Br, I, OCF$_3$, CH$_3$, and CF$_3$. In some embodiments, D$_1$ is not substituted.

In some embodiments, B$_5$ is optionally mono or multiply substituted

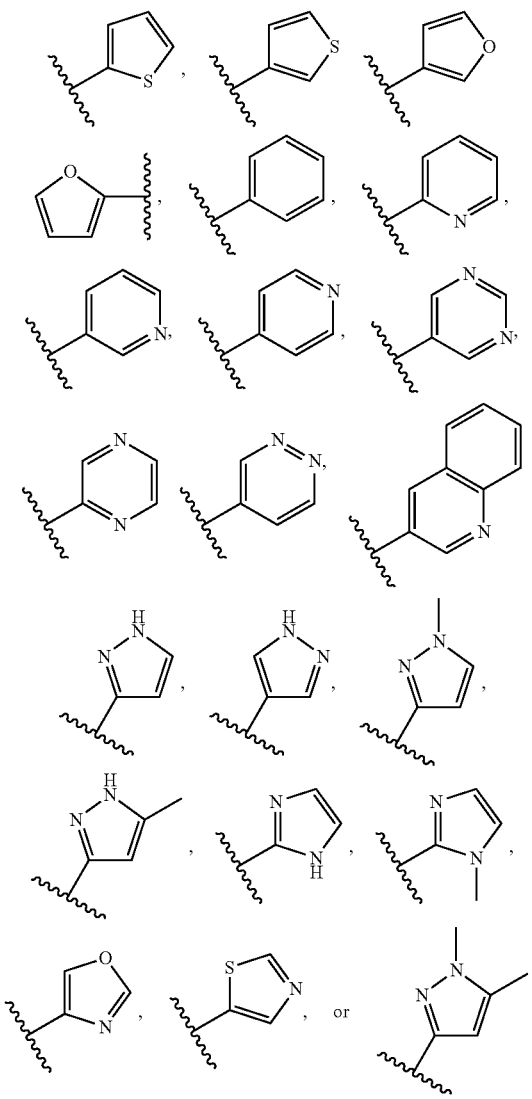

In some embodiments, B$_5$ is substituted with one or more of Cl, Br, F, I, OMe, CN, CH$_3$, methanesulfonyl, and CF$_3$. In some embodiments, B$_5$ is substituted with two or more of Cl, Br, F, I, OMe, CN, CH$_3$, CF$_3$, and methanesulfonyl, or a combination thereof. That is $B_5$ can have two or more substituents but not all of the plurality of substituents needs to be the same.

In some embodiments, compounds having structures of Formula VII-1, VII-2, or VII-3

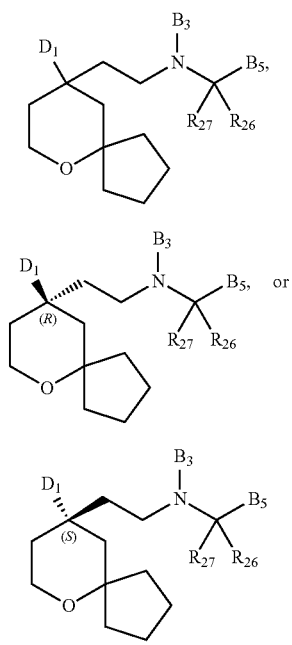

are provided, wherein $D_1$ is an optionally substituted heteroaryl or aryl, $B_3$ is H or alkyl, $B_5$ is an optionally substituted aryl or heteroaryl, and $R_{26}$ and $R_{27}$ are each hydrogen or an isotope thereof. In some embodiments, $R_{26}$ and $R_{27}$ are deuterium. In some embodiments, $R_{26}$ or $R_{27}$ are independently alkyl. In some embodiments, $B_3$ is $C_1$-$C_5$ alkyl.

In some embodiments, the compound has a structure of Formula VIII or an enantiomer thereof.

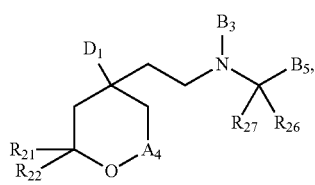

wherein D1 is an optionally substituted heteroaryl or aryl, B3 is H or alkyl, B5 is an optionally substituted aryl or heteroaryl, and R26 and R27 are each hydrogen or an isotope thereof. In some embodiments, R26 and R27 are deuterium. In some embodiments, R26 or R27 are independently alkyl. A4 is as described herein. In some embodiments, B3 is C1-C5 alkyl. In some embodiments, the enantiomer is the R or S enantiomer at the carbon that is connected to D1.

In some embodiments, a compound has the structure of Formula IX or an enantiomer thereof

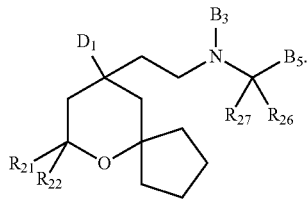

In some embodiments, the enantiomer is the R or S enantiomer at the carbon that is connected to $D_1$.

In some embodiments, a compound has the structure of Formula X or an enantiomer thereof

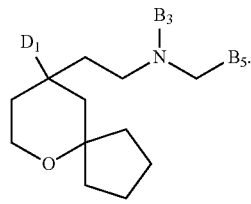

In some embodiments, the enantiomer is the R or S enantiomer at the carbon that is connected to D1.

In some embodiments of the structures described herein, D1 is an optionally substituted pyridyl group or phenyl group. In some embodiments, D1 is an optionally substituted 2-pyridyl, 3-pyridyl, or 4-pyridyl group or phenyl group. In some embodiments, D1 is optionally substituted with one or more of, H, OH, alkyl alcohol, halo, alkyl, amide, cyano, alkoxy, haloalkyl, or alkylsulfonyl. In some embodiments, D1 is optionally substituted with one or more of H, OH, Cl, Br, F, I, OMe, CN, $CH_3$, $CF_3$.

In some embodiments of the structures described herein, $B_5$ is an optionally substituted thiophene group. In some embodiments, $B_5$ is substituted with an alkoxy group. In some embodiments, $B_5$ is substituted with a $C_1$-$C_5$ alkoxy group. In some embodiments, $B_5$ is substituted with a methoxy group. In some embodiments, $B_5$ is

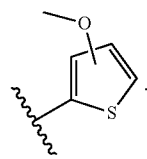

In some embodiments, $B_5$ is

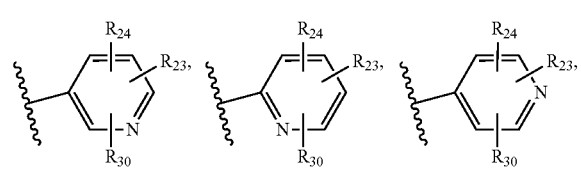

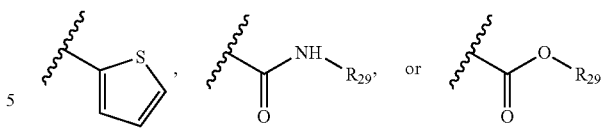

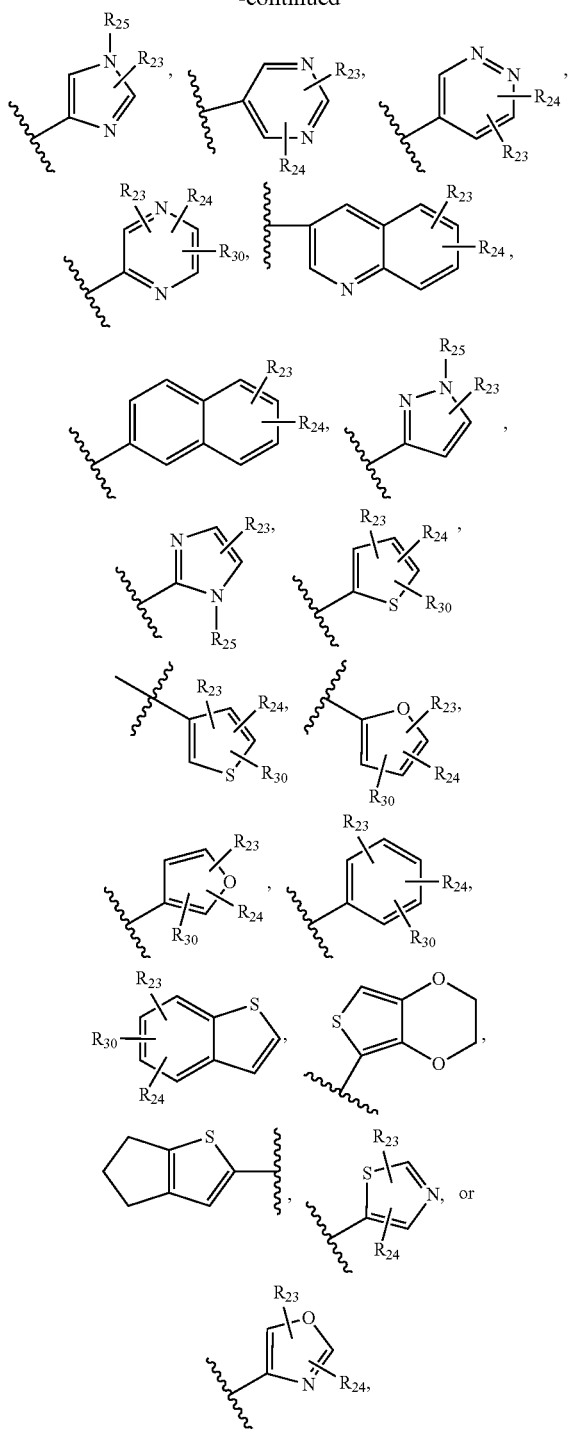

wherein $R_{23}$, $R_{24}$, and $R_{30}$ are each independently null, H, OH, cycle, aryl, branched or unbranched alkyl alcohol, halo, branched or unbranched alkyl, amide, cyano, alkoxy, haloalkyl, alkylsulfonyl, nitrite, alkylsulfanyl, and $R_{25}$ is H or alkyl. In some embodiments, $R_{23}$ and $R_{24}$ together form a aryl or cycle that is attached to one or more of the atoms of $B_5$. $R_{23}$ $R_{24}$, and $R_{30}$ can also be further substituted. In some embodiments, $R_{23}$, $R_{24}$, and $R_{30}$ are each independently H, $NH_2$, OH, Cl, Br, F, I, OMe, CN, $CH_3$, phenyl, $C_3$-$C_6$ carbocycle, methanesulfonyl, $CF_3$, wherein $R_{29}$ is H or an alkyl. In some embodiments, $R_{29}$ is a $C_1$-$C_6$ alkyl. In some embodiments, one of $R_{23}$, $R_{24}$, and $R_{30}$ is H. In some embodiments, at least one of $R_{23}$, $R_{24}$, and $R_{30}$ is H. In some embodiments, two of $R_{23}$, $R_{24}$, and $R_{30}$ are H.

The following compounds and others described herein have agonist activity for OR mediated signal transduction:

[(4-chlorophenyl)methyl]({2-[4-(4-methoxyphenyl)-2,2-dimethyloxan-4-yl]ethyl})amine

[(3,4-dimethoxyphenyl)methyl][2-(2,2-dimethyl-4-phenyloxan-4-yl)ethyl]amine

2-[({2-[2-ethyl-2-methyl-4-(4-methylphenyl)oxan-4-yl]ethyl}amino)methyl]phenol

[2-(2,2-dimethyl-4-phenyloxan-4-yl)ethyl][(2-fluorophenyl)methyl]amine

4-[({2-[4-(2-methoxyphenyl)-2,2-dimethyloxan-4-yl]ethyl}amino)methyl]-N,N-dimethylaniline 2-[({2-[2-ethyl-4-(4-fluorophenyl)-2-methyloxan-4-yl]ethyl}amino)methyl]phenol

[(3-methoxythiophen-2-yl)methyl]({2-[(9R)-9-(pyridin-2-yl)-6-oxaspiro[4.5]decan-9-yl]ethyl})amine.

In some embodiments, compounds, such as the ones described herein are provided. In some embodiments, a compound selected from the compounds described in the Examples is provided. The compounds can be used in any of the methods described herein, including, but not limited to, treating pain.

Thus, the application provides methods of generating agonist activity in OR mediated signal transduction through administration of one or more of the above recited compounds to a subject or subject in need thereof.

Various atoms in the compositions described herein can be isotopes that occur at lower frequency. Hydrogen can be replaced at any position in the compositions described herein with deuterium. Optionally, hydrogen can also be replaced with tritium. Carbon ($^{12}C$) can be replaced at any position in the compositions described herein with $^{13}C$ or $^{14}C$. Nitrogen ($^{14}N$) can be replaced with $^{15}N$. Oxygen ($^{16}O$) can be replaced at any position in the compositions described herein with $^{17}O$ or $^{18}O$, Sulfur ($^{32}S$) can be replaced at any position in the compositions described herein with $^{33}S$, $^{34}S$ or $^{36}S$. Chlorine ($^{35}Cl$) can be replaced at any position in the compositions described herein with $^{37}Cl$. Bromine ($^{79}Br$) can be replaced at any position in the compositions described herein with $^{81}Br$.

Selected compounds described herein are agonists and antagonists of Opioid Receptors (ORs). The ability of the compounds to stimulate OR mediated signaling may be measured using any assay known in the art to detect OR mediated signaling or OR activity, or the absence of such signaling/activity. "OR activity" refers to the ability of an OR to transduce a signal. Such activity can be measured, e.g., in a heterologous cell, by coupling an OR (or a chimeric OR) to a downstream effector such as adenylate cyclase.

A "natural ligand-induced activity" as used herein, refers to activation of the OR by a natural ligand of the OR. Activity can be assessed using any number of endpoints to measure OR activity.

Generally, assays for testing compounds that modulate OR-mediated signal transduction include the determination of any parameter that is indirectly or directly under the influence of a OR, e.g., a functional, physical, or chemical effect.

Samples or assays comprising ORs that are treated with a potential activator, inhibitor, or modulator are compared to control samples without the inhibitor, activator, or modulator to examine the extent of inhibition. Control samples (untreated with inhibitors) are assigned a relative OR activity value of 100%. Inhibition of an OR is achieved when the OR activity value relative to the control is about 80%, 50%, or 25%. Activation of an OR is achieved when the OR activity value relative to the control (untreated with activators) is 110%, 150%, 200-500% (i.e., two to five fold higher relative to the control) or, 1000-3000% or higher.

The effects of the compounds upon the function of an OR can be measured by examining any of the parameters described above. Any suitable physiological change that affects OR activity can be used to assess the influence of a compound on the ORs and natural ligand-mediated OR activity. When the functional consequences are determined using intact cells or animals, one can also measure a variety of effects such as changes in intracellular second messengers such as cAMP.

Modulators of OR activity are tested using OR polypeptides as described above, either recombinant or naturally occurring. The protein can be isolated, expressed in a cell, expressed in a membrane derived from a cell, expressed in tissue or in an animal. For example, neuronal cells, cells of the immune system, transformed cells, or membranes can be used to test the GPCR polypeptides described above. Modulation is tested using one of the in vitro or in vivo assays described herein. Signal transduction can also be examined in vitro with soluble or solid state reactions, using a chimeric molecule such as an extracellular domain of a receptor covalently linked to a heterologous signal transduction domain, or a heterologous extracellular domain covalently linked to the transmembrane and or cytoplasmic domain of a receptor. Furthermore, ligand-binding domains of the protein of interest can be used in vitro in soluble or solid state reactions to assay for ligand binding.

Ligand binding to an OR, a domain, or chimeric protein can be tested in a number of formats. Binding can be performed in solution, in a bilayer membrane, attached to a solid phase, in a lipid monolayer, or in vesicles. Typically, in an assay described herein, the binding of the natural ligand to its receptor is measured in the presence of a candidate modulator. Alternatively, the binding of the candidate modulator may be measured in the presence of the natural ligand. Often, competitive assays that measure the ability of a compound to compete with binding of the natural ligand to the receptor are used. Binding can be tested by measuring, e.g., changes in spectroscopic characteristics (e.g., fluorescence, absorbance, refractive index), hydrodynamic (e.g., shape) changes, or changes in chromatographic or solubility properties.

Modulators may also be identified using assays involving β-arrestin recruitment. β-arrestin serves as a regulatory protein that is distributed throughout the cytoplasm in unactivated cells. Ligand binding to an appropriate OR is associated with redistribution of β-arrestin from the cytoplasm to the cell surface, where it associates with the OR. Thus, receptor activation and the effect of candidate modulators on ligand-induced receptor activation, can be assessed by monitoring β-arrestin recruitment to the cell surface. This is frequently performed by transfecting a labeled β-arrestin fusion protein (e.g., β-arrestin-green fluorescent protein (GFP)) into cells and monitoring its distribution using confocal microscopy (see, e.g., Groarke et al., J. Biol. Chem. 274(33):23263 69 (1999)).

Another technology that can be used to evaluate OR-protein interactions in living cells involves bioluminescence resonance energy transfer (BRET). A detailed discussion regarding BRET can be found in Kroeger et al., J. Biol. Chem., 276(16):12736 43 (2001).

Other assays can involve determining the activity of receptors which, when activated by ligand binding, result in a change in the level of intracellular cyclic nucleotides, e.g., cAMP, by activating or inhibiting downstream effectors such as adenylate cyclase. Changes in intracellular cAMP can be measured using immunoassays. The method described in Offermanns & Simon, J. Biol. Chem. 270:15175 15180 (1995) may be used to determine the level of cAMP. Also, the method described in Felley-Bosco et al., Am. J. Resp. Cell and Mol. Biol. 11:159 164 (1994) may be used to determine the level of cGMP. Further, an assay kit for measuring cAMP a is described in U.S. Pat. No. 4,115,538, herein incorporated by reference.

Transcription levels can be measured to assess the effects of a test compound on ligand-induced signal transduction. A host cell containing the protein of interest is contacted with a test compound in the presence of the natural ligand for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using reporter genes may be used as described in U.S. Pat. No. 5,436,128, herein incorporated by reference. The reporter genes can be, e.g., chloramphenicol acetyltransferase, firefly luciferase, bacterial luciferase, β-galactosidase and alkaline phosphatase. Furthermore, the protein of interest can be used as an indirect reporter via attachment to a second reporter such as green fluorescent protein (see, e.g., Mistili & Spector, Nature Biotechnology 15:961 964 (1997)).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

Pharmaceutical Compositions/Formulations

Pharmaceutical compositions can be formulated by standard techniques using one or more physiologically acceptable carriers or excipients. The formulations may contain a buffer and/or a preservative. The compounds and their physiologically acceptable salts and solvates can be formulated for administration by any suitable route, including via inhalation, topically, nasally, orally, parenterally (e.g., intravenously, intraperitoneally, intravesically or intrathecally) or rectally in a vehicle comprising one or more pharmaceutically acceptable carriers, the proportion of which is determined by the solubility and chemical nature of the compound, chosen route of administration and standard biological practice.

Pharmaceutical compositions can include effective amounts of one or more compound(s) described herein together with, for example, pharmaceutically acceptable diluents, preservatives, solubilizers, emulsifiers, adjuvants and/or other carriers. Such compositions may include diluents of various buffer content (e.g., TRIS or other amines, carbonates, phosphates, amino acids, for example, glycinamide hydrochloride (especially in the physiological pH range), N-glycylglycine, sodium or potassium phosphate (dibasic, tribasic), etc. or TRIS-HCl or acetate), pH and ionic strength; additives such as detergents and solubilizing agents (e.g., surfactants such as Pluronics, Tween 20, Tween 80 (Polysorbate 80), Cremophor, polyols such as polyethylene glycol, propylene glycol, etc.), anti-oxidants (e.g., ascorbic acid, sodium metabisulfite), preservatives (e.g., Thimersol, benzyl alcohol, parabens, etc.) and bulking substances (e.g., sugars such as sucrose, lactose, mannitol, polymers such as polyvinylpyrrolidones or dextran, etc.); and/or incorporation of the material into particulate preparations of polymeric compounds such as polylactic acid, polyglycolic acid, etc. or into liposomes. Hyaluronic acid may also be used. Such compositions can be employed to influence the physical state, stability, rate of in vivo release, and rate of in vivo clearance of a compound described herein. See, e.g., Remington's Pharmaceutical Sciences, 18th Ed. (1990, Mack Publishing Co., Easton, Pa. 18042) pages 1435-1712 which are herein incorporated by reference. The compositions can, for example, be prepared in liquid form, or can be in dried powder, such as lyophilized form. Particular methods of administering such compositions are described infra.

Where a buffer is to be included in the formulations described herein, the buffer can be selected from sodium acetate, sodium carbonate, citrate, glycylglycine, histidine, glycine, lysine, arginine, sodium dihydrogen phosphate, disodium hydrogen phosphate, sodium phosphate, and tris (hydroxymethyl)-aminomethane, or mixtures thereof. The buffer can also be glycylglycine, sodium dihydrogen phosphate, disodium hydrogen phosphate, and sodium phosphate or mixtures thereof.

Where a pharmaceutically acceptable preservative is to be included in a formulation of one of the compounds described herein, the preservative can be selected from phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, or mixtures thereof. The preservative can also be phenol or m-cresol.

The preservative is present in a concentration from about 0.1 mg/ml to about 50 mg/ml, in a concentration from about 0.1 mg/ml to about 25 mg/ml, or in a concentration from about 0.1 mg/ml to about 10 mg/ml.

The use of a preservative in pharmaceutical compositions is well-known to the skilled person. For convenience reference is made to Remington: The Science and Practice of Pharmacy, 19th edition, 1995.

The formulation may further comprise a chelating agent where the chelating agent may be selected from salts of ethlenediaminetetraacetic acid (EDTA), citric acid, and aspartic acid, and mixtures thereof.

The chelating agent can be present in a concentration from 0.1 mg/ml to 5 mg/ml, from 0.1 mg/ml to 2 mg/ml or from 2 mg/ml to 5 mg/ml.

The use of a chelating agent in pharmaceutical compositions is well-known to the skilled person. For convenience reference is made to Remington: The Science and Practice of Pharmacy, 19th edition, 1995.

The formulation of the compounds described herein may further comprise a stabilizer selected from high molecular weight polymers and low molecular compounds where such stabilizers include, but are not limited to, polyethylene glycol (e.g. PEG 3350), polyvinylalcohol (PVA), polyvinylpyrrolidone, carboxymethylcellulose, different salts (e.g. sodium chloride), L-glycine, L-histidine, imidazole, arginine, lysine, isoleucine, aspartic acid, tryptophan, and threonine or any mixture thereof. The stabilizer can also be L-histidine, imidazole or arginine.

The high molecular weight polymer can be present in a concentration from 0.1 mg/ml to 50 mg/m, from 0.1 mg/ml to 5 mg/ml, from 5 mg/ml to 10 mg/ml, from 10 mg/ml to 20 mg/ml, from 20 mg/ml to 30 mg/ml or from 30 mg/ml to 50 mg/ml.

The low molecular weight compound can be present in a concentration from 0.1 mg/ml to 50 mg/ml, from 0.1 mg/ml to 5 mg/ml, from 5 mg/ml to 10 mg/ml, from 10 mg/ml to 20 mg/ml, from 20 mg/ml to 30 mg/ml or from 30 mg/ml to 50 mg/ml.

The use of a stabilizer in pharmaceutical compositions is well-known to the skilled person. For convenience reference is made to Remington: The Science and Practice of Pharmacy, 19th edition, 1995.

The formulation of the compounds described herein may further include a surfactant. IN some embodiments, the surfactant may be selected from a detergent, ethoxylated castor oil, polyglycolyzed glycerides, acetylated monoglycerides, sorbitan fatty acid esters, poloxamers, such as 188 and 407, polyoxyethylene sorbitan fatty acid esters, polyoxyethylene derivatives such as alkylated and alkoxylated derivatives (tweens, e.g. Tween-20, or Tween-80), monoglycerides or ethoxylated derivatives thereof, diglycerides or polyoxyethylene derivatives thereof, glycerol, cholic acid or derivatives thereof, lecithins, alcohols and phospholipids, glycerophospholipids (lecithins, kephalins, phosphatidyl serine), glyceroglycolipids (galactopyransoide), sphingophospholipids (sphingomyelin), and sphingoglycolipids (ceramides, gangliosides), DSS (docusate sodium, docusate calcium, docusate potassium, SDS (sodium dodecyl sulfate or sodium lauryl sulfate), dipalmitoyl phosphatidic acid, sodium caprylate, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, palmitoyl lysophosphatidyl-L-serine, lysophospholipids (e.g. 1-acyl-sn-glycero-3-phosphate esters of ethanolamine, choline, serine or threonine), alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, zwitterionic surfactants (e.g. N-alkyl-N,N-dimethylammonio-1-propanesulfonates, 3-cholamido-1-propyldimethylammonio-1-propanesulfonate, dodecylphosphocholine, myristoyl lysophosphatidylcholine, hen egg lysolecithin), cationic surfactants (quarternary ammonium bases) (e.g. cetyl-trimethylammonium bromide, cetylpyridinium chloride), non-ionic surfactants, polyethyleneoxide/polypropyleneoxide block copolymers (Pluronics/Tetronics, Triton X-100, Dodecyl β-D-glucopyranoside) or polymeric surfactants (Tween-40, Tween-80, Brij-35), fusidic acid derivatives—(e.g. sodium tauro-dihydrofusidate etc.), long-chain fatty acids and salts thereof C6-C12 (e.g. oleic acid and caprylic acid), acylcarnitines and derivatives, $N_\alpha$-acylated derivatives of lysine, arginine or histidine, or side-chain acylated derivatives of lysine or arginine, $N_\alpha$-acylated derivatives of dipeptides comprising any combination of lysine, arginine or histidine and a neutral or acidic amino acid, $N_\alpha$-acylated derivative of a tripeptide comprising any combination of a neutral amino acid and two charged amino acids, or the surfactant may be selected from the group of imidazoline derivatives, or mixtures thereof.

The use of a surfactant in pharmaceutical compositions is well-known to the skilled person. For convenience reference is made to Remington: The Science and Practice of Pharmacy, 19th edition, 1995.

Pharmaceutically acceptable sweeteners can be part of the formulation of the compounds described herein. Pharmaceutically acceptable sweeteners include at least one intense sweetener such as saccharin, sodium or calcium saccharin, aspartame, acesulfame potassium, sodium cyclamate, alitame, a dihydrochalcone sweetener, monellin, stevioside or sucralose (4,1',6'-trichloro-4,1',6'-trideoxygalactosucrose), saccharin, sodium or calcium saccharin, and optionally a bulk sweetener such as sorbitol, mannitol, fructose, sucrose, maltose, isomalt, glucose, hydrogenated glucose syrup, xylitol, caramel, and honey.

Intense sweeteners are conveniently employed in low concentrations. For example, in the case of sodium saccharin, the concentration may range from 0.04% to 0.1% (w/v) based on the total volume of the final formulation, or is about 0.06% in the low-dosage formulations and about 0.08% in the high-dosage ones. The bulk sweetener can effectively be used in larger quantities ranging from about 10% to about 35%, or from about 10% to 15% (w/v).

The formulations of the compounds described herein may be prepared by conventional techniques, e.g. as described in Remington's Pharmaceutical Sciences, 1985 or in Remington: The Science and Practice of Pharmacy, 19th edition, 1995, where such conventional techniques of the pharmaceutical industry involve dissolving and mixing the ingredients as appropriate to give the desired end product.

The phrase "pharmaceutically acceptable" or "therapeutically acceptable" refers to molecular entities and compositions that are physiologically tolerable and preferably do not typically produce an allergic or similar untoward reaction, such as gastric upset, dizziness and the like, when administered to a human. As used herein, the term "pharmaceutically acceptable" means approved by a regulatory agency of the Federal or a State government or listed in the U.S. Pharmacopeia or other generally recognized pharmacopeia (e.g., Remington's Pharmaceutical Sciences, Mack Publishing Co. (A. R. Gennaro edit. 1985)) for use in animals, and more particularly in humans.

Administration of the compounds described herein may be carried out using any method known in the art. For example, administration may be transdermal, parenteral, intravenous, intra-arterial, subcutaneous, intramuscular, intracranial, intraorbital, ophthalmic, intraventricular, intracapsular, intraspinal, intracisternal, intraperitoneal, intracerebroventricular, intrathecal, intranasal, aerosol, by suppositories, or oral administration. A pharmaceutical composition of the compounds described herein can be for administration for injection, or for oral, pulmonary, nasal, transdermal, ocular administration.

For oral administration, the pharmaceutical composition of the compounds described herein can be formulated in unit dosage forms such as capsules or tablets. The tablets or capsules may be prepared by conventional means with pharmaceutically acceptable excipients, including binding agents, for example, pregelatinised maize starch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate; or wetting agents, for example, sodium lauryl sulphate. Tablets can be coated by methods well known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparation's can also contain buffer salts, flavoring, coloring, and/or sweetening agents as appropriate. If desired, preparations for oral administration can be suitably formulated to give controlled release of the active compound.

For topical administration, the pharmaceutical composition of the compounds described herein can be formulated in a pharmaceutically acceptable vehicle containing 0.1 to 10 percent, or 0.5 to 5 percent, of the active compound(s). Such formulations can be in the form of a cream, lotion, sublingual tablet, aerosols and/or emulsions and can be included in a transdermal or buccal patch of the matrix or reservoir type as are conventional in the art for this purpose.

For parenteral administration, the compounds described herein are administered by either intravenous, subcutaneous, or intramuscular injection, in compositions with pharmaceutically acceptable vehicles or carriers. The compounds can be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents, for example, suspending, stabilizing, and/or dispersing agents. Alternatively, the active ingredient can be in powder form for constitution with a suitable vehicle, for example, sterile pyrogen-free water, before use.

For administration by injection, the compound(s) can be used in solution in a sterile aqueous vehicle which may also contain other solutes such as buffers or preservatives as well as sufficient quantities of pharmaceutically acceptable salts or of glucose to make the solution isotonic. The pharmaceutical compositions of the compounds described herein may be formulated with a pharmaceutically acceptable carrier to provide sterile solutions or suspensions for injectable administration. Injectables can be prepared in conventional forms, either as liquid solutions or suspensions, solid forms suitable for solution or suspensions in liquid prior to injection or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized. Suitable pharmaceutical carriers are described in "Remington's pharmaceutical Sciences" by E. W. Martin.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch. For intranasal administration the compounds described herein may be used, for example, as a liquid spray, as a powder or in the form of drops.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

The compounds described herein also include derivatives referred to as prodrugs, which can be prepared by modifying functional groups present in the compounds in such a way that the modifications are cleaved, either in routine manipulation or in vivo, to the parent compounds. Examples of prodrugs include compounds of the invention as described herein that contain one or more molecular moieties appended to a hydroxyl, amino, sulfhydryl, or carboxyl group of the compound, and that when administered to a patient, cleaves in vivo to form the free hydroxyl, amino, sulfhydryl, or carboxyl group, respectively. Examples of prodrugs include, but are not limited to, acetate, formate and benzoate derivatives of alcohol and amine functional groups in the compounds of the invention. Preparation and use of prodrugs is discussed in T. Higuchi et al., "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference in their entireties.

Dosages

The compounds described herein may be administered to a patient at therapeutically effective doses to prevent, treat, or control one or more diseases and disorders mediated, in whole or in part, by an OR-ligand interaction. Pharmaceutical compositions comprising one or more of compounds described herein may be administered to a patient in an amount sufficient to elicit an effective protective or therapeutic response in the patient. An amount adequate to accomplish this is defined as "therapeutically effective dose." The dose will be determined by the efficacy of the particular compound employed and the condition of the subject, as well as the body weight or surface area of the area to be treated. The size of the dose also will be determined by the existence, nature, and extent of any adverse effects that accompany the administration of a particular compound or vector in a particular subject.

Toxicity and therapeutic efficacy of such compounds can be determined by standard pharmaceutical procedures in cell cultures or experimental animals, for example, by determining the LD50 (the dose lethal to 50% of the population) and the ED50 (the dose therapeutically effective in 50% of the population). The dose ratio between toxic and therapeutic effects is the therapeutic index and can be expressed as the ratio, LD50/ED50. In some embodiments, compounds that exhibit large therapeutic indices are used. While compounds that exhibit toxic side effects can be used, care should be taken to design a delivery system that targets such compounds to the site of affected tissue to minimize potential damage to normal cells and, thereby, reduce side effects.

The data obtained from cell culture assays and animal studies can be used to formulate a dosage range for use in humans. In some embodiments, the dosage of such compounds lies within a range of circulating concentrations that include the ED50 with little or no toxicity. The dosage can vary within this range depending upon the dosage form employed and the route of administration. For any compound described herein, the therapeutically effective dose can be estimated initially from cell culture assays. A dose can be formulated in animal models to achieve a circulating plasma concentration range that includes the IC50 (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a modulator is from about 1 ng/kg to 10 mg/kg for a typical subject.

The amount and frequency of administration of the compounds described herein and/or the pharmaceutically acceptable salts thereof will be regulated according to the judgment of the attending clinician considering such factors as age, condition and size of the patient as well as severity of the symptoms being treated. An ordinarily skilled physician or veterinarian can readily determine and prescribe the effective amount of the drug required to prevent, counter or arrest the progress of the condition. In general it is contemplated that an effective amount would be from 0.001 mg/kg to 10 mg/kg body weight, and in particular from 0.01 mg/kg to 1 mg/kg body weight. It may be appropriate to administer the required dose as two, three, four or more sub-doses at appropriate intervals throughout the day. Said sub-doses may be formulated as unit dosage forms, for example, containing 0.01 to 500 mg, and in particular 0.1 mg to 200 mg of active ingredient per unit dosage form.

In some embodiments, the pharmaceutical preparation is in a unit dosage form. In such form, the preparation is subdivided into suitably sized unit doses containing appropriate quantities of the active component, e.g., an effective amount to achieve the desired purpose. The quantity of active compound in a unit dose of preparation may be varied or adjusted from about 0.01 mg to about 1000 mg, from about 0.01 mg to about 750 mg, from about 0.01 mg to about 500 mg, or from about 0.01 mg to about 250 mg, according to the particular application. The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

In some embodiments, one or more compounds described herein are administered with another compound. The administration may be sequentially or concurrently. The combination may be in the same dosage form or administered as separate doses. In some embodiments, the another compound is another analgesic or pain reliever. In some embodiments, the another compound is a non-opioid analgesic. Examples of useful non-opioid analgesics include, but, are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Other suitable non-opioid analgesics include the following, non-limiting, chemical classes of analgesic, antipyretic, nonsteroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Inset, Analgesic-Antipyretic and Anti-inflammatory Agents and Drugs Employed in the Treatment of Gout, in Goodman & Gilman's The Pharmacological Basis of Therapeutics 617-57 (Perry B. Molinhoff and Raymond W. Ruddon eds., 9.sup.th ed 1996); and Glen R. Hanson, Analgesic, Antipyretic and Anti-Inflammatory Drugs in Remington: The Science and Practice of Pharmacy Vol II 1196-1221 (A. R. Gennaro ed. 19.sup.th ed. 1995), which are hereby incorporated by reference in their entireties.

The compounds described herein can also be administered Cox-II inhibitors. Examples of useful Cox-II inhibitors and 5-lipoxygenase inhibitors, as well as combinations thereof, are described in U.S. Pat. No. 6,136,839, which is hereby incorporated by reference in its entirety. Examples of Cox-II inhibitors include, but are not limited to, rofecoxib and celecoxib.

The compounds described herein can also be administered with antimigraine agents. Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

The compounds described herein can also be administered with anti-constipation agents. Examples of anti-constipation agents include, but are not limited to, laxatives or stool softners. Examples of anti-constipation agents include, but are not limited to, be docusate, poloxamer 188, psyllium, methylcellulose, carboxymethyl cellulose, polycarbophil, bisacodyl, castor oil, magnesium citrate, magnesium hydroxide, magnesium sulfate, dibasic sodium phosphate, monobasic sodium phosphate, sodium biphosphate or any combination thereof.

Medical Use

The compositions described herein may be useful for treating pain or pain associated disorders. The compositions described herein may be useful for treating immune dysfunction, inflammation, esophageal reflux, neurological and psychiatric conditions, urological and reproductive conditions, medicaments for drug and alcohol abuse, agents for treating gastritis and diarrhea, cardiovascular agents and agents for the treatment of respiratory diseases and cough.

In some embodiments, methods of treating pain are provided. In some embodiments, one or more compound described herein are administered to a subject to treat the pain. In some embodiments, the pain can be post-operative pain. In some embodiments, the pain is caused by cancer. In some embodiments, the pain is neuropathic pain. In some embodiments, the pain is caused by trauma, such as but not limited to, blunt force trauma. In some embodiments, the pain is caused by inflammation.

In some embodiments, the one or more compounds described herein can be administered by any suitable route, including, but not limited to, via inhalation, topically, nasally, orally, parenterally (e.g., intravenously, intraperitoneally, intravesically or intrathecally) or rectally in a vehicle comprising one or more pharmaceutically acceptable carriers, the proportion of which is determined by the solubility and chemical nature of the compound, chosen route of administration and standard practice.

Definitions

Unless otherwise defined, all technical and scientific terms used herein have the same meaning as commonly understood by one of ordinary skill in the art. Although methods and materials similar or equivalent to those described herein can be used in the practice or testing of the compositions and compounds described herein, suitable methods and materials are described below. All publications, patent applications, patents, and other references mentioned herein are incorporated by reference in their entirety. In the case of conflict, the present specification, including definitions, will control. In addition, the materials, methods, and examples are illustrative only not intended to be limiting. Other features and advantages of the compositions and compounds described herein will be apparent from the following detailed description and claims.

The general chemical terms used throughout have their usual meanings. For example, the term alkyl refers to a branched or unbranched saturated hydrocarbon group. The term "n-alkyl" refers to an unbranched alkyl group. The term "$C_x$-$C_y$ alkyl" refers to an alkyl group having from x to y carbon atoms, inclusively, in the branched or unbranched hydrocarbon group. By way of illustration, but without limitation, the term "$C_1$-$C_4$ alkyl" refers to a straight chain or branched hydrocarbon moiety having from 1 to 4 carbon atoms, including methyl, ethyl, n-propyl, isopropyl, n-butyl, isobutyl, sec-butyl, and tert-butyl. The term "$C_1$-$C_4$ n-alkyl" refers to straight chain hydrocarbon moieties having from 1 to 4 carbon atoms including methyl, ethyl, n-propyl, and n-butyl. $C_x$-$C_y$, x can be from 1 to 10 and y is from 2 to 20. The term "$C_3$-$C_6$ cycloalkyl" refers to cyclopropyl, cyclobutyl, cyclopentyl, and cyclohexyl. The term "$C_3$-$C_7$ cycloalkyl" also includes cycloheptyl. Cycloalkylalkyl refers to cycloalkyl moieties linked through an alkyl linker chain, as for example, but without limitation, cyclopropylmethyl, cyclopropylethyl, cyclopropylpropyl, cyclopropylbutyl, cyclobutylmethyl, cyclobutylethyl, cyclobutylpropyl, cyclopentylmethyl, cyclopentylethyl, cyclopentylpropyl, cyclohexylmethyl, cyclohexylethyl, and cyclohexylpropyl. Each alkyl, cycloalkyl, and cycloalkylalkyl group may be optionally substituted, such as, but not limited to, as specified herein. In some embodiments, the alkyl is a $C_1$-$C_3$, $C_1$-$C_4$, $C_1$-$C_6$, $C_4$-$C_6$, or $C_1$-$C_{10}$ alkyl.

The terms "alkoxy", "phenyloxy", "benzoxy" and "pyrimidinyloxy" refer to an alkyl group, phenyl group, benzyl group, or pyrimidinyl group, respectively, that is bonded through an oxygen atom. Each of these groups may be optionally substituted.

The terms "alkylthio", "phenylthio", and "benzylthio" refer to an alkyl group, phenyl group, or benzyl group, respectively, that is bonded through a sulfur atom. Each of these groups may be optionally substituted.

The term "$C_1$-$C_4$ acyl" refers to a formyl group or a $C_1$-$C_3$ alkyl group bonded through a carbonyl moiety. The term "$C_1$-$C_4$ alkoxycarbonyl" refers to a $C_1$-$C_4$ alkoxy group bonded through a carbonyl moiety.

The term "halo" refers to fluoro, chloro, bromo, or iodo. In some embodiments, the halo groups are fluoro, chloro, and bromo. In some embodiments, the halo groups are fluoro and chloro.

As used herein, "carbocycle" or "carbocyclic ring" is intended to mean, unless otherwise specified, any stable 3, 4, 5, 6, 7, 8, 9, 10, 11, or 12-membered monocyclic, bicyclic or tricyclic ring, any of which can be saturated, unsaturated (including partially and fully unsaturated), or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, and tetrahydronaphthyl. As shown above, bridged rings are also included in the definition of carbocycle (e.g., [2.2.2]bicyclooctane). A bridged ring occurs when one or more carbon atoms link two non-adjacent carbon atoms. In some embodiments, the bridges are one or two carbon atoms. It is noted that a bridge always converts a monocyclic ring into a tricyclic ring. When a ring is bridged, the substituents recited for the ring can also be present on the bridge. Fused (e.g., naphthyl and tetrahydronaphthyl) and spiro rings are also included.

The term "heterocycle" is taken to mean a saturated or unsaturated 5- or 6-membered ring containing from 1 to 3 heteroatoms selected from nitrogen, oxygen and sulfur, said ring optionally being benzofused. Exemplary heterocycles include furanyl, thiophenyl (thienyl), pyrrolyl, pyrrolidinyl, pyridinyl, N-methylpyrrolyl, oxazolyl, isoxazolyl, pyrazolyl, imidazolyl, triazolyl, oxadiazolyl, thiadiazolyl, thiazolyl, thiazolidinyl, N-acetylthiazolidinyl, pyrimidinyl, pyrazinyl, pyridazinyl, and the like. Benzofused heterocyclic rings include isoquinolinyl, benzoxazolyl, benzodioxolyl, benzothiazolyl, quinolinyl, benzofuranyl, benzothiophenyl, indolyl, and the like, all of which may be optionally substituted, which also of course includes optionally substituted on the benzo ring when the heterocycle is benzofused.

The term "cycle" group is taken to mean a carbocyclic ring, a carbocycle or a heterocarbocycle.

As used herein, the phrase a "cycle of the formula" refers to a ring that can be formed with the variable referred to. For example, in the structure

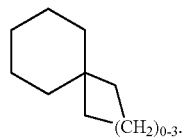

wherein A can be a cycle of the formula $C(CH_2)_n$, where n=2-5, it means that A is a carbon and forms a ring with itself with 2-5 $CH_2$ groups, which could also be represented structurally as

The variable "A" is not limited to carbon and can be another atom, such as, but not limited to, a heteroatom, but the context in which the variable is used will indicate the type of atom "A" could be. This is just a non-limiting example. Additionally, the ring that is formed with "A" can also be substituted. Exemplary substituents are described herein.

In some embodiments, heterocycles include, but are not limited to, pyridinyl, indolyl, furanyl, benzofuranyl, thiophenyl, benzodioxolyl, and thiazolidinyl, all of which may be optionally substituted.

As used herein, the term "aromatic heterocycle" or "heteroaryl" is intended to mean a stable 5, 6, 7, 8, 9, 10, 11, or 12-membered monocyclic or bicyclic aromatic ring which consists of carbon atoms and one or more heteroatoms, e.g., 1 or 1-2 or 1-3 or 1-4 or 1-5 or 1-6 heteroatoms, independently selected from nitrogen, oxygen, and sulfur. In the case of bicyclic heterocyclic aromatic rings, only one of the two rings needs to be aromatic (e.g., 2,3-dihydroindole), though both can be (e.g., quinoline). The second ring can also be fused or bridged as defined above for heterocycles. The nitrogen atom can be substituted or unsubstituted (i.e., N or NR wherein R is H or another substituent, as defined). The nitrogen and sulfur heteroatoms can optionally be oxidized (i.e., N→O and $S(O)_p$, wherein p=1 or 2). In certain compounds, the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2, 5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2, 4-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Substituted alkyl, cycloalkyl, cycloalkylalkyl, alkoxy, or alkylthio, means an alkyl, cycloalkyl, cycloalkylalkyl, alkoxy, or alkylthio group, respectively, substituted one or more times independently with a substituent selected from the group consisting of halo, hydroxy, and $C_1$-$C_3$ alkoxy. By way of illustration, but without limitation, examples include trifluoromethyl, pentafluoroethyl, 5-fluoro-2-bromopentyl, 3-hydroxypropyloxy, 4-hydroxycyclohexyloxy, 2-bromoethylthio, 3-ethoxypropyloxy, 3-ethoxy-4-chlorocyclohexyl, and the like. In some embodiments, substitutions include substitution 1-5 times with halo, each independently selected, or substituted 1-3 times with halo and 1-2 times independently with a group selected from hydroxy and $C_1$-$C_3$ alkoxy, or substituted 1-3 times independently with a group selected from hydroxy and $C_1$-$C_3$ alkoxy, provided that no more than one hydroxy and/or alkoxy substituent may be attached through the same carbon.

The terms "substituted phenyl" and "substituted heterocycle" are taken to mean that the cyclic moiety in either case is substituted. They can be substituted independently with one or more substituents. They can be substituted independently with 1, 2, 3, 4, 5, 1-3, 1-4, or 1-5 substituents. The substitution can be, independently, halo, alkyl, such as, but not limited to, $C_1$-$C_4$ alkyl, alkoxy, such as but not limited to, $C_1$-$C_4$ alkoxy, and alkylthio, such as but not limited to, $C_1$-$C_4$ alkylthio, wherein each alkyl, alkoxy and alkylthio substituent can be further substituted independently with $C_1$-$C_2$ alkoxy or with one to five halo groups; or substituted with one substituent selected from the group consisting of phenyloxy, benzyloxy, phenylthio, benzylthio, and pyrimidinyloxy, wherein the phenyloxy, benzyloxy, phenylthio, benzylthio, and pyrimidinyloxy moiety can be further substituted with one to two substituents selected from the group consisting of halo, $C_1$-$C_2$ alkyl, and $C_1$-$C_2$ alkoxy; or substituted with one substituent selected from the group consisting of $C_1$-$C_4$ acyl and $C_1$-$C_4$ alkoxycarbonyl, and further substituted with zero to one substituent selected from the group consisting of halo, $C_1$-$C_4$ alkyl, $C_1$-$C_4$ alkoxy, and $C_1$-$C_4$ alkylthio. When a substituent is halo, in some embodiments, the halo groups are fluoro, chloro, and bromo. The halo can also be iodo.

DMF means N,N-dimethylformamide.

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

By "pharmaceutical formulation" it is further meant that the carrier, solvent, excipients and salt must be compatible with the active ingredient of the formulation (e.g. a compound described herein). It is understood by those of ordinary skill in this art that the terms "pharmaceutical formulation" and "pharmaceutical composition" are generally interchangeable, and they are so used for the purposes of this application.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary, ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, and toluene sulfonic. The present disclosure includes pharmaceutically acceptable salts of any compound(s) described herein.

Pharmaceutically acceptable salts can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile, and the like. Lists of suitable salts are found in *Remington's Pharmaceutical Sciences,* 18th ed., Mack Publishing Company, Easton, Pa., USA, p. 1445 (1990).

Since prodrugs are known to enhance numerous desirable qualities of pharmaceuticals (e.g., solubility, bioavailability, manufacturing, etc.) the compounds described herein can be delivered in prodrug form and can be administered in this form for the treatment of disease. "Prodrugs" are intended to include any covalently bonded carriers that release an active parent drug of described herein in vivo when such prodrug is administered to a mammalian subject. Prodrugs are prepared by modifying functional groups present in the compound in such a way that the modifications are cleaved, either in routine manipulation or in vivo, to the parent compound. Prodrugs include compounds described herein wherein a hydroxy, amino, or sulfhydryl group is bonded to any group that, when the prodrug is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds described herein.

"Stable compound" and "stable structure" are meant to indicate a compound that is sufficiently robust to survive isolation to a useful degree of purity from a reaction mixture, and formulation into an efficacious therapeutic agent.

As used herein, "treating" or "treatment" includes any effect e.g., lessening, reducing, modulating, or eliminating, that results in the improvement of the condition, disease, disorder, etc. "Treating" or "treatment" of a disease state means the treatment of a disease-state in a mammal, particularly in a human, and include: (a) inhibiting an existing disease-state, i.e., arresting its development or its clinical symptoms; and/or (c) relieving the disease-state, i.e., causing regression of the disease state.

As used herein, "preventing" means causing the clinical symptoms of the disease state not to develop i.e., inhibiting the onset of disease, in a subject that may be exposed to or predisposed to the disease state, but does not yet experience or display symptoms of the disease state.

As used herein, "mammal" refers to human and non-human patients.

As used herein, the term "therapeutically effective amount" refers to a compound, or a combination of compounds, described herein present in or on a recipient in an amount sufficient to elicit biological activity, e.g. pain relief. In some embodiments, the combination of compounds is a synergistic combination. Synergy, as described, for example, by Chou and Talalay, *Adv. Enzyme Regul.* vol. 22, pp. 27-55 (1984), occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased decrease in pain, or some other beneficial effect of the combination compared with the individual components.

All percentages and ratios used herein, unless otherwise indicated, are by weight.

Throughout the description, where compositions are described as having, including, or comprising specific components, or where processes are described as having, including, or comprising specific process steps, it is contemplated that compositions described herein also consist essentially of, or consist of, the recited components, and that the processes described herein also consist essentially of, or consist of, the recited processing steps. Further, it should be understood that the order of steps or order for performing certain actions are immaterial so long as the process remains operable. Moreover, two or more steps or actions can be conducted simultaneously.

All enantiomers, diastereomers, and mixtures thereof, are included within the scope of compounds described herein. In some embodiments, a composition comprising the R enantiomer is free or substantially free of the S enantiomer. In some embodiments, a composition comprising the S enantiomer is free or substantially free of the R enantiomer. In some embodiments, a composition comprises an enantiomeric excess of at least, or about, 80, 85, 90, 91, 92, 93, 94, 95, 96, 97, 98, 99% of either the R or the S enantiomer.

As used throughout this disclosure, the singular forms "a," "an," and "the" include plural reference unless the context clearly dictates otherwise. Thus, for example, a reference to "a composition" includes a plurality of such compositions, as well as a single composition; and a reference to "a therapeutic agent" is a reference to one or more therapeutic and/or pharmaceutical agents and equivalents thereof known to those skilled in the art, and so forth. Thus, for example, a reference to "a host cell" includes a plurality of such host cells, and a reference to "an antibody" is a reference to one or more antibodies and equivalents thereof known to those skilled in the art, and so forth.

The claimed compounds in this invention can be prepared from the procedures described in the schemes below.

Schemes

The following representative schemes illustrate how compounds described herein can be prepared. The specific solvents and reaction conditions referred to are also illustrative and are not intended to be limited. Compounds not described are either commercially available or are readily prepared by one skilled in the art using available starting materials.

Scheme 1: Synthesis of Spirocyclic Nitrile

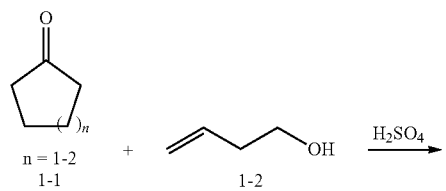

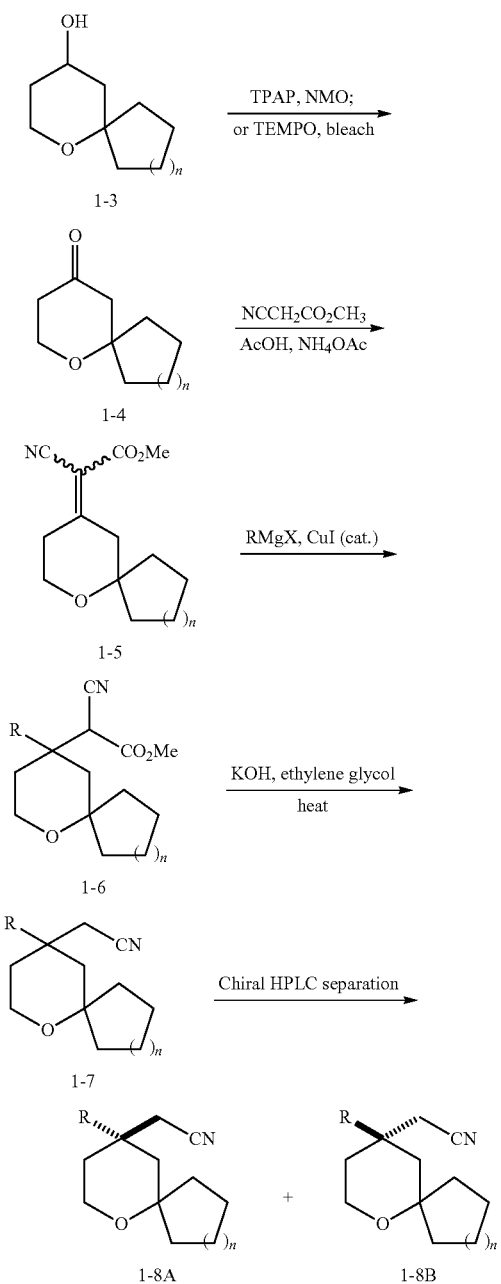

Scheme 2: Converting the nitrile to the opioid receptor ligand (Approach 1)

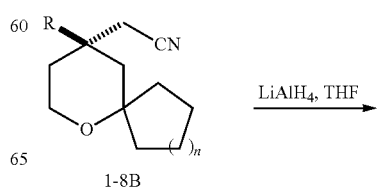

-continued

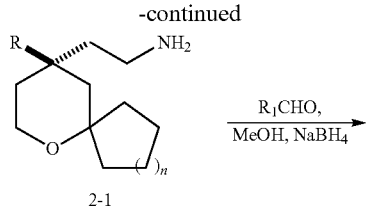
2-1

R₁CHO, MeOH, NaBH₄ →

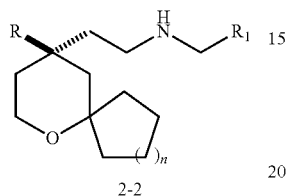
2-2

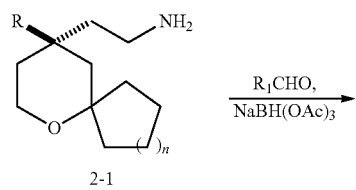
2-1

R₁CHO, NaBH(OAc)₃ →

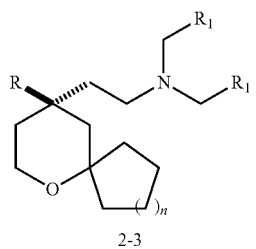
2-3

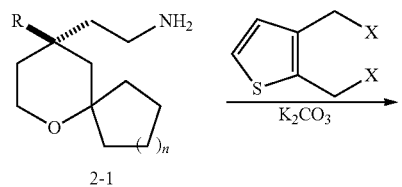
2-1

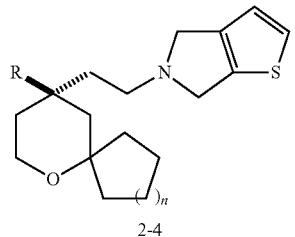
2-4 n = 1-2
R and R₁ are independent
R and R₁ = phenyl, substituted phenyl, aryl, substituted aryl, pyridyl, substituted pyridyl, heteroaryl, substituted heteroaryl, carbocycle, heterocycle and etc.

In some embodiments, the same scheme is applied to 1-7 and 1-8A.

Scheme 3: Converting the nitrile to the opioid receptor ligand (Approach 2)

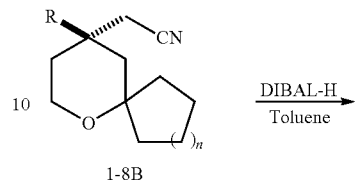
1-8B

DIBAL-H, Toluene →

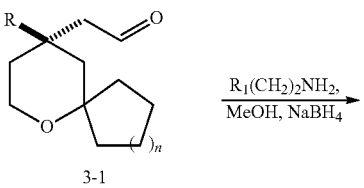
3-1

R₁(CH₂)₂NH₂, MeOH, NaBH₄ →

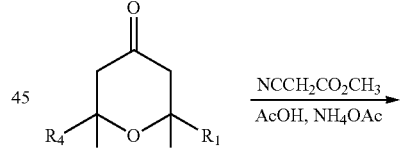
3-2 n = 1-2
R and R₁ are independent
R and R₁ = phenyl, substituted phenyl, aryl, substituted aryl, pyridyl, substituted pyridyl, heteroaryl, substituted heteroaryl, carbocycle, heterocycle and etc.

In some embodiments, the same scheme is applied to 1-7 and 1-8A.

Scheme 4: Synthesis of Non-Spirocyclic Nitrile

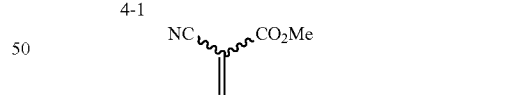
4-1

NCCH₂CO₂CH₃, AcOH, NH₄OAc →

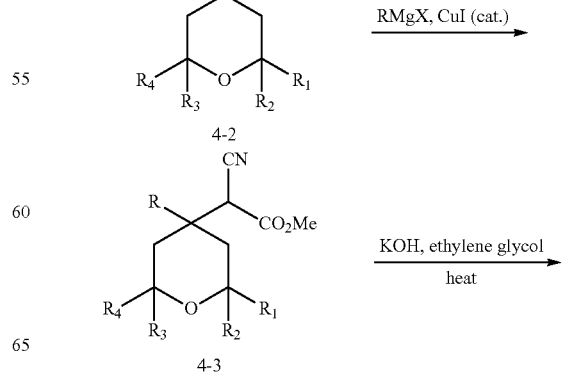
4-2

RMgX, CuI (cat.) →

4-3

KOH, ethylene glycol, heat →

-continued

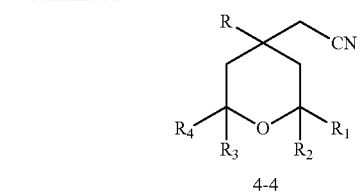
4-4

R = phenyl, substituted phenyl, aryl,
substituted aryl, pyridyl, substituted pyridyl,
heteroaryl, substituted heteroaryl,
carbocycle, heterocycle and etc.

In some embodiments, 4-1 is selected from the group consisting of

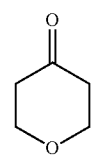
4-1A

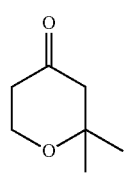
4-1B

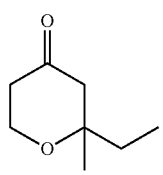
4-1C

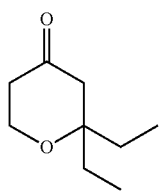
4-1D

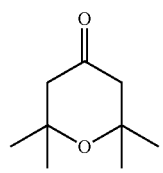
4-1E

Following a sequence outlined in Scheme 2 or 3, intermediate 4-4 can be converted to the opioid receptor ligands.

Scheme 5: Synthesis of Other Spirocyclic Derived Opioid Ligands

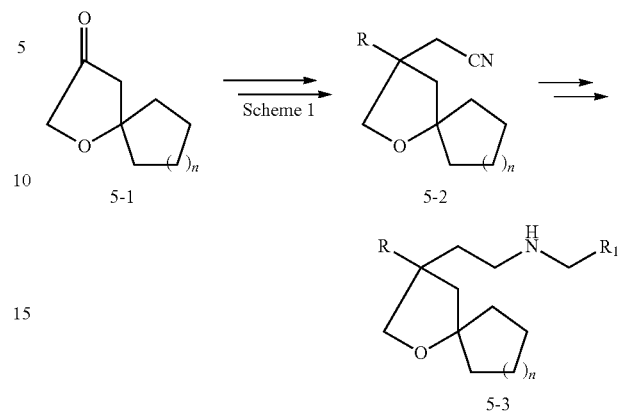

$n = 1-2$
R and $R_1$ are independent
R and $R_1$ = phenyl, substituted phenyl, aryl,
substituted aryl, pyridyl, substituted pyridyl,
heteroaryl, substituted heteroaryl,
carbocycle, heterocycle and etc.

Other schemes can also be used. For example, the following schemes can be used alone or in combination with other schemes to prepare the compounds described herein.

Scheme 6: Allyltrimethylsilane Approach to Access the Quaternary Carbon Center

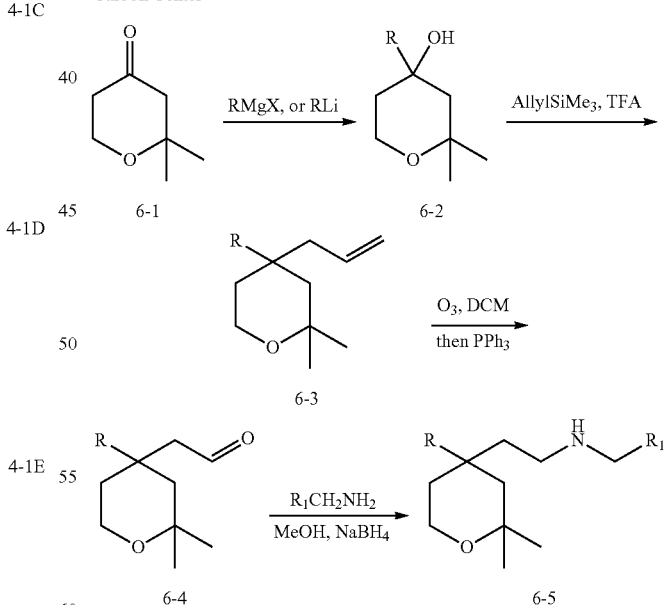

$n = 1-2$
R and $R_1$ are independent
R and $R_1$ = phenyl, substituted phenyl, aryl,
substituted aryl, pyridyl, substituted pyridyl,
heteroaryl, substituted heteroaryl,
carbocycle, heterocycle and etc.

Scheme 7: N-linked Pyrrazole Opioid Receptor Ligand
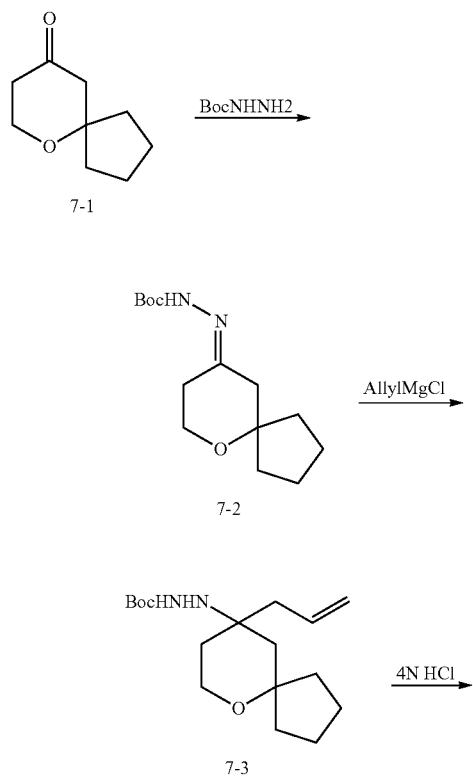
Scheme 8
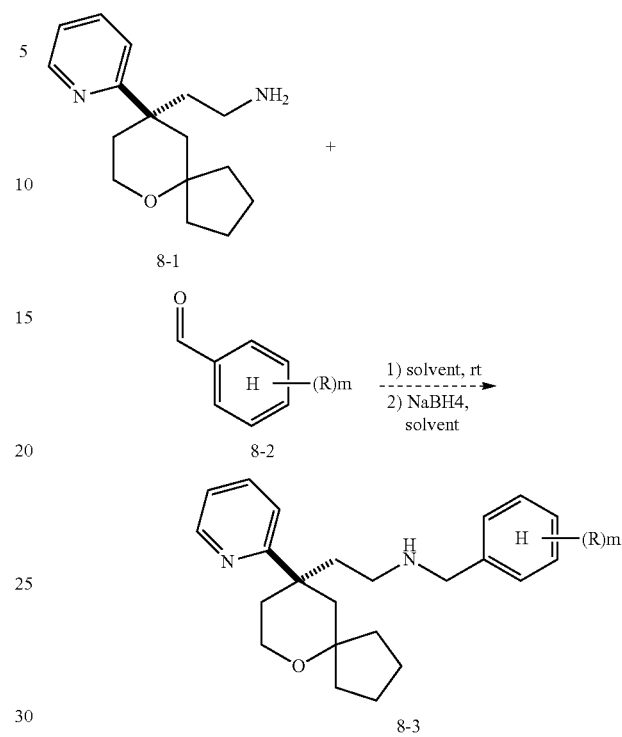
Scheme 9
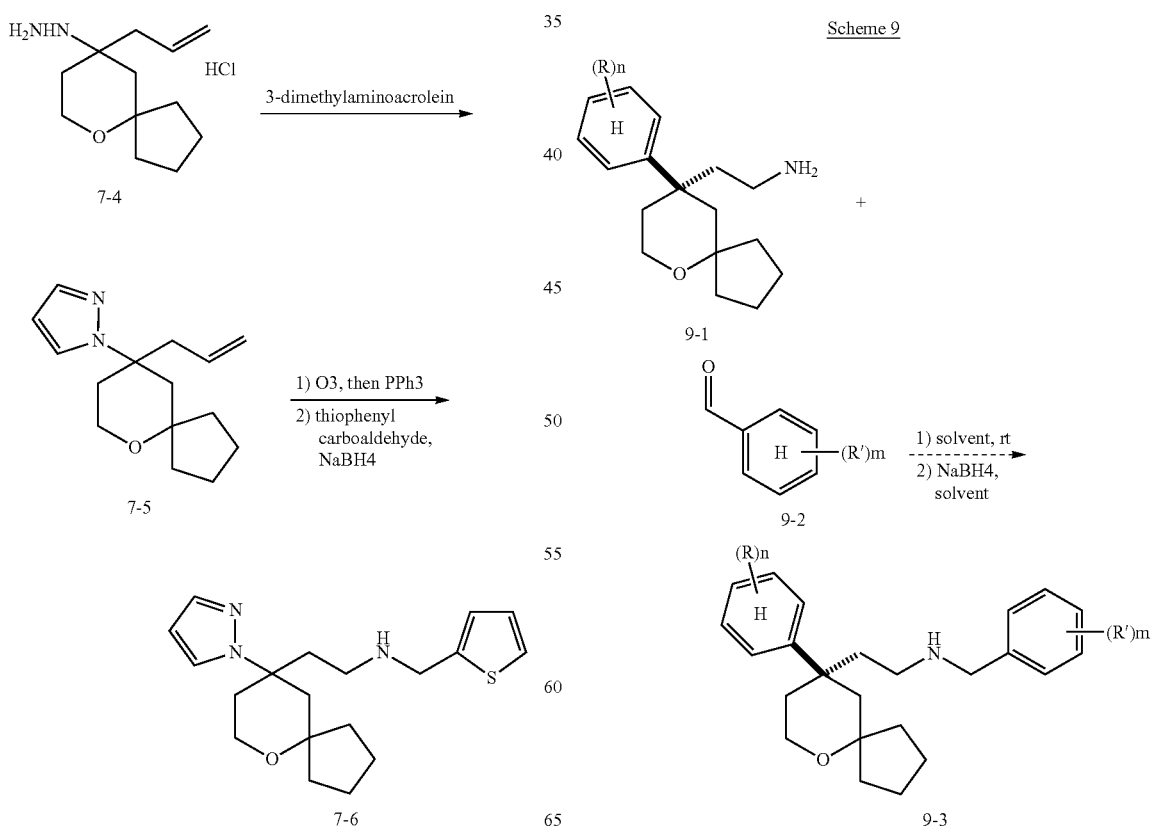

Scheme 10

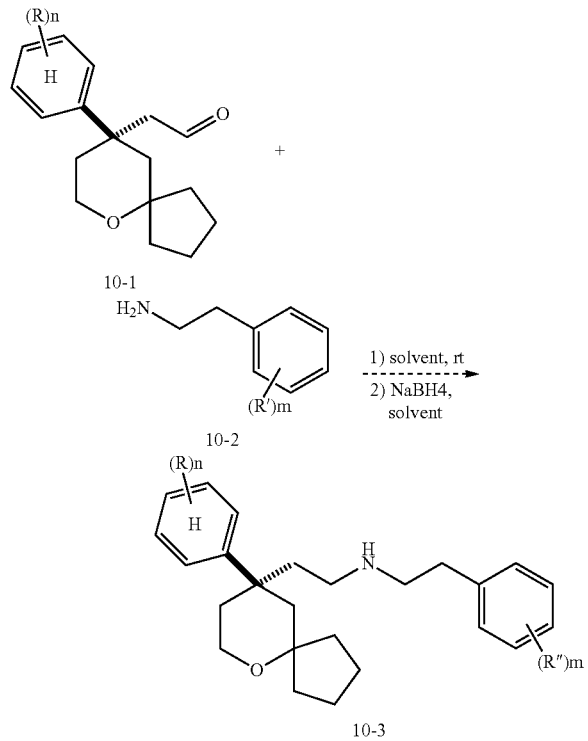

In some embodiments, a process for preparing a compound having the structure of IV-1

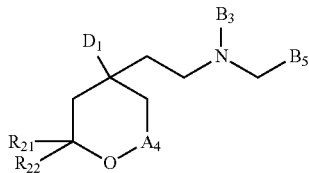

is provided. In some embodiments, the process comprises contacting

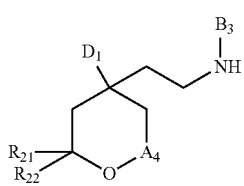

with

under suitable conditions to form a compound having the structure of

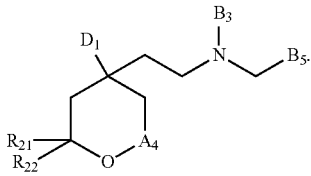

IV-1

In some embodiments, the process is performed at room temperature. In some embodiments, the process is performed in the presence of a borohydrate salt. In some embodiments, the process is performed in the presence of sodium borohydrate. Solvents can also be used to facilitate the preparation. The process can be modified to yield different alkyl groups, such as, but not limited to, the scheme shown in Scheme 10.

EXAMPLES

The following examples are illustrative, but not limiting, of the methods and compositions described herein. Other suitable modifications and adaptations of the variety of conditions and parameters normally encountered in therapy and that are obvious to those skilled in the art are within the spirit and scope of the compounds and methods described herein.

Example 1

Intermediate 1 methyl 2-cyano-2-(oxan-4-ylidene)acetate

A 50 ml round-bottom flask equipped with a Dean-Stark distillation setup and condenser was charged with tetrahydro-4H-pyran-4-one (4.61 ml, 50 mmol), methyl cyanoacetate (5.3 ml, 60 mmol), ammonium acetate (1 g, 13 mmol), acetic acid (0.57 ml, 10 mmol) and benzene (30 ml). The mixture was refluxed until no more water collected in the Dean-Stark (2 hours), cooled, benzene (30 ml) added and the organic layer washed with water (50 ml). The aqueous layer was extracted with $CH_2Cl_2$ (3×50 ml). The combined organic phase was washed with sat. $NaHCO_3$ (100 ml), brine (100 ml) dried ($MgSO_4$), filtered and concentrated. Purified by normal phase $SiO_2$ chromatography (10 to 60% EtOAc/hexanes) to afford methyl 2-cyano-2-(oxan-4-ylidene)acetate as a colorless oil (6.30 g, 70%, m/z: 181.1 [M+H]$^+$ observed).

Intermediate 2 methyl 2-cyano-2-[4-(4-fluorophenyl)oxan-4-yl]acetate

A round bottom flask was equipped with a condenser, addition funnel and rubber septum with nitrogen inlet was charged with a solution of p-fluorophenylmagnesium bromide (2.0 M in diethyl ether, 1.99 ml, 3.97 mmol) and CuI (63 mg, 0.331 mmol) in 10 ml dry diethyl ether (10 ml). Methyl 2-cyano-2-(oxan-4-ylidene)acetate (600 mg, 3.31 mmol) in diethyl ether (10 ml) was added drop-wise over 30 min while cooling the reaction flask in an ice bath. The mixture was then stirred for 3 h. The reaction mixture was poured into a 50 g ice/1 N HCl (25 ml) mixture. The product was extracted with $Et_2O$ (3×50 ml), washed with brine (50 ml), dried ($NA_2SO_4$) and concentrated. Purified by normal phase $SiO_2$ chromatography (7% to 60% EtOAc/hexanes) to give methyl 2-cyano- 2-[4-(4-fluorophenyl)oxan-4-yl]acetate as a white solid (730 mg, 80%, m/z: 277.1 [M+Na]$^+$ observed).

Intermediate 3

2-[4-(4-fluorophenyl)oxan-4-yl]acetonitrile

To a pre-dissolved solution of KOH (441 mg, 7.87 mmol) in ethylene glycol (20 ml) was added methyl 2-cyano-2-[4-(4-fluorophenyl)oxan-4-yl]acetate (1.09 g, 3.93 mmol). The mixture was heated to 120° C. for 3 h, and then cooled. H$_2$O was added (50 ml), the product extracted with Et$_2$O (3×50 ml), washed with H$_2$O (50 ml), dried over NA$_2$SO$_4$, filtered and concentrated. Purified by normal phase SiO$_2$ chromatography (5 to 40% EtOAc/hexanes) to give 2-[4-(4-fluorophenyl)oxan-4-yl]acetonitrile as a colorless oil (450 mg, 78%, m/z: 219.1 [M+H]$^+$ observed).

Intermediate 4

2-[4-(4-fluorophenyl)oxan-4-yl]ethan-1-amine

To a solution of 2-[4-(4-fluorophenyl)oxan-4-yl]acetonitrile (450 mg, 2.05 mmol) in anhydrous ether (15 ml) at 0° C. was added dropwise LAH (1.0 M in Et$_2$O, 4.1 ml, 4.11 mmol). After 2 h the reaction was quenched with 1 ml H$_2$O, 0.1 ml 15% NaOH and then 1 ml H$_2$O. The reaction mixture was extracted with Et$_2$O (3×20 ml), dried over NA$_2$SO$_4$ and concentrated to give 2-[4-(4-fluorophenyl)oxan-4-yl]ethan-1-amine as an yellow oil, which used without further purification (450 mg, 94%, m/z: 223.1 [M+H]$^+$ observed).

Example 2 benzyl({2-[4-(4-fluorophenyl)oxan-4-yl]ethyl}) amine (Compound 8)

To a solution of 2-[4-(4-fluorophenyl)oxan-4-yl]ethan-1-amine (250 mg, 1.12 mmol) in anhydrous CH$_2$Cl$_2$ (5 ml) and NA$_2$SO$_4$ (159 mg, 1.12 mmol) at rt was added benzaldehyde (0.17 ml, 1.68 mmol). The reaction was stirred overnight. The reaction mixture was filtered and concentrated. The residue was dissolved in 5 ml MeOH at 0° C. and NaBH$_4$ added in one portion (51 mg, 1.34 mmol). The reaction was stirred at 0° C. for 1 h. The solution was then quenched with H$_2$O (10 ml), extracted with CH$_2$Cl$_2$ (3×20 ml), washed with brine (10 ml) and dried over NA$_2$SO$_4$. Purified by normal phase SiO$_2$ chromatography (0 to 10% MeOH/CH$_2$Cl$_2$) to give benzyl({2-[4-(4-fluorophenyl) oxan-4-yl]ethyl})amine as a colorless oil (200 mg, 60%, m/z: 314.2 [M+H]$^+$ observed).

Intermediate 5

2,2-dimethyl-4-(4-methylphenyl)oxan-4-ol n-BuLi (26.3 ml, 1.6 M in hexane, 42 mmol) was added dropwise to a solution of 4-bromo-toluene (7.70 g, 45 mmol) in THF (100 ml) at −78° C. under N$_2$. The resulting mixture was stirred at −78° C. for 30 min and a solution of tetrahydro-2,2-dimethyl-4H-pyran-4-one (3.84 g, 30 mmol) in THF (20 ml) was added. The resulting mixture was stirred at −78° C. for another 20 min and quenched by adding MeOH (10 ml). The reaction was concentrated under vacuum and the resulting residue was diluted with EtOAc (500 ml) and washed with sat. NH$_4$Cl (250 ml), brine (250 ml), dried and concentrated to give 2,2-dimethyl-4-(4-methylphenyl)oxan-4-ol as a white solid, which was used without further purification (5.41 g, 82%).

$^1$H NMR (400 MHz, CDCl$_3$) δ 7.36-7.26 (m, 2H), 7.11 (d, J=8.0, 2H), 4.10 (td, J=12.0, 2.2, 1H), 3.71 (ddd, J=11.8, 5.0, 2.1, 1H), 2.28 (s, 3H), 2.11 (ddd, J=13.7, 12.2, 5.0, 1H), 1.72 (dt, J=14.2, 8.3, 2H), 1.58 (dq, J=13.8, 2.2, 1H), 1.44 (s, 3H), 1.38 (s, 1H), 1.14 (s, 3H).

Intermediate 6

2,2-dimethyl-4-(4-methylphenyl)-4-(prop-2-en-1-yl) oxane

Allyltrimethylsilane (4.34 ml, 27.2 mmol) was added to a solution of 2,2-dimethyl-4-(4-methylphenyl)oxan-4-ol (3.0 g, 13.6 mmol) in dry CH$_2$Cl$_2$ (100 ml) at 0° C., followed by BF$_3$—OEt$_2$ (3.42 ml, 27.2 mmol). The resulting mix was stirred at 0° C. for 1 h. The reaction was quenched with H$_2$O (10 ml) and diluted with CH$_2$Cl$_2$ (10 ml), and washed with sat. NaHCO$_3$ (20 ml), brine (20 ml), dried and concentrated. Purified by normal phase SiO$_2$ chromatography (5 to 40% EtOAc/hexanes) to give 2,2-dimethyl-4-(4-methylphenyl)-4-(prop-2-en-1-yl)oxane as a colorless oil, which was used crude (2.49 g, 75%).

Intermediate 7

2-[2,2-dimethyl-4-(4-methylphenyl)oxan-4-yl]acetaldehyde

O$_3$ gas was passed through a solution of 2,2-dimethyl-4-(4-methylphenyl)-4-(prop-2-en-1-yl)oxane (1.21 g, 5 mmol) in CH$_2$Cl$_2$ (50 ml) at −78° C. until the solution turned light blue (about 5 min). After additional 5 minutes, the reaction mix was purged with oxygen gas for 15 min before adding triphenylphosphine (2.62 g, 10 mmol). The reaction was stirred at rt for 4 h and concentrated. Purified by normal phase SiO$_2$ chromatography (10 to 60% EtOAc/hexanes) to give 2-[2,2-dimethyl-4-(4-methylphenyl)oxan-4-yl]acetaldehyde as a colorless oil (641 mg, 52%).

$^1$H NMR (400 MHz, CDCl$_3$) δ 9.42-9.27 (m, 1H), 7.26 (dd, J=9.9, 8.0, 2H), 7.20 (t, J=8.7, 2H), 3.94-3.75 (m, 2H), 2.69 (dd, J=14.6, 2.5, 1H), 2.51-2.38 (m, 2H), 2.35 (s, 3H), 2.26 (dd, J=13.9, 2.3, 1H), 1.84 (ddd, J=14.3, 11.0, 4.6, 1H), 1.76 (d, J=13.9, 1H), 1.23 (s, 3H), 0.73 (s, 3H).

Example 3

{2-[2,2-dimethyl-4-(4-methylphenyl)oxan-4-yl] ethyl}[(3-methylphenyl)methyl]amine (Compound 32)

A mixture of 2-[2,2-dimethyl-4-(4-methylphenyl)oxan-4-yl]acetaldehyde (61.6 mg, 0.25 mmol), 3-methylbenzylamine (63 μl, 0.5 mmol) and acetic acid (50 μl, 8.6 mmol) in CH$_2$Cl$_2$ (3 ml) was stirred at rt for 1 h before it adding sodium triacetoxyborohydride (106 mg, 0.50 mmol). The resulting mixture was stirred at rt for 18 h. The mix was concentrated and dissolved in MeOH and purified by HPLC to give {2-[2,2-dimethyl-4-(4-methylphenyl)oxan-4-yl]ethyl}[(3-methylphenyl)methyl]amine as a white solid (35 mg, 40%, m/z: 352.3 [M+H]$^+$ observed).

Intermediate 8 methyl 2-cyano-2-[(9Z)-6-oxaspiro[4.5]decan-9-ylidene]acetate

A 100 ml round-bottom flask equipped with a Dean-Stark distillation setup and condenser was charged with 6-oxaspiro[4.5]decan-9-one (6 g, 39 mmol, which was prepared according to Hanschke, E. *Chem. Ber.* 1955, 88, 1053), methyl cyanoacetate (4.1 ml, 46.7 mmol), ammonium acetate (780 mg, 10.1 mmol), acetic acid (0.44 ml, 7.8 mmol) and benzene (40 ml). The mixture was refluxed until no more water collected in the Dean-Stark (2 hours), cooled, benzene (30 ml) added and the organic washed with water (50 ml). The aqueous layer was extracted with $CH_2Cl_2$ (3×50 ml). The combined organic phase was washed with sat. $NaHCO_3$ (100 ml), brine (100 ml) dried ($MgSO_4$), filtered and concentrated. Purified by normal phase $SiO_2$ chromatography (7% to 60% EtOAc/hexanes) to give methyl 2-cyano-2-[(9Z)-6-oxaspiro[4.5]decan-9-ylidene]acetate as a colorless oil (8.93 g, 97.5%, m/z 235.1 $[M+H]^+$ observed).

By the procedure for the preparation of intermediate 8 substituting 2,2-diethyloxan-4-one for 6-oxaspiro[4.5]decan-9-one, methyl 2-cyano-2-[(4Z)-2,2-diethyloxan-4-ylidene]acetate was prepared (m/z 237.1 $[M+H]^+$ observed).

By the procedure for the preparation of intermediate 8 substituting 1-oxaspiro[5.5]undecan-4-one for 6-oxaspiro[4.5]decan-9-one, methyl 2-cyano-2-[(4Z)-1-oxaspiro[5.5]undecan-4-ylidene]acetate was prepared (m/z 249.1 $[M+H]^+$ observed).

Intermediate 9 methyl 2-cyano-2-[9-(4-fluorophenyl)-6-oxaspiro[4.5]decan-9-yl]acetate

A round bottom flask was equipped with a condenser, addition funnel and rubber septum with nitrogen inlet was charged with a solution of 4-fluoromagnesium bromide (2.0 M in diethyl ether, 7.5 ml, 12.5 mmol) and CuI (200 mg, 1.0 mmol) in 35 ml dry diethyl ether. Methyl 2-cyano-2-[(9Z)-6-oxaspiro[4.5]decan-9-ylidene]acetate (2.5 g, 10.5 mmol) in diethyl ether (35 ml) was added drop-wise over 30 min while cooling the reaction flask in an ice bath. The mixture was then stirred at room temperature for 1 h. The reaction mixture was poured into a 25 g ice/1 N HCl (20 ml) mixture. The product was extracted with $Et_2O$ (3×50 ml), washed with brine (50 ml), dried ($NA_2SO_4$) and concentrated. Purified by normal phase $SiO_2$ chromatography (8% to 60% EtOAc/hexanes) to give methyl 2-cyano-2-[9-(4-fluorophenyl)-6-oxaspiro[4.5]decan-9-yl]acetate as a colorless oil (3.24 g, 93%, m/z 331.2 $[M+H]^+$ observed).

By the procedure described in the preparation of intermediate 9 substituting methyl 2-cyano-2-[(4Z)-2,2-diethyloxan-4-ylidene]acetate for methyl 2-cyano-2-[(9Z)-6-oxaspiro[4.5]decan-9-ylidene]acetate, methyl 2-cyano-2-[2,2-diethyl-4-(4-fluorophenyl)oxan-4-yl]acetate was prepared (m/z 333.2 $[M+H]^+$ observed).

By the procedure described in the preparation of intermediate 9 substituting methyl 2-cyano-2-[(4Z)-1-oxaspiro[5.5]undecan-4-ylidene]acetate for methyl 2-cyano-2-[(9Z)-6-oxaspiro[4.5]decan-9-ylidene]acetate, methyl 2-cyano-2-[4-(4-fluorophenyl)-1-oxaspiro[5.5]undecan-4-yl]acetate was prepared (m/z 345.2 $[M+H]^+$ observed).

Intermediate 10

2-[(9R)-9-(4-fluorophenyl)-6-oxaspiro[4.5]decan-9-yl]acetonitrile

To a pre-dissolved solution of KOH (1.1 g, 19.5 mmol) in ethylene glycol (50 ml) was added methyl 2-cyano-2-[9-(4-fluorophenyl)-6-oxaspiro[4.5]decan-9-yl]acetate (3.24 g, 9.8 mmol). The mixture was heated to 120° C. for 3 h, then cooled. $H_2O$ was added (50 ml), the product extracted with $Et_2O$ (3×50 ml), washed with $H_2O$ (50 ml), dried over $NA_2SO_4$, filtered and concentrated. (7% to 60% EtOAc/hexanes) to give methyl 2-cyano-2-[9-(4-fluorophenyl)-6-oxaspiro[4.5]decan-9-yl]acetate (1.96 g, 73%, m/z 273.2 $[M+H]^+$ observed).

1.96 g of the enantiomers were separated by SFC on an AD-3 column using 15% MeOH (0.05% DEA) as a modifier to give 2-[(9S)-9-(4-fluorophenyl)-6-oxaspiro[4.5]decan-9-yl]acetonitrile as a colorless oil (faster eluting enantiomer, 635 mg, 24%, m/z 274.2 $[M+H]^+$ observed) and 2-[(9R)-9-(4-fluorophenyl)-6-oxaspiro[4.5]decan-9-yl]acetonitrile as a colorless oil (slower eluting enantiomer, 703 mg, 26%, m/z 273.2 $[M+H]^+$ observed).

By the procedure described in the preparation of intermediate 10 substituting methyl 2-cyano-2-[2,2-diethyl-4-(4-fluorophenyl)oxan-4-yl]acetate for methyl 2-cyano-2-[9-(-fluorophenyl)-6-oxaspiro[4.5]decan-9-yl]acetate, 2-[2,2-diethyl-4-(4-fluorophenyl)oxan-4-yl]acetonitrile was prepared (m/z 275.2 $[M+H]^+$ observed).

By the procedure described in the preparation of intermediate 10 substituting methyl 2-cyano-2-[4-(4-fluorophenyl)-1-oxaspiro[5.5]undecan-4-yl]acetate for methyl 2-cyano-2-[9-(4-fluorophenyl)-6-oxaspiro[4.5]decan-9-yl]acetate, 2-[4-(4-fluorophenyl)-1-oxaspiro[5.5]undecan-4-yl]acetonitrile was prepared (m/z 287.2 $[M+H]^+$ observed).

Intermediate 11

2-[(9R)-9-(4-fluorophenyl)-6-oxaspiro[4.5]decan-9-yl]ethan-1-amine

To a solution of 2-[(9R)-9-(4-fluorophenyl)-6-oxaspiro[4.5]decan-9-yl]acetonitrile (500 mg, 1.8 mmol) in anhydrous ether (30 ml) at 0° C. was added dropwise LAH (1.0 M in $Et_2O$, 3.7 ml, 3.7 mmol). The reaction was then warmed up to room temperature. After 2 h the reaction was quenched with 1 ml $H_2O$, 0.2 ml 15% NaOH and then 1 ml $H_2O$. The reaction mixture was extracted with $Et_2O$ (3×30 ml), dried over $NA_2SO_4$ and concentrated to give 2-[(9R)-9-(4-fluorophenyl)-6-oxaspiro[4.5]decan-9-yl]ethan-1-amine as an yellow oil, which used without further purification (500 mg, 100%, m/z 277.2 $[M+H]^+$ observed).

By the procedure described in the preparation of intermediate 11 substituting 2-[2, 2-diethyl-4-(4-fluorophenyl)oxan-4-yl]acetonitrile for 2-[(9R)-9-(4-fluorophenyl)-6-oxaspiro[4.5]decan-9-yl]acetonitrile, 2-[2,2-diethyl-4-(4-fluorophenyl)oxan-4-yl]ethan-1-amine was prepared (m/z 279.2 $[M+H]^+$ observed).

By the procedure described in the preparation of intermediate 11 substituting 2-[4-(4-fluorophenyl)-1-oxaspiro[5.5]undecan-4-yl]acetonitrile for 2-[(9R)-9-(4-fluorophenyl)-6-oxaspiro[4.5]decan-9-yl]acetonitrile, 2-[4-(4-fluorophenyl)-1-oxaspiro[5.5]undecan-4-yl]ethan-1-amine was prepared (m/z 291.2 [M+H]$^+$ observed).

Example 4 benzyl({2-[(9R)-9-(4-fluorophenyl)-6-oxaspiro[4.5]decan-9-yl]ethyl})amine (Compound 81)

To a solution of amine 2-[(9R)-9-(4-fluorophenyl)-6-oxaspiro[4.5]decan-9-yl]ethan-1-amine (100 mg, 0.361 mmol) in anhydrous $CH_2Cl_2$ (6 ml) and $NA_2SO_4$ (256 mg, 1.80 mmol) at rt was added benzaldehyde (0.055 ml; 0.541 mmol). The reaction was stirred overnight. The reaction mixture was filtered and concentrated. The residue was dissolved in 6 ml MeOH at 0° C. and $NaBH_4$ added in one portion (16 mg, 0.433 mmol). The reaction was stirred at 0° C. for 1 h. The solution was then quenched with $H_2O$ (20 ml), extracted with $CH_2Cl_2$ (3×30 ml), washed with brine (10 ml) and dried over $NA_2SO_4$. The mixture was purified by HPLC to give benzyl({2-[(9R)-9-(4-fluorophenyl)-6-oxaspiro[4.5]decan-9-yl]ethyl})amine as a white solid (121 mg, 92%, m/z 368.3 [M+H]$^+$ observed).

Intermediate 12

2,2-diethyloxan-4-ol

To a mixture of 3-butene-1-ol (19.8 ml; 233 mmol) and 3-pentenone (12.3 ml; 116 mmol) was added 75% sulfuric acid (19.8; 334 mmol; prepared by diluting 79 ml of conc. sulfuric acid to 100 ml with distilled water) drop-wise at 0° C. The reaction was allowed to warm to room temperature and stirred overnight. Water (70 ml) was added to the mixture then neutralized with NaOH (pellets) to pH 8 and extracted with diethyl ether (3×150 ml). The ether extract was washed with an aqueous sodium bisulfite solution (40 ml), dried over $K_2CO_3$ and the ether evaporated in vacuo. The residue was distilled under reduced pressure to give 2,2-diethyloxan-4-ol (4.89 g, 27%, B. Pt. 65-70° C. at 1 mm Hg).
$^1$H NMR (400 MHz, $CDCl_3$) δ 4.04-3.86 (m, 1H), 3.84-3.66 (m, 1H), 3.65-3.38 (m, 1H), 2.06-1.95 (m, 1H), 1.92-1.76 (m, 2H), 1.78-1.63 (m, 1H), 1.63-1.50 (m, 1H), 1.51-1.31 (m, 3H), 1.28-1.10 (m, 1H), 0.92-0.68 (m, 6H).

Intermediate 13

2,2-diethyloxan-4-one

To a solution of crude 2,2-diethyloxan-4-ol (500 mg, 3.2 mmol) in $CH_2Cl_2$ (10 ml) were added NMO (750 mg, 6.41 mmol) and 4 A molecular sieves (2 g). The solution was stirred for 30 mins and then TPAP (34 mg, 0.096 mmol) was added in one portion. The reaction was allowed to stir for 10 h. After checking the TLC, the alcohol was gone. It was filtered through a short pad of $SiO_2$. The filtrate was concentrated and purified by normal phase $SiO_2$ chromatography (0% to 50% EtOAc/hexanes) to give 2,2-diethyloxan-4-one (365 mg, 73%).
$^1$H NMR (400 MHz, $CDCl_3$) δ 3.75-3.66 (m, 2H), 3.44-3.29 (m, 2H), 2.51-2.31 (m, 4H), 1.25-1.4 (m, 4H), 0.75 (m, 6H).

Intermediate 14

2-(bromomagnesio)pyridine

Into a flask was placed isopropylmagnesium chloride 2.0M in THF (6 mL, 12 mmole), 2-bromopyridine (1.2 mL, 12 mmol) in anhydrous $Et_2O$ (4 ml) added dropwise. The reaction mixture was stirred at rt. for 3 h. The resulting mixture was used as is as 1M Grignard solution.

Example 5 dibenzyl({2-[(9R)-9-(4-fluorophenyl)-6-oxaspiro[4.5]decan-9-yl]ethyl})amine (Compound 225)

To a solution of 2-[(9R)-9-(4-fluorophenyl)-6-oxaspiro[4.5]decan-9-yl]acetonitrile (30 mg, 0.13 mmol) in anhydrous $CH_2Cl_2$ (3 ml) and $NA_2SO_4$ (92.3 mg, 0.65 mmol) at rt was added 2.3 eq benzaldehyde (0.032 ml, 0.32 mmol); The reaction was stirred overnight. $NaBH(OAc)_3$ (6.6 mg, 0.31 mmol) added in one portion. The solution was then quenched with $H_2O$ (10 ml), extracted with $CH_2Cl_2$ (3×20 ml), washed with brine (10 ml) and dried over $NA_2SO_4$. The solvent was evaporated in vacuo and the residue was purified by HPLC to obtain dibenzyl({2-[(9R)-9-(4-fluorophenyl)-6-oxaspiro[4.5]decan-9-yl]ethyl})amine (37.4 mg, 50%, m/z 458.3 [M+H]$^+$ observed).

Example 6

{2-[(9R)-9-(4-fluorophenyl)-6-oxaspiro[4.5]decan-9-yl]ethyl}[(3-methylphenyl)methyl]amine (Compound 122)

Following an analogueous procedure described for Compound 81, Compound 122 was obtained from the corresponding intermediate after a chiral HPLC separation (The slower moving fraction on AD-3 column. The absolute configuration of Ex. 122 was determined by an X-ray crystallography.

Example 7

{2-[(9R)-9-(pyridin-2-yl)-6-oxaspiro[4.5]decan-9-yl]ethyl}[2-(pyridin-3-yl)ethyl]amine (Compound 75)

1.0 M DIBAL solution in toluene (3.0 ml, 3 mmol) was added drop-wise to a solution of 2-[(9R)-9-(pyridin-2-yl)-6-oxaspiro[4.5]decan-9-yl]acetonitrile (350 mg, 1.4 mmol) in 7 mL toluene at −78° C. The resulting mixture was stirred at −78° C. until completion (1.5 h). The reaction was then quenched with 5 eq of MeOH (0.28 mL) and 0.1 mL water, stir while warming, 175 mg $NA_2SO_4$ added, stir at room temp. 2 h to give 310 mg (80%) of 2-[(9R)-9-(pyridin-2-yl)-6-oxaspiro[4.5]decan-9-yl]acetaldehyde. LCMS m/z 250.6 (M+1) observed.
To a solution of 2-[(9R)-9-(pyridin-2-yl)-6-oxaspiro[4.5]decan-9-yl]acetaldehyde (50 mg, 0.19 mmole), 5 mL DCM and $NA_2SO_4$ (134 mg, 0.95 mmole) was added 2-(pyridin-3-yl)ethan-1-amine (31 mg, 0.25 mmole) and the reaction was stirred overnight. $NaBH_4$ (9.5 mg, 0.25 mmole) added, stir 10 minutes, 2 drops MeOH added, stir 1 h, quenched with water, organics separated off and evaporated. The residue was passed through a Gilson reverse phase HPLC to give {2-[(9R)-9-(pyridin-2-yl)-6-oxaspiro[4.5]decan-9-yl]ethyl}[2-(pyridin-3-yl)ethyl]amine, 65.3 mg (71%). LCMS m/z 367.1 (M+1) observed.

Example 8

2-[(9R)-9-(2-{4H,5H,6H-thieno[2,3-c]pyrrol-5-yl}ethyl)-6-oxaspiro[4.5]decan-9-yl]pyridine (Compound 82)

To a stirred solution of 2-[(9R)-9-(pyridin-2-yl)-6-oxaspiro[4.5]decan-9-yl]ethan-1-amine (0.030 g, 0.115 mmol; prepared by following a sequence described for Compound 81 in dried ACN (5.8 mL) was added 2,3-bis(bromomethyl)thiophene (31.1 mg, 0.115 mmol) followed by addition of $K_2CO_3$ (79.62 mg, 0.576 mmol). After 30 min, LCMS showed that the reaction was done and the major peak had the corresponding mass to the desired product. It was then subjected to HPLC purification. HPLC purification method: Luna acid medium column, 10-50% acetonitrile in $H_2O$ over 15 min, followed by flashing with 100% acetonitrile, 0.1% TFA modifier was employed. The fractions containing the desired product were pooled, basified with 2N NaOH and extracted with DCM (3×20 mL). The combined organics were concentrated and purified with flash chromatography (10 g silica gel column, eluted by 0-10% MeOH in DCM, based upon TLC measurement: DCM/MeOH (10/1) Rf=0.60) to afford 5 mg of 2-[(9R)-9-(2-{4H,5H,6H-thieno[2, 3-c]pyrrol-5-yl}ethyl)-6-oxaspiro[4.5]decan-9-yl]pyridine as a colorless oil in 12% yield.

LCMS m/z 369 (M+1) observed.

Example 9

{2-[9-(1H-pyrazol-1-yl)-6-oxaspiro[4.5]decan-9-yl]ethyl}(thiophen-2-ylmethyl)amine (Compound 26)

An oven-dried flask equipped with a Dean-Stork apparatus and condenser was cooled to rt under a stream of $N_2$ and was charged with 6-oxaspiro[4.5]decan-9-one (0.50 g, 3.24 mmol), (tert-butoxy)carbohydrazide (0.42 g, 3.24 mmol) and hexane (10 mL). The resulting solution was heated to reflux overnight.

It was cooled to rt and the solid collected by vacuum filtration. The solid was washed with hexane and air-dried to give (tert-butoxy)-N'-[(9Z)-6-oxaspiro[4.5]decan-9-ylidene]carbohydrazide (0.84 g, 96% yield). LCMS m/z 213 (M+1-t-butyl) observed.

An oven-dried flask was charged with (tert-butoxy)-N'-[(9Z)-6-oxaspiro[4.5]decan-9-ylidene]carbohydrazide (0.42 g, 1.56 mmol) and THF. The solution was cooled to 0° C. and allylmagnesiumchloride (2.0 M, 1.60 mL) was added dropwise. The reaction was stirred at 0° C. for 1 h and the warmed to rt overnight. LC-MS indicated the reaction didn't go to completion. Another 2 equivalent of allylmagnesiumchloride was added at rt. The solution was stirred for 1 h before it was quenched with MeOH. The solution was diluted with DCM (60 mL) and $H_2O$ (20 mL). A lot of precipitates were formed and the solid was filtered through a pad of celite. The organic was then separated and the aqueous layer was extracted with 10 mL of EtOAc. The combined organic layers were concentrated and the residue was purified on 25 g Snap column (0-20% tOAc in Hex, 12 CV) to give (tert-butoxy)-N'-[9-(prop-2-en-1-yl)-6-oxaspiro[4.5]decan-9-yl]carbohydrazide (0.33 g, 68% yield). LCMS m/z 333 (M+Na) observed.

A solution of (tert-butoxy)-N'-[9-(prop-2-en-1-yl)-6-oxaspiro[4.5]decan-9-yl]carbohydrazide (0.33 g, 1.06 mmol) in 4 mL of EtOAc was added 4M HCl in dioxane at rt. The solution was stirred at rt until reaction completion, monitored by LC-MS (30 h). The solvent was then removed to give [9-(prop-2-en-1-yl)-6-oxaspiro[4.5]decan-9-yl]hydrazine (250 mg). LCMS m/z 211.1 (M+1) observed.

A solution of [9-(prop-2-en-1-yl)-6-oxaspiro[4.5]decan-9-yl]hydrazine (250 mg, 1.0 mmol) in 4 mL of i-PrOH were added Et3N and 3-dimethylaminoacrolein. The solution was refluxed for 3 h and then at 50° C. for 2 d. The solvent removed and the residue was purified on 25 g Biotage snap column, eluted with 0-18% EtOAc in Hex (12 CV) to give 1-[9-(prop-2-en-1-yl)-6-oxaspiro[4.5]decan-9-yl]-1H-pyrazole (80 mg, 31% yield).

LCMS m/z 247.1 (M+1) observed.

To a solution of 1-[9-(prop-2-en-1-yl)-6-oxaspiro[4.5]decan-9-yl]-1H-pyrazole (80 mg, 0.32 mmol) in DCM (5 mL) at −78° C. was bubbled with $O_3$ until the solution turned blue. The resulting solution was bubbled with $N_2$ for 5 min. To it was added PPh3 (168 mg, 0.64 mmol). And the solution was stirred for 4 h at rt. After removal of the solvent, the residue was purified by flash column chromatography to give 2-[9-(1H-pyrazol-1-yl)-6-oxaspiro[4.5]decan-9-yl]acetaldehyde (15 mg, 23% yield). LCMS m/z 249 (M+1) observed.

To a mixture of 2-[9-(1H-pyrazol-1-yl)-6-oxaspiro[4.5]decan-9-yl]acetaldehyde (15 mg, 0.06 mmol) and thiophen-2-ylmethanamine (19 uL, 0.18 mmol) was stirred at rt for 1 h before NaBH(OAc)3 (25.4 mg, 0.12 mmol) was added. The solution stirred overnight. After removal of solvent, the residue was purified by HPLC to provide {2-[9-(1H-pyrazol-1-yl)-6-oxaspiro[4.5]decan-9-yl]ethyl}(thiophen-2-ylmethyl)amine (17 mg, 61% yield) as a TFA salt. LCMS m/z 346 (M+1) observed.

Example 10

Basic Procedure for Making Compounds of the Formula

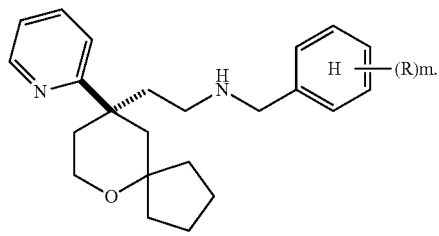

Following Scheme 8 2-[(9R)-9-(pyridin-2-yl)-6-oxaspiro[4.5]decan-9-yl]ethan-1-amine, which can be prepared by following a sequence as described for Compound 81 (Compound 4) and a sequence similar to for Intermediate 11 reacts with an appropriately substituted heteroaromatic aldehyde or appropriately substituted aromatic aldehyde (1 equivalent) in the presence of an organic solvent (i.e. DCM, MeOH, EtOH) to form a corresponding imine, which is reduced by an appropriate reducing agent the compound. The $(R)_n$ and the $R_m$ refers to the optional substituents Additionally, the phenyl groups can be replaced with other cycles or aryl groups as described herein.

Example 11

Basic Procedures for Making Compounds of the Formula

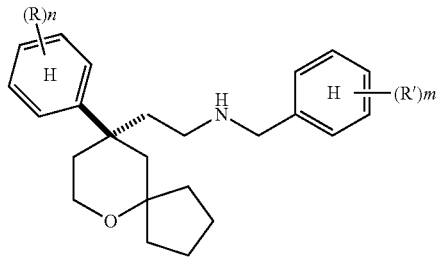

Following Scheme 9, 9-1, which can be prepared by following a sequence described for Compound 81 (Compound 4) and a sequence similar to for Intermediate 11, reacts with an appropriately substituted heteroaromatic aldehyde or appropriately substituted aromatic aldehyde (1 equivalent) in the presence of an organic solvent (i.e. DCM, MeOH, EtOH and etc) to form a corresponding imine, which is reduced by an appropriate reducing agent (i.e. NaBH$_4$) to give the compound. The $(R)_n$ and the $R_m$ refers to the optional substituents Additionally, the phenyl groups can be replaced with other cycles or aryl groups as described herein.

Example 12

Opioid Receptor Ligands

The opioid receptor ligands and compounds listed in the following tables can be or were prepared according to the procedures described above from appropriate starting materials and appropriate reagents. Compounds that have been made lists NMR data and prophetic examples do not list NMR data.

TABLE 1

| Compounds with chemical name and characterization data | | | |
|---|---|---|---|
| Compound. | Name | MS (m/z) [M + H]$^+$ | 1H NMR |
| 1 | 2-[9-(pyridin-2-yl)-6-oxaspiro[4.5]decan-9-yl]ethan-1-amine | 261.1 | δ 8.58 (ddd, J = 4.8, 1.9, 0.9, 1H), 7.63 (m, 1H), 7.30 (m, 1H), 7.12 (ddd, J = 7.4, 4.8, 1.0, 1H), 3.76 (m, 2H), 2.55 (td, J = 11.6, 5.1, 1H), 2.46 (ddd, J = 13.7, 5.1, 2.7, 1H), 2.37 (dd, J = 13.7, 2.1, 1H), 2.14 (td, J = 11.6, 5.0, 1H), 1.92 (m, 2H), 1.70 (m, 4H), 1.46 (m, 4H), 1.13 (m, 1H), 0.71 (dt, J = 13.4, 8.8, 1H). |
| 2 | 2-[(9R)-9-(pyridin-2-yl)-6-oxaspiro[4.5]decan-9-yl]ethan-1-amine | 261.2 | δ 8.58 (ddd, J = 4.8, 1.7, 0.7, 1H), 7.64 (td, J = 7.8, 1.9, 1H), 7.28 (m, 1H), 7.12 (ddd, J = 7.4, 4.8, 0.9, 1H), 3.76 (m, 2H), 2.55 (m, 1H), 2.46 (ddd, J = 13.7, 5.1, 2.7, 1H), 2.37 (m, 1H), 2.14 (m, 1H), 1.91 (m, 2H), 1.71 (m, 4H), 1.47 (m, 4H), 1.13 (m, 1H), 0.71 (m, 1H). |
| 3 | 2-[9-(2-aminoethyl)-6-oxaspiro[4.5]decan-9-yl]pyridin-4-ol | 277.1 | δ 7.60 (d, J = 6.8, 1H), 7.60 (d, J = 6.8, 1H), 7.21 (s, 2H), 6.79 (d, J = 332.9, 3H), 6.54 (m, 5H), 6.37 (s, 1H), 6.29 (d, J = 6.5, 1H), 5.97 (m, 6H), 4.84 (d, J = 169.9, 3H), 3.69 (dt, J = 23.7, 11.7, 3H), 3.69 (dt, J = 23.7, 11.7, 3H), 3.40 (s, 2H), 3.40 (s, 2H), 2.64 (s, 1H), 2.64 (s, 1H), 2.32 (d, J = 12.0, 1H), 2.26 (dd, J = 46.7, 13.0, 2H), 2.20 (d, J = 13.9, 1H), 2.09 (d, J = 13.8, 1H), 2.09 (d, J = 13.8, 1H), 1.84 (t, J = 15.9, 2H), 1.60 (m, 15H), 1.55 (m, 11H), 0.89 (m, 2H), 0.89 (m, 1H). |
| 4 | 6-[9-(2-aminoethyl)-6-oxaspiro[4.5]decan-9-yl]pyridin-3-ol | 277.1 | δ 8.05 (m, 1H), 7.01 (d, J = 8.6, 1H), 6.87 (dd, J = 8.6, 2.9, 1H), 5.37 (s, 2H), 3.66 (dd, J = 13.7, 7.2, 2H), 2.60 (ddd, J = 12.3, 10.1, 5.6, 1H), 2.22 (m, 3H), 1.88 (tt, J = 10.0, 7.9, 1H), 1.77 (d, J = 13.6, 1H), 1.58 (m, 4H), 1.37 (m, 5H), 1.08 (dd, J = 15.4, 4.9, 1H), 0.63 (dt, J = 13.7, 8.9, 1H). |
| 5 | 6-[9-(2-aminoethyl)-6-oxaspiro[4.5]decan-9-yl]pyridin-2-ol | 277.1 | δ 7.38 (dd, J = 9.0, 7.1, 1H), 6.40 (d, J = 9.0, 1H), 6.09 (d, J = 7.1, 1H), 5.28 (s, 1H), 3.73 (s, 2H), 2.69 (m, 1H), 2.37 (m, 2H), 2.13 (m, 2H), 1.66 (m, 12H), 0.97 (dt, J = 12.4, 7.6, 1H). |
| 6 | 2-[(9R)-9-(2-aminoethyl)-6-oxaspiro[4.5]decan-9-yl]-1-oxidopyridin-1-ium | 277.1 | δ 8.23 (m, 1H), 7.31 (dd, J = 5.8, 2.0, 2H), 7.23 (m, 1H), 4.03 (s, 2H), 3.81 (s, 2H), 3.27 (d, J = 13.9, 1H), 2.95 (td, J = 12.8, 5.1, 1H), 2.65 (td, J = 11.8, 5.1, 1H), 2.25 (s, 2H), 1.65 (ddd, J = 38.7, 17.6, 11.7, 9H), 1.24 (s, 1H), 0.84 (dt, J = 13.1, 8.8, 1H). |
| 7 | benzyl({2-[1-(4-fluorophenyl)cyclohexyl]ethyl})amine | 312.2 | δ 9.72 (t, J = 1.5, 1H), 7.91 (m, 2H), 7.23 (m, 3H), 7.06 (m, 2H), 6.92 (m, 2H), 2.91 (t, J = 6.9, 2H), 2.44 (m, 4H), 2.09 (dd, J = 13.2, 5.3, 2H), 1.68 (m, 4H), 1.46 (m, 1H), 1.33 (dd, J = 15.4, 6.7, 4H). |
| 8 | benzyl({2-[4-(4-fluorophenyl)oxan-4-yl]ethyl})amine | 314.2 | δ 7.38-7.16 (m, 7H), 7.09-6.99 (m, 2H), 3.79 (ddd, J = 11.5, 5.7, 3.6, 2H), 3.64 (s, 2H), 3.56 (ddd, J = 11.6, 8.8, 2.8, 2H), 2.39-2.29 (m, 2H), 2.24-2.01 (m, 4H), 1.86 (ddd, J = 13.8, 7.9, 3.5, 2H). |

TABLE 1-continued

Compounds with chemical name and characterization data

| Compound. | Name | MS (m/z) [M + H]⁺ | 1H NMR |
|---|---|---|---|
| 9 | [(2-methylphenyl)methyl]({2-[4-(4-methylphenyl)oxan-4-yl]ethyl})amine | 324.2 | δ 7.16 (m, 8H), 3.79 (ddd, J = 11.5, 5.2, 3.8, 2H), 3.58 (m, 4H), 2.41 (m, 2H), 2.36 (s, 3H), 2.27 (s, 3H), 2.16 (m, 2H), 1.86 (ddd, J = 12.3, 8.6, 4.6, 4H), 1.58 (s, 1H) |
| 10 | N-{2-[2,2-dimethyl-4-(4-methylphenyl)oxan-4-yl]ethyl}aniline | 324.3 | δ 7.25 (dt, J = 5.9, 2.9, 3H), 7.11 (m, 2H), 6.98 (dd, J = 25.0, 8.2, 4H), 3.65 (dd, J = 8.9, 6.7, 2H), 2.95 (d, J = 4.6, 1H), 2.50 (d, J = 4.7, 1H), 2.23 (s, 3H), 2.10 (d, J = 13.9, 1H), 1.89 (m, 3H), 1.43 (m, 2H), 1.21 (m, 1H), 1.05 (s, 3H), 0.53 (s, 3H). |
| 11 | 2-[({2-[4-(4-methylphenyl)oxan-4-yl]ethyl}amino)methyl]phenol | 326.2 | δ 7.15 (m, 5H), 6.88 (dd, J = 7.4, 1.3, 1H), 6.79 (dd, J = 8.1, 1.0, 1H), 6.73 (td, J = 7.4, 1.1, 1H), 3.76 (m, 4H), 3.54 (ddd, J = 11.7, 9.4, 2.5, 2H), 2.37 (m, 5H), 2.13 (m, 2H), 1.82 (m, 4H) |
| 12 | 2-[({2-[4-(4-fluorophenyl)oxan-4-yl]ethyl}amino)methyl]phenol | 330.2 | δ 8.26 (s, 2H), 7.07 (m, 3H), 6.95 (dd, J = 14.3, 5.8, 2H), 6.86 (d, J = 6.3, 1H), 6.78 (d, J = 8.1, 1H), 6.71 (t, J = 7.4, 1H), 3.96 (d, J = 7.0, 2H), 3.80 (s, 2H), 3.64 (dt, J = 8.8, 3.9, 2H), 3.41 (t, J = 9.3, 2H), 2.45 (s, 2H), 1.95 (d, J = 14.7, 2H), 1.85 (m, 2H), 1.67 (m, 2H). |
| 13 | benzyl({2-[3-(pyridin-2-yl)-1-oxaspiro[4.4]nonan-3-yl]ethyl})amine | 337.1 | δ 9.76 (s, 2H), 8.59 (d, J = 4.7, 1H), 8.11 (t, J = 7.8, 1H), 7.69 (d, J = 8.1, 1H), 7.63-7.52 (m, 1H), 7.35 (s, 5H), 4.13 (d, J = 9.7, 1H), 4.03 (s, 2H), 3.91 (d, J = 9.7, 1H), 2.92 (d, J = 26.5, 2H), 2.53 (ddd, J = 14.6, 9.5, 5.4, 1H), 2.38 (dd, J = 19.0, 8.5, 2H), 2.28 (d, J = 13.6, 1H), 1.99-1.81 (m, 1H), 1.84-1.52 (m, 6H), 1.51-1.35 (m, 1H). |
| 14 | benzyl({2-[2,2-dimethyl-4-(4-methylphenyl)oxan-4-yl]ethyl})amine | 338.3 | δ 8.54 (d, J = 226.0, 2H), 7.22 (q, J = 6.7, 3H), 7.03 (dd, J = 19.0, 8.3, 6H), 6.23 (d, J = 186.3, 2H), 3.69 (m, 4H), 2.66 (s, 1H), 2.25 (s, 4H), 2.10 (dd, J = 22.7, 13.3, 2H), 1.83 (m, 1H), 1.64 (m, 1H), 1.49 (m, 2H), 1.11 (s, 3H), 0.57 (s, 3H). |
| 15 | {2-[2,2-dimethyl-4-(4-methylphenyl)oxan-4-yl]ethyl}(pyridin-2-ylmethyl)amine | 339.3 | δ 8.48 (dd, J = 5.2, 0.9, 1H), 8.26 (s, 1H), 7.98 (dd, J = 7.8, 1.6, 1H), 7.59 (d, J = 7.9, 1H), 7.54 (m, 1H), 7.07 (s, 4H), 4.17 (q, J = 13.9, 2H), 3.73 (m, 2H), 2.88 (d, J = 4.8, 1H), 2.42 (d, J = 4.8, 1H), 2.21 (m, 4H), 2.10 (dd, J = 13.9, 2.1, 1H), 2.00 (d, J = 4.6, 1H), 1.78 (d, J = 4.6, 1H), 1.58 (m, 2H), 1.12 (s, 3H), 0.59 (s, 3H). |
| 16 | {2-[2,2-dimethyl-4-(4-methylphenyl)oxan-4-yl]ethyl}(pyridin-3-ylmethyl)amine | 339.3 | δ 8.92 (s, 1H), 8.52 (s, 1H), 8.25 (d, J = 8.0, 1H), 7.67 (m, 1H), 7.08 (m, 4H), 5.92 (s, 4H), 4.09 (s, 2H), 3.71 (m, 2H), 2.85 (d, J = 12.0, 7.9, 1H), 2.34 (m, 1H), 2.23 (m, 4H), 2.10 (d, J = 13.9, 1H), 1.94 (m, 1H), 1.74 (dd, J = 12.5, 4.3, 1H), 1.55 (m, 2H), 1.10 (s, 3H), 0.57 (s, 3H). |
| 17 | [(2-methoxyphenyl)methyl]({2-[4-(4-methylphenyl)oxan-4-yl]ethyl})amine | 340.2 | δ 7.21 (m, 1H), 7.13 (s, 4H), 7.07 (dd, J = 7.4, 1.7, 1H), 6.84 (ddd, J = 12.1, 9.3, 4.6, 2H), 3.78 (m, 5H), 3.63 (s, 2H), 3.54 (ddd, J = 11.6, 9.1, 2.7, 2H), 2.38 (d, J = 1.3, 1H), 2.32 (m, 5H), 2.10 (m, 2H), 1.84 (m, 4H) |
| 18 | (furan-3-ylmethyl)({2-[(9R)-9-(pyridin-2-yl)-6-oxaspiro[4.5]decan-9-yl]ethyl})amine | 341.1 | δ 8.72 (d, J = 4.6, 1H), 8.23 (t, J = 7.3, 1H), 7.84-7.57 (m, 2H), 7.46 (s, 1H), 7.38 (t, J = 1.6, 1H), 7.28 (s, 1H), 3.89 (s, 2H), 3.82 (dt, J = 12.4, 4.2, 1H), 3.72 (dd, J = 16.1, 6.2, 1H), 2.96 (d, J = 4.4, 1H), 2.40 (ddd, J = 36.0, 24.7, 12.8, 4H), 2.20 (d, J = 12.7, 4.8, 1H), 2.01 (d, J = 14.2, 1H), 1.95-1.77 (m, 2H), 1.69 (dd, J = 9.6, 4.4, 1H), 1.63-1.39 (m, 4H), 1.21-1.08 (m, 1H), 0.91-0.60 (m, 1H). |
| 19 | (1H-imidazol-2-ylmethyl)({2-[(9R)-9-(pyridin-2-yl)-6-oxaspiro[4.5]decan-9-yl]ethyl})amine | 341.1 | δ 8.70 (d, J = 5.1, 1H), 8.40 (t, J = 7.9, 1H), 7.92 (d, J = 8.2, 1H), 7.87-7.74 (m, 1H), 7.31 (d, J = 18.0, 2H), 4.66 (d, J = 14.3, 1H), 4.49 (d, J = 14.3, 1H), 4.02-3.81 (m, 1H), 3.74 (d, J = 9.7, 1H), 3.10 (d, J = 4.9, 1H), 2.84-2.48 (m, 2H), 2.37 (t, J = 12.7, 3H), 2.17-2.00 (m, 1H), 2.00-1.82 (m, 2H), 1.70 (s, 1H), 1.65-1.41 (m, 4H), 1.21 (s, 1H), 0.82 (d, J = 13.1, 1H). |
| 20 | (1,3-oxazol-4-ylmethyl)({2-[(9R)-9-(pyridin-2-yl)-6-oxaspiro[4.5]decan-9-yl]ethyl})amine | 342.1 | δ 8.77 (dd, J = 5.5, 1.4, 1H), 8.26 (td, J = 8.0, 1.7, 1H), 7.90 (s, 1H), 7.82 (s, 1H), 7.79-7.60 (m, 2H), 4.08 (s, 2H), 3.86 (d, J = 12.9, 1H), 3.81-3.66 (m, 1H), 3.13 (d, J = 5.6, 1H), 2.76-2.60 (m, 1H), 2.48 (s, 1H), 2.42-2.25 (m, 3H), 2.16-2.01 (m, 1H), 1.89 (dd, J = 9.6, 4.0, 2H), 1.79-1.63 (m, 1H), 1.63-1.35 (m, 4H), 1.19 (s, 1H), 0.80 (d, J = 13.2, 1H). |
| 21 | {2-[3-(pyridin-2-yl)-1-oxaspiro[4.4]nonan-3-yl]ethyl}(thiophen-2-ylmethyl)amine | 343 | δ 10.01 (s, 3H), 8.62 (d, J = 4.5, 1H), 8.11 (td, J = 8.0, 1.4, 1H), 7.70 (d, J = 8.1, 1H), 7.63-7.46 (m, 1H), 7.33 (dd, J = 5.1, 1.0, 1H), 7.16 (d, J = 2.8, 1H), 7.00 (dd, J = 5.1, 3.6, 1H), 4.29 (s, 2H), 4.14 (d, J = 9.7, |

TABLE 1-continued

Compounds with chemical name and characterization data

| Compound. | Name | MS (m/z) [M + H]+ | 1H NMR |
|---|---|---|---|
| | | | 1H), 3.92 (d, J = 9.7, 1H), 2.97 (qd, J = 18.1, 12.2, 2H), 2.53 (ddd, J = 14.4, 9.0, 5.7, 1H), 2.45-2.21 (m, 3H), 2.00-1.82 (m, 1H), 1.67 (tt, J = 22.6, 8.0, 6H), 1.44 (dd, J = 14.3, 10.0, 1H). |
| 22 | {2-[3-(pyridin-2-yl)-1-oxaspiro[4.4]nonan-3-yl]ethyl}(thiophen-3-ylmethyl)amine | 343 | δ 11.15 (s, 2H), 9.70 (s, 2H), 8.64 (d, J = 4.4, 1H), 8.17 (td, J = 8.0, 1.5, 1H), 7.74 (d, J = 8.1, 1H), 7.63 (dd, J = 6.7, 5.7, 1H), 7.40 (dd, J = 2.8, 1.1, 1H), 7.33 (dd, J = 5.0, 3.0, 1H), 7.10 (dd, J = 5.0, 1.2, 1H), 4.23-4.07 (m, 3H), 3.94 (d, J = 9.8, 1H), 2.90 (d, J = 33.7, 2H), 2.67-2.50 (m, 1H), 2.50-2.24 (m, 3H), 1.91 (dd, J = 13.7, 4.9, 1H), 1.83-1.52 (m, 6H), 1.43 (td, J = 7.7, 3.9, 1H). |
| 23 | (cyclopentylmethyl)({2-[(9R)-9-(pyridin-2-yl)-6-oxaspiro[4.5]decan-9-yl]ethyl})amine | 343.3 | δ 8.77 (d, J = 4.6, 2H), 8.26 (t, J = 7.6, 1H), 7.89-7.60 (m, 2H), 3.85 (dd, J = 8.5, 4.2, 1H), 3.73 (t, J = 10.1, 1H), 3.00 (s, 1H), 2.81 (s, 2H), 2.42 (dt, J = 23.0, 9.5, 4H), 2.25 (t, J = 10.8, 1H), 2.19-1.98 (m, 2H), 1.98-1.33 (m, 13H), 1.16 (s, 3H), 0.76 (dt, J = 13.1, 8.9, 1H). |
| 24 | {2-[2,2-dimethyl-4-(4-methylphenyl)oxan-4-yl]ethyl}(thiophen-2-ylmethyl)amine | 344.2 | δ 8.87 (d, J = 194.4, 2H), 3.91 (s, 3H), 3.69 (m, 2H), 2.66 (d, J = 7.9, 1H), 2.24 (m, 4H), 2.10 (ddd, J = 30.6, 14.0, 2.1, 2H), 1.84 (td, J = 12.5, 4.9, 1H), 1.65 (m, 1H), 1.49 (m, 2H), 1.11 (d, J = 6.1, 3H), 0.57 (s, 3H). |
| 25 | {2-[4-(4-fluorophenyl)oxan-4-yl]ethyl}[(2-methoxyphenyl)methyl]amine | 344.2 | δ 7.20 (ddd, J = 7.6, 4.8, 2.0, 3H), 7.03 (m, 3H), 6.84 (ddd, J = 11.7, 9.1, 4.5, 2H), 3.77 (m, 5H), 3.61 (s, 2H), 3.54 (ddd, J = 11.6, 8.8, 2.8, 2H), 2.27 (m, 2H), 2.08 (m, 2H), 1.84 (ddd, J = 10.5, 8.4, 3.0, 4H), 1.58 (s, 1H) |
| 26 | {2-[9-(1H-pyrazol-1-yl)-6-oxaspiro[4.5]decan-9-yl]ethyl}(thiophen-2-ylmethyl)amine | 346 | δ 9.87 (s, 1H), 9.00 (d, J = 145.4, 2H), 7.46 (dd, J = 12.7, 2.1, 2H), 7.28 (dd, J = 5.1, 1.1, 1H), 7.01 (d, J = 0.8, 1H), 6.93 (dd, J = 5.1, 3.5, 1H), 6.34-6.24 (m, 1H), 5.22 (s, 1H), 4.10 (q, J = 14.2, 2H), 3.68 (d, J = 2.7, 2H), 2.94 (s, 1H), 2.50 (s, 1H), 2.31 (s, 2H), 2.24-2.08 (m, 1H), 1.99 (dt, J = 14.7, 7.3, 1H), 1.93-1.76 (m, 2H), 1.75-1.63 (m, 1H), 1.57 (ddd, J = 23.2, 14.0, 8.1, 1H), 1.51 (s, 4H), 1.17-1.04 (m, 1H), 0.69 (dt, J = 13.3, 8.7, 1H). |
| 27 | benzyl({2-[(9S)-9-(pyridin-2-yl)-6-oxaspiro[4.5]decan-9-yl]ethyl})amine | 351.1 | δ 8.67 (d, J = 4.7, 1H), 8.17 (t, J = 7.7, 1H), 7.64 (m, 2H), 7.35 (m, 5H), 6.51 (s, 4H), 4.72 (s, 1H), 3.94 (s, 2H), 3.75 (m, 2H), 2.95 (s, 1H), 2.49 (s, 1H), 2.33 (m, 3H), 2.19 (m, 1H), 1.98 (d, J = 14.1, 1H), 1.81 (dt, J = 13.4, 7.5, 2H), 1.68 (m, 1H), 1.49 (ddd, J = 20.8, 14.7, 7.2, 4H), 1.15 (s, 1H), 0.75 (m, 1H). |
| 28 | benzyl({2-[(9R)-9-(pyridin-2-yl)-6-oxaspiro[4.5]decan-9-yl]ethyl})amine | 351.1 | δ 8.61 (s, 1H), 8.18 (t, J = 7.7, 1H), 7.65 (m, 2H), 7.26 (m, 5H), 6.90 (d, J = 26.0, 4H), 3.88 (s, 2H), 3.72 (d, J = 12.7, 1H), 3.60 (t, J = 10.0, 1H), 2.90 (s, 1H), 2.39 (d, J = 34.6, 2H), 2.20 (t, J = 13.3, 3H), 1.92 (d, J = 14.8, 2H), 1.75 (m, 2H), 1.59 (d, J = 4.9, 1H), 1.41 (m, 4H), 1.08 (s, 1H), 0.68 (dt, J = 13.2, 9.0, 1H). |
| 29 | benzyl({2-[3-(pyridin-2-yl)-1-oxaspiro[4.5]decan-3-yl]ethyl})amine | 351.1 | δ 9.67 (s, 2H), 8.61 (s, 1H), 8.19 (t, J = 7.5, 1H), 7.80 (d, J = 8.1, 1H), 7.64 (s, 1H), 7.36 (s, 5H), 4.22 (d, J = 10.0, 1H), 4.05 (s, 2H), 3.98 (d, J = 10.0, 1H), 3.00 (s, 1H), 2.84 (s, 1H), 2.64 (s, 1H), 2.39 (d, J = 8.7, 1H), 2.18 (d, J = 13.6, 1H), 2.09 (d, J = 13.6, 1H), 1.75-1.52 (m, 4H), 1.33 (dd, J = 28.9, 16.2, 7H). |
| 30 | benzyl({2-[9-(pyridin-2-yl)-6-oxaspiro[4.5]decan-9-yl]ethyl})amine | 351.2 | δ 8.49 (s, 1H), 8.03 (s, 1H), 7.53 (d, J = 8.0, 2H), 7.18 (m, 5H), 3.82 (s, 2H), 3.63 (s, 1H), 3.53 (dd, J = 23.8, 13.7, 1H), 2.84 (s, 1H), 2.38 (s, 1H), 2.27 (d, J = 7.4, 1H), 2.13 (d, J = 14.1, 3H), 1.84 (d, J = 14.2, 1H), 1.67 (m, 2H), 1.52 (d, J = 5.0, 1H), 1.32 (m, 4H), 1.01 (s, 1H), 0.61 (dt, J = 13.0, 8.9, 1H). |
| 31 | {2-[2,2-dimethyl-4-(4-methylphenyl)oxan-4-yl]ethyl}[(2-methylphenyl)methyl]amine | 352.2 | δ 7.09 (d, J = 8.3, 2H), 7.02 (ddd, J = 8.1, 6.1, 3.3, 6H), 3.69 (m, 2H), 3.47 (s, 2H), 2.41 (td, J = 10.8, 5.4, 1H), 2.25 (m, 4H), 2.11 (m, 5H), 1.75 (ddd, J = 13.2, 10.4, 5.2, 1H), 1.56 (m, 4H), 1.11 (s, 3H), 0.59 (s, 3H). |
| 32 | {2-[2,2-dimethyl-4-(4-methylphenyl)oxan-4-yl]ethyl}[(3-methylphenyl)methyl]amine | 352.3 | δ 9.13 (s, 1H), 8.69 (s, 1H), 7.04 (m, 6H), 6.86 (m, 2H), 3.65 (m, 6H), 2.59 (s, 1H), 2.12 (m, 9H), 1.83 (td, J = 12.4, 4.5, 1H), 1.64 (m, 1H), 1.48 (m, 2H), 1.10 (s, 3H), 0.57 (s, 3H). |
| 33 | {2-[2,2-dimethyl-4-(4-methylphenyl)oxan-4-yl]ethyl}[(4-methylphenyl)methyl]amine | 352.3 | δ 8.68 (d, J = 205.9, 2H), 7.02 (dd, J = 16.8, 9.0, 6H), 6.93 (d, J = 8.1, 2H), 3.67 (dd, J = 6.6, 2.7, 2H), 3.57 (s, 2H), 3.44 (s, 3H), 2.61 (s, 1H), 2.25 (d, J = 11.2, 3H), 2.17 (s, 3H), 2.08 (dd, J = 20.3, 14.0, 2H), 1.84 (m, 1H), 1.67 (d, J = 7.6, 1H), 1.48 (m, 2H), 1.09 (s, 3H), 0.56 (s, 3H). |

TABLE 1-continued

Compounds with chemical name and characterization data

| Compound. | Name | MS (m/z) [M + H]+ | 1H NMR |
|---|---|---|---|
| 34 | {2-[2,2-dimethyl-4-(4-methylphenyl)oxan-4-yl]ethyl}[(1R)-1-phenylethyl]amine | 352.3 | δ 9.07 (dd, J = 228.2, 166.6, 2H), 7.24 (ddd, J = 9.3, 6.4, 3.4, 3H), 7.15 (m, 2H), 6.94 (m, 4H), 3.91 (s, 1H), 3.61 (dd, J = 7.0, 4.0, 2H), 2.42 (d, J = 33.9, 1H), 2.21 (d, J = 11.7, 6H), 2.00 (m, 2H), 1.82 (m, 1H), 1.62 (dd, J = 8.6, 4.1, 1H), 1.42 (m, 5H), 1.05 (s, 3H), 0.53 (d, J = 3.4, 3H). |
| 35 | {2-[2,2-dimethyl-4-(4-methylphenyl)oxan-4-yl]ethyl}[(1S)-1-phenylethyl]amine | 352.3 | δ 8.92 (dd, J = 238.8, 174.0, 2H), 7.24 (m, 3H), 7.14 (td, J = 7.5, 2.2, 2H), 6.95 (m, 4H), 3.89 (d, J = 19.3, 1H), 3.62 (m, 2H), 2.96 (s, 2H), 2.42 (m, 1H), 2.21 (d, J = 11.6, 3H), 2.00 (m, 3H), 1.82 (m, 1H), 1.63 (m, 1H), 1.40 (m, 5H), 1.06 (s, 3H), 0.53 (d, J = 3.6, 3H). |
| 36 | benzyl({2-[2,2-dimethyl-4-(4-methylphenyl)oxan-4-yl]ethyl})methylamine | 352.3 | δ 11.09 (s, 2H), 7.39 (m, 3H), 7.23 (m, 1H), 7.15 (m, 5H), 4.19 (dd, J = 25.7, 12.6, 1H), 3.91 (dd, J = 17.4, 8.4, 1H), 3.78 (m, 2H), 2.91 (d, J = 127.4, 1H), 2.56 (dd, J = 17.7, 7.2, 3H), 2.37 (d, J = 4.8, 3H), 2.24 (ddd, J = 22.0, 12.2, 2.2, 3H), 2.05 (m, 1H), 1.88 (td, J = 12.5, 4.7, 1H), 1.64 (m, 2H), 1.21 (s, 3H), 382.30.67 (d, J = 1.2, 3H). |
| 37 | {2-[2,2-dimethyl-4-(4-methylphenyl)oxan-4-yl]ethyl}(2-phenylethyl)amine | 352.3 | δ 9.06 (d, J = 128.6, 2H), 7.17 (m, 3H), 7.02 (m, 6H), 3.68 (dd, J = 11.8, 10.1, 2H), 2.77 (dt, J = 36.5, 30.4, 7H), 2.19 (m, 5H), 1.99 (m, 1H), 1.89 (td, J = 12.5, 4.6, 1H), 1.69 (m, 1H), 1.49 (m, 2H), 1.00 (s, 3H), 0.52 (s, 3H). |
| 38 | (pyrazin-2-ylmethyl)({2-[(9R)-9-(pyridin-2-yl)-6-oxaspiro[4.5]decan-9-yl]ethyl})amine | 353.1 | δ 8.79 (dd, J = 5.6, 1.4, 1H), 8.68-8.54 (m, 2H), 8.51 (dd, J = 2.3, 1.6, 1H), 8.32 (td, J = 8.0, 1.6, 1H), 7.93-7.66 (m, 3H), 4.30 (s, 2H), 3.85 (dt, J = 12.3, 4.2, 1H), 3.72 (t, J = 9.9, 1H), 3.19 (td, J = 11.7, 5.2, 1H), 2.72 (td, J = 11.8, 4.0, 1H), 2.62-2.45 (m, 1H), 2.45-2.27 (m, 3H), 2.10 (d, J = 14.2, 1H), 2.00-1.79 (m, 2H), 1.69 (dt, J = 9.9, 6.6, 1H), 1.63-1.41 (m, 4H), 1.19 (dd, J = 12.6, 6.5, 1H), 0.78 (dt, J = 13.1, 8.9, 1H). |
| 39 | benzyl({2-[2,2-diethyl-4-(pyridin-2-yl)oxan-4-yl]ethyl})amine | 353.3 | δ 8.71 (dd, J = 5.5, 1.4, 1H), 8.21 (td, J = 8.0, 1.7, 1H), 7.67 (m, 2H), 7.33 (m, 5H), 3.95 (s, 2H), 3.79 (m, 1H), 3.67 (d, J = 10.8, 1H), 3.01 (d, J = 5.2, 1H), 2.40 (m, 4H), 2.10 (s, 1H), 1.73 (t, J = 16.5, 2H), 1.55 (dd, J = 14.1, 7.5, 1H), 1.39 (dd, J = 14.1, 7.4, 1H), 0.81 (m, 5H), 0.56 (t, J = 7.3, 3H). |
| 40 | benzyl({2-[2,2,6,6-tetramethyl-4-(pyridin-2-yl)oxan-4-yl]ethyl})amine | 353.3 | δ 8.74-8.62 (m, 1H), 8.24 (td, J = 8.1, 1.5, 1H), 7.87 (d, J = 8.2, 1H), 7.76-7.65 (m, 1H), 7.47-7.18 (m, 7H), 3.96 (s, 2H), 2.75 (m, 2H), 2.50 (d, J = 14.7, 2H), 2.43-2.28 (m, 2H), 1.89 (d, J = 14.8, 2H), 1.30 (s, 6H), 0.97 (s, 6H). |
| 41 | 4-[({2-[2,2-dimethyl-4-(4-methylphenyl)oxan-4-yl]ethyl}amino)methyl]phenol | 354.2 | δ 8.58 (d, J = 187.3, 2H), 7.05 (q, J = 8.3, 4H), 6.91 (d, J = 8.3, 2H), 6.58 (d, J = 8.4, 2H), 3.67 (d, J = 10.4, 2H), 3.58 (s, 2H), 2.63 (d, J = 18.2, 1H), 2.26 (s, 4H), 2.07 (d, J = 14.3, 4H), 1.84 (t, J = 10.2, 1H), 1.49 (d, J = 13.9, 3H), 1.09 (s, 3H), 0.56 (s, 3H). |
| 42 | 2-[({2-[2,2-dimethyl-4-(4-methylphenyl)oxan-4-yl]ethyl}amino)methyl]phenol | 354.3 | δ 8.15 (d, J = 107.7, 2H), 7.03 (dt, J = 26.2, 8.3, 5H), 6.82 (m, 2H), 6.64 (t, J = 7.4, 1H), 3.68 (m, 6H), 2.58 (s, 1H), 2.24 (d, J = 6.8, 4H), 2.05 (dd, J = 21.0, 14.9, 2H), 1.78 (d, J = 4.4, 1H), 1.58 (s, 1H), 1.44 (dd, J = 21.2, 9.8, 2H), 1.10 (d, J = 18.7, 3H), 0.57 (d, J = 24.3, 3H). |
| 43 | 3-[({2-[2,2-dimethyl-4-(4-methylphenyl)oxan-4-yl]ethyl}amino)methyl]phenol | 354.3 | δ 8.50 (d, J = 165.4, 2H), 7.02 (m, 5H), 6.68 (d, J = 7.5, 2H), 6.47 (d, J = 7.4, 1H), 3.67 (d, J = 9.4, 2H), 3.59 (s, 2H), 2.63 (s, 2H), 2.23 (s, 4H), 2.09 (dd, J = 27.3, 13.5, 2H), 1.84 (d, J = 7.8, 1H), 1.66 (d, J = 8.6, 1H), 1.52 (d, J = 13.9, 2H), 1.09 (s, 3H), 0.56 (s, 3H). |
| 44 | [(5-methylfuran-2-yl)methyl]({2-[(9R)-9-(pyridin-2-yl)-6-oxaspiro[4.5]decan-9-yl]ethyl})amine | 355.1 | δ 8.73 (d, J = 4.2, 1H), 8.18 (td, J = 8.0, 1.5, 1H), 7.80-7.53 (m, 2H), 7.29 (s, 1H), 4.00 (d, J = 1.4, 2H), 3.83 (dt, J = 12.4, 4.3, 1H), 3.79-3.63 (m, 1H), 3.10-2.86 (m, 1H), 2.64-2.44 (m, 1H), 2.45-2.27 (m, 3H), 2.27-2.11 (m, 4H), 2.02 (d, J = 14.2, 1H), 1.95-1.77 (m, 2H), 1.68 (dd, J = 9.5, 4.1, 1H), 1.62-1.39 (m, 4H), 1.26-1.05 (m, 1H), 0.77 (dt, J = 13.3, 9.0, 1H). |
| 45 | [(5-methylfuran-2-yl)methyl]({2-[9-(pyrazin-2-yl)-6-oxaspiro[4.5]decan-9-yl]ethyl})amine | 356.1 | δ 8.66 (s, 1H), 8.56 (s, 1H), 8.50 (s, 1H), 6.27 (d, J = 3.2, 1H), 6.05-5.83 (m, 1H), 3.94 (d, J = 1.9, 2H), 3.85-3.59 (m, 2H), 2.89 (d, J = 5.0, 1H), 2.49 (d, J = 5.1, 1H), 2.38 (t, J = 16.0, 2H), 2.24 (s, 4H), 2.02 (dd, J = 18.2, 6.8, 2H), 1.96-1.88 (m, 2H), 1.59-1.37 (m, 5H), 1.09 (s, 1H), 0.66 (d, J = 13.4, 1H). |
| 46 | benzyl({2-[9-(thiophen-2-yl)-6- | 356.2 | δ 9.56 (s, 1H), 9.11 (s, 1H), 7.31 (m, 3H), 7.23 (m, 2H), 7.19 (dd, J = 5.1, 1.0, 1H), 6.91 (dd, J = 5.1, 3.6, |

TABLE 1-continued

Compounds with chemical name and characterization data

| Compound. | Name | MS (m/z) [M + H]+ | 1H NMR |
|---|---|---|---|
| | oxaspiro[4.5]decan-9-yl]ethyl})amine | | 1H), 6.74 (d, J = 3.5, 1H), 3.72 (m, 4H), 2.74 (m, 1H), 2.44 (m, 1H), 2.01 (d, J = 13.9, 2H), 1.95 (dd, J = 11.7, 5.0, 1H), 1.87 (m, 2H), 1.73 (s, 5H), 1.66 (m, 2H), 1.50 (m, 3H), 1.00 (dd, J = 13.6, 8.5, 1H). |
| 47 | {2-[2,2-dimethyl-4-(4-methylphenyl)oxan-4-yl]ethyl}[(2-fluorophenyl)methyl]amine | 356.3 | δ 7.15 (m, 1H), 7.06 (m, 5H), 6.94 (dt, J = 18.3, 8.1, 2H), 3.69 (t, J = 7.7, 2H), 3.60 (s, 2H), 2.44 (dd, J = 11.0, 5.2, 1H), 2.22 (d, J = 20.4, 4H), 2.11 (m, 2H), 1.77 (dd, J = 6.6, 4.0, 1H), 1.57 (qd, J = 10.9, 5.5, 3H), 1.11 (s, 3H), 0.59 (s, 3H). |
| 48 | {2-[2,2-dimethyl-4-(4-methylphenyl)oxan-4-yl]ethyl}[(3-fluorophenyl)methyl]amine | 356.3 | δ 8.79 (d, J = 198.9, 2H), 7.19 (m, 2H), 7.05 (d, J = 8.2, 2H), 7.00 (d, J = 8.4, 2H), 6.94 (td, J = 8.4, 2.2, 1H), 6.86 (d, J = 7.6, 1H), 6.79 (d, J = 8.9, 1H), 6.36 (s, 2H), 3.69 (m, 4H), 2.65 (s, 1H), 2.24 (s, 3H), 2.11 (ddd, J = 18.3, 15.7, 11.3, 3H), 1.81 (dt, J = 12.3, 6.2, 1H), 1.63 (m, 1H), 1.48 (m, 2H), 1.10 (s, 3H), 0.56 (s, 3H). |
| 49 | {2-[2,2-dimethyl-4-(4-methylphenyl)oxan-4-yl]ethyl}[(4-fluorophenyl)methyl]amine | 356.3 | δ 8.73 (d, J = 173.6, 2H), 7.03 (m, 6H), 6.88 (t, J = 8.5, 2H), 5.32 (s, 2H), 3.68 (m, 4H), 2.61 (s, 1H), 2.24 (s, 3H), 2.11 (m, 3H), 1.78 (dt, J = 12.3, 6.2, 1H), 1.61 (m, 1H), 1.47 (m, 2H), 1.10 (s, 3H), 0.56 (s, 3H). |
| 50 | benzyl(2-{9-cyclohexyl-6-oxaspiro[4.5]decan-9-yl}ethyl)amine | 356.3 | δ 9.09 (d, J = 38.9, 2H), 7.35 (m, 5H), 6.43 (s, 2H), 3.93 (s, 2H), 3.54 (m, 2H), 2.85 (s, 2H), 1.63 (m, 16H), 1.10 (m, 7H), 0.84 (q, J = 11.8, 2H). |
| 51 | {2-[3-(pyridin-2-yl)-1-oxaspiro[4.5]decan-3-yl]ethyl}(thiophen-2-ylmethyl)amine | 357 | δ 9.79 (s, 2H), 8.66 (s, 1H), 8.21 (t, J = 7.5, 1H), 7.80 (d, J = 8.1, 1H), 7.66 (s, 1H), 7.33 (d, J = 5.0, 1H), 7.16 (s, 1H), 7.06-6.98 (m, 1H), 4.29 (s, 2H), 4.23 (d, J = 9.9, 1H), 3.99 (d, J = 10.0, 1H), 3.00 (s, 1H), 2.87 (s, 1H), 2.63 (t, J = 9.5, 1H), 2.39 (d, J = 8.6, 1H), 2.20 (d, J = 13.5, 1H), 2.10 (d, J = 13.6, 1H), 1.77-1.49 (m, 4H), 1.47-1.19 (m, 6H). |
| 52 | {2-[3-(pyridin-2-yl)-1-oxaspiro[4.5]decan-3-yl]ethyl}(thiophen-3-ylmethyl)amine | 357 | δ 9.72 (s, 2H), 8.64 (s, 1H), 8.21 (t, J = 7.5, 1H), 7.80 (d, J = 8.1, 1H), 7.66 (t, J = 5.9, 1H), 7.44-7.31 (m, 2H), 7.09 (d, J = 4.8, 1H), 4.23 (d, J = 9.9, 1H), 4.10 (s, 2H), 3.99 (d, J = 10.0, 1H), 2.95 (s, 1H), 2.80 (s, 1H), 2.64 (s, 1H), 2.39 (d, J = 8.7, 1H), 2.21 (d, J = 13.7, 1H), 2.10 (d, J = 13.6, 1H), 1.77-1.50 (m, 4H), 1.49-1.22 (m, 6H). |
| 53 | {2-[9-(pyridin-2-yl)-6-oxaspiro[4.5]decan-9-yl]ethyl}(thiophen-2-ylmethyl)amine | 357.1 | δ 8.67 (d, J = 4.3, 1H), 8.14 (s, 1H), 7.66 (d, J = 8.2, 1H), 7.59 (s, 1H), 7.33 (dd, J = 5.1, 1.1, 1H), 7.12 (d, J = 2.7, 1H), 7.00 (dd, J = 5.1, 3.5, 1H), 4.22 (s, 2H), 3.80 (s, 1H), 3.72 (t, J = 9.8, 1H), 3.33-2.70 (m, 1H), 2.70-2.50 (m, 1H), 2.30 (d, J = 14.0, 3H), 2.19 (dd, J = 18.0, 7.1, 1H), 1.98 (d, J = 14.1, 1H), 1.83 (d, J = 4.6, 2H), 1.76-1.62 (m, 1H), 1.50 (dd, J = 20.1, 13.3, 5H), 1.16 (s, 1H), 0.75 (dt, J = 13.1, 9.1, 1H). |
| 54 | {2-[(9R)-9-(pyridin-2-yl)-6-oxaspiro[4.5]decan-9-yl]ethyl}(thiophen-2-ylmethyl)amine | 357.2 | δ 8.67 (d, J = 4.3, 1H), 8.14 (s, 1H), 7.66 (d, J = 8.2, 1H), 7.59 (s, 1H), 7.33 (dd, J = 5.1, 1.1, 1H), 7.12 (d, J = 2.7, 1H), 7.00 (dd, J = 5.1, 3.5, 1H), 4.22 (s, 2H), 3.80 (s, 1H), 3.72 (t, J = 9.8, 1H), 3.33-2.70 (m, 1H), 2.70-2.50 (m, 1H), 2.30 (d, J = 14.0, 3H), 2.19 (dd, J = 18.0, 7.1, 1H), 1.98 (d, J = 14.1, 1H), 1.83 (d, J = 4.6, 2H), 1.76-1.62 (m, 1H), 1.50 (dd, J = 20.1, 13.3, 5H), 1.16 (s, 1H), 0.75 (dt, J = 13.1, 9.1, 1H). |
| 55 | {2-[(9R)-9-(pyridin-2-yl)-6-oxaspiro[4.5]decan-9-yl]ethyl}(thiophen-3-ylmethyl)amine | 357.2 | δ 8.73 (d, J = 5.0, 1H), 8.27 (t, J = 7.5, 2H), 7.88-7.62 (m, 2H), 7.48-7.23 (m, 1H), 7.04 (dd, J = 4.9, 1.0, 1H), 4.02 (s, 2H), 3.90-3.76 (m, 1H), 3.69 (t, J = 10.0, 1H), 2.95 (s, 1H), 2.62-2.12 (m, 4H), 2.13-1.95 (m, 1H), 1.95-1.76 (m, 2H), 1.68 (dt, J = 13.5, 7.9, 1H), 1.62-1.30 (m, 5H), 1.16 (dd, J = 13.2, 6.6, 1H), 0.76 (dt, J = 13.0, 8.9, 1H). |
| 56 | {2-[(9R)-9-(pyridin-2-yl)-6-oxaspiro[4.5]decan-9-yl]ethyl}(1,3-thiazol-2-ylmethyl)amine | 358 | δ 8.77 (d, J = 4.3, 1H), 8.27 (t, J = 7.3, 1H), 7.86-7.65 (m, 2H), 7.43 (d, J = 3.1, 1H), 7.28 (s, 1H), 4.56-4.39 (m, 2H), 3.79 (dddd, J = 21.9, 19.5, 10.8, 7.1, 2H), 3.19 (td, J = 11.5, 5.3, 1H), 2.81-2.63 (m, 1H), 2.62-2.43 (m, 1H), 2.43-2.26 (m, 3H), 2.14-1.99 (m, 1H), 2.00-1.79 (m, 2H), 1.79-1.63 (m, 1H), 1.63-1.38 (m, 4H), 1.20 (dd, J = 13.0, 6.5, 1H), 0.79 (dt, J = 13.0, 8.9, 1H). |
| 57 | {2-[(9R)-9-(pyridin-2-yl)-6-oxaspiro[4.5]decan-9-yl]ethyl}(1,3-thiazol-5-ylmethyl)amine | 358 | δ 8.76 (d, J = 4.7, 1H), 8.37 (td, J = 8.1, 1.4, 1H), 8.12-7.72 (m, 3H), 7.29 (s, 1H), 4.37 (s, 2H), 3.93-3.58 (m, 2H), 3.05 (td, J = 11.7, 5.1, 1H), 2.66-2.43 (m, 2H), 2.42-2.22 (m, 3H), 2.18-1.96 (m, 1H), 1.96-1.79 (m, 2H), 1.79-1.39 (m, 5H), 1.18 (dd, J = 12.1, 5.5, 1H), 0.77 (dt, J = 12.9, 8.9, 1H). |

TABLE 1-continued

Compounds with chemical name and characterization data

| Compound. | Name | MS (m/z) [M + H]+ | 1H NMR |
|---|---|---|---|
| 58 | {2-[9-(pyrazin-2-yl)-6-oxaspiro[4.5]decan-9-yl]ethyl}(thiophen-2-ylmethyl)amine | 358 | δ 8.63 (s, 1H), 8.55 (s, 1H), 8.49 (d, J = 2.3, 1H), 7.33 (dd, J = 5.1, 1.1, 1H), 7.08 (d, J = 2.6, 1H), 7.05-6.97 (m, 1H), 3.73 (d, J = 36.7, 2H), 3.17-2.73 (m, 1H), 2.54-2.43 (m, 1H), 2.35 (d, J = 13.0, 2H), 2.24-2.11 (m, 1H), 2.05-2.15 (m, 4H), 1.51 (s, 5H), 1.14-1.01 (m, 1H), 0.66 (s, 1H). |
| 59 | {2-[2,2-diethyl-4-(pyridin-2-yl)oxan-4-yl]ethyl}(thiophen-3-ylmethyl)amine | 359.2 | δ 8.72 (dd, J = 5.5, 1.4, 1H), 8.21 (td, J = 8.0, 1.7, 1H), 7.68 (m, 2H), 7.35 (dd, J = 2.9, 1.2, 1H), 7.30 (m, 2H), 7.04 (dd, J = 5.0, 1.3, 1H), 4.02 (s, 2H), 3.80 (dd, J = 10.0, 6.3, 1H), 3.68 (d, J = 10.8, 1H), 3.00 (m, 1H), 2.42 (m, 4H), 2.08 (d, J = 4.4, 1H), 1.78 (s, 1H), 1.71 (d, J = 14.5, 1H), 1.56 (dd, J = 14.1, 7.5, 1H), 1.40 (dd, J = 14.1, 7.4, 1H), 0.81 (m, 5H), 0.57 (t, J = 7.3, 3H). |
| 60 | {2-[2,2-diethyl-4-(pyridin-2-yl)oxan-4-yl]ethyl}(thiophen-2-ylmethyl)amine | 359.2 | δ 8.70 (dd, J = 5.4, 1.4, 1H), 8.15 (d, J = 1.6, 1H), 7.66 (dd, J = 8.2, 1H), 7.60 (dd, J = 6.7, 5.5, 1H), 7.33 (dd, J = 5.1, 1.2, 1H), 7.11 (d, J = 2.6, 1H), 6.99 (dd, J = 5.1, 3.6, 1H), 3.73 (d, J = 44.0, 4H), 4.02 (s, 2H), 3.80 (dd, J = 10.0, 6.3, 1H), 3.68 (d, J = 10.8, 1H), 3.00 (m, 1H), 2.42 (m, 4H), 2.08 (d, J = 4.4, 1H), 1.78 (s, 1H), 1.71 (d, J = 14.5, 1H), 1.56 (dd, J = 14.1, 7.5, 1H), 1.40 (dd, J = 14.1, 7.4, 1H), 0.81 (m, 5H), 0.57 (t, J = 7.3, 3H). |
| 61 | {2-[2,2,6,6-tetramethyl-4-(pyridin-2-yl)oxan-4-yl]ethyl}(thiophen-2-ylmethyl)amine | 359.2 | δ 8.63 (dd, J = 5.6, 1.3, 1H), 8.18 (td, J = 8.1, 1.6, 1H), 7.81 (d, J = 8.2, 1H), 7.63 (dd, J = 6.8, 5.8, 1H), 7.36-7.16 (m, 2H), 7.05-6.96 (m, 2H), 6.88 (dd, J = 5.1, 3.6, 2H), 4.13 (s, 2H), 2.80-2.60 (m, 2H), 2.43 (d, J = 14.7, 2H), 2.33-2.17 (m, 2H), 1.81 (d, J = 14.8, 2H), 1.21 (d, J = 12.2, 6H), 0.89 (s, 6H). |
| 62 | {2-[2,2,6,6-tetramethyl-4-(pyridin-2-yl)oxan-4-yl]ethyl}(thiophen-3-ylmethyl)amine | 359.2 | δ 8.62 (dd, J = 5.6, 1.4, 1H), 8.19 (td, J = 8.0, 1.7, 1H), 7.81 (d, J = 8.2, 2H), 7.67-7.60 (m, 1H), 7.27 (dd, J = 2.9, 1.2, 1H), 7.23-7.17 (m, 2H), 6.95 (dd, J = 5.0, 1.3, 1H), 3.95 (s, 2H), 2.62 (d, J = 8.1, 2H), 2.41 (d, J = 14.7, 2H), 2.34-2.08 (m, 2H), 1.82 (d, J = 14.8, 2H), 1.21 (d, J = 13.1, 6H), 0.89 (s, 6H). |
| 63 | {2-[9-(thiophen-2-yl)-6-oxaspiro[4.5]decan-9-yl]ethyl}(thiophen-2-ylmethyl)amine | 362.2 | δ 9.60 (s, 1H), 9.27 (s, 1H), 7.29 (dd, J = 5.1, 1.1, 2H), 7.21 (dd, J = 5.1, 1.0, 1H), 7.03 (d, J = 2.6, 1H), 6.94 (ddd, J = 9.9, 5.1, 3.6, 2H), 6.77 (dd, J = 3.6, 1.1, 1H), 4.03 (s, 2H), 3.74 (m, 2H), 2.80 (td, J = 11.9, 4.9, 1H), 2.50 (td, J = 11.8, 5.0, 1H), 1.96 (m, 4H), 1.71 (m, 4H), 1.48 (m, 6H), 1.00 (dt, J = 12.7, 8.1, 1H). |
| 64 | {2-[9-(thiophen-2-yl)-6-oxaspiro[4.5]decan-9-yl]ethyl}(thiophen-3-ylmethyl)amine | 362.2 | δ 9.46 (s, 1H), 9.23 (s, 1H), 7.27 (m, 2H), 7.21 (dd, J = 5.1, 1.0, 1H), 7.00 (dt, J = 7.5, 4.4, 1H), 6.93 (dd, J = 5.1, 3.5, 1H), 6.75 (dd, J = 3.6, 1.1, 1H), 3.85 (s, 2H), 3.74 (m, 2H), 2.73 (m, 1H), 2.43 (s, 1H), 2.12 (m, 1H), 2.03 (m, 2H), 1.96 (dd, J = 12.4, 7.6, 1H), 1.87 (m, 2H), 1.70 (m, 3H), 1.48 (m, 5H), 1.00 (dt, J = 12.8, 8.1, 1H). |
| 65 | (cyclopentylmethyl)({2-[2,2-diethyl-4-(4-fluorophenyl)oxan-4-yl]ethyl})amine | 362.3 | δ 9.23 (m, 1H), 8.73 (m, 1H), 7.25 (dd, J = 8.9, 5.2, 2H), 7.07 (t, J = 8.6, 2H), 3.73 (d, J = 10.9, 2H), 2.69 (s, 2H), 2.10 (m, 4H), 1.78 (d, J = 18.1, 3H), 1.64 (m, 7H), 1.38 (s, 2H), 1.28 (s, 1H), 1.10 (d, J = 16.3, 3H), 0.84 (m, 4H), 0.53 (s, 3H). |
| 66 | (cyclopentylmethyl)({2-[4-(4-fluorophenyl)-2,2,6,6-tetramethyloxan-4-yl]ethyl})amine | 362.3 | δ 8.64 (s, 2H), 7.22 (dd, J = 8.9, 5.1, 2H), 6.95 (t, J = 8.6, 2H), 3.25 (s, 2H), 2.61 (s, 2H), 2.43 (s, 2H), 2.24 (d, J = 14.3, 2H), 1.91 (m, 2H), 1.68 (m, 2H), 1.60 (d, J = 14.3, 2H), 1.49 (m, 4H), 1.18 (s, 6H), 1.03 (dd, J = 12.4, 7.3, 2H), 0.93 (s, 6H). |
| 67 | (2-{9-cyclohexyl-6-oxaspiro[4.5]decan-9-yl}ethyl)(thiophen-2-ylmethyl)amine | 362.3 | δ 9.21 (d, J = 25.7, 2H), 7.33 (dd, J = 5.1, 1.1, 2H), 7.14 (d, J = 2.7, 1H), 7.00 (dd, J = 5.1, 3.6, 1H), 4.19 (s, 2H), 3.56 (m, 2H), 2.92 (s, 2H), 1.65 (m, 17H), 1.12 (m, 7H), 0.87 (dd, J = 23.8, 11.9, 2H). |
| 68 | (2-{9-cyclohexyl-6-oxaspiro[4.5]decan-9-yl}ethyl)(thiophen-3-ylmethyl)amine | 362.3 | δ 9.07 (d, J = 31.8, 2H), 7.37 (ddd, J = 7.9, 3.9, 2.1, 2H), 7.10 (dd, J = 5.0, 1.3, 1H), 6.37 (s, 2H), 4.04 (s, 2H), 3.55 (m, 2H), 2.87 (s, 2H), 1.64 (m, 16H), 1.12 (m, 7H), 0.85 (q, J = 11.8, 2H). |
| 69 | 2-{2-[(9R)-9-(pyridin-2-yl)-6-oxaspiro[4.5]decan-9-yl]ethyl}-2,3-dihydro-1H-isoindole | 363.1 | δ 8.77 (d, J = 4.0, 1H), 8.09 (td, J = 8.0, 1.7, 1H), 7.64 (d, J = 8.1, 1H), 7.55 (dd, J = 7.1, 5.8, 1H), 7.35 (dd, J = 5.6, 3.2, 2H), 7.24 (d, J = 3.6, 2H), 4.76 (m, 4H), 4.21 (brs, 1H), 3.77 (m, 2H), 3.30 (m, 1H), 2.80 (td, J = 12.3, 4.4, 1H), 2.49 (td, J = 12.9, 4.5, 1H), 2.38 (t, J = 15.1, 2H), 2.23 (td, J = 12.9, 4.2, 1H), 2.07 (d, J = 14.0, 1H), 1.87 (ddd, J = 24.1, 11.9, 7.1, 2H), 1.69 (m, 1H), 1.51 (dt, J = 24.2, 10.9, 4H), 1.15 (m, 1H), 0.78 (dt, J = 13.4, 9.0, 1H). |

TABLE 1-continued

Compounds with chemical name and characterization data

| Compound. | Name | MS (m/z) [M + H]+ | 1H NMR |
|---|---|---|---|
| 70 | {2-[2,2-diethyl-4-(4-fluorophenyl)oxan-4-yl]ethyl}dipropylamine | 364.4 | δ 11.44 (s, 1H), 7.28 (m, 2H), 7.10 (m, 2H), 3.75 (m, 2H), 2.88 (m, 5H), 2.27 (m, 3H), 1.97 (td, J = 12.7, 3.9, 1H), 1.80 (td, J = 12.6, 4.9, 1H), 1.66 (m, 2H), 1.46 (m, 6H), 1.04 (m, 1H), 0.88 (m, 10H), 0.55 (m, 3H). |
| 71 | (2-phenylethyl)({2-[(9R)-9-(pyridin-2-yl)-6-oxaspiro[4.5]decan-9-yl]ethyl})amine | 365.1 | δ 8.51 (dd, J = 5.3, 1.3, 1H), 8.04 (td, J = 7.9, 1.7, 1H), 7.56 (d, J = 8.1, 1H), 7.49 (dd, J = 7.1, 5.8, 1H), 7.25-7.12 (m, 6H), 7.10-7.03 (m, 2H), 3.88-3.47 (m, 3H), 3.01 (d, J = 7.5, 2H), 2.85 (t, J = 7.8, 2H), 2.44 (s, 1H), 2.38-2.17 (m, 3H), 2.17-1.99 (m, 1H), 1.92 (d, J = 14.1, 1H), 1.84-1.66 (m, 3H), 1.58 (d, J = 5.1, 1H), 1.40 (ddd, J = 15.2, 12.1, 8.9, 4H), 1.05 (d, J = 6.5, 1H), 0.65 (d, J = 13.4, 1H). |
| 72 | (2-phenylethyl)({2-[9-(pyridin-2-yl)-6-oxaspiro[4.5]decan-9-yl]ethyl})amine | 365.3 | δ 8.58 (d, J = 4.8, 1H), 8.07 (t, J = 7.9, 1H), 7.61 (s, 1H), 7.52 (dd, J = 12.0, 6.3, 1H), 7.27 (m, 3H), 7.20 (m, 2H), 4.04 (d, J = 3.2, 2H), 3.76 (ddd, J = 19.4, 12.6, 8.9, 2H), 3.05 (s, 1H), 2.53 (m, 2H), 2.29 (d, J = 43.6, 5H), 1.96 (d, J = 13.9, 1H), 1.80 (m, 2H), 1.68 (s, 1H), 1.50 (ddd, J = 20.5, 13.1, 7.0, 4H), 1.17 (s, 1H), 0.75 (m, 1H). |
| 73 | benzyl({2-[9-(6-methylpyridin-2-yl)-6-oxaspiro[4.5]decan-9-yl]ethyl})amine | 365.7 | δ 9.49 (s, 2H), 8.18 (t, J = 7.9, 1H), 7.55 (dd, J = 23.1, 7.8, 2H), 7.35 (s, 5H), 5.87 (s, 3H), 4.00 (s, 2H), 3.88-3.66 (m, 2H), 3.00 (s, 1H), 2.80 (s, 3H), 2.65 (d, J = 12.5, 1H), 2.53 (s, 1H), 2.31 (d, J = 14.3, 2H), 2.20 (d, J = 13.5, 1H), 2.11-2.00 (m, 1H), 1.97-1.80 (m, 2H), 1.70 (d, J = 5.3, 1H), 1.52 (ddd, J = 29.7, 17.1, 7.4, 4H), 1.28 (t, J = 7.1, 1H), 0.95-0.79 (m, 1H). (ddd, J = 29.7, 17.1, 7.4, 4H), 1.28 (t, J = 7.1, 1H), 0.92-0.77 (m, 1H). |
| 74 | {2-[2,2-dimethyl-4-(4-methylphenyl)oxan-4-yl]ethyl}(2-phenylpropan-2-yl)amine | 366.3 | 1H NMR (400 MHz324.3, CDCl3) δ 8.50 (d, J = 223.4, 2H), 7.25 (s, 5H), 6.95 (d, 338.3 J = 8.1, 2H), 6.87 (d, J = 8.3, 2H), 5.69 (s, 3H), 3.62 (dd, J = 6.8, 2.5, 2H), 2.38 (dd, J = 15.7, 13.2, 1H), 2.22 (s, 3H), 1.98 (m, 2H), 1.80 (m, 2H), 1.63 (m, 1H), 1.56 (s, 3H), 1.51 (s, 3H), 1.47 (d, J = 14.1, 1H), 1.39 (dd, J = 10.5, 4.0, 1H), 1.06 (s, 3H), 0.53 (s, 3H). |
| 75 | {2-[(9R)-9-(pyridin-2-yl)-6-oxaspiro[4.5]decan-9-yl]ethyl}[2-(pyridin-3-yl)ethyl]amine | 367.1 | δ 8.90 (s, 1H), 8.75 (d, J = 4.4, 1H), 8.61 (d, J = 5.2, 1H), 8.41-8.28 (m, 2H), 7.87-7.70 (m, 3H), 3.81 (s, 1H), 3.71 (s, 1H), 3.29 (t, J = 10.5, 3H), 2.97 (d, J = 7.3, 1H), 2.44 (s, 2H), 2.33 (t, J = 11.9, 2H), 2.21 (dt, J = 24.1, 11.9, 1H), 2.07 (d, J = 14.3, 1H), 1.88 (d, J = 10.3, 2H), 1.65 (dd, J = 16.4, 9.9, 1H), 1.60-1.44 (m, 5H), 1.19 (s, 1H), 0.81 (d, J = 13.1, 1H). |
| 76 | [(2-methylpyrimidin-5-yl)methyl]({2-[(9R)-9-(pyridin-2-yl)-6-oxaspiro[4.5]decan-9-yl]ethyl})amine | 367.1 | δ 8.57 (s, 2H), 7.83-7.66 (m, 1H), 7.33 (s, 4H), 7.21 (dt, J = 10.8, 2.9, 1H), 3.93 (s, 1H), 3.69 (s, 2H), 2.65 (s, 1H), 2.40-2.20 (m, 3H), 2.09 (s, 2H), 1.87 (s, 2H), 1.76-1.50 (m, 3H), 1.42 (ddd, J = 33.3, 13.0, 3.9, 2H), 1.22 (td, J = 7.3, 1.9, 1H), 1.02 (s, 1H), 0.71-0.54 (m, 1H). |
| 77 | {2-[2,2-dimethyl-4-(4-methylphenyl)oxan-4-yl]ethyl}[(2-methoxyphenyl)methyl]amine | 368.3 | δ 7.16 (m, 6H), 6.85 (dd, J = 18.0, 7.8, 2H), 3.80 (s, 3H), 3.61 (d, J = 1.9, 2H), 3.51 (s, 2H), 2.45 (d, J = 5.2, 1H), 2.35 (s, 4H), 2.15 (m, 2H), 1.81 (m, 1H), 1.66 (s, 4H), 1.20 (s, 3H), 0.69 (s, 3H). |
| 78 | {2-[2,2-dimethyl-4-(4-methylphenyl)oxan-4-yl]ethyl}[(3-methoxyphenyl)methyl]amine | 368.3 | δ 9.28 (s, 1H), 8.80 (s, 1H), 7.10 (m, 1H), 7.01 (q, J = 8.4, 4H), 6.74 (dd, J = 8.2, 2.0, 1H), 6.65 (dd, J = 15.6, 4.8, 2H), 3.66 (m, 7H), 2.64 (s, 4H), 2.24 (s, 3H), 2.09 (m, 3H), 1.82 (m, 1H), 1.64 (m, 1H), 1.48 (ddd, J = 13.4, 13.4, 9.8, 8.8, 2H), 1.10 (s, 3H), 0.57 (s, 3H). |
| 79 | benzyl({2-[9-(4-fluorophenyl)-6-oxaspiro[4.5]decan-9-yl]ethyl})amine | 368.3 | δ 8.82 (d, J = 134.2, 2H), 7.31 (m, 3H), 7.16 (m, 4H), 7.00 (dd, J = 10.7, 6.5, 2H), 3.72 (m, 4H), 2.70 (s, 1H), 2.28 (s, 1H), 1.92 (m, 6H), 1.62 (m, 2H), 1.46 (m, 4H), 1.23 (m, 1H), 0.77 (dt, J = 13.6, 8.8, 1H). |
| 80 | benzyl({2-[(9S)-9-(4-fluorophenyl)-6-oxaspiro[4.5]decan-9-yl]ethyl})amine | 368.3 | δ 9.09 (s, 1H), 8.74 (s, 1H), 7.31 (m, 3H), 7.16 (m, 4H), 7.00 (t, J = 8.6, 2H), 3.73 (m, 4H), 2.67 (s, 1H), 2.26 (s, 1H), 2.02 (s, 1H), 1.94 (td, J = 12.6, 4.7, 1H), 1.85 (d, J = 13.9, 3H), 1.62 (s, 3H), 1.46 (dd, J = 7.8, 4.0, 4H), 1.24 (d, J = 12.7, 1H), 0.77 (dt, J = 13.6, 8.7, 1H) |
| 81 | benzyl({2-[(9R)-9-(4-fluorophenyl)-6-oxaspiro[4.5]decan-9-yl]ethyl})amine | 368.3 | δ 7.24-7.17 (m, 2H), 7.16-7.09 (m, 3H), 7.01 (d, J = 7.8, 2H), 6.89 (d, J = 8.0, 2H), 3.68 (ddd, J = 11.8, 5.0, 1.3, 1H), 3.62-3.49 (m, 3H), 2.32 (t, J = 7.3, 2H), 2.25 (s, 3H), 2.22-2.13 (m, 1H), 1.93 (dtd, J = 15.7, 7.7, 3.8, 1H), 1.81-1.66 (m, 2H), 1.65-1.56 (m, 1H), 1.37 (d, J = 20.2, 1H), 1.20-1.05 (m, 2H), 1.01-1.02 (m, 2H), 0.86 (t, J = 12.7, 1H). |

TABLE 1-continued

Compounds with chemical name and characterization data

| Compound. | Name | MS (m/z) [M + H]+ | 1H NMR |
|---|---|---|---|
| 82 | 2-[(9R)-9-(2-{4H,5H,6H-thieno[2,3-c]pyrrol-5-yl}ethyl)-6-oxaspiro[4.5]decan-9-yl]pyridine | 369 | δ 8.59 (ddd, J = 4.8, 1.9, 0.9, 1H), 7.64 (m, 1H), 7.32 (t, J = 5.9, 1H), 7.15 (d, J = 4.9, 1H), 7.12 (ddd, J = 7.5, 4.8, 1.0, 1H), 6.74 (d, J = 4.9, 1H), 3.80 (m, 4H), 3.68 (m, 2H), 2.63 (td, J = 11.6, 5.1, 1H), 2.49 (dd, J = 13.8, 2.2, 1H), 2.37 (dd, J = 13.7, 2.0, 1H), 2.16 (td, J = 11.6, 4.4, 1H), 2.05 (m, 1H), 1.79 (m, 3H), 1.62 (d, J = 7.8, 2H), 1.50 (m, 3H), 1.40 (m, 1H), 1.14 (ddd, J = 9.7, 7.6, 3.2, 1H), 0.72 (dt, J = 13.4, 8.9, 1H). |
| 83 | [(4,5-dimethylfuran-2-yl)methyl]({2-[(9R)-9-(pyridin-2-yl)-6-oxaspiro[4.5]decan-9-yl]ethyl})amine | 369.1 | δ 10.28 (brs, 1H), 9.39 (brs, 1H), 8.70 (d, J = 4.6, 1H), 8.12 (t, J = 7.5, 1H), 7.65 (d, J = 8.1, 1H), 7.58 (m, 1H), 6.14 (s, 1H), 3.91 (q, J = 14.4, 2H), 3.75 (m, 2H), 2.95 (dd, J = 10.9, 5.9, 1H), 2.51 (t, J = 9.7, 1H), 2.33 (m, 3H), 2.10 (s, 3H), 1.99 (d, J = 14.1, 1H), 1.82 (m, 5H), 1.68 (m, 1H), 1.48 (m, 4H), 1.15 (m, 1H), 0.74 (dt, J = 13.2, 8.9, 1H). |
| 84 | {2-[(9R)-9-(4-fluorophenyl)-6-oxaspiro[4.5]decan-9-yl]ethyl}(pyridin-4-ylmethyl)amine | 369.2 | δ 8.53 (s, 2H), 7.78 (s, 3H), 7.29-7.05 (m, 6H), 6.96 (t, J = 8.4, 3H), 4.07 (s, 2H), 3.66 (d, J = 12.5, 2H), 2.83 (s, 1H), 2.37 (s, 1H), 2.11 (d, J = 13.7, 1H), 2.01 (d, J = 13.3, 2H), 1.83 (d, J = 14.0, 2H), 1.49 (t, J = 61.9, 9H), 1.17 (s, 1H), 0.70 (dt, J = 17.4, 8.9, 1H). |
| 85 | 2-[({2-[4-(4-methoxyphenyl)-2,2-dimethyloxan-4-yl]ethyl}amino)methyl]phenol | 370.3 | δ 8.05 (d, J = 152.9, 2H), 7.08 (m, 1H), 7.01 (d, J = 8.9, 2H), 6.82 (m, 2H), 6.76 (d, J = 8.8, 2H), 6.69 (t, J = 7.3, 1H), 4.00 (s, 2H), 3.77 (s, 2H), 3.70 (s, 3H), 3.65 (dd, J = 6.9, 2.6, 2H), 2.61 (s, 1H), 2.23 (s, 1H), 2.04 (dd, J = 23.7, 13.9, 2H), 1.93 (s, 1H), 1.81 (td, J = 12.5, 4.9, 1H), 1.60 (td, J = 12.7, 4.8, 1H), 1.48 (d, J = 13.9, 2H), 1.08 (s, 3H), 0.55 (s, 3H). |
| 86 | benzyl({2-[2,2-diethyl-4-(4-fluorophenyl)oxan-4-yl]ethyl})amine | 370.3 | δ 7.26-7.14 (m, 3H), 7.13-7.02 (m, 4H), 6.91 (t, J = 8.6, 2H), 3.69-3.47 (m, 4H), 2.51 (td, J = 12.2, 4.7, 1H), 2.14-1.94 (m, 3H), 1.83 (td, J = 12.7, 4.3, 1H), 1.64 (td, J = 12.6, 4.7, 1H), 1.56-1.35 (m, 3H), 1.27 (tt, J = 27.2, 13.7, 1H), 0.95 (dq, J = 14.7, 7.4, 1H), 0.84-0.58 (m, 4H), 0.43 (t, J = 7.4, 3H). |
| 87 | benzyl({2-[4-(4-fluorophenyl)-2,2,6,6-tetramethyloxan-4-yl]ethyl})amine | 370.3 | δ 9.15 (s, 2H), 7.32 (m, 3H), 7.25 (m, 2H), 7.18 (dd, J = 7.3, 2.1, 2H), 6.99 (dd, J = 12.0, 5.3, 2H), 3.72 (s, 2H), 2.34 (dd, J = 53.2, 23.4, 2H), 1.91 (dd, J = 10.4, 6.5, 2H), 1.68 (d, J = 14.3, 2H), 1.27 (s, 6H), 1.02 (s, 6H). |
| 88 | [(2,3-dimethoxyphenyl)methyl]({2-[4-(4-methylphenyl)oxan-4-yl]ethyl})amine | 370.3 | δ 7.13 (s, 4H), 6.95 (m, 1H), 6.80 (dd, J = 8.2, 1.4, 1H), 6.72 (dd, J = 7.6, 1.4, 1H), 3.83 (s, 3H), 3.75 (m, 5H), 3.63 (s, 2H), 3.54 (ddd, J = 11.6, 9.1, 2.7, 2H), 2.31 (m, 5H), 2.10 (m, 3H), 1.82 (ddd, J = 13.3, 8.3, 3.7, 4H) |
| 89 | [(3-methylthiophen-2-yl)methyl]({2-[(9R)-9-(pyridin-2-yl)-6-oxaspiro[4.5]decan-9-yl]ethyl})amine | 371.1 | δ 9.68 (s, 1H), 8.75 (s, 1H), 8.16 (m, 1H), 7.74 (d, J = 27.0, 2H), 7.27 (d, J = 1.5, 1H), 6.85 (d, J = 5.1, 1H), 4.10 (m, 2H), 3.84 (d, J = 12.7, 1H), 3.66 (d, J = 10.3, 1H), 2.96 (m, 1H), 2.69 (m, 1H), 2.54 (m, 3H), 2.35 (m, 4H), 2.11 (d, J = 14.0, 1H), 1.87 (m, 10.3, 3H), 1.57 (m, 5H), 1.06 (m, 1H) 0.78 (dt, J = 12.8, 1H). |
| 90 | {2-[(9R)-9-(pyridin-2-yl)-6-oxaspiro[4.5]decan-9-yl]ethyl}[2-(thiophen-2-yl)ethyl]amine | 371.1 | δ 8.80-8.66 (m, 1H), 8.45-8.25 (m, 1H), 7.84-7.63 (m, 2H), 7.16 (dd, J = 5.1, 1.1, 1H), 6.91 (dd, J = 5.1, 3.5, 1H), 6.83 (dd, J = 3.4, 0.9, 1H), 3.83 (tt, J = 13.7, 6.9, 1H), 3.69 (dd, J = 20.1, 10.1, 1H), 3.16 (s, 4H), 3.02 (s, 1H), 2.61-2.22 (m, 5H), 2.20-1.98 (m, 1H), 1.98-1.77 (m, 2H), 1.76-1.63 (m, 1H), 1.50 (tdd, J = 12.3, 10.9, 5.3, 4H), 1.17 (dd, J = 7.9, 5.2, 1H), 0.76 (dt, J = 13.0, 8.8, 1H). |
| 91 | [(2-methylthiophen-3-yl)methyl]({2-[(9R)-9-(pyridin-2-yl)-6-oxaspiro[4.5]decan-9-yl]ethyl})amine | 371.1 | δ 8.68 (d, J = 5.4, 1H), 8.26 (s, 1H), 7.82-7.63 (m, 2H), 7.05 (t, J = 10.0, 1H), 6.94 (d, J = 5.3, 1H), 3.96 (s, 2H), 3.82 (s, 1H), 3.72 (s, 1H), 3.03 (s, 1H), 2.50 (d, J = 15.9, 2H), 2.39 (s, 3H), 2.30 (dd, J = 12.6, 7.5, 3H), 2.02 (d, J = 14.2, 1H), 1.92-1.79 (m, 2H), 1.70 (dt, J = 14.5, 10.2, 1H), 1.64-1.38 (m, 4H), 1.25-1.13 (m, 1H), 0.79 (d, J = 13.2, 1H). |
| 92 | [(5-methylthiophen-2-yl)methyl]({2-[(9R)-9-(pyridin-2-yl)-6-oxaspiro[4.5]decan-9-yl]ethyl})amine | 371.2 | δ 8.71 (d, J = 4.7, 1H), 8.14 (t, J = 7.6, 1H), 7.78-7.48 (m, 2H), 6.86 (d, J = 3.4, 1H), 6.78-6.53 (m, 1H), 4.09 (s, 2H), 3.76 (ddd, J = 40.6, 14.3, 7.2, 2H), 3.17-2.85 (m, 1H), 2.64-2.23 (m, 4H), 2.16 (dd, J = 16.4, 8.6, 1H), 1.99 (d, J = 14.2, 1H), 1.89-1.75 (m, 2H), 1.75-1.61 (m, 1H), 1.61-1.35 (m, 4H), 1.24-1.05 (m, 1H), 0.74 (dt, J = 13.2, 8.9, 1H). |
| 93 | {2-[9-(6-methylpyridin-2-yl)-6-oxaspiro[4.5]decan-9- | 371.2 | δ 9.47 (d, J = 86.3, 2H), 8.17 (t, J = 8.0, 1H), 7.58 (d, J = 8.0, 1H), 7.52 (d, J = 7.8, 1H), 7.39 (d, J = 1.9, 1H), 7.31-7.29 (m, 1H), 7.08 (dd, J = 5.0, 1.0, 1H), |

TABLE 1-continued

Compounds with chemical name and characterization data

| Compound. | Name | MS (m/z) [M + H]+ | 1H NMR |
|---|---|---|---|
| | yl]ethyl}(thiophen-3-ylmethyl)amine | | 6.43 (s, 3H), 4.11-3.95 (m, 2H), 3.91-3.67 (m, 2H), 2.97 (s, 1H), 2.81 (s, 3H), 2.61 (t, J = 12.6, 1H), 2.47 (t, J = 10.1, 1H), 2.43-2.15 (m, 3H), 2.15-1.99 (m, 1H), 1.87 (dd, J = 12.2, 6.8, 2H), 1.70 (dt, J = 12.7, 6.2, 1H), 1.63-1.40 (m, 4H), 1.28-1.20 (m, 1H), 0.84 (dt, J = 13.3, 9.0, 1H). |
| 94 | {2-[4-(4-fluorophenyl)-1-oxaspiro[5.5]undecan-4-yl]ethyl}(1H-pyrrol-2-ylmethyl)amine | 371.3 | δ 7.09 (dd, J = 8.9, 5.1, 2H), 6.93 (dd, J = 11.7, 5.5, 2H), 6.71 (d, J = 2.3, 1H), 5.98 (s, 2H), 3.83 (s, 2H), 3.61 (m, 2H), 2.56 (m, 1H), 2.08 (t, J = 12.1, 3H), 1.68 (s, 3H), 1.48 (d, J = 14.6, 2H), 1.40 (d, J = 14.1, 2H), 1.29 (m, 3H), 1.05 (m, 3H), 0.58 (s, 1H). |
| 95 | {2-[9-(6-methylpyridin-2-yl)-6-oxaspiro[4.5]decan-9-yl]ethyl}(thiophen-2-ylmethyl)amine | 371.3 | δ 9.48 (s, 1H), 8.08 (t, J = 7.9, 1H), 7.48 (d, J = 8.0, 1H), 7.42 (d, J = 7.8, 1H), 7.22 (dd, J = 5.1, 0.8, 1H), 7.04 (d, J = 2.9, 1H), 6.88 (dd, J = 5.1, 3.5, 1H), 5.95 (s, 3H), 4.13 (s, 2H), 3.66 (ddd, J = 18.7, 12.8, 9.1, 2H), 2.91 (s, 1H), 2.71 (s, 3H), 2.60-2.40 (m, 2H), 2.18 (dd, J = 48.6, 14.1, 3H), 1.96 (d, J = 14.2, 1H), 1.88-1.68 (m, 2H), 1.71-1.54 (m, 1H), 1.56-1.31 (m, 4H), 1.20-1.05 (m, 1H), 0.83-0.63 (m, 1H). |
| 96 | [(4-methylthiophen-2-yl)methyl]({2-[(9R)-9-(pyridin-2-yl)-6-oxaspiro[4.5]decan-9-yl]ethyl})amine | 371.3 | δ 9.63 (s, 1H), 8.61 (d, J = 4.1, 1H), 8.08 (t, J = 7.8, 1H), 7.61 (d, J = 8.1, 1H), 7.53 (dd, J = 7.0, 5.6, 1H), 6.91 (s, 1H), 6.88 (s, 1H), 4.14 (m, 2H), 3.75 (dt, J = 19.0, 11.1, 2H), 3.02 (m, 1H), 2.61 (m, 1H), 2.40 (brs, 1H), 2.27 (m, 4H), 2.19 (d, J = 0.8, 3H), 1.95 (d, J = 14.0, 1H), 1.79 (m, 2H), 1.66 (dd, J = 12.1, 5.9, 1H), 1.47 (m, 4H), 1.16 (m, 1H), 0.74 (dt, J = 13.1, 8.9, 1H). |
| 97 | {2-[(9R)-9-(4-fluorophenyl)-6-oxaspiro[4.5]decan-9-yl]ethyl}[(5-methylfuran-2-yl)methyl]amine | 372 | δ 7.12 (dd, J = 8.9, 5.2, 2H), 6.94 (t, J = 8.6, 2H), 6.10 (d, J = 3.1, 1H), 5.79 (dd, J = 3.1, 0.9, 1H), 3.77 (m, 2H), 3.72-3.49 (m, 2H), 2.63 (s, 1H), 2.19 (s, 1H), 2.13-2.08 (m, 3H), 2.06 (s, 1H), 1.98 (dd, J = 13.8, 1.3, 1H), 1.89 (td, J = 12.7, 4.5, 1H), 1.80 (dd, J = 13.1, 7.1, 2H), 1.71 (dd, J = 13.2, 6.0, 1H), 1.59 (ddd, J = 14.2, 9.4, 5.4, 2H), 1.50-1.28 (m, 4H), 1.25-1.09 (m, 1H), 0.71 (dt, J = 13.5, 8.8, 1H). |
| 98 | [(4-methyl-1,3-thiazol-2-yl)methyl]({2-[(9R)-9-(pyridin-2-yl)-6-oxaspiro[4.5]decan-9-yl]ethyl})amine | 372.1 | δ 8.68 (dd, J = 5.3, 1.2, 1H), 8.25 (s, 1H), 8.09 (td, J = 8.0, 1.7, 1H), 7.63 (d, J = 8.1, 1H), 7.54 (dd, J = 7.1, 5.7, 1H), 6.94 (d, J = 0.9, 1H), 4.37 (m, 2H), 3.76 (m, 2H), 3.14 (td, J = 11.2, 5.9, 1H), 2.73 (td, J = 11.4, 4.7, 1H), 2.40 (m, 4H), 2.27 (m, 3H), 2.00 (m, 1H), 1.83 (ddd, J = 13.8, 9.3, 4.4, 2H), 1.66 (m, 1H), 1.49 (m, 4H), 1.19 (m, 1H), 0.78 (dt, J = 13.3, 9.0, 1H). |
| 99 | [(2-methyl-1,3-thiazol-5-yl)methyl]({2-[(9R)-9-(pyridin-2-yl)-6-oxaspiro[4.5]decan-9-yl]ethyl})amine | 372.1 | δ 8.71 (d, J = 4.3, 1H), 8.33 (td, J = 8.0, 1.5, 1H), 7.77 (m, 2H), 7.69 (s, 1H), 5.53 (s, 1H), 4.28 (m, 2H), 3.78 (m, 2H), 3.04 (td, J = 11.4, 5.4, 1H), 2.73 (s, 3H), 2.56 (m, 2H), 2.30 (t, J = 15.3, 3H), 2.04 (m, 1H), 1.88 (ddd, J = 19.6, 11.5, 7.0, 2H), 1.68 (m, 1H), 1.49 (m, 4H), 1.18 (m, 1H), 0.77 (dt, J = 13.1, 9.0, 1H). |
| 100 | [(4-methyl-1,3-thiazol-5-yl)methyl]({2-[(9R)-9-(pyridin-2-yl)-6-oxaspiro[4.5]decan-9-yl]ethyl})amine | 372.1 | δ 13.17 (s, 1H), 9.91 (s, 1H), 8.88 (s, 1H), 8.69 (d, J = 4.9, 1H), 8.31 (t, J = 7.4, 1H), 7.75 (t, J = 7.9, 2H), 4.25 (m, 2H), 3.77 (m, 2H), 3.04 (td, J = 11.5, 5.0, 1H), 2.57 (dt, J = 10.7, 7.9, 1H), 2.34 (m, 7H), 2.02 (m, 1H), 1.86 (ddd, J = 26.5, 13.3, 8.2, 2H), 1.66 (dt, J = 13.6, 8.4, 1H), 1.50 (m, 4H), 1.15 (dd, J = 13.2, 6.6, 1H), 0.73 (dt, J = 13.0, 8.9, 1H). |
| 101 | [(2-chlorophenyl)methyl]({2-[2,2-dimethyl-4-(4-methylphenyl)oxan-4-yl]ethyl})amine | 372.2 | δ 7.21 (m, 1H), 7.07 (m, 5H), 7.02 (d, J = 8.2, 2H), 3.69 (m, 2H), 3.58 (d, J = 1.0, 2H), 2.37 (td, J = 10.9, 5.3, 1H), 2.22 (m, 4H), 2.07 (ddd, J = 14.2, 9.9, 3.8, 2H), 1.74 (ddd, J = 13.2, 10.5, 5.1, 1H), 1.55 (m, 3H), 1.43 (s, 2H), 1.10 (s, 3H), 0.58 (s, 3H). |
| 102 | [(3-chlorophenyl)methyl]({2-[2,2-dimethyl-4-(4-methylphenyl)oxan-4-yl]ethyl})amine | 372.2 | δ 9.27 (d, J = 168.2, 2H), 7.19 (m, 2H), 7.11 (m, 2H), 7.04 (d, J = 8.2, 2H), 6.99 (d, J = 8.2, 3H), 3.67 (m, 2H), 3.58 (s, 2H), 2.57 (s, 1H), 2.33 (d, J = 12.1, 2H), 2.23 (s, 3H), 2.07 (m, 3H), 1.80 (td, J = 12.5, 4.6, 1H), 1.62 (m, 1H), 1.47 (m, 2H), 1.09 (s, 3H), 0.56 (s, 3H). |
| 103 | [(4-chlorophenyl)methyl]({2-[2,2-dimethyl-4-(4-methylphenyl)oxan-4-yl]ethyl})amine | 372.2 | δ 8.80 (d, J = 192.6, 2H), 7.19 (t, J = 4.2, 3H), 7.02 (m, 6H), 4.06 (s, 3H), 3.68 (dd, J = 12.4, 10.2, 4H), 2.62 (s, 1H), 2.24 (d, J = 13.6, 3H), 2.11 (ddd, J = 21.2, 15.6, 7.6, 3H), 1.80 (dt, J = 12.3, 6.3, 1H), 1.64 (m, 1H), 1.49 (m, 2H), 1.11 (s, 3H), 0.57 (s, 3H). |
| 104 | 6-{9-{2-[(thiophen-2-ylmethyl)amino]ethyl}-6-oxaspiro[4.5]decan-9- | 373 | 1H NMR (400 MHz, CD3CN) δ 8.18 (t, J = 1.7, 1H), 8.11 (brs, 1H), 7.49 (dd, J = 5.1, 1.1, 1H), 7.34 (d, J = 1.7, 2H), 7.18 (d, J = 2.7, 1H), 7.06 (dd, J = 5.1, 3.6, 1H), 4.24 (s, 2H), 3.67 (m, 2H), 2.95 (m, 1H), |

TABLE 1-continued

Compounds with chemical name and characterization data

| Compound. | Name | MS (m/z) [M + H]+ | 1H NMR |
|---|---|---|---|
| | yl]pyridin-3-ol | | 2.73 (brs, 1H), 2.51 (d, J = 4.3, 1H), 2.29 (t, J = 11.0, 2H), 2.08 (m, 2H), 1.84 (m, 2H), 1.72 (t, J = 8.5, 1H), 1.62 (dd, J = 14.4, 6.5, 2H), 1.48 (dt, J = 23.5, 7.0, 4H), 1.15 (m, 1H), 0.73 (dt, J = 12.7, 8.7, 1H). |
| 105 | 6-[9-{2-[(thiophen-2-ylmethyl)amino]ethyl}-6-oxaspiro[4.5]decan-9-yl]pyridin-2-ol | 373 | δ 7.52 (d, J = 16.2, 1H), 7.29 (d, J = 1.1, 1H), 7.12 (d, J = 2.7, 1H), 6.97 (dd, J = 5.1, 3.6, 1H), 6.51 (d, J = 8.9, 1H), 6.27 (d, J = 7.2, 1H), 4.16 (s, 2H), 3.71 (s, 2H), 2.85 (dd, J = 13.9, 7.6, 1H), 2.68 (dd, J = 18.4, 9.5, 1H), 2.31 (m, 2H), 1.94 (d, J = 13.6, 2H), 1.59 (m, 10H), 0.90 (m, 1H). |
| 106 | [(5-methylthiophen-2-yl)methyl]({2-[2,2,6,6-tetramethyl-4-(pyridin-2-yl)oxan-4-yl]ethyl})amine | 373.2 | δ 8.73 (dd, J = 5.5, 1.4, 2H), 8.24 (td, J = 8.0, 1.6, 1H), 7.87 (d, J = 8.2, 1H), 7.69 (dd, J = 7.0, 6.1, 1H), 6.83 (dd, J = 20.2, 3.4, 1H), 6.67-6.48 (m, 1H), 4.09 (s, 2H), 2.83-2.69 (m, 2H), 2.52 (dd, J = 19.1, 11.7, 3H), 2.41 (d, J = 0.5, 3H), 2.37-2.21 (m, 2H), 1.89 (d, J = 14.8, 2H), 1.31 (s, 6H), 0.98 (s, 6H). |
| 107 | 2-(9-{2-[(thiophen-2-ylmethyl)amino]ethyl}-6-oxaspiro[4.5]decan-9-yl)pyridin-4-ol | 373.2 | δ 9.46 (m, 2H), 7.95 (d, J = 6.6, 1H), 7.25 (d, J = 5.1, 1H), 7.10 (s, 1H), 7.03 (t, J = 5.8, 2H), 6.90 (dd, J = 5.1, 3.6, 1H), 4.10 (s, 2H), 3.62 (m, 2H), 2.84 (s, 1H), 2.49 (s, 1H), 2.28 (s, 1H), 2.06 (dd, J = 44.3, 14.1, 3H), 1.66 (m, 4H), 1.35 (ddd, J = 72.6, 39.8, 18.9, 6H), 0.68 (s, 1H). |
| 108 | [(4-methylthiophen-2-yl)methyl]({2-[2,2,6,6-tetramethyl-4-(pyridin-2-yl)oxan-4-yl]ethy})amine | 373.3 | δ 8.75 (d, J = 4.6, 1H), 8.35 (td, J = 8.1, 1.3, 1H), 7.96 (d, J = 8.2, 1H), 7.86-7.74 (m, 1H), 6.95-6.80 (m, 2H), 4.14 (s, 2H), 2.87-2.68 (m, 2H), 2.52 (d, J = 14.8, 2H), 2.45-2.29 (m, 2H), 2.18 (d, J = 0.7, 3H), 1.93 (d, J = 14.9, 2H), 1.31 (s, 6H), 0.98 (s, 6H). |
| 109 | dibutyl({2-[(9R)-9-(pyridin-2-yl)-6-oxaspiro[4.5]decan-9-yl]ethyl})amine | 373.4 | δ 8.78 (d, J = 4.6, 1H), 8.05 (t, J = 7.5, 1H), 7.62 (d, J = 8.0, 1H), 7.50 (m, 1H), 3.80 (m, 2H), 3.06 (t, J = 10.5, 1H), 2.90 (s, 4H), 2.42 (m, 4H), 2.02 (m, 2H), 1.83 (m, 2H), 1.68 (tt, J = 13.3, 6.8, 1H), 1.43 (m, 12H), 1.15 (dd, J = 13.2, 5.7, 1H), 0.91 (dt, J = 11.8, 7.1, 6H), 0.72 (dt, J = 13.3, 9.0, 1H). |
| 110 | {2-[(9R)-9-(4-fluorophenyl)-6-oxaspiro[4.5]decan-9-yl]ethyl}(thiophen-3-ylmethyl)amine | 374.2 | δ 7.33-7.23 (m, 7H), 7.19 (dd, J = 8.9, 5.2, 2H), 7.04 (t, J = 8.6, 2H), 6.98 (dd, J = 5.0, 1.3, 1H), 3.84 (s, 2H), 3.79-3.69 (m, 2H), 2.67 (s, 1H), 2.19-1.74 (m, 22H), 1.66 (ddd, J = 14.0, 9.3, 4.6, 3H), 1.48 (ddd, J = 23.7, 15.2, 8.6, 4H), 1.28 (s, 1H), 0.99-0.64 (m, 1H). |
| 111 | {2-[(9R)-9-(4-fluorophenyl)-6-oxaspiro[4.5]decan-9-yl]ethyl}(thiophen-2-ylmethyl)amine | 374.2 | δ 9.04 (d, J = 106.1, 2H), 7.21 (dd, J = 5.1, 1.1, 1H), 7.10 (m, 2H), 6.92 (m, 3H), 6.86 (dd, J = 5.1, 3.6, 1H), 3.93 (s, 2H), 3.64 (m, 3H), 2.63 (d, J = 7.9, 1H), 2.22 (t, J = 9.7, 1H), 2.05 (d, J = 14.1, 1H), 1.97 (d, J = 13.9, 1H), 1.88 (td, J = 12.7, 4.6, 1H), 1.75 (m, 3H), 1.57 (m, 2H), 1.38 (m, 3H), 1.17 (dd, J = 14.1, 6.1, 1H), 0.70 (dt, J = 13.6, 8.8, 1H). |
| 112 | (cyclopentylmethyl)({2-[4-(4-fluorophenyl)-1-oxaspiro[5.5]undecan-4-yl]ethyl})amine | 374.3 | δ 7.15 (dd, J = 8.9, 5.2, 2H), 6.96 (s, 2H), 3.64 (d, J = 13.0, 3H), 2.59 (s, 3H), 2.11 (m, 3H), 1.94 (dd, J = 10.4, 5.7, 2H), 1.68 (dd, J = 12.4, 4.8, 2H), 1.53 (m, 8H), 1.31 (d, J = 19.9, 4H), 1.03 (s, 7H), 0.65 (m, 1H). |
| 113 | {2-[2,2-diethyl-4-(4-fluorophenyl)oxan-4-yl]ethyl}(thiophen-3-ylmethyl)amine | 376.2 | δ 7.20-7.13 (m, 8H), 7.09 (dd, J = 8.9, 5.2, 2H), 6.93 (t, J = 8.6, 2H), 6.87 (dd, J = 4.9, 1.3, 1H), 3.70 (s, 2H), 3.61 (d, J = 2.3, 2H), 2.56 (s, 1H), 2.02 (d, J = 14.1, 3H), 1.75 (s, 11H), 1.44 (d, J = 14.2, 5H), 0.95 (dd, J = 14.5, 7.4, 1H), 0.73 (t, J = 7.5, 5H), 0.43 (t, J = 7.4, 4H). |
| 114 | {2-[2,2-diethyl-4-(4-fluorophenyl)oxan-4-yl]ethyl}(thiophen-2-ylmethyl)amine | 376.2 | δ 7.25-7.15 (m, 3H), 7.15-7.02 (m, 4H), 6.91 (t, J = 8.6, 2H), 3.82-3.36 (m, 4H), 2.51 (td, J = 12.2, 4.7, 1H), 2.12-1.94 (m, 3H), 1.83 (td, J = 12.7, 4.3, 1H), 1.64 (td, J = 12.6, 4.7, 1H), 1.55-1.35 (m, 3H), 1.28 (dq, J = 14.7, 7.4, 1H), 0.95 (dq, J = 14.7, 7.4, 1H), 0.80-0.64 (m, 4H), 0.43 (t, J = 7.4, 3H). |
| 115 | {2-[4-(4-fluorophenyl)-2,2,6,6-tetramethyloxan-4-yl]ethyl}(thiophen-3-ylmethyl)amine | 376.2 | δ 7.28 (m, 4H), 7.00 (ddd, J = 6.7, 6.3, 3.2, 3H), 3.82 (s, 3H), 2.46 (s, 1H), 2.28 (d, J = 14.3, 1H), 1.92 (m, 1H), 1.57 (m, 2H), 1.69 (d, J = 14.4, 2H), 1.28 (s, 6H), 1.02 (s, 6H). |
| 116 | {2-[4-(4-fluorophenyl)-2,2,6,6-tetramethyloxan-4-yl]ethyl}(thiophen-2-ylmethyl)amine | 376.2 | δ 7.29 (m, 3H), 7.01 (s, 4H), 3.98 (s, 2H), 2.50 (m, 2H), 2.30 (d, J = 14.2, 2H), 1.94 (m, 2H), 1.69 (d, J = 14.4, 2H), 1.28 (s, 6H), 1.03 (s, 6H). |
| 117 | benzyl({2-[9-(2-methoxyphenyl)-6-oxaspiro[4.5]decan-9-yl]ethyl})amine | 380.3 | δ 8.86 (d, J = 149.6, 2H), 7.25-7.19 (m, 3H), 7.18-7.12 (m, 1H), 7.09 (d, J = 7.4, 2.0, 2H), 6.96 (dd, J = 7.8, 1.5, 1H), 6.85-6.75 (m, 2H), 3.74-3.63 (m, 7H), 2.55 (dd, J = 15.6, 7.9, 3H), 2.11 (d, J = 14.8, |

TABLE 1-continued

Compounds with chemical name and characterization data

| Compound. | Name | MS (m/z) [M + H]+ | 1H NMR |
|---|---|---|---|
| | | | 2H), 1.75-1.46 (m, 5H), 1.46-1.32 (m, 3H), 1.32-1.22 (m, 1H), 1.17 (d, J = 4.1, 1H), 0.74-0.60 (m, 1H). |
| 118 | benzyl({2-[9-(6-methoxypyridin-2-yl)-6-oxaspiro[4.5]decan-9-yl]ethyl})amine | 381.3 | δ 9.43 (s, 1H), 9.20 (s, 1H), 7.52 (m, 2H), 7.30 (dd, J = 5.1, 1.8, 3H), 7.21 (m, 2H), 6.78 (d, J = 7.3, 1H), 6.57 (d, J = 8.1, 1H), 3.83 (s, 3H), 3.77 (s, 2H), 3.71 (dd, J = 7.8, 2.7, 2H), 2.77 (s, 1H), 2.32 (d, J = 13.6, 2H), 2.25 (d, J = 11.5, 1H), 2.06 (td, J = 11.9, 4.8, 1H), 1.76 (m, 3H), 1.59 (m, 3H), 1.47 (m, 3H), 1.38 (m, 1H), 1.15 (m, 1H), 0.70 (m, 1H). |
| 119 | {2-[2,2-dimethyl-4-(4-methylphenyl)oxan-4-yl]ethyl}[(2-methoxyphenyl)methyl]methylamine | 382.3 | δ 10.17 (m, 3H), 7.41 (tdd, J = 8.3, 4.8, 1.6, 1H), 7.13 (m, 5H), 6.93 (m, 2H), 4.20 (dd, J = 14.9, 5.8, 1H), 3.98 (ddd, J = 32.2, 12.9, 4.8, 1H), 3.80 (dd, J = 7.4, 2.6, 5H), 2.94 (d, J = 114.3, 1H), 2.35 (m, 9H), 2.05 (ddd, J = 17.1, 12.7, 6.5, 1H), 1.89 (dt, J = 12.8, 6.2, 1H), 1.67 (ddd, J = 22.2, 14.2, 5.0, 2H), 1.23 (d, J = 10.7, 3H), 0.69 (t, J = 9.5, 3H). |
| 120 | {2-[9-(4-fluorophenyl)-6-oxaspiro[4.5]decan-9-yl]ethyl}[(3-methylphenyl)methyl]amine | 382.3 | δ 8.90 (d, J = 138.8, 2H), 7.15 (tt, J = 13.7, 7.6, 4H), 6.97 (m, 4H), 3.70 (m, 4H), 2.67 (s, 1H), 2.27 (s, 4H), 2.00 (m, 3H), 1.82 (m, 3H), 1.63 (m, 2H), 1.46 (m, 4H), 1.24 (d, J = 9.6, 1H), 0.78 (dt, J = 13.6, 8.8, 1H) |
| 121 | {2-[(9S)-9-(4-fluorophenyl)-6-oxaspiro[4.5]decan-9-yl]ethyl}[(3-methylphenyl)methyl]amine | 382.3 | δ 8.73 (d, J = 138.2, 2H), 7.16 (m, 4H), 7.00 (dd, J = 10.5, 6.7, 2H), 6.94 (m, 2H), 3.72 (m, 4H), 2.69 (m, 1H), 2.27 (s, 4H), 2.05 (m, 2H), 1.94 (td, J = 12.6, 4.7, 1H), 1.83 (m, 3H), 1.63 (ddd, J = 14.1, 9.6, 4.6, 2H), 1.47 (m, 4H), 1.23 (m, 1H), 0.78 (dt, J = 13.9, 8.9, 1H) |
| 122 | {2-[(9R)-9-(4-fluorophenyl)-6-oxaspiro[4.5]decan-9-yl]ethyl}[(3-methylphenyl)methyl]amine | 382.3 | δ 8.96 (d, J = 123.7, 2H), 7.15 (m, 4H), 6.98 (m, 4H), 3.71 (m, 4H), 2.66 (s, 1H), 2.25 (d, J = 14.0, 4H), 2.05 (m, 2H), 1.94 (td, J = 12.7, 4.6, 1H), 1.81 (m, 3H), 1.63 (ddd, J = 14.2, 7.7, 3.4, 2H), 1.47 (m, 4H), 1.23 (m, 1H), 0.77 (dt, J = 13.7, 8.9, 1H) |
| 123 | benzyl({2-[4-(4-fluorophenyl)-1-oxaspiro[5.5]undecan-4-yl]ethyl})amine | 382.3 | δ 7.23 (m, 3H), 7.10 (dd, J = 4.6, 2.6, 4H), 6.92 (s, 2H), 3.64 (s, 2H), 2.63 (m, 1H), 2.07 (t, J = 13.9, 3H), 1.74 (s, 2H), 1.48 (d, J = 8.3, 3H), 1.40 (d, J = 14.0, 2H), 1.29 (m, 3H), 1.06 (m, 4H), 0.57 (m, 1H). |
| 124 | {2-[(9R)-9-(4-fluorophenyl)-6-oxaspiro[4.5]decan-9-yl]ethyl}[(1R)-1-phenylethyl]amine | 382.3 | δ 7.47-7.32 (m, 3H), 7.31-7.22 (m, 2H), 7.11 (dd, J = 8.9, 5.2, 2H), 6.98 (t, J = 8.6, 2H), 6.28 (s, 2H), 4.03 (s, 1H), 3.79-3.58 (m, 2H), 2.51 (s, 1H), 2.19 (d, J = 14.5, 1H), 2.07-1.90 (m, 3H), 1.89-1.71 (m, 3H), 1.72-1.32 (m, 9H), 1.32-1.10 (m, 1H), 0.78 (dt, J = 13.6, 8.8, 1H). |
| 125 | {2-[(9R)-9-(4-fluorophenyl)-6-oxaspiro[4.5]decan-9-yl]ethyl}[(1S)-1-phenylethyl]amine | 382.3 | δ 7.47-7.32 (m, 3H), 7.31-7.22 (m, 2H), 7.11 (dd, J = 8.9, 5.2, 2H), 6.98 (t, J = 8.6, 2H), 6.28 (s, 2H), 4.03 (s, 1H), 3.79-3.58 (m, 2H), 2.51 (s, 1H), 2.19 (d, J = 14.5, 1H), 2.07-1.90 (m, 3H), 1.89-1.71 (m, 3H), 1.72-1.32 (m, 9H), 1.32-1.10 (m, 1H), 0.78 (dt, J = 13.6, 8.8, 1H). |
| 126 | {2-[2,2-dimethyl-4-(4-methylphenyl)oxan-4-yl]ethyl}[(2-nitrophenyl)methyl]amine | 383.3 | δ 7.94 (dd, J = 8.1, 1.2, 1H), 7.53 (td, J = 7.6, 1.3, 1H), 7.40 (m, 2H), 7.15 (m, 4H), 3.80 (m, 4H), 2.48 (td, J = 10.9, 5.4, 1H), 2.32 (m, 4H), 2.18 (ddd, J = 12.7, 7.8, 3.7, 2H), 1.84 (ddd, J = 13.2, 10.4, 5.1, 1H), 1.63 (m, 4H), 1.21 (s, 3H), 0.69 (s, 3H). |
| 127 | {2-[2,2-dimethyl-4-(4-methylphenyl)oxan-4-yl]ethyl}[(3-nitrophenyl)methyl]amine | 383.3 | δ 9.09 (d, J = 219.1, 2H), 8.12 (dd, J = 8.2, 1.6, 1H), 8.01 (s, 1H), 7.45 (dt, J = 15.6, 7.7, 2H), 7.03 (q, J = 8.5, 4H), 3.87 (s, 2H), 3.69 (m, 2H), 3.42 (s, 1H), 3.22 (s, 2H), 2.73 (d, J = 4.5, 1H), 2.24 (d, J = 8.2, 4H), 2.12 (m, 2H), 1.85 (m, 1H), 1.69 (dd, J = 12.1, 4.5, 1H), 1.52 (m, 2H), 1.11 (s, 3H), 0.57 (s, 3H). |
| 128 | 2-[({2-[9-(4-fluorophenyl)-6-oxaspiro[4.5]decan-9-yl]ethyl}amino)methyl]phenol | 384.2 | δ 8.36 (d, J = 129.4, 2H), 7.20 (dd, J = 11.0, 4.6, 1H), 7.14 (dd, J = 8.9, 5.1, 2H), 7.00 (t, J = 8.6, 2H), 6.92 (m, 2H), 6.79 (t, J = 7.1, 1H), 3.88 (s, 2H), 3.68 (m, 2H), 2.67 (m, 1H), 2.29 (m, 1H), 1.98 (m, 3H), 1.79 (m, 3H), 1.51 (m, 6H), 1.20 (s, 1H), 0.74 (dt, J = 13.8, 8.9, 1H) |
| 129 | {2-[4-(4-methoxyphenyl)-2,2-dimethyloxan-4-yl]ethyl}[(2-methoxyphenyl)methyl]amine | 384.3 | δ 8.47 (d, J = 196.5, 2H), 7.36 (td, J = 8.3, 1.7, 1H), 7.12 (dd, J = 9.5, 2.6, 2H), 7.08 (dd, J = 7.5, 1.6, 1H), 6.91 (td, J = 7.5, 0.8, 1H), 6.86 (d, J = 8.8, 3H), 5.77 (s, 2H), 3.91 (s, 2H), 3.82 (s, 3H), 3.79 (s, 3H), 3.77 (m, 2H), 2.76 (s, 1H), 2.33 (s, 1H), 2.16 (m, 2H), 1.96 (d, J = 4.6, 1H), 1.77 (d, J = 4.7, 1H), 1.59 (m, 2H), 1.19 (s, 3H), 0.66 (s, 3H). |
| 130 | [(5-ethylthiophen-2-yl)methyl]({2-[(9R)-9-(pyridin-2- | 385.1 | δ 8.73 (d, J = 4.6, 1H), 8.20 (t, J = 7.7, 2H), 7.80-7.55 (m, 2H), 6.88 (d, J = 3.4, 1H), 6.64 (d, J = 3.4, 1H), 4.11 (s, 2H), 3.81 (dd, J = 8.4, 4.3, 1H), 3.70 (t, J = 10.0, |

TABLE 1-continued

Compounds with chemical name and characterization data

| Compound. | Name | MS (m/z) [M + H]+ | 1H NMR |
|---|---|---|---|
| | yl)-6-oxaspiro[4.5]decan-9-yl]ethyl})amine | | 1H), 3.00 (d, J = 4.6, 1H), 2.86-2.70 (m, 2H), 2.53 (t, J = 10.1, 1H), 2.45-2.25 (m, 3H), 2.18 (t, J = 10.0, 1H), 2.00 (d, J = 14.2, 1H), 1.93-1.75 (m, 2H), 1.68 (dd, J = 9.5, 4.4, 1H), 1.62-1.38 (m, 4H), 1.26 (t, J = 7.5, 3H), 1.20-1.07 (m, 1H), 0.75 (dt, J = 12.9, 8.8, 1H). |
| 131 | [(3,5-dimethylthiophen-2-yl)methyl]({2-[(9R)-9-(pyridin-2-yl)-6-oxaspiro[4.5]decan-9-yl]ethyl})amine | 385.1 | δ 9.45 (brs, 1H), 8.70 (d, J = 5.0, 1H), 8.26 (t, J = 7.7, 1H), 7.75 (d, J = 8.1, 1H), 7.70 (m, 1H), 6.46 (d, J = 0.8, 1H), 4.07 (s, 2H), 3.76 (ddd, J = 44.9, 13.9, 7.2, 2H), 3.05 (m, 1H), 2.58 (m, 1H), 2.43 (t, J = 10.6, 1H), 2.36 (d, J = 0.7, 3H), 2.24 (dd, J = 31.9, 17.7, 3H), 2.03 (m, 4H), 1.85 (m, 2H), 1.66 (dd, J = 13.8, 8.8, 1H), 1.48 (m, 4H), 1.15 (d, J = 7.9, 1H), 0.75 (dt, J = 13.1, 8.9, 1H). |
| 132 | {2-[2,2-diethyl-4-(4-fluorophenyl)oxan-4-yl]ethyl}[(6-methylpyridin-3-yl)methyl]amine | 385.3 | δ 8.84 (s, 1H), 8.24 (d, J = 8.2, 1H), 7.53 (d, J = 8.2, 1H), 7.17 (m, 3H), 6.96 (t, J = 8.6, 2H), 4.08 (d, J = 13.9, 2H), 3.63 (d, J = 10.5, 2H), 2.84 (dd, J = 12.0, 8.2, 1H), 2.68 (s, 3H), 2.24 (m, 2H), 2.07 (d, J = 14.1, 1H), 1.96 (m, 1H), 1.74 (dd, J = 12.5, 8.6, 1H), 1.57 (m, 1H), 1.48 (d, J = 14.2, 1H), 1.41 (m, 1H), 1.28 (dd, J = 14.0, 7.4, 1H), 0.96 (dd, J = 14.5, 7.4, 1H), 0.73 (td, J = 7.3, 3.9, 4H), 0.44 (t, J = 7.4, 3H). |
| 133 | {2-[4-(4-fluorophenyl)-2,2,6,6-tetramethyloxan-4-yl]ethyl}[(6-methylpyridin-3-yl)methyl]amine | 385.3 | δ 8.85 (s, 1H), 8.24 (d, J = 8.2, 1H), 7.54 (d, J = 8.3, 2H), 7.24 (dd, J = 8.9, 5.1, 1H), 6.92 (m, 2H), 4.12 (s, 2H), 2.61 (m, 5H), 2.25 (d, J = 14.3, 2H), 1.91 (dd, J = 10.4, 6.2, 2H), 1.65 (d, J = 14.4, 2H), 1.19 (d, J = 8.9, 6H), 0.94 (s, 6H). |
| 134 | [(4,5-dimethylthiophen-2-yl)methyl]({2-[(9R)-9-(pyridin-2-yl)-6-oxaspiro[4.5]decan-9-yl]ethyl})amine | 385.3 | δ 9.46 (s, 1H), 8.62 (d, J = 4.2, 1H), 8.07 (t, J = 7.3, 1H), 7.60 (d, J = 8.1, 1H), 7.52 (m, 1H), 6.76 (s, 1H), 4.06 (q, J = 13.9, 2H), 3.75 (m, 2H), 3.01 (m, 1H), 2.57 (s, 1H), 2.29 (m, 7H), 2.19 (m, 1H), 2.04 (s, 3H), 1.95 (d, J = 14.0, 1H), 1.81 (m, 2H), 1.67 (d, J = 8.2, 1H), 1.47 (m, 4H), 1.15 (m, 1H), 0.74 (dt, J = 13.1, 8.8, 1H). |
| 135 | [(2,4-dimethyl-1,3-thiazol-5-yl)methyl]({2-[(9R)-9-(pyridin-2-yl)-6-oxaspiro[4.5]decan-9-yl]ethyl})amine | 386.1 | δ 9.59 (s, 1H), 8.68 (dd, J = 5.6, 1.4, 1H), 8.35 (td, J = 8.0, 1.6, 1H), 7.80 (dd, J = 12.0, 7.0, 2H), 4.22 (m, 2H), 3.83 (dt, J = 12.5, 4.4, 1H), 3.72 (m, 1H), 3.05 (dt, J = 11.2, 5.6, 1H), 2.73 (s, 3H), 2.57 (m, 2H), 2.31 (m, 6H), 2.04 (m, 1H), 1.88 (ddd, J = 19.2, 11.4, 6.9, 2H), 1.68 (m, 1H), 1.52 (m, 4H), 1.19 (dd, J = 12.2, 5.9, 1H), 0.76 (dt, J = 13.1, 8.9, 1H). |
| 136 | {2-[9-(pyrazin-2-yl)-6-oxaspiro[4.5]decan-9-yl]ethyl}(thiophen-2-ylmethyl)amine | 386.1 | δ 8.90 (s, 1H), 8.55 (s, 1H), 8.40 (s, 1H), 6.60 (s, 1H), 3.88 (d, J = 12.3, 2H), 3.79-3.66 (m, 1H), 3.58 (dd, J = 16.8, 6.5, 1H), 2.81 (s, 1H), 2.40 (s, 1H), 2.35-2.22 (m, 2H), 2.16 (s, 3H), 2.12-2.00 (m, 1H), 1.97-1.88 (m, 4H), 1.85 (t, J = 9.1, 1H), 1.75-1.49 (m, 3H), 1.49-1.27 (m, 4H), 0.98 (d, J = 11.4, 1H), 0.55 (dt, J = 13.3, 9.0, 1H). |
| 137 | [(4,5-dimethylfuran-2-yl)methyl]({2-[(9R)-9-(4-fluorophenyl)-6-oxaspiro[4.5]decan-9-yl]ethyl})amine | 386.1 | δ 9.14 (s, 1H), 8.85 (s, 1H), 7.24 (ddd, J = 11.5, 6.2, 3.3, 2H), 7.05 (s, 2H), 6.06 (s, 1H), 3.89-3.66 (m, 4H), 2.72 (s, 1H), 2.29 (s, 1H), 2.22-2.13 (m, 1H), 2.11 (s, 4H), 1.85 (s, 7H), 1.76-1.62 (m, 2H), 1.60-1.36 (m, 4H), 1.33-1.24 (m, 1H), 0.82 (dt, J = 13.6, 8.8, 1H). |
| 138 | {2-[9-(2-methoxyphenyl)-6-oxaspiro[4.5]decan-9-yl]ethyl}(thiophen-2-ylmethyl)amine | 386.2 | δ 8.90 (d, J = 150.1, 2H), 7.19 (dd, J = 3.7, 1.4, 1H), 7.18-7.14 (m, 1H), 6.99 (dd, J = 7.8, 1.5, 1H), 6.94-6.76 (m, 4H), 4.66 (s, 2H), 3.94 (s, 2H), 3.80-3.63 (m, 5H), 2.73-2.45 (m, 3H), 2.30-2.08 (m, 2H), 1.76-1.48 (m, 5H), 1.39 (dt, J = 7.0, 6.3, 3H), 1.30 (d, J = 5.2, 1H), 1.18 (d, J = 4.1, 1H), 0.68 (dd, J = 8.7, 5.0, 1H). |
| 139 | {2-[9-(2-methoxyphenyl)-6-oxaspiro[4.5]decan-9-yl]ethyl}(thiophen-3-ylmethyl)amine | 386.2 | δ 9.28 (d, J = 95.5, 2H), 7.18-7.12 (m, 3H), 6.97 (dd, J = 7.8, 1.5, 1H), 6.93-6.86 (m, 1H), 6.86-6.71 (m, 2H), 3.80-3.61 (m, 7H), 2.55 (dd, J = 19.5, 5.1, 3H), 2.12 (d, J = 12.8, 2H), 1.85 (s, 2H), 1.76-1.47 (m, 5H), 1.46-1.32 (m, 3H), 1.31-1.22 (m, 1H), 1.17 (d, J = 4.2, 1H), 0.74-0.60 (m, 1H). |
| 140 | [(3-methoxythiophen-2-yl)methyl]({2-[(9R)-9-(pyridin-2-yl)-6-oxaspiro[4.5]decan-9-yl]ethyl})amine | 387 | δ 11.70 (brs, 1H), 9.14 (d, J = 66.6, 2H), 8.72 (d, J = 4.3, 1H), 8.19 (td, J = 8.0, 1.4, 1H), 7.70 (d, J = 8.1, 1H), 7.63 (dd, J = 7.0, 5.8, 1H), 7.22 (d, J = 5.5, 1H), 6.78 (d, J = 5.6, 1H), 4.08 (m, 2H), 3.80 (m, 4H), 3.69 (dd, J = 11.2, 8.7, 1H), 2.99 (d, J = 4.8, 1H), 2.51 (t, J = 9.9, 1H), 2.35 (m, 3H), 2.18 (td, J = 13.5, 5.4, 1H), 1.99 (d, J = 14.2, 1H), 1.82 (m, 2H), 1.65 (m, 1H), |

TABLE 1-continued

Compounds with chemical name and characterization data

| Compound. | Name | MS (m/z) [M + H]+ | 1H NMR |
|---|---|---|---|
| | | | 1.47 (m, 4H), 1.14 (m, 1H), 0.73 (dt, J = 13.2, 8.9, 1H). |
| 141 | [(3-methoxythiophen-2-yl)methyl]({2-[9-(pyridin-2-yl)-6-oxaspiro[4.5]decan-9-yl]ethyl})amine | 387 | δ 9.03 (d, J = 80.0, 2H), 8.75 (d, J = 5.3, 1H), 8.31 (t, J = 7.9, 1H), 7.76 (m, 2H), 7.26 (t, J = 4.0, 1H), 6.81 (d, J = 5.6, 1H), 4.12 (s, 2H), 3.82 (s, 4H), 3.69 (dd, J = 24.9, 14.9, 1H), 3.04 (s, 1H), 2.56 (s, 1H), 2.45 (dd, J = 17.7, 7.6, 1H), 2.29 (ddd, J = 17.8, 13.5, 5.8, 3H), 2.05 (d, J = 14.3, 1H), 1.87 (dt, J = 14.4, 6.7, 1H), 1.67 (ddd, J = 27.6, 16.0, 6.9, 1H), 1.52 (m, 4H), 1.20 (m, 1H), 0.78 (dt, J = 13.0, 8.9, 1H). |
| 142 | {2-[9-(6-methoxypyridin-2-yl)-6-oxaspiro[4.5]decan-9-yl]ethyl}(thiophen-2-ylmethyl)amine | 387.2 | δ 9.37 (s, 1H), 9.11 (s, 0H), 7.55 (dd, J = 8.2, 7.5, 1H), 7.30 (dd, J = 5.1, 1.1, 1H), 7.03 (d, J = 2.6, 1H), 6.96 (dd, J = 5.1, 3.6, 1H), 6.81 (d, J = 7.3, 1H), 6.60 (d, J = 8.0, 1H), 4.07 (s, 2H), 3.86 (s, 3H), 3.73 (dd, J = 7.7, 2.7, 2H), 2.87 (m, 1H), 2.75 (brs, 1H), 2.47 (m, 1H), 2.32 (dd, J = 24.5, 13.6, 2H), 2.09 (m, 1H), 1.80 (m, 3H), 1.63 (dt, J = 15.1, 7.4, 2H), 1.49 (m, 3H), 1.39 (d, J = 4.5, 1H), 1.16 (m, 1H), 0.72 (dt, J = 13.4, 8.8, 1H). |
| 143 | {2-[9-(6-methoxypyridin-2-yl)-6-oxaspiro[4.5]decan-9-yl]ethyl}(thiophen-3-ylmethyl)amine | 387.2 | δ 9.40 (s, 1H), 9.21 (s, 1H), 7.53 (m, 1H), 7.28 (d, J = 3.0, 2H), 6.99 (dd, J = 4.8, 1.4, 1H), 6.80 (d, J = 7.4, 1H), 6.59 (d, J = 8.2, 1H), 3.86 (d, J = 6.4, 5H), 3.72 (dd, J = 7.7, 2.7, 2H), 2.78 (m, 1H), 2.30 (dd, J = 28.1, 12.5, 3H), 2.09 (m, 1H), 2.02 (brs, 1H), 1.79 (m, 3H), 1.61 (m, 2H), 1.47 (m, 4H), 1.16 (m, 1H), 0.71 (dt, J = 13.4, 8.7, 1H). |
| 144 | {2-[4-(4-chlorophenyl)-2,2-dimethyloxan-4-yl]ethyl}[(2-methoxyphenyl)methyl]amine | 388.2 | δ 8.48 (d, J = 152.7, 2H), 7.28 (td, J = 8.3, 1.7, 1H), 7.22 (dd, J = 6.6, 4.8, 1H), 7.06 (m, 2H), 6.97 (dd, J = 7.5, 1.6, 1H), 6.81 (ddd, J = 19.8, 13.2, 4.6, 2H), 6.03 (s, 1H), 3.82 (s, 2H), 3.66 (m, 5H), 2.64 (s, 1H), 2.15 (s, 1H), 2.05 (ddd, J = 22.5, 14.1, 2.1, 2H), 1.85 (m, 1H), 1.72 (dd, J = 12.5, 4.7, 1H), 1.53 (m, 2H), 1.11 (s, 3H), 0.57 (s, 3H). |
| 145 | {2-[(9R)-9-(4-fluorophenyl)-6-oxaspiro[4.5]decan-9-yl]ethyl}[(5-methylthiophen-2-yl)methyl]amine | 388.2 | δ 7.28 (s, 4H), 7.25-7.15 (m, 2H), 7.04 (t, J = 8.6, 2H), 6.77 (d, J = 3.5, 1H), 6.59 (dd, J = 3.4, 1.1, 1H), 3.91 (s, 2H), 3.85-3.64 (m, 2H), 2.73 (t, J = 9.7, 1H), 2.41 (d, J = 0.7, 3H), 2.37-1.75 (m, 18H), 1.67 (dd, J = 11.7, 7.1, 2H), 1.59-1.34 (m, 4H), 1.26 (s, 1H), 0.81 (dt, J = 14.0, 8.9, 1H). |
| 146 | {2-[4-(4-fluorophenyl)-1-oxaspiro[5.5]undecan-4-yl]ethyl}(thiophen-3-ylmethyl)amine | 388.2 | δ 7.18 (s, 1H), 7.15 (s, 1H), 7.10 (dd, J = 8.9, 5.2, 2H), 6.92 (dd, J = 10.8, 6.4, 2H), 6.87 (m, 1H), 3.67 (d, J = 35.8, 3H), 2.66 (m, 1H), 2.07 (s, 3H), 1.83 (m, 2H), 1.56 (s, 3H), 1.41 (d, J = 13.9, 2H), 1.33 (m, 3H), 1.02 (m, 4H), 0.58 (m, 1H). |
| 147 | {2-[(9R)-9-(4-fluorophenyl)-6-oxaspiro[4.5]decan-9-yl]ethyl}[(3-methylthiophen-2-yl)methyl]amine | 388.2 | δ 9.01 (d, J = 137.9, 2H), 7.15-7.02 (m, 3H), 6.94 (t, J = 8.6, 2H), 6.77-6.63 (m, 1H), 4.82 (s, 1H), 3.83 (d, J = 19.1, 2H), 3.73-3.54 (m, 2H), 2.64 (s, 1H), 2.18 (d, J = 10.4, 1H), 2.12-1.64 (m, 9H), 1.65-1.50 (m, 2H), 1.50-1.27 (m, 4H), 1.27-1.08 (m, 1H), 0.69 (dt, J = 13.5, 8.8, 1H). |
| 148 | {2-[(9R)-9-(4-fluorophenyl)-6-oxaspiro[4.5]decan-9-yl]ethyl}[(4-methylthiophen-2-yl)methyl]amine | 388.2 | δ 9.31 (d, J = 89.1, 2H), 7.15-7.05 (m, 2H), 6.93 (t, J = 8.6, 2H), 6.80-6.65 (m, 2H), 3.80 (s, 2H), 3.73-3.57 (m, 2H), 2.93 (s, 1H), 2.60 (s, 1H), 2.17 (s, 1H), 2.04 (dd, J = 16.0, 3.3, 4H), 1.91 (ddd, J = 17.5, 16.7, 9.1, 2H), 1.84-1.65 (m, 3H), 1.57 (ddd, J = 13.2, 9.0, 4.4, 2H), 1.50-1.25 (m, 4H), 1.17 (dd, J = 14.9, 5.0, 1H), 0.70 (dt, J = 13.6, 8.8, 1H). |
| 149 | {2-[4-(4-fluorophenyl)-1-oxaspiro[5.5]undecan-4-yl]ethyl}(thiophen-2-ylmethyl)amine | 388.3 | δ 7.28 (s, 3H), 7.22 (dd, J = 8.6, 4.9, 2H), 7.01 (m, 2H), 4.01 (s, 2H), 3.74 (s, 1H), 2.26 (m, 1H), 1.73 (m, 11H), 1.52 (d, J = 14.1, 2H), 1.39 (m, 2H), 1.13 (s, 2H), 0.69 (m, 1H). |
| 150 | {2-[(9R)-9-(4-fluorophenyl)-6-oxaspiro[4.5]decan-9-yl]ethyl}[(4-methyl-1,3-thiazol-2-yl)methyl]amine | 389 | δ 7.22 (dd, J = 8.9, 5.2, 2H), 7.02 (dd, J = 14.0, 5.4, 2H), 6.92 (d, J = 0.9, 1H), 4.25 (q, J = 14.7, 2H), 3.73 (m, 2H), 2.89 (td, J = 11.8, 4.8, 1H), 2.50 (td, J = 11.7, 5.0, 1H), 2.38 (d, J = 0.8, 3H), 2.15 (m, 1H), 2.08 (m, 2H), 1.98 (m, 1H), 1.91 (d, J = 13.9, 1H), 1.79 (d, J = 9.3, 1H), 1.69 (m, 2H), 1.48 (m, 5H), 1.25 (m, 1H), 0.81 (dt, J = 13.3, 8.7, 1H). |
| 151 | {2-[2,2-diethyl-4-(4-fluorophenyl)oxan-4-yl]ethyl}[(5- | 390.2 | δ 7.15-7.02 (m, 2H), 6.94 (t, J = 8.6, 2H), 6.67 (d, J = 3.5, 1H), 6.49 (s, 1H), 3.78 (s, 2H), 3.62 (dd, J = 10.4, 8.1, 3H), 2.61 (s, 1H), 2.30 (s, 4H), 2.08 (dd, J = 31.6, |

TABLE 1-continued

Compounds with chemical name and characterization data

| Compound. | Name | MS (m/z) [M + H]+ | 1H NMR |
|---|---|---|---|
| | methylthiophen-2-yl)methyl]amine | | 14.0, 4H), 1.88 (d, J = 4.6, 1H), 1.79-1.34 (m, 19H), 1.29 (dd, J = 14.0, 7.4, 2H), 0.96 (dd, J = 14.5, 7.3, 1H), 0.74 (t, J = 7.5, 5H), 0.44 (t, J = 7.4, 4H). |
| 152 | [(5-chlorothiophen-2-yl)methyl]({2-[(9R)-9-(pyridin-2-yl)-6-oxaspiro[4.5]decan-9-yl]ethyl})amine | 391 | δ 8.75 (d, J = 4.8, 1H), 8.24 (t, J = 7.7, 1H), 7.86-7.58 (m, 2H), 6.44 (d, J = 3.3, 1H), 6.28 (d, J = 3.3, 1H), 4.07 (s, 2H), 3.94-3.79 (m, 1H), 3.72 (t, J = 10.1, 1H), 3.01 (dd, J = 11.1, 6.0, 1H), 2.56 (t, J = 9.9, 1H), 2.49-2.11 (m, 4H), 2.05 (d, J = 14.1, 1H), 1.88 (ddd, J = 18.8, 11.0, 6.5, 2H), 1.78-1.31 (m, 5H), 1.31-1.07 (m, 1H), 0.77 (dt, J = 13.1, 8.9, 1H) |
| 153 | dibutyl({2-[4-(4-fluorophenyl)-2,2,6,6-tetramethyloxan-4-yl]ethyl})amine | 392.4 | δ 7.37 (m, 2H), 7.07 (m, 2H), 2.83 (dd, J = 16.3, 9.4, 4H), 2.68 (m, 2H), 2.38 (d, J = 14.3, 2H), 2.09 (s, 4H), 1.93 (m, 2H), 1.77 (d, J = 14.3, 2H), 1.33 (m, 10H), 1.05 (d, J = 8.6, 6H), 0.91 (t, J = 7.2, 6H). |
| 154 | {2-[(9R)-9-(4-fluorophenyl)-6-oxaspiro[4.5]decan-9-yl]ethyl}(2-phenylpropan-2-yl)amine | 396.3 | δ 7.37 (s, 5H), 7.28 (s, 0H), 7.17-6.99 (m, 3H), 6.93 (t, J = 8.6, 2H), 3.81-3.57 (m, 2H), 2.45 (d, J = 9.0, 1H), 2.04-1.72 (m, 7H), 1.66 (t, J = 10.7, 6H), 1.62-1.53 (m, 2H), 1.52-1.34 (m, 4H), 1.23 (s, 1H), 0.78 (d, J = 13.8, 1H). |
| 155 | {4H,5H,6H-cyclopenta[b]thiophen-2-ylmethyl}({2-[(9R)-9-(pyridin-2-yl)-6-oxaspiro[4.5]decan-9-yl]ethyl})amine | 397.1 | δ 9.57 (brs, 1H), 8.62 (d, J = 3.9, 1H), 8.02 (t, J = 7.1, 1H), 7.57 (d, J = 8.1, 1H), 7.48 (dd, J = 6.9, 5.5, 1H), 6.80 (s, 1H), 5.30 (brs, 1H), 4.06 (q, J = 14.1, 2H), 3.74 (m, 2H), 2.99 (m, 1H), 2.82 (t, J = 7.2, 2H), 2.65 (t, J = 7.2, 2H), 2.57 (m, 1H), 2.34 (ddd, J = 33.3, 21.0, 10.4, 5H), 2.16 (dd, J = 9.9, 5.6, 1H), 1.94 (d, J = 13.9, 1H), 1.78 (m, 2H), 1.66 (d, J = 8.0, 1H), 1.46 (ddd, J = 16.6, 12.7, 5.7, 4H), 1.14 (m, 1H), 0.72 (dt, J = 13.4, 9.0, 1H). |
| 156 | {2-[4-(4-fluorophenyl)-1-oxaspiro[5.5]undecan-4-yl]ethyl}[(6-methylpyridin-3-yl)methyl]amine | 397.3 | δ 8.22 (d, J = 8.0, 1H), 7.49 (t, J = 16.4, 1H), 7.17 (m, 8H), 6.96 (t, J = 8.6, 2H), 4.09 (s, 2H), 3.66 (s, 4H), 2.84 (s, 1H), 2.68 (s, 3H), 2.29 (s, 1H), 2.20 (d, J = 13.2, 1H), 2.10 (d, J = 14.1, 1H), 1.93 (s, 1H), 1.73 (s, 1H), 1.59 (m, 1H), 1.45 (d, J = 14.0, 3H), 1.30 (m, 2H), 1.10 (m, 3H), 0.62 (d, J = 11.1, 1H). |
| 157 | [(2,3-dimethoxyphenyl)methyl]({2-[2,2-dimethyl-4-(4-methylphenyl)oxan-4-yl]ethyl})amine | 398.3 | δ 7.05 (dd, J = 19.6, 8.3, 4H), 6.88 (m, 1H), 6.74 (dd, J = 8.2, 1.4, 1H), 6.62 (dd, J = 7.6, 1.4, 1H), 3.77 (s, 3H), 3.68 (m, 5H), 3.55 (d, J = 2.3, 2H), 2.37 (m, 1H), 2.22 (m, 4H), 2.06 (ddd, J = 13.8, 8.6, 4.1, 2H), 1.73 (dd, J = 6.6, 4.3, 1H), 1.56 (m, 4H), 1.10 (s, 3H), 0.58 (s, 3H). |
| 158 | [(2,4-dimethoxyphenyl)methyl]({2-[2,2-dimethyl-4-(4-methylphenyl)oxan-4-yl]ethyl})amine | 398.3 | δ 8.09 (s, 1H), 7.68 (d, J = 33.5, 1H), 7.55 (s, 1H), 7.02 (q, J = 8.4, 4H), 6.86 (m, 1H), 6.32 (dd, J = 6.6, 2.2, 2H), 3.77 (d, J = 10.4, 2H), 3.69 (m, 8H), 2.67 (s, 1H), 2.24 (s, 4H), 2.10 (m, 2H), 1.87 (d, J = 4.5, 1H), 1.67 (d, J = 4.4, 1H), 1.51 (m, 2H), 1.10 (s, 3H), 0.57 (s, 3H). |
| 159 | {2-[9-(4-fluorophenyl)-6-oxaspiro[4.5]decan-9-yl]ethyl}[(4-methoxyphenyl)methyl]amine | 398.3 | δ 9.06 (d, J = 131.9, 2H), 7.17 (m, 2H), 7.08 (d, J = 8.7, 2H), 7.00 (t, J = 8.6, 2H), 6.79 (d, J = 8.7, 2H), 3.69 (m, 7H), 2.62 (s, 1H), 2.20 (s, 1H), 1.99 (m, 3H), 1.81 (m, 3H), 1.62 (m, 2H), 1.46 (m, 4H), 1.24 (d, J = 9.5, 1H), 0.77 (dt, J = 13.4, 8.8, 1H) |
| 160 | [(5-propylthiophen-2-yl)methyl]({2-[(9R)-9-(pyridin-2-yl)-6-oxaspiro[4.5]decan-9-yl]ethyl})amine | 399.1 | δ 9.43 (s, 2H), 8.72 (d, J = 4.6, 1H), 8.21 (t, J = 7.3, 1H), 7.72 (d, J = 8.1, 2H), 6.88 (d, J = 3.5, 1H), 6.63 (d, J = 3.5, 1H), 4.11 (s, 2H), 3.87-3.65 (m, 2H), 3.00 (s, 1H), 2.71 (t, J = 7.5, 2H), 2.54 (s, 1H), 2.32 (s, 3H), 2.27-2.11 (m, 1H), 2.02 (s, 1H), 1.84 (dd, J = 16.6, 7.3, 2H), 1.64 (dd, J = 15.0, 7.4, 7H), 1.22-1.10 (m, 1H), 0.95 (t, J = 7.3, 3H), 0.83-0.72 (m, 1H). |
| 161 | 1-{5-[({2-[(9R)-9-(pyridin-2-yl)-6-oxaspiro[4.5]decan-9-yl]ethyl}amino)methyl]thiophen-2-yl}ethan-1-ol | 401.1 | δ 9.38 (s, 2H), 8.76 (d, J = 4.6, 1H), 8.29 (t, J = 7.9, 1H), 7.84-7.69 (m, 2H), 6.92-6.74 (m, 4H), 5.02 (d, J = 6.4, 1H), 4.13 (s, 2H), 3.87-3.60 (m, 2H), 3.03 (s, 1H), 2.52 (s, 1H), 2.34 (t, J = 15.7, 3H), 2.20 (t, J = 12.6, 1H), 2.03 (dd, J = 14.2, 4.7, 1H), 1.96-1.78 (m, 2H), 1.81-1.65 (m, 1H), 1.65-1.43 (m, 7H), 1.15 (s, 1H), 0.77 (s, 1H). |
| 162 | 6-[9-(2-{[(4,5-dimethylthiophen-2-yl)methylamino]ethyl)-6-oxaspiro[4.5]decan-9-yl]pyridin-3-ol | 401.1 | 1H NMR (400 MHz, CD3CN) δ 8.18 (dd, J = 2.3, 1.2, 1H), 7.72 (s, 1H), 7.32 (d, J = 2.3, 2H), 6.82 (s, 1H), 4.10 (s, 2H), 3.67 (m, 2H), 2.95 (m, 1H), 2.50 (m, 1H), 2.32 (s, 3H), 2.27 (d, J = 13.9, 2H), 2.09 (m, 4H), 2.03 (m, 1H), 1.88 (m, 1H), 1.83 (t, J = 9.2, 2H), 1.71 (m, 1H), 1.63 (m, 2H), 1.48 (ddd, J = 16.6, 12.3, 7.6, 4H), 1.13 (dd, J = 11.7, 5.4, 1H), 0.72 (dt, J = 13.7, 9.0, 1H). |

TABLE 1-continued

Compounds with chemical name and characterization data

| Compound. | Name | MS (m/z) [M + H]+ | 1H NMR |
|---|---|---|---|
| 163 | 6-[9-(2-{[(4,5-dimethylthiophen-2-yl)methyl]amino}ethyl)-6-oxaspiro[4.5]decan-9-yl]pyridin-2-ol | 401.1 | δ 7.49 (m, 1H), 6.76 (s, 1H), 6.51 (d, J = 8.9, 1H), 6.25 (d, J = 7.0, 1H), 3.99 (s, 2H), 3.71 (m, 2H), 2.83 (dd, J = 16.5, 11.3, 1H), 2.61 (dd, J = 17.0, 5.8, 1H), 2.27 (d, J = 21.1, 5H), 1.99 (m, 6H), 1.65 (m, 10H), 0.98 (dd, J = 18.1, 5.5, 1H). |
| 164 | 2-[9-(2-{[(4,5-dimethylthiophen-2-yl)methyl]amino}ethyl)-6-oxaspiro[4.5]decan-9-yl]pyridin-4-ol | 401.2 | δ 9.21 (d, J = 64.7, 2H), 8.00 (s, 1H), 7.07 (m, 2H), 6.67 (s, 1H), 3.95 (s, 2H), 3.62 (m, 2H), 2.84 (s, 1H), 2.44 (s, 1H), 2.27 (d, J = 12.2, 1H), 2.16 (s, 4H), 2.03 (d, J = 13.5, 2H), 1.94 (m, 3H), 1.83 (d, J = 13.9, 1H), 1.65 (m, 3H), 1.37 (m, 5H), 0.75 (s, 1H). |
| 165 | [(5-nitrothiophen-2-yl)methyl]({2-[(9R)-9-(pyridin-2-yl)-6-oxaspiro[4.5]decan-9-yl]ethyl})amine | 402 | δ 8.59 (d, J = 4.0, 1H), 8.15 (t, J = 7.0, 1H), 7.79 (d, J = 4.1, 1H), 7.66 (d, J = 8.2, 1H), 7.60 (m, 1H), 7.16 (d, J = 4.2, 1H), 4.23 (s, 2H), 3.78 (m, 2H), 3.04 (d, J = 6.0, 1H), 2.65 (m, 1H), 2.43 (d, J = 9.8, 1H), 2.29 (m, 3H), 1.98 (d, J = 14.1, 1H), 1.83 (d, J = 5.4, 2H), 1.67 (m, 1H), 1.48 (m, 4H), 1.16 (m, 1H), 0.75 (d, J = 13.2, 1H). |
| 166 | [(3,5-dimethylthiophen-2-yl)methyl]({2-[(9R)-9-(4-fluorophenyl)-6-oxaspiro[4.5]decan-9-yl]ethyl})amine | 402.1 | δ 7.19 (dd, J = 8.9, 5.1, 2H), 7.01 (dd, J = 13.7, 5.0, 2H), 6.43 (s, 1H), 3.87 (m, 2H), 3.72 (m, 2H), 3.02 (s, 1H), 2.72 (dd, J = 14.6, 8.9, 1H), 2.31 (dd, J = 31.1, 10.4, 4H), 2.15 (d, J = 13.8, 1H), 2.05 (d, J = 14.0, 1H), 1.98 (m, 4H), 1.87 (m, 2H), 1.77 (d, J = 9.7, 1H), 1.67 (ddd, J = 15.6, 10.3, 5.4, 2H), 1.46 (m, 4H), 1.25 (t, J = 7.1, 1H), 0.79 (dt, J = 13.7, 8.9, 1H). |
| 167 | [(5-ethylthiophen-2-yl)methyl]({2-[(9R)-9-(4-fluorophenyl)-6-oxaspiro[4.5]decan-9-yl]ethyl})amine | 402.1 | δ 7.21 (dd, J = 8.9, 5.2, 2H), 7.04 (t, J = 8.6, 2H), 6.79 (d, J = 3.5, 1H), 6.62 (d, J = 3.5, 1H), 3.92 (s, 2H), 3.80-3.67 (m, 3H), 2.82-2.67 (m, 2H), 2.32 (s, 1H), 2.16 (d, J = 14.3, 1H), 2.06 (s, 1H), 2.00 (td, J = 12.8, 4.9, 1H), 1.91 (d, J = 13.9, 2H), 1.84-1.75 (m, 1H), 1.69 (s, 2H), 1.50 (d, J = 3.7, 4H), 1.25 (t, J = 7.5, 4H), 0.81 (dt, J = 13.4, 8.7, 1H). |
| 168 | {2-[4-(4-fluorophenyl)-1-oxaspiro[5.5]undecan-4-yl]ethyl}[(5-methylthiophen-2-yl)methyl]amine | 402.3 | δ 7.12 (m, 2H), 6.93 (s, 2H), 6.66 (d, J = 3.4, 1H), 6.49 (d, J = 2.5, 1H), 3.80 (s, 2H), 3.63 (s, 2H), 2.65 (m, 1H), 2.31 (s, 3H), 2.12 (m, 2H), 1.85 (m, 1H), 1.61 (s, 3H), 1.43 (d, J = 14.0, 2H), 1.33 (m, 3H), 1.03 (s, 4H), 0.59 (m, 1H). |
| 169 | [(4,5-dimethylthiophen-2-yl)methyl]({2-[(9R)-9-(4-fluorophenyl)-6-oxaspiro[4.5]decan-9-yl]ethyl})amine | 402.3 | δ 8.92 (d, J = 108.6, 2H), 7.15-7.05 (m, 2H), 6.93 (t, J = 8.6, 2H), 6.51 (s, 1H), 5.31 (s, 1H), 3.75 (s, 2H), 3.69-3.54 (m, 2H), 2.63 (s, 1H), 2.27-2.10 (m, 4H), 2.06 (d, J = 14.0, 1H), 1.98 (d, J = 13.9, 1H), 1.93-1.84 (m, 4H), 1.84-1.65 (m, 3H), 1.58 (ddd, J = 17.0, 8.4, 3.8, 2H), 1.51-1.27 (m, 4H), 1.17 (dd, J = 13.9, 6.2, 1H), 0.71 (dt, J = 13.6, 8.8, 1H). |
| 170 | {[5-(methylsulfanyl)thiophen-2-yl]methyl}({2-[(9R)-9-(pyridin-2-yl)-6-oxaspiro[4.5]decan-9-yl]ethyl})amine | 403 | δ 9.54 (s, 1H), 8.71 (d, J = 4.5, 1H), 8.26 (t, J = 7.2, 2H), 7.80-7.67 (m, 2H), 6.92 (dd, J = 21.5, 3.6, 2H), 4.15 (s, 2H), 3.76 (d, J = 40.3, 2H), 3.02 (d, J = 11.4, 5.3, 1H), 2.62-2.51 (m, 1H), 2.48 (s, 3H), 2.42 (s, 1H), 2.31 (t, J = 13.3, 3H), 2.03 (d, J = 14.2, 1H), 1.92-1.78 (m, 2H), 1.78-1.63 (m, 1H), 1.64-1.36 (m, 4H), 1.25-1.12 (m, 1H), 0.79 (s, 1H). |
| 171 | 6-[9-(2-{[(3-methoxythiophen-2-yl)methyl]amino}ethyl)-6-oxaspiro[4.5]decan-9-yl]pyridin-3-ol | 403 | 1H NMR (400 MHz, CD3CN) δ 8.15 (d, J = 1.5, 1H), 7.60 (s, 1H), 7.43 (d, J = 5.6, 1H), 7.31 (m, 2H), 6.97 (d, J = 5.6, 1H), 4.11 (s, 2H), 3.86 (s, 3H), 3.66 (dd, J = 7.8, 2.9, 2H), 2.97 (m, 1H), 2.51 (m, 1H), 2.28 (m, 2H), 2.02 (m, 1H), 1.87 (m, 2H), 1.80 (d, J = 13.5, 2H), 1.70 (d, J = 9.8, 1H), 1.61 (dd, J = 13.8, 7.1, 2H), 1.49 (m, 4H), 1.12 (m, 1H), 0.71 (d, J = 13.5, 1H). |
| 172 | 6-[9-(2-{[(3-methoxythiophen-2-yl)methyl]amino}ethyl)-6-oxaspiro[4.5]decan-9-yl]pyridin-2-ol | 403 | δ 9.47 (brs, 1H), 7.51 (dd, J = 9.0, 7.2, 1H), 7.23 (d, J = 5.6, 1H), 6.80 (d, J = 5.5, 1H), 6.52 (d, J = 8.9, 1H), 6.27 (d, J = 7.1, 1H), 4.10 (s, 2H), 3.82 (s, 3H), 3.73 (dd, J = 6.8, 3.4, 2H), 2.83 (dd, J = 11.9, 5.7, 1H), 2.60 (t, J = 10.0, 1H), 2.27 (t, J = 15.0, 2H), 2.00 (t, J = 12.3, 2H), 1.65 (m, 10H), 0.97 (d, J = 13.4, 1H). |
| 173 | 2-[(9R)-9-(2-{[(3-methoxythiophen-2-yl)methyl]amino}ethyl)-6-oxaspiro[4.5]decan-9-yl]-1-oxidopyridin-1-ium | 403.2 | δ 9.84 (s, 1H), 8.76 (s, 1H), 8.32 (d, J = 5.3, 1H), 7.60 (t, J = 7.7, 1H), 7.52 (m, 1H), 7.41 (m, 1H), 7.25 (d, J = 5.5, 1H), 6.81 (d, J = 5.5, 1H), 4.16 (m, 2H), 3.82 (m, 4H), 3.71 (m, 1H), 3.05 (d, J = 13.4, 2H), 2.85 (d, J = 9.1, 1H), 2.53 (s, 2H), 2.27 (d, J = 14.3, 1H), 2.14 (m, 1H), 1.99 (t, J = 11.3, 1H), 1.85 (m, 2H), 1.66 (ddd, J = 18.0, 10.0, 5.8, 1H), 1.51 (m, 4H), 1.22 (dd, J = 12.3, 6.0, 1H), 0.90 (dt, J = 13.0, 8.7, 1H). |

TABLE 1-continued

Compounds with chemical name and characterization data

| Compound. | Name | MS (m/z) [M + H]+ | 1H NMR |
|---|---|---|---|
| 174 | 2-[9-(2-{[(3-methoxythiophen-2-yl)methyl]amino}ethyl)-6-oxaspiro[4.5]decan-9-yl]pyridin-4-ol | 403.2 | δ 9.17 (d, J = 50.2, 2H), 8.00 (d, J = 6.5, 1H), 7.16 (d, J = 5.6, 3H), 6.72 (d, J = 5.6, 1H), 4.00 (s, 2H), 3.73 (s, 5H), 2.82 (s, 1H), 2.34 (d, J = 39.9, 2H), 2.11 (dd, J = 51.0, 13.1, 3H), 1.84 (d, J = 13.9, 1H), 1.43 (m, 9H), 0.75 (s, 1H). |
| 175 | {2-[(9R)-9-(4-fluorophenyl)-6-oxaspiro[4.5]decan-9-yl]ethyl}[(3-methoxythiophen-2-yl)methyl]amine | 404 | δ 7.24 (s, 3H), 7.03 (dd, J = 11.7, 5.6, 2H), 6.80 (d, J = 5.5, 1H), 4.00 (s, 2H), 3.81 (m, 5H), 2.78 (m, 1H), 2.39 (m, 1H), 2.17 (m, 1H), 2.06 (s, 2H), 1.86 (m, 2H), 1.66 (m, 3H), 1.51 (m, 3H), 1.26 (m, 2H), 0.80 (m, 1H). |
| 176 | {2-[2,2-dimethyl-4-(4-methylphenyl)oxan-4-yl]ethyl}({[3-(trifluoromethyl)phenyl]methyl})amine | 406.3 | δ 9.43 (d, J = 141.7, 2H), 7.47 (d, J = 7.2, 1H), 7.39 (s, 1H), 7.31 (m, 2H), 6.99 (q, J = 8.3, 4H), 3.67 (m, 4H), 2.54 (d, J = 8.4, 1H), 2.20 (d, J = 7.1, 3H), 2.06 (m, 3H), 1.92 (m, 2H), 1.60 (td, J = 12.5, 4.7, 1H), 1.46 (m, 2H), 1.08 (s, 3H), 0.55 (s, 3H). |
| 177 | (1-benzothiophen-2-ylmethyl)({2-[(9R)-9-(pyridin-2-yl)-6-oxaspiro[4.5]decan-9-yl]ethyl})amine | 407.1 | δ 8.51 (dd, J = 5.5, 1.3, 1H), 8.02 (d, J = 1.4, 1H), 7.73-7.52 (m, 3H), 7.43 (d, J = 1.0, 1H), 7.35-7.23 (m, 3H), 3.67 (s, 3H), 2.96 (td, J = 11.5, 5.7, 1H), 2.56-2.43 (m, 1H), 2.43-2.28 (m, 1H), 2.16 (d, J = 13.6, 3H), 1.89 (d, J = 14.2, 1H), 1.73 (ddd, J = 19.7, 11.9, 7.2, 2H), 1.55 (dt, J = 15.0, 5.7, 1H), 1.48-1.22 (m, 4H), 1.06 (s, 1H), 0.66 (dt, J = 13.2, 8.9, 1H). |
| 178 | (1-benzothiophen-3-ylmethyl)({2-[(9R)-9-(pyridin-2-yl)-6-oxaspiro[4.5]decan-9-yl]ethyl})amine | 407.1 | δ 11.71 (s, 2H), 9.34 (d, J = 85.8, 1H), 8.48 (d, J = 5.0, 1H), 8.10 (s, 1H), 7.71 (dd, J = 6.2, 2.8, 1H), 7.58 (ddd, J = 22.1, 9.6, 4.3, 3H), 7.47 (s, 1H), 7.36-7.24 (m, 2H), 4.12 (s, 2H), 3.64 (s, 2H), 2.93 (s, 1H), 2.51-2.23 (m, 2H), 2.13 (t, J = 14.3, 3H), 1.94-1.83 (m, 1H), 1.80-1.64 (m, 2H), 1.62-1.49 (m, 1H), 1.37 (dd, J = 39.4, 7.2, 4H), 1.06 (d, J = 13.0, 1H), 0.64 (dt, J = 13.1, 9.0, 1H). |
| 179 | [(5-chlorothiophen-2-yl)methyl]({2-[(9R)-9-(4-fluorophenyl)-6-oxaspiro[4.5]decan-9-yl]ethyl})amine | 408.2 | δ 7.11 (dd, J = 8.9, 5.2, 2H), 6.94 (dd, J = 15.9, 7.2, 2H), 6.75-6.56 (m, 2H), 3.79 (s, 2H), 3.71-3.52 (m, 2H), 2.61 (s, 1H), 2.18 (s, 1H), 1.84 (dddd, J = 31.4, 25.9, 23.7, 13.1, 12H), 1.58 (td, J = 9.4, 4.6, 2H), 1.39 (ddd, J = 23.7, 14.8, 9.2, 5H), 1.17 (s, 2H), 0.69 (dd, J = 8.7, 5.1, 1H). |
| 180 | 2-{[(2-{2,2-dimethyl-4-[4-(trifluoromethyl)phenyl]oxan-4-yl}ethyl)amino]methyl}phenol | 408.3 | δ 8.34 (d, J = 45.4, 2H), 7.50 (d, J = 8.3, 2H), 7.24 (d, J = 8.2, 2H), 7.10 (s, 1H), 6.77 (m, 3H), 3.80 (s, 2H), 3.66 (m, 2H), 3.31 (s, 3H), 2.63 (s, 1H), 2.09 (dd, J = 26.1, 13.9, 3H), 1.87 (t, J = 10.4, 1H), 1.71 (t, J = 10.4, 1H), 1.58 (d, J = 14.0, 2H), 1.10 (s, 3H), 0.53 (s, 3H). |
| 181 | [(5-chlorothiophen-2-yl)methyl]({2-[2,2-diethyl-4-(4-fluorophenyl)oxan-4-yl]ethyl})amine | 410.1 | δ 7.12 (dd, J = 8.9, 5.2, 2H), 6.96 (t, J = 8.6, 2H), 6.69 (q, J = 3.8, 2H), 3.79 (s, 2H), 3.63 (dd, J = 12.2, 7.1, 2H), 2.63 (dd, J = 12.2, 7.5, 1H), 2.29-1.77 (m, 8H), 1.67 (td, J = 12.5, 4.7, 1H), 1.44 (dd, J = 24.5, 10.8, 3H), 1.31 (d, J = 7.5, 1H), 0.95 (s, 1H), 0.74 (t, J = 7.5, 4H), 0.44 (t, J = 7.4, 3H). |
| 182 | {[5-(2-methylpropyl)thiophen-2-yl]methyl}({2-[(9R)-9-(pyridin-2-yl)-6-oxaspiro[4.5]decan-9-yl]ethyl})amine | 413.1 | δ 9.56 (brs, 1H), 8.66 (d, J = 4.7, 1H), 8.09 (t, J = 7.5, 1H), 7.62 (d, J = 8.1, 1H), 7.55 (m, 1H), 6.87 (d, J = 3.4, 1H), 6.59 (d, J = 3.4, 1H), 4.08 (m, 2H), 3.75 (m, 2H), 2.96 (d, J = 4.8, 1H), 2.57 (d, J = 7.0, 2H), 2.50 (t, J = 9.6, 1H), 2.31 (m, 3H), 2.14 (td, J = 13.5, 5.4, 1H), 1.96 (d, J = 14.1, 1H), 1.80 (m, 3H), 1.66 (m, 1H), 1.47 (m, 4H), 1.14 (d, J = 13.0, 1H), 0.89 (d, J = 6.6, 6H), 0.73 (dt, J = 13.6, 9.0, 1H). |
| 183 | [(5-butylthiophen-2-yl)methyl]({2-[(9R)-9-(pyridin-2-yl)-6-oxaspiro[4.5]decan-9-yl]ethyl})amine | 413.1 | δ 10.87 (brs, 1H), 9.42 (brs, 1H), 8.70 (d, J = 4.8, 1H), 8.17 (t, J = 7.7, 1H), 7.68 (d, J = 8.1, 1H), 7.62 (m, 1H), 6.85 (d, J = 3.5, 1H), 6.60 (d, J = 3.4, 1H), 4.08 (s, 2H), 3.79 (m, 1H), 3.67 (t, J = 10.0, 1H), 2.97 (d, J = 4.3, 1H), 2.70 (t, J = 7.6, 2H), 2.50 (t, J = 9.9, 1H), 2.33 (m, 3H), 2.16 (td, J = 13.1, 5.0, 1H), 1.98 (t, J = 9.4, 1H), 1.80 (t, J = 9.6, 2H), 1.54 (m, 7H), 1.33 (dq, J = 14.5, 7.3, 2H), 1.14 (m, 1H), 0.90 (t, J = 7.3, 3H), 0.73 (dt, J = 13.0, 8.9, 1H). |
| 184 | {4H,5H,6H-cyclopenta[b]thiophen-2-ylmethyl}({2-[(9R)-9-(4-fluorophenyl)-6-oxaspiro[4.5]decan-9-yl]ethyl})amine | 414 | δ 7.20 (m, 2H), 7.01 (dd, J = 13.5, 4.7, 2H), 6.65 (s, 1H), 3.88 (s, 2H), 3.72 (m, 3H), 2.78 (t, J = 7.2, 3H), 2.61 (t, J = 7.2, 2H), 2.34 (dt, J = 14.5, 7.3, 3H), 2.15 (d, J = 14.1, 1H), 2.06 (d, J = 13.9, 1H), 1.99 (m, 1H), 1.89 (m, 2H), 1.78 (m, 1H), 1.67 (ddd, J = 18.6, 11.9, 7.0, 2H), 1.46 (m, 4H), 1.25 (m, 1H), 0.79 (dt, J = 13.4, 8.7, 1H). |

TABLE 1-continued

Compounds with chemical name and characterization data

| Compound. | Name | MS (m/z) [M + H]+ | 1H NMR |
|---|---|---|---|
| 185 | {2-[(9R)-9-(pyridin-2-yl)-6-oxaspiro[4.5]decan-9-yl]ethyl}({2H,3H-thieno[3,4-b][1,4]dioxin-5-ylmethyl})amine | 415 | δ 9.37 (s, 1H), 8.65 (dd, J = 5.3, 1.3, 1H), 8.12 (td, J = 7.9, 1.6, 1H), 7.65 (d, J = 8.2, 1H), 7.56 (dd, J = 7.1, 5.7, 1H), 6.34 (s, 1H), 5.94 (s, 1H), 4.16 (dt, J = 8.2, 6.0, 4H), 4.05 (m, 2H), 3.77 (m, 2H), 3.06 (dd, J = 17.1, 11.1, 1H), 2.61 (t, J = 8.9, 1H), 2.29 (m, 4H), 1.99 (t, J = 8.8, 1H), 1.82 (ddd, J = 13.6, 9.4, 4.3, 2H), 1.67 (m, 1H), 1.48 (ddd, J = 14.5, 12.7, 6.9, 4H), 1.19 (m, 1H), 0.74 (dt, J = 13.3, 9.0, 1H). |
| 186 | {2-[2,2-dimethyl-4-(4-methylphenyl)oxan-4-yl]ethyl}[(2-methanesulfonylphenyl)methyl]amine | 416.3 | δ 8.66 (d, J = 167.7, 2H), 7.92 (m, 1H), 7.52 (m, 3H), 7.05 (s, 4H), 4.21 (s, 2H), 3.71 (m, 2H), 3.49 (s, 1H), 3.06 (s, 3H), 2.85 (s, 1H), 2.47 (d, J = 4.8, 1H), 2.20 (m, 4H), 2.09 (dd, J = 13.9, 2.1, 1H), 1.94 (d, J = 4.6, 1H), 1.72 (s, 1H), 1.55 (m, 2H), 1.10 (s, 3H), 0.57 (s, 3H). |
| 187 | [(4-bromofuran-2-yl)methyl]({2-[(9R)-9-(pyridin-2-yl)-6-oxaspiro[4.5]decan-9-yl]ethyl})amine | 419 | δ 9.52 (s, 1H), 8.77 (s, 1H), 8.38 (s, 1H), 7.83 (d, J = 7.6, 2H), 7.40 (s, 1H), 6.51 (s, 1H), 4.09 (s, 2H), 3.78 (d, J = 48.0, 2H), 3.03 (s, 1H), 2.63-2.41 (m, 2H), 2.33 (dd, J = 28.3, 13.9, 3H), 2.09 (d, J = 14.2, 1H), 1.90 (s, 2H), 1.82-1.63 (m, 1H), 1.53 (ddd, J = 12.9, 10.9, 4.5, 4H), 1.19 (s, 1H), 0.79 (dt, J = 13.0, 8.9, 1H). |
| 188 | {2-[(9R)-9-(4-fluorophenyl)-6-oxaspiro[4.5]decan-9-yl]ethyl}({[5-(methylsulfanyl)thiophen-2-yl]methyl})amine | 420 | δ 7.22 (dd, J = 8.9, 5.2, 2H), 7.05 (t, J = 8.6, 2H), 6.85 (dd, J = 10.8, 3.7, 2H), 3.95 (s, 2H), 3.75 (d, J = 4.6, 2H), 2.75 (s, 1H), 2.47 (s, 3H), 2.32 (s, 1H), 2.17 (d, J = 14.4, 1H), 2.09 (d, J = 13.8, 1H), 1.99 (dt, J = 12.3, 6.4, 1H), 1.91 (d, J = 13.9, 2H), 1.80 (d, J = 10.5, 1H), 1.74-1.61 (m, 2H), 1.49 (dt, J = 18.7, 11.7, 4H), 1.26 (s, 1H), 0.89-0.75 (m, 1H). |
| 189 | {2-[(9R)-9-(pyridin-2-yl)-6-oxaspiro[4.5]decan-9-yl]ethyl}({[6-(trifluoromethyl)pyridin-3-yl]methyl})amine | 420.3 | δ 8.83-8.56 (m, 2H), 8.35 (t, J = 7.6, 1H), 7.96 (dd, J = 19.3, 8.7, 1H), 7.87-7.75 (m, 2H), 7.71 (t, J = 9.2, 1H), 4.16 (s, 2H), 3.84 (dd, J = 8.5, 4.4, 1H), 3.71 (t, J = 10.0, 1H), 3.07 (dd, J = 11.7, 6.8, 1H), 2.55 (dt, J = 25.6, 11.9, 2H), 2.43-2.21 (m, 3H), 2.10 (d, J = 14.2, 1H), 1.90 (ddd, J = 26.1, 14.9, 6.7, 2H), 1.76-1.62 (m, 1H), 1.60-1.34 (m, 4H), 1.33-1.09 (m, 1H), 0.76 (dt, J = 12.8, 8.8, 1H). |
| 190 | [(5-bromofuran-2-yl)methyl]({2-[(9R)-9-(pyridin-2-yl)-6-oxaspiro[4.5]decan-9-yl]ethyl})amine | 421 | δ 8.75 (d, J = 4.8, 1H), 8.24 (t, J = 7.7, 1H), 7.86-7.58 (m, 2H), 6.44 (d, J = 3.3, 1H), 6.28 (d, J = 3.3, 1H), 4.07 (s, 2H), 3.94-3.79 (m, 1H), 3.72 (t, J = 10.1, 1H), 3.01 (dd, J = 11.1, 6.0, 1H), 2.56 (t, J = 9.9, 1H), 2.49-2.11 (m, 4H), 2.05 (d, J = 14.1, 1H), 1.88 (ddd, J = 18.8, 11.0, 6.5, 2H), 1.78-1.31 (m, 5H), 1.31-1.07 (m, 1H), 0.77 (dt, J = 13.1, 8.9, 1H) |
| 191 | (2-{2,2-dimethyl-4-[4-(trifluoromethyl)phenyl]oxan-4-yl}ethyl)[(2-methoxyphenyl)methyl]amine | 422.3 | δ 8.49 (d, J = 118.7, 2H), 7.50 (d, J = 8.3, 2H), 7.25 (dd, J = 10.3, 4.6, 3H), 6.96 (dd, J = 7.5, 1.5, 1H), 6.79 (ddd, J = 22.1, 14.4, 4.4, 2H), 6.08 (s, 1H), 3.84 (d, J = 9.2, 2H), 3.68 (m, 5H), 2.64 (s, 1H), 2.09 (m, 3H), 1.90 (m, 1H), 1.77 (dd, J = 12.7, 4.5, 1H), 1.58 (ddd, J = 14.0, 10.8, 10.1, 2H), 1.12 (s, 3H), 0.55 (s, 3H). |
| 192 | {2-[2,2,6,6-tetramethyl-4-(pyridin-2-yl)oxan-4-yl]ethyl}({[6-(trifluoromethyl)pyridin-3-yl]methyl})amine | 422.3 | δ 8.79-8.63 (m, 2H), 8.31 (t, J = 7.9, 1H), 8.05-7.90 (m, 2H), 7.87-7.61 (m, 2H), 4.16 (s, 2H), 2.82 (dd, J = 10.0, 6.6, 2H), 2.54 (d, J = 14.7, 2H), 2.46-2.30 (m, 2H), 1.95 (d, J = 14.8, 2H), 1.32 (s, 5H), 0.98 (s, 5H). |
| 193 | {[5-(furan-2-yl)thiophen-2-yl]methyl}({2-[(9R)-9-(pyridin-2-yl)-6-oxaspiro[4.5]decan-9-yl]ethyl})amine | 423.1 | δ 9.59 (s, 1H), 8.56 (d, J = 4.7, 1H), 8.05 (t, J = 7.4, 1H), 7.57 (d, J = 8.1, 1H), 7.46 (dd, J = 12.2, 6.3, 1H), 7.35-7.26 (m, 1H), 6.93 (dd, J = 19.9, 3.7, 2H), 6.46-6.30 (m, 2H), 4.08 (s, 2H), 3.78-3.54 (m, 2H), 3.00-2.81 (m, 2H), 2.46 (t, J = 9.7, 1H), 2.30 (t, J = 10.6, 1H), 2.13 (ddd, J = 17.3, 16.1, 9.3, 3H), 1.89 (d, J = 14.2, 1H), 1.72 (ddd, J = 13.9, 9.5, 4.3, 2H), 1.54 (dd, J = 21.6, 14.5, 1H), 1.48-1.23 (m, 4H), 1.06 (d, J = 13.2, 1H), 0.65 (dt, J = 13.3, 8.9, 1H). |
| 194 | [(5-chlorothiophen-2-yl)methyl]({2-[4-(4-fluorophenyl)-1-oxaspiro[5.5]undecan-4-yl]ethyl})amine | 423.2 | δ 7.13 (dd, J = 8.9, 5.1, 2H), 6.95 (dd, J = 15.5, 6.8, 2H), 6.69 (q, J = 3.9, 2H), 3.81 (s, 2H), 3.62 (d, J = 13.8, 2H), 2.68 (m, 1H), 2.11 (dd, J = 22.2, 13.8, 3H), 1.84 (m, 1H), 1.54 (m, 4H), 1.30 (m, 4H), 1.05 (d, J = 11.4, 4H), 0.63 (m, 1H). |
| 195 | (1-benzothiophen-2-ylmethyl)({2-[(9R)-9-(4-fluorophenyl)-6-oxaspiro[4.5]decan-9- | 424 | δ 9.53 (d, J = 105.8, 2H), 7.77-7.66 (m, 2H), 7.36-7.32 (m, 2H), 7.15 (dd, J = 8.8, 5.2, 3H), 6.96 (t, J = 8.6, 2H), 3.96 (s, 2H), 3.75-3.63 (m, 2H), 2.75 (s, 1H), 2.33 (s, 1H), 2.19-2.16 (m, 0H), 2.15-1.71 (m, |

TABLE 1-continued

Compounds with chemical name and characterization data

| Compound. | Name | MS (m/z) [M + H]⁺ | 1H NMR |
|---|---|---|---|
| | yl]ethyl})amine | | 6H), 1.71-1.29 (m, 6H), 1.22 (s, 1H), 0.77 (dt, J = 13.5, 9.0, 1H). |
| 196 | (1-benzothiophen-3-ylmethyl)({2-[(9R)-9-(4-fluorophenyl)-6-oxaspiro[4.5]decan-9-yl]ethyl})amine | 424 | δ 8.67 (d, J = 139.8, 2H), 7.76-7.61 (m, 1H), 7.56-7.39 (m, 1H), 7.34-7.25 (m, 3H), 6.98 (dd, J = 8.8, 5.1, 2H), 6.84 (t, J = 8.6, 2H), 3.89 (s, 2H), 3.71-3.54 (m, 2H), 2.66 (s, 1H), 2.21 (s, 1H), 2.07-1.89 (m, 2H), 1.89-1.60 (m, 4H), 1.60-1.45 (m, 2H), 1.44-1.24 (m, 4H), 1.19-1.07 (m, 1H), 0.67 (dt, J = 13.8, 8.9, 1H). |
| 197 | [(5-fluoro-1-benzothiophen-2-yl)methyl]({2-[(9R)-9-(pyridin-2-yl)-6-oxaspiro[4.5]decan-9-yl]ethyl})amine | 425 | δ 8.47 (s, 1H), 7.69 (s, 2H), 7.42 (d, J = 9.2, 1H), 7.30 (dd, J = 10.5, 9.5, 3H), 7.13 (s, 2H), 4.21 (d, J = 13.3, 2H), 3.73 (s, 2H), 3.16-2.91 (m, 1H), 2.82-2.52 (m, 1H), 2.27 (d, J = 14.8, 2H), 2.21-2.09 (m, 1H), 2.08-1.94 (m, 1H), 1.85 (d, J = 13.6, 1H), 1.65 (s, 4H), 1.43 (d, J = 38.4, 3H), 1.18-1.02 (m, 1H), 0.75-0.60 (m, 1H). |
| 198 | [(5-cyclopentylthiophen-2-yl)methyl]({2-[(9R)-9-(pyridin-2-yl)-6-oxaspiro[4.5]decan-9-yl]ethyl})amine | 425.1 | δ 12.19-12.13 (m, 0H), 8.69 (d, J = 4.7, 1H), 8.18 (s, 1H), 7.80-7.59 (m, 2H), 6.90 (d, J = 3.5, 1H), 6.67 (d, J = 2.9, 1H), 4.14 (s, 2H), 3.82 (d, J = 12.7, 2H), 3.73, (d, J = 9.7, 1H), 3.17 (t, J = 8.3, 1H), 3.02 (s, 1H), 2.58 (s, 1H), 2.31 (d, J = 14.1, 4H), 2.05 (dd, J = 33.0, 10.0, 3H), 1.90-1.74 (m, 4H), 1.68 (dt, J = 12.1, 9.1, 3H), 1.51 (ddd, J = 13.4, 10.8, 5.9, 6H), 1.18 (s, 1H), 0.79 (s, 1H). |
| 199 | [(4-phenylphenyl)methyl]({2-[(9R)-9-(pyridin-2-yl)-6-oxaspiro[4.5]decan-9-yl]ethyl})amine | 427.3 | δ 8.59 (d, J = 4.9, 1H), 8.18 (t, J = 7.4, 1H), 7.75-7.52 (m, 2H), 7.47-7.38 (m, 4H), 7.35-7.29 (m, 2H), 7.29-7.21 (m, 3H), 3.91 (s, 2H), 3.70 (dt, J = 12.3, 4.2, 1H), 3.57 (t, J = 9.7, 1H), 2.92 (s, 1H), 2.40 (dd, J = 26.0, 12.7, 2H), 2.30-2.04 (m, 3H), 2.04-1.84 (m, 1H), 1.76 (ddd, J = 27.2, 15.3, 6.8, 2H), 1.65-1.21 (m, 5H), 1.07 (dd, J = 14.4, 5.6, 1H), 0.67 (dt, J = 13.0, 9.0, 1H). |
| 200 | [(3-phenylphenyl)methyl]({2-[(9R)-9-(pyridin-2-yl)-6-oxaspiro[4.5]decan-9-yl]ethyl})amine | 427.3 | δ 8.44 (d, J = 4.1, 1H), 7.96 (t, J = 7.1, 1H), 7.53-7.43 (m, 5H), 7.42-7.26 (m, 3H), 7.19 (s, 3H), 3.94 (s, 1H), 3.82-3.45 (m, 2H), 2.73 (s, 2H), 2.44 (s, 1H), 2.31 (d, J = 10.6, 1H), 2.15 (d, J = 13.2, 3H), 1.86 (d, J = 14.1, 1H), 1.70 (t, J = 9.7, 1H), 1.56 (s, 1H), 1.50-1.22 (m, 5H), 1.06 (s, 1H), 0.66 (dd, J = 13.3, 9.0, 1H). |
| 201 | benzyl({2-[9-(4-bromophenyl)-6-oxaspiro[4.5]decan-9-yl]ethyl})amine | 428.2 | δ 9.51 (s, 1H), 9.15 (s, 1H), 7.42 (d, J = 8.6, 2H), 7.30 (m, 3H), 7.16 (dd, J = 7.3, 2.1, 2H), 7.06 (d, J = 8.7, 2H), 3.68 (m, 4H), 2.62 (m, 1H), 2.19 (m, 1H), 2.04 (dd, J = 22.4, 13.9, 2H), 1.93 (m, 1H), 1.85 (m, 3H), 1.60 (m, 2H), 1.45 (ddd, J = 21.1, 16.1, 8.8, 5H), 1.25 (m, 2H), 0.77 (dt, J = 13.2, 8.7, 1H). |
| 202 | 2-amino-4-chloro-5-[({2-[(9R)-9-(pyridin-2-yl)-6-oxaspiro[4.5]decan-9-yl]ethyl}amino)methyl]thiophene-3-carbonitrile | 431 | 1H NMR (400 MHz, CD3CN) δ 8.57 (dd, J = 4.9, 1.0, 1H), 7.83 (m, 1H), 7.48 (d, J = 8.1, 1H), 7.31 (ddd, J = 7.5, 4.9, 0.9, 1H), 6.13 (s, 2H), 4.06 (s, 2H), 3.69 (m, 2H), 2.96 (m, 1H), 2.42 (m, 2H), 2.08 (m, 2H), 1.92 (m, 1H), 1.87 (d, J = 13.5, 1H), 1.57 (m, 8H), 1.10 (m, 1H), 0.71 (m, 1H). |
| 203 | {2-[(9R)-9-(4-fluorophenyl)-6-oxaspiro[4.5]decan-9-yl]ethyl}({2H,3H-thieno[3,4-b][1,4]dioxin-5-ylmethyl})amine | 432 | δ 7.21 (dd, J = 9.0, 5.1, 2H), 7.03 (t, J = 8.6, 2H), 6.33 (s, 1H), 4.13 (s, 4H), 3.90 (s, 2H), 3.74 (m, 2H), 3.01 (brs, 1H), 2.77 (t, J = 13.7, 1H), 2.35 (m, 1H), 2.17 (d, J = 14.0, 1H), 2.02 (dt, J = 14.7, 9.5, 2H), 1.89 (m, 2H), 1.78 (d, J = 10.1, 1H), 1.68 (ddd, J = 16.9, 10.6, 5.8, 2H), 1.46 (ddd, J = 17.8, 10.0, 5.9, 4H), 1.25 (m, 1H), 0.79 (dt, J = 13.5, 8.8, 1H). |
| 204 | [(4-phenylthiophen-2-yl)methyl]({2-[(9R)-9-(pyridin-2-yl)-6-oxaspiro[4.5]decan-9-yl]ethyl})amine | 433.1 | δ 9.71 (s, 4H), 8.53 (d, J = 5.0, 1H), 8.09 (t, J = 7.6, 1H), 7.62 (d, J = 8.1, 1H), 7.54-7.44 (m, 1H), 7.43-7.35 (m, 2H), 7.32-7.19 (m, 5H), 4.12 (s, 2H), 3.77-3.52 (m, 2H), 3.00-2.76 (m, 1H), 2.41 (dt, J = 25.0, 11.5, 2H), 2.18 (t, J = 17.1, 3H), 1.90 (d, J = 14.1, 1H), 1.73 (ddd, J = 19.6, 11.4, 6.9, 2H), 1.55 (dd, J = 10.0, 4.9, 1H), 1.48-1.26 (m, 4H), 1.04 (s, 1H), 0.72-0.56 (m, 1H). |
| 205 | [(5-phenylthiophen-2-yl)methyl]({2-[(9R)-9-(pyridin-2-yl)-6-oxaspiro[4.5]decan-9-yl]ethyl})amine | 433.1 | δ 9.74 (brs, 1H), 7.62 (d, J = 8.1, 1H), 7.50 (m, 3H), 7.37 (m, 2H), 7.31 (m, 1H), 7.12 (d, J = 3.7, 1H), 7.04 (d, J = 3.7, 1H), 5.23 (brs, 1H), 4.19 (mz, 2H), 3.72 (m, 2H), 3.02 (d, J = 6.5, 1H), 2.59 (t, J = 9.1, 1H), 2.39 (t, J = 10.1, 1H), 2.22 (dd, J = 29.2, 10.0, 3H), 1.96 (d, J = 14.1, 1H), 1.80 (t, J = 11.0, 2H), 1.62 (dd, J = 14.1, 7.4, 1H), 1.44 (ddd, J = 16.8, 16.4, 7.5, 4H), 1.13 (m, 1H), 0.73 (dt, J = 12.7, 8.8, 1H). |

TABLE 1-continued

Compounds with chemical name and characterization data

| Compound. | Name | MS (m/z) [M + H]⁺ | 1H NMR |
|---|---|---|---|
| 206 | [(5-methanesulfonylthiophen-2-yl)methyl]({2-[(9R)-9-(pyridin-2-yl)-6-oxaspiro[4.5]decan-9-yl]ethyl})amine | 435 | δ 8.67 (d, J = 5.0, 1H), 8.32 (t, J = 8.0, 1H), 7.79 (d, J = 7.9, 2H), 7.59 (d, J = 3.8, 1H), 7.22 (d, J = 3.8, 1H), 4.31 (d, J = 6.2, 2H), 3.84 (s, 1H), 3.74 (s, 1H), 3.18 (s, 1H), 3.05 (s, 2H), 2.54 (t, J = 10.3, 2H), 2.31 (d, J = 13.3, 2H), 2.14-2.00 (m, 2H), 1.89 (d, J = 13.8, 3H), 1.81-1.64 (m, 1H), 1.64-1.37 (m, 3H), 1.28 (s, 2H), 0.81 (d, J = 13.2, 1H). |
| 207 | [(4-bromothiophen-3-yl)methyl]({2-[(9R)-9-(pyridin-2-yl)-6-oxaspiro[4.5]decan-9-yl]ethyl})amine | 435 | δ 11.51 (s, 1H), 9.44 (s, 1H), 8.69-8.58 (m, 1H), 8.14 (td, J = 8.0, 1.6, 1H), 7.68-7.56 (m, 2H), 7.52 (d, J = 3.4, 1H), 7.21 (d, J = 3.3, 1H), 4.01 (s, 2H), 3.82-3.54 (m, 2H), 2.97 (td, J = 11.5, 5.7, 1H), 2.62-2.43 (m, 1H), 2.41-2.12 (m, 4H), 2.02-1.89 (m, 1H), 1.78 (ddd, J = 18.6, 11.9, 6.5, 2H), 1.60 (dt, J = 13.5, 7.7, 1H), 1.55-1.30 (m, 4H), 1.10 (d, J = 4.1, 0H), 0.67 (dt, J = 13.1, 8.9, 1H). |
| 208 | [(4-bromothiophen-2-yl)methyl]({2-[(9R)-9-(pyridin-2-yl)-6-oxaspiro[4.5]decan-9-yl]ethyl})amine | 435.1 | δ 8.59 (d, J = 4.0, 1H), 8.13 (t, J = 7.1, 1H), 7.65 (d, J = 8.2, 1H), 7.59 (m, 1H), 7.23 (d, J = 1.4, 1H), 7.04 (d, J = 1.2, 1H), 4.19 (s, 2H), 3.75 (m, 2H), 3.01 (m, 1H), 2.84 (s, 1H), 2.60 (m, 1H), 2.40 (m, 1H), 2.25 (d, J = 13.0, 3H), 1.97 (d, J = 14.0, 1H), 1.83 (d, J = 9.4, 2H), 1.67 (m, 1H), 1.48 (dd, J = 24.0, 15.8, 4H), 1.17 (brs, 1H), 0.77 (m, 1H). |
| 209 | [(5-bromothiophen-2-yl)methyl]({2-[(9R)-9-(pyridin-2-yl)-6-oxaspiro[4.5]decan-9-yl]ethyl})amine | 435.1 | δ 8.61 (d, J = 4.3, 1H), 8.14 (t, J = 7.9, 1H), 7.65 (d, J = 8.1, 1H), 7.60 (m, 1H), 6.94 (d, J = 3.8, 1H), 6.89 (d, J = 3.8, 1H), 4.14 (s, 2H), 3.76 (m, 3H), 2.99 (m, 1H), 2.58 (m, 1H), 2.38 (d, J = 9.8, 1H), 2.26 (d, J = 13.9, 3H), 1.97 (d, J = 14.1, 1H), 1.82 (t, J = 9.7, 2H), 1.67 (s, 1H), 1.47 (m, 4H), 1.16 (s, 1H), 0.75 (dt, J = 13.4, 9.2, 1H). |
| 210 | [(2-bromothiophen-3-yl)methyl]({2-[(9R)-9-(pyridin-2-yl)-6-oxaspiro[4.5]decan-9-yl]ethyl})amine | 436 | δ 8.66 (d, J = 5.3, 1H), 8.21 (d, J = 7.2, 1H), 7.85-7.58 (m, 2H), 7.33 (d, J = 5.7, 1H), 7.09 (d, J = 5.7, 1H), 4.02-3.63 (m, 3H), 3.10-2.97 (m, 2H), 2.61 (t, J = 9.1, 1H), 2.43 (t, J = 11.0, 1H), 2.30 (d, J = 13.6, 3H), 2.04 (s, 1H), 1.94-1.80 (m, 2H), 1.69 (s, 1H), 1.64-1.40 (m, 4H), 1.20 (s, 1H), 0.86-0.68 (m, 1H). |
| 211 | [(5-bromofuran-2-yl)methyl]({2-[(9R)-9-(4-fluorophenyl)-6-oxaspiro[4.5]decan-9-yl]ethyl})amine | 436 | δ 9.07 (d, J = 116.7, 2H), 7.16-7.06 (m, 2H), 7.01-6.89 (m, 2H), 6.25 (d, J = 3.4, 1H), 6.17 (s, 1H), 3.83 (s, 2H), 3.76-3.58 (m, 2H), 2.66 (s, 1H), 2.23 (s, 1H), 2.09 (d, J = 14.0, 1H), 2.04-1.96 (m, 1H), 1.95-1.66 (m, 4H), 1.66-1.50 (m, 2H), 1.50-1.28 (m, 4H), 1.28-1.13 (m, 1H), 0.71 (dt, J = 13.6, 8.8, 1H). |
| 212 | {2-[(9R)-9-(4-fluorophenyl)-6-oxaspiro[4.5]decan-9-yl]ethyl}({[6-(trifluoromethyl)pyridin-3-yl]methyl})amine | 437.2 | δ 8.63 (s, 1H), 7.83 (d, J = 8.3, 1H), 7.68 (d, J = 8.0, 1H), 7.29 (s, 1H), 7.21 (dd, J = 8.9, 5.1, 3H), 7.05 (s, 2H), 3.93 (s, 2H), 3.75 (dd, J = 11.3, 7.3, 2H), 2.84-2.58 (m, 1H), 2.44-2.04 (m, 10H), 2.02-1.75 (m, 5H), 1.74-1.56 (m, 3H), 1.59-1.33 (m, 5H), 1.33-1.19 (m, 1H), 0.78 (d, J = 13.6, 1H). |
| 213 | [(4-bromofuran-2-yl)methyl]({2-[(9R)-9-(4-fluorophenyl)-6-oxaspiro[4.5]decan-9-yl]ethyl})amine | 437.9 | δ 7.38 (d, J = 0.6, 1H), 7.28 (s, 1H), 7.22 (d, J = 5.2, 2H), 7.08 (d, J = 8.5, 2H), 3.75 (dd, J = 11.7, 7.1, 2H), 2.73 (s, 1H), 2.30 (d, J = 4.5, 2H), 2.17 (d, J = 13.5, 1H), 2.10 (d, J = 13.9, 1H), 2.05-1.95 (m, 1H), 1.94 (s, 2H), 1.79 (d, J = 9.8, 1H), 1.74-1.62 (m, 2H), 1.49 (dt, J = 16.4, 10.6, 4H), 1.28 (s, 2H), 0.80 (d, J = 13.7, 1H). |
| 214 | {2-[(9R)-9-(pyridin-2-yl)-6-oxaspiro[4.5]decan-9-yl]ethyl}({[5-(thiophen-2-yl)thiophen-2-yl]methyl})amine | 439 | δ 8.52 (d, J = 5.3, 1H), 7.96 (t, J = 7.9, 1H), 7.50 (d, J = 8.1, 1H), 7.40 (dd, J = 16.2, 10.4, 1H), 7.24-7.10 (m, 1H), 7.03 (dd, J = 3.6, 1.0, 1H), 6.98-6.81 (m, 3H), 4.07 (s, 2H), 3.80-3.49 (m, 2H), 2.90 (d, J = 11.1, 2H), 2.16 (s, 5H), 1.87 (d, J = 14.0, 1H), 1.71 (dd, J = 11.5, 7.2, 2H), 1.54 (d, J = 6.1, 1H), 1.36 (ddd, J = 16.8, 12.9, 6.1, 5H), 1.05 (s, 1H), 0.82-0.54 (m, 1H). |
| 215 | {2-[2,2-diethyl-4-(4-fluorophenyl)oxan-4-yl]ethyl}({[6-(trifluoromethyl)pyridin-3-yl]methyl})amine | 439.3 | δ 8.62 (s, 1H), 7.84 (d, J = 8.2, 1H), 7.66 (d, J = 8.2, 1H), 7.20 (m, 1H), 7.04 (s, 2H), 3.90 (s, 2H), 3.71 (d, J = 12.1, 2H), 2.77 (m, 1H), 2.19 (m, 3H), 1.98 (m, 1H), 1.68 (M, 3H), 1.40 (d, J = 7.6, 2H), 1.04 (s, 1H), 0.83 (t, J = 7.5, 4H), 0.54 (d, J = 7.3, 3H). |
| 216 | [(5-chloro-1-benzothiophen-3-yl)methyl]({2-[(9R)-9-(pyridin-2-yl)-6-oxaspiro[4.5]decan-9-yl]ethyl})amine | 442 | δ 8.61 (d, J = 4.9, 1H), 8.44 (s, 1H), 8.17 (s, 1H), 7.93 (d, J = 5.5, 1H), 7.69 (d, J = 8.1, 1H), 7.60 (s, 1H), 7.50 (d, J = 5.5, 1H), 7.28 (s, 1H), 3.82 (s, 3H), 3.17 (dd, J = 16.8, 10.9, 1H), 2.75 (t, J = 8.9, 1H), 2.47 (t, J = 9.7, 1H), 2.32 (d, J = 13.9, 3H), 2.10-1.98 (m, 1H), 1.87 (dd, J = 12.1, 7.1, 2H), 1.78-1.62 (m, 1H), 1.48 (dd, |

TABLE 1-continued

Compounds with chemical name and characterization data

| Compound. | Name | MS (m/z) [M + H]+ | 1H NMR |
|---|---|---|---|
| | | | J = 23.5, 18.9, 5H), 1.18 (s, 1H), 0.77 (dt, J = 13.2, 9.0, 1H). |
| 217 | [(5-bromo-4-methylthiophen-2-yl)methyl]({2-[(9R)-9-(pyridin-2-yl)-6-oxaspiro[4.5]decan-9-yl]ethyl})amine | 449 | δ 10.10-9.21 (m, 1H), 8.53 (d, J = 3.9, 1H), 7.90 (td, J = 7.9, 1.6, 1H), 7.45 (d, J = 8.1, 1H), 7.38 (dd, J = 7.0, 5.4, 1H), 6.69 (s, 1H), 4.02-3.86 (m, 2H), 3.74-3.55 (m, 2H), 2.85 (dd, J = 11.4, 5.9, 1H), 2.47-2.33 (m, 1H), 2.31-2.09 (m, 3H), 2.09-1.93 (m, 4H), 1.87 (d, J = 14.0, 1H), 1.69 (dt, J = 14.4, 6.1, 2H), 1.57 (d, J = 5.4, 1H), 1.38 (ddd, J = 26.7, 14.6, 8.4, 4H), 1.04 (s, 1H), 0.73-0.56 (m, 1H). |
| 218 | [(4-bromo-5-methylthiophen-2-yl)methyl]({2-[(9R)-9-(pyridin-2-yl)-6-oxaspiro[4.5]decan-9-yl]ethyl})amine | 449 | δ 8.72 (d, J = 4.9, 1H), 8.26 (d, J = 7.7, 1H), 7.74 (dd, J = 16.7, 7.1, 2H), 6.92 (s, 1H), 4.21 (d, 1H), 3.90-3.78 (m, 2H), 3.74 (d, J = 9.6, 1H), 3.02 (s, 1H), 2.51 (dd, J = 52.4, 11.0, 2H), 2.39-2.16 (m, 6H), 2.05 (d, J = 13.8, 1H), 1.87 (d, J = 9.5, 2H), 1.69 (s, 1H), 1.63-1.41 (m, 4H), 1.24 (d, J = 30.9, 1H), 0.81 (s, 1H). |
| 219 | [(3-bromo-5-methylthiophen-2-yl)methyl]({2-[(9R)-9-(pyridin-2-yl)-6-oxaspiro[4.5]decan-9-yl]ethyl})amine | 449 | δ 8.61 (d, J = 4.9, 1H), 8.02 (d, J = 7.9, 1H), 7.69-7.41 (m, 2H), 6.68 (d, J = 1.0, 1H), 4.23 (q, J = 14.2, 2H), 3.90-3.59 (m, 2H), 3.10 (s, 1H), 2.75 (m, 2H), 2.36-2.13 (m, 5H), 1.96 (d, J = 13.9, 1H), 1.82 (d, J = 9.9, 2H), 1.75-1.62 (m, 1H), 1.62-1.38 (m, 4H), 1.24-1.05 (m, 1H), 0.74 (d, J = 13.2, 1H). |
| 220 | [(4-bromo-3-methylthiophen-2-yl)methyl]({2-[(9R)-9-(pyridin-2-yl)-6-oxaspiro[4.5]decan-9-yl]ethyl})amine | 449 | δ 8.61 (d, J = 5.2, 1H), 8.09 (t, J = 7.7, 1H), 7.71-7.49 (m, 2H), 7.30 (s, 1H), 4.21 (d, J = 4.3, 2H), 4.00-3.59 (m, 2H), 3.05 (s, 1H), 2.64 (s, 1H), 2.31 (d, J = 14.5, 2H), 2.25 (d, J = 13.7, 2H), 2.18 (s, 3H), 1.96 (d, J = 13.9, 1H), 1.82 (dd, J = 12.0, 7.2, 2H), 1.68 (s, 1H), 1.61-1.40 (m, 4H), 1.17 (s, 1H), 0.92-0.64 (m, 1H). |
| 221 | {2-[4-(4-fluorophenyl)-1-oxaspiro[5.5]undecan-4-yl]ethyl}({[6-(trifluoromethyl)pyridin-3-yl]methyl})amine | 451.2 | δ 8.52 (s, 1H), 7.73 (d, J = 9.6, 1H), 7.57 (d, J = 8.0, 1H), 7.11 (dd, J = 9.0, 5.2, 2H), 6.94 (t, J = 8.4, 2H), 3.83 (s, 2H), 3.63 (d, J = 18.0, 2H), 2.69 (m, 1H), 2.12 (t, J = 13.9, 3H), 1.70 (m, 5H), 1.31 (d, J = 18.3, 4H), 1.03 (s, 4H), 0.57 (m, 1H). |
| 222 | [(4-bromothiophen-3-yl)methyl]({2-[(9R)-9-(4-fluorophenyl)-6-oxaspiro[4.5]decan-9-yl]ethyl})amine | 451.9 | δ 9.26 (d, J = 136.7, 2H), 7.39 (dd, J = 22.6, 19.3, 2H), 7.10 (dd, J = 8.8, 5.2, 2H), 6.92 (dd, J = 10.6, 6.6, 2H), 3.82 (s, 2H), 3.71-3.53 (m, 2H), 2.64 (s, 1H), 2.20 (s, 1H), 2.05 (d, J = 14.1, 1H), 1.97 (d, J = 13.9, 1H), 1.89 (td, J = 12.6, 4.6, 1H), 1.83-1.64 (m, 3H), 1.57 (ddd, J = 14.0, 9.6, 4.7, 2H), 1.49-1.25 (m, 4H), 1.17 (d, J = 13.2, 1H), 0.69 (dt, J = 13.8, 8.8, 1H). |
| 223 | [(4-bromothiophen-2-yl)methyl]({2-[(9R)-9-(4-fluorophenyl)-6-oxaspiro[4.5]decan-9-yl]ethyl})amine | 452.1 | δ 9.38 (d, J = 89.0, 2H), 7.16-7.03 (m, 3H), 6.96 (t, J = 8.6, 2H), 6.84 (d, J = 1.3, 1H), 3.86 (s, 2H), 3.70-3.55 (m, 2H), 2.62 (dd, J = 12.1, 7.7, 1H), 2.18 (dd, J = 11.9, 7.8, 1H), 2.02 (dd, J = 32.5, 14.0, 2H), 1.91-1.63 (m, 4H), 1.64-1.50 (m, 2H), 1.49-1.25 (m, 4H), 1.16 (dd, J = 14.0, 6.1, 1H), 0.69 (dt, J = 13.5, 8.8, 1H). |
| 224 | [(5-bromothiophen-2-yl)methyl]({2-[(9R)-9-(4-fluorophenyl)-6-oxaspiro[4.5]decan-9-yl]ethyl})amine | 452.1 | δ 9.31 (d, J = 92.6, 2H), 7.15-7.04 (m, 2H), 6.95 (t, J = 8.6, 2H), 6.82 (d, J = 3.8, 1H), 6.67 (d, J = 3.8, 1H), 3.82 (s, 2H), 3.70-3.53 (m, 2H), 3.44 (s, 1H), 2.62 (dd, J = 12.0, 7.6, 1H), 2.18 (dd, J = 11.8, 7.9, 1H), 2.02 (dd, J = 31.6, 14.0, 2H), 1.93-1.64 (m, 4H), 1.57 (ddd, J = 12.1, 8.5, 3.8, 2H), 1.52-1.25 (m, 4H), 1.16 (dd, J = 14.9, 5.1, 1H), 0.69 (dt, J = 13.6, 8.8, 1H). |
| 225 | dibenzyl({2-[(9R)-9-(4-fluorophenyl)-6-oxaspiro[4.5]decan-9-yl]ethyl})amine | 458.3 | δ 7.27 (m, 17H), 7.00 (dd, J = 8.9, 5.2, 2H), 6.86 (t, J = 8.6, 2H), 4.24 (s, 2H), 3.90 (m, 2H), 3.55 (d, J = 3.4, 2H), 2.59 (m, 1H), 2.22 (m, 12H), 1.86 (dd, J = 75.2, 14.8, 7H), 1.59 (dd, J = 44.5, 9.1, 2H), 1.38 (m, 6H), 1.18 (s, 1H), 1.11 (s, 1H), 0.68 (m, 1H). |
| 226 | dibenzyl({2-[2,2-diethyl-4-(4-fluorophenyl)oxan-4-yl]ethyl})amine | 460.3 | δ 7.27 (d, J = 34.4, 7H), 7.18 (s, 4H), 6.98 (dd, J = 8.9, 5.2, 2H), 6.84 (t, J = 8.6, 2H), 4.25 (s, 2H), 3.85 (d, J = 46.4, 2H), 3.53 (m, 2H), 2.57 (d, J = 4.7, 2H), 2.12 (d, J = 4.0, 2H), 1.97 (m, 3H), 1.73 (d, J = 4.8, 1H), 1.44 (s, 1H), 1.38 (dd, J = 13.8, 7.5, 3H), 1.23 (m, 1H), 0.90 (m, 1H), 0.70 (dt, J = 10.8, 7.4, 4H), 0.40 (t, J = 7.4, 3H). |
| 227 | [(4-bromo-3-methylthiophen-2-yl)methyl]({2-[(9R)-9- | 465.9 | δ 7.19 (dd, J = 8.9, 5.1, 2H), 7.04 (t, J = 8.6, 2H), 3.94 (d, J = 16.3, 2H), 3.72 (m, 2H), 2.72 (dd, J = 13.8, 6.5, 1H), 2.31 (m, 1H), 2.15 (d, J = 12.1, 2H), 2.07 (s, 3H), |

TABLE 1-continued

Compounds with chemical name and characterization data

| Compound. | Name | MS (m/z) [M + H]+ | 1H NMR |
|---|---|---|---|
| | (4-fluorophenyl)-6-oxaspiro[4.5]decan-9-yl]ethyl})amine | | 1.90 (m, 5H), 1.65 (m, 2H), 1.47 (m, 4H), 1.25 (s, 1H), 0.78 (m, 1H). |
| 228 | [(4-bromo-5-methylthiophen-2-yl)methyl]({2-[(9R)-9-(4-fluorophenyl)-6-oxaspiro[4.5]decan-9-yl]ethyl})amine | 465.9 | δ 9.06 (d, J = 100.4, 2H), 7.15-7.04 (m, 2H), 6.95 (s, 2H), 6.68 (s, 1H), 3.80 (s, 2H), 3.73-3.57 (m, 2H), 2.64 (s, 1H), 2.21 (s, 4H), 2.07 (d, J = 14.1, 1H), 1.99 (d, J = 13.9, 1H), 1.94-1.64 (m, 4H), 1.64-1.51 (m, 2H), 1.51-1.26 (m, 4H), 1.17 (dd, J = 13.9, 6.3, 1H), 0.70 (dt, J = 13.7, 8.8, 1H). |
| 229 | [(3-bromo-5-methylthiophen-2-yl)methyl]({2-[(9R)-9-(4-fluorophenyl)-6-oxaspiro[4.5]decan-9-yl]ethyl})amine | 466 | δ 7.20 (m, 2H), 7.01 (dd, J = 11.1, 6.1, 2H), 6.61 (d, J = 1.1, 1H), 4.01 (s, 2H), 3.72 (m, 2H), 2.75 (m, 1H), 2.61 (brs, 1H), 2.41 (d, J = 0.9, 3H), 2.32 (m, 1H), 2.15 (d, J = 14.2, 1H), 2.07 (d, J = 13.9, 1H), 1.99 (m, 1H), 1.89 (m, 2H), 1.77 (m, 1H), 1.67 (ddd, J = 17.0, 10.6, 5.6, 2H), 1.46 (m, 4H), 1.25 (m, 1H), 0.78 (dt, J = 13.9, 8.9, 1H). |
| 230 | [(5-bromo-4-methylthiophen-2-yl)methyl]({2-[(9R)-9-(4-fluorophenyl)-6-oxaspiro[4.5]decan-9-yl]ethyl})amine | 466.9 | δ 7.20 (d, J = 5.2, 2H), 7.06 (d, J = 8.5, 2H), 6.85 (t, J = 3.6, 1H), 3.91 (s, 2H), 3.81-3.62 (m, 2H), 2.71 (s, 1H), 2.28 (s, 1H), 2.07 (s, 6H), 1.91 (d, J = 13.8, 2H), 1.79 (d, J = 10.3, 1H), 1.69 (ddd, J = 14.1, 9.4, 4.7, 2H), 1.59-1.37 (m, 4H), 1.28 (s, 1H), 0.80 (dd, J = 8.8, 4.9, 1H). |
| 231 | {2-[2,2-diethyl-4-(4-fluorophenyl)oxan-4-yl]ethyl}bis(thiophen-2-ylmethyl)amine | 472.2 | δ 7.31 (d, J = 4.9, 2H), 7.07 (dd, J = 8.9, 5.2, 2H), 6.99 (s, 2H), 6.95 (d, J = 4.5, 2H), 6.89 (t, J = 8.6, 2H), 4.24 (s, 2H), 3.58 (dt, J = 23.8, 6.6, 2H), 2.66 (m, 1H), 2.06 (d, J = 14.0, 4H), 1.82 (m, 1H), 1.51 (d, J = 14.3, 3H), 1.25 (m, 2H), 0.94 (dd, J = 14.6, 7.4, 1H), 0.74 (t, J = 7.5, 4H), 0.42 (t, J = 7.4, 3H). |
| 232 | [(4,5-dibromothiophen-2-yl)methyl]({2-[(9R)-9-(pyridin-2-yl)-6-oxaspiro[4.5]decan-9-yl]ethyl})amine | 514.8 | δ 8.61 (dd, J = 5.3, 1.3, 1H), 8.13 (td, J = 8.0, 1.7, 1H), 7.64 (d, J = 8.2, 1H), 7.60 (m, 1H), 6.94 (s, 1H), 4.40 (brs, 1H), 4.11 (s, 2H), 3.77 (ddd, J = 36.9, 13.7, 7.2, 2H), 2.98 (td, J = 11.3, 6.0, 1H), 2.54 (td, J = 11.2, 4.3, 1H), 2.38 (m, 1H), 2.22 (m, 3H), 1.98 (d, J = 14.0, 1H), 1.83 (dt, J = 18.5, 9.2, 2H), 1.68 (m, 1H), 1.48 (m, 4H), 1.21 (d, J = 37.1, 1H), 0.75 (dt, J = 13.1, 9.0, 1H). |
| 233 | [(3,4-dibromothiophen-2-yl)methyl]({2-[(9R)-9-(pyridin-2-yl)-6-oxaspiro[4.5]decan-9-yl]ethyl})amine | 514.8 | δ 8.39 (d, J = 4.0, 1H), 7.67 (t, J = 7.0, 1H), 7.38 (s, 1H), 7.28 (d, J = 8.1, 1H), 7.18 (s, 1H), 4.22 (d, J = 18.2, 2H), 3.65 (dd, J = 11.2, 7.1, 2H), 3.09-2.85 (m, 1H), 2.60 (s, 1H), 2.22 (dd, J = 25.9, 13.8, 2H), 2.10-1.83 (m, 2H), 1.87-1.50 (m, 4H), 1.36 (dd, J = 18.7, 10.7, 3H), 1.02 (s, 2H), 0.68-0.50 (m, 1H). |
| 234 | [(4,5-dibromothiophen-2-yl)methyl]({2-[(9R)-9-(4-fluorophenyl)-6-oxaspiro[4.5]decan-9-yl]ethyl})amine | 531.8 | δ 7.20 (m, 2H), 7.05 (t, J = 8.6, 2H), 6.81 (s, 1H), 3.91 (s, 2H), 3.74 (m, 2H), 3.60 (brs, 1H), 2.74 (m, 1H), 2.31 (td, J = 12.1, 4.7, 1H), 2.15 (d, J = 14.1, 1H), 2.08 (d, J = 13.9, 1H), 1.88 (m, 4H), 1.67 (ddd, J = 15.1, 10.2, 5.0, 2H), 1.46 (ddd, J = 27.4, 14.5, 7.2, 4H), 1.24 (dd, J = 10.5, 5.6, 1H), 0.78 (dt, J = 13.5, 8.8, 1H). |
| 235 | [(3,4-dibromothiophen-2-yl)methyl]({2-[(9R)-9-(4-fluorophenyl)-6-oxaspiro[4.5]decan-9-yl]ethyl})amine | 531.8 | δ 7.35 (s, 1H), 7.11-7.06 (m, 2H), 6.94 (dd, J = 14.3, 5.7, 2H), 4.05 (s, 2H), 3.75-3.56 (m, 2H), 2.70 (dd, J = 11.9, 7.4, 1H), 2.25 (dd, J = 11.7, 7.3, 1H), 2.08 (d, J = 14.7, 1H), 1.99 (d, J = 13.9, 1H), 1.95-1.65 (m, 4H), 1.65-1.50 (m, 2H), 1.50-1.29 (m, 4H), 1.16 (dd, J = 14.8, 7.3, 1H), 0.70 (dt, J = 13.6, 8.8, 1H). |
| 236 | [(2-fluorophenyl)methyl]({2-[(9R)-9-(pyridin-2-yl)-6-oxaspiro[4.5]decan-9-yl]ethyl})amine | 369 | δ 8.82 (s, 2H), 8.61 (dd, J = 4.8, 1.2, 1H), 7.85 (td, J = 7.8, 1.8, 1H), 7.51 (m, 3H), 7.30 (m, 3H), 5.22 (s, 2H), 4.12 (d, J = 5.3, 2H), 3.66 (m, 2H), 2.90 (d, J = 4.5, 1H), 2.39 (m, 3H), 2.08 (td, J = 12.8, 4.4, 1H), 1.54 (m, 7H), 1.02 (dd, J = 12.3, 5.8, 1H), 0.68 (dt, J = 13.3, 8.9, 1H). |
| 237 | [(2-bromophenyl)methyl]({2-[(9R)-9-(pyridin-2-yl)-6-oxaspiro[4.5]decan-9-yl]ethyl})amine | 429 | δ 8.93 (s, 2H), 8.60 (dd, J = 4.8, 1.2, 1H), 7.83 (td, J = 7.8, 1.9, 1H), 7.71 (dd, J = 8.0, 1.1, 1H), 7.50 (m, 3H), 7.33 (m, 2H), 4.18 (s, 2H), 3.65 (m, 2H), 2.94 (s, 1H), 2.43 (t, J = 12.2, 3H), 2.11 (td, J = 12.8, 4.4, 1H), 1.89 (m, 2H), 1.55 (m, 7H), 1.01 (m, 1H), 0.67 (dt, J = 13.3, 8.9, 1H). |
| 238 | [(2-chlorophenyl)methyl]({2-[(9R)-9-(pyridin-2-yl)-6-oxaspiro[4.5]decan-9-yl]ethyl})amine | 385 | δ 8.75 (dd, J = 5.4, 1.2, 1H), 8.52 (s, 3H), 8.22 (td, J = 8.0, 1.7, 1H), 7.77 (d, J = 8.2, 1H), 7.67 (ddd, J = 7.5, 5.4, 0.9, 1H), 7.42 (m, 4H), 4.20 (d, J = 14.0, 2H), 3.72 (m, 2H), 3.05 (td, J = 12.0, 5.1, 1H), 2.53 (td, J = 12.0, 4.4, 1H), 2.36 (m, 3H), 2.17 (m, 1H), 2.01 (d, J = 14.2, 1H), |

TABLE 1-continued

Compounds with chemical name and characterization data

| Compound. | Name | MS (m/z) [M + H]+ | 1H NMR |
|---|---|---|---|
| | | | 1.79 (ddd, J = 9.3, 6.7, 3.4, 2H), 1.52 (m, 5H), 1.17 (m, 1H), 0.78 (dt, J = 12.9, 8.8, 1H). |
| 239 | [(2-methylphenyl)methyl]({2-[(9R)-9-(pyridin-2-yl)-6-oxaspiro[4.5]decan-9-yl]ethyl})amine | 365.1 | δ 8.81 (dd, J = 5.7, 1.3, 1H), 8.43 (td, J = 8.0, 1.7, 1H), 7.98 (s, 1H), 7.92 (d, J = 8.2, 1H), 7.86 (ddd, J = 7.6, 5.7, 1.0, 1H), 7.27 (m, 2H), 7.18 (m, 2H), 3.98 (s, 2H), 3.75 (m, 2H), 2.98 (d, J = 4.4, 1H), 2.44 (m, 2H), 2.36 (m, 5H), 2.25 (dd, J = 13.5, 5.4, 1H), 2.07 (d, J = 14.3, 1H), 1.84 (m, 2H), 1.55 (m, 5H), 1.23 (m, 1H), 0.83 (dt, J = 13.0, 8.8, 1H). |
| 240 | {2-[(9R)-9-(pyridin-2-yl)-6-oxaspiro[4.5]decan-9-yl]ethyl}({[2-(trifluoromethyl)phenyl]methyl})amine | 419.1 | δ 8.71 (dd, J = 5.3, 1.2, 1H), 8.18 (td, J = 8.0, 1.7, 1H), 7.79 (d, J = 7.8, 1H), 7.75 (d, J = 8.2, 1H), 7.70 (m, 2H), 7.62 (ddd, J = 13.7, 6.8, 1.2, 2H), 6.71 (s, 3H), 4.23 (s, 2H), 3.75 (ddd, J = 17.6, 8.8, 3.7, 2H), 3.08 (m, 1H), 2.56 (m, 1H), 2.36 (m, 3H), 2.19 (m, 1H), 1.79 (dq, J = 7.2, 4.7, 2H), 1.53 (m, 5H), 1.19 (m, 1H), 0.79 (m, 1H). |
| 241 | 2-[({2-[(9R)-9-(pyridin-2-yl)-6-oxaspiro[4.5]decan-9-yl]ethyl}amino)methyl]phenol | 367 | δ 8.74 (m, 1H), 8.21 (td, J = 8.0, 1.8, 1H), 7.75 (d, J = 8.2, 1H), 7.66 (ddd, J = 7.6, 5.4, 1.0, 1H), 7.27 (m, 1H), 7.20 (dd, J = 7.6, 1.6, 1H), 6.90 (m, 4H), 4.05 (s, 2H), 3.72 (ddd, J = 12.4, 11.1, 5.4, 2H), 2.96 (d, J = 5.2, 1H), 2.35 (m, 4H), 2.13 (m, 1H), 1.78 (m, 2H), 1.51 (m, 5H), 1.15 (dd, J = 4.0, 2.0, 1H), 0.78 (m, 1H). |
| 242 | [(2-methoxyphenyl)methyl]({2-[(9R)-9-(pyridin-2-yl)-6-oxaspiro[4.5]decan-9-yl]ethyl})amine | 381.1 | δ 9.66 (s, 3H), 8.80 (dd, J = 5.5, 1.2, 1H), 8.31 (td, J = 8.0, 1.7, 1H), 7.77 (m, 3H), 7.42 (ddd, J = 15.9, 8.0, 1.6, 1H), 7.25 (dd, J = 7.5, 1.6, 1H), 7.04 (m, 1H), 6.96 (td, J = 7.5, 1.0, 1H), 4.04 (s, 2H), 3.85 (m, 4H), 3.73 (m, 2H), 2.97 (d, J = 4.9, 1H), 2.37 (m, 4H), 2.19 (dd, J = 13.2, 5.2, 1H), 2.04 (d, J = 14.1, 1H), 1.81 (ddd, J = 14.0, 9.5, 4.5, 2H), 1.81 (ddd, J = 14.0, 9.5, 4.5, 2H), 1.54 (m, 5H), 1.18 (m, 1H), 0.80 (m, 1H). |
| 243 | [(3-fluorophenyl)methyl]({2-[(9R)-9-(pyridin-2-yl)-6-oxaspiro[4.5]decan-9-yl]ethyl})amine | 369 | δ 8.77 (dd, J = 5.4, 1.5, 1H), 8.38 (s, 1H), 8.29 (td, J = 8.0, 1.7, 1H), 7.82 (d, J = 8.2, 1H), 7.74 (dd, J = 7.1, 6.1, 1H), 7.43 (ddd, J = 13.8, 7.5, 1.4, 1H), 7.19 (m, 3H), 6.90 (s, 3H), 4.03 (d, J = 2.0, 2H), 3.74 (m, 2H), 2.98 (dt, J = 11.4, 5.6, 1H), 2.42 (ddd, J = 29.2, 13.0, 3.8, 4H), 2.18 (m, 1H), 2.03 (d, J = 14.1, 1H), 1.81 (ddd, J = 13.9, 9.4, 4.5, 2H), 1.55 (m, 5H), 1.20 (ddd, J = 9.9, 6.9, 2.4, 1H), 0.80 (dt, J = 12.9, 8.8, 1H). |
| 244 | [(3-bromophenyl)methyl]({2-[(9R)-9-(pyridin-2-yl)-6-oxaspiro[4.5]decan-9-yl]ethyl})amine | 431 | δ 8.75 (dd, J = 5.4, 1.2, 1H), 8.41 (s, 1H), 8.25 (td, J = 8.0, 1.8, 1H), 7.79 (d, J = 8.2, 1H), 7.70 (ddd, J = 7.6, 5.5, 0.9, 1H), 7.59 (m, 2H), 7.36 (ddd, J = 22.8, 10.9, 4.6, 2H), 6.76 (s, 3H), 4.01 (d, J = 2.3, 2H), 3.74 (ddd, J = 12.3, 11.0, 5.4, 2H), 2.97 (d, J = 5.0, 1H), 2.38 (m, 4H), 2.16 (m, 1H), 2.00 (m, 1H), 1.79 (ddd, J = 8.6, 7.8, 4.7, 2H), 1.53 (m, 5H), 1.20 (m, 1H), 0.80 (m, 1H). |
| 245 | [(3-chlorophenyl)methyl]({2-[(9R)-9-(pyridin-2-yl)-6-oxaspiro[4.5]decan-9-yl]ethyl})amine | 385 | δ 8.72 (dd, J = 5.4, 1.1, 1H), 8.57 (s, 1H), 8.19 (td, J = 8.0, 1.8, 1H), 7.74 (d, J = 8.2, 1H), 7.64 (ddd, J = 7.6, 5.4, 0.9, 1H), 7.37 (m, 5H), 3.99 (d, J = 2.3, 2H), 3.70 (m, 2H), 2.95 (m, 1H), 2.36 (m, 4H), 2.12 (td, J = 12.9, 5.1, 1H), 1.76 (ddd, J = 14.2, 9.3, 5.1, 2H), 1.50 (m, 5H), 0.77 (dt, J = 13.0, 8.9, 1H). |
| 246 | [(3-methylphenyl)methyl]({2-[(9R)-9-(pyridin-2-yl)-6-oxaspiro[4.5]decan-9-yl]ethyl})amine | 365 | δ 8.81 (dd, J = 5.7, 1.3, 1H), 8.43 (td, J = 8.0, 1.7, 1H), 7.98 (s, 1H), 7.92 (d, J = 8.2, 1H), 7.86 (ddd, J = 7.6, 5.7, 1.0, 1H), 7.24 (dq, J = 19.8, 7.4, 4H), 3.98 (s, 2H), 3.75 (m, 2H), 2.98 (d, J = 4.4, 1H), 2.44 (m, 2H), 2.36 (m, 5H), 2.25 (dd, J = 13.5, 5.4, 1H), 2.07 (d, J = 14.3, 1H), 1.84 (m, 2H), 1.55 (m, 5H), 1.23 (m, 1H), 0.83 (dt, J = 13.0, 8.8, 1H). |
| 247 | methyl 3-[({2-[(9R)-9-(pyridin-2-yl)-6-oxaspiro[4.5]decan-9-yl]ethyl}amino)methyl]benzoate | 409.1 | δ 8.78 (dd, J = 5.5, 1.3, 1H), 8.33 (td, J = 8.0, 1.7, 1H), 8.24 (s, 1H), 8.04 (m, 2H), 7.85 (d, J = 8.2, 1H), 7.78 (m, 1H), 7.63 (m, 2H), 7.55 (d, J = 7.7, 1H), 4.10 (d, J = 2.0, 2H), 3.90 (s, 3H), 3.75 (ddd, J = 12.2, 11.0, 5.4, 2H), 3.00 (dd, J = 11.5, 7.1, 1H), 2.40 (m, 4H), 2.21 (m, 1H), 2.04 (d, J = 14.2, 1H), 1.83 (ddd, J = 13.9, 9.2, 4.3, 2H), 1.51 (dddd, J = 17.6, 10.1, 8.1, 3.0, 5H); 1.21 (s, 1H), 0.82 (dd, J = 15.6, 6.6, 1H). |

TABLE 1-continued

Compounds with chemical name and characterization data

| Compound. | Name | MS (m/z) [M + H]+ | 1H NMR |
|---|---|---|---|
| 248 | 3-[({2-[(9R)-9-(pyridin-2-yl)-6-oxaspiro[4.5]decan-9-yl]ethyl}amino)methyl]phenol | 367 | δ 8.77 (dd, J = 5.5, 1.2, 1H), 8.30 (td, J = 8.0, 1.7, 1H), 7.81 (s, 1H), 7.75 (ddd, J = 7.6, 5.5, 1.0, 1H), 7.23 (t, J = 8.1, 1H), 6.85 (dt, J = 3.2, 2.1, 3H), 6.65 (s, 3H), 3.96 (s, 2H), 3.73 (dd, J = 13.8, 7.3, 2H), 2.96 (s, 1H), 2.36 (m, 4H), 2.15 (ddd, J = 9.9, 8.5, 4.7, 1H), 2.03 (d, J = 14.2, 1H), 1.80 (dt, J = 11.2, 4.8, 2H), 1.52 (ddd, J = 21.7, 12.8, 7.4, 5H), 1.20 (m, 1H), 0.80 (d, J = 13.3, 1H). |
| 249 | {2-[(9R)-9-(pyridin-2-yl)-6-oxaspiro[4.5]decan-9-yl]ethyl}({[3-(trifluoromethyl)phenyl]methyl})amine | 419.1 | δ 8.66 (m, 1H), 8.07 (td, J = 7.9, 1.8, 1H), 7.72 (m, 2H), 7.65 (m, 2H), 7.54 (m, 2H), 6.22 (s, 2H), 4.08 (d, J = 3.1, 2H), 3.71 (m, 2H), 2.97 (d, J = 5.0, 1H), 2.34 (dddd, J = 25.4, 19.6, 16.7, 4.4, 4H), 2.09 (m, 1H), 1.74 (m, 2H), 1.49 (m, 5H), 0.76 (m, 1H). |
| 250 | N-methyl-5-[({2-[(9R)-9-(pyridin-2-yl)-6-oxaspiro[4.5]decan-9-yl]ethyl}amino)methyl]thiophene-2-carboxamide | 414.1 | δ 8.78 (dd, J = 5.6, 1.3, 1H), 8.36 (td, J = 8.0, 1.7, 1H), 7.86 (d, J = 8.2, 1H), 7.79 (ddd, J = 7.6, 5.6, 1.0, 1H), 7.38 (d, J = 3.8, 1H), 7.14 (d, J = 3.8, 1H), 7.06 (d, J = 3.9, 1H), 4.21 (s, 2H), 3.72 (m, 2H), 2.97 (td, J = 12.0, 5.1, 1H), 2.84 (d, J = 4.7, 3H), 2.34 (m, 4H), 2.16 (m, 1H), 2.03 (d, J = 14.2, 1H), 1.80 (dd, J = 12.2, 3.0, 2H), 1.50 (m, 5H), 1.20 (m, 1H), 0.82 (s, 1H). |
| 251 | N-ethyl-5-[({2-[(9R)-9-(pyridin-2-yl)-6-oxaspiro[4.5]decan-9-yl]ethyl}amino)methyl]thiophene-2-carboxamide | 428.1 | δ 8.78 (dd, J = 5.6, 1.2, 1H), 8.35 (td, J = 8.0, 1.7, 1H), 7.86 (d, J = 8.2, 1H), 7.79 (ddd, J = 7.6, 5.6, 0.9, 1H), 7.40 (d, J = 3.8, 1H), 7.14 (t, J = 10.7, 2H), 6.20 (s, 4H), 4.21 (d, J = 1.2, 2H), 3.72 (m, 2H), 3.34 (m, 2H), 2.97 (m, 1H), 2.39 (m, 4H), 2.18 (m, 1H), 2.03 (d, J = 14.2, 1H), 1.81 (m, 2H), 1.52 (m, 5H), 1.19 (m, 4H), 0.80 (m, 1H). |
| 252 | N-methyl-3-[({2-[(9R)-9-(pyridin-2-yl)-6-oxaspiro[4.5]decan-9-yl]ethyl}amino)methyl]benzamide | 408.1 | δ 8.75 (dd, J = 5.4, 1.2, 1H), 8.24 (td, J = 8.0, 1.7, 1H), 7.89 (s, 1H), 7.77 (m, 2H), 7.69 (ddd, J = 7.6, 5.5, 0.9, 1H), 7.49 (ddd, J = 18.3, 10.6, 4.6, 2H), 7.33 (s, 1H), 4.07 (s, 2H), 3.73 (m, 2H), 2.98 (m, 1H), 2.88 (d, J = 4.6, 3H), 2.47 (t, J = 10.7, 1H), 2.36 (dd, J = 12.8, 7.5, 3H), 2.16 (d, J = 4.8, 1H), 1.79 (m, 2H), 1.50 (ddd, J = 18.7, 13.3, 6.9, 5H), 1.19 (ddd, J = 8.3, 7.0, 1.8, 1H), 0.80 (d, J = 13.3, 1H). |
| 253 | N-ethyl-3-[({2-[(9R)-9-(pyridin-2-yl)-6-oxaspiro[4.5]decan-9-yl]ethyl}amino)methyl]benzamide | 422.1 | δ 8.70 (dd, J = 5.3, 1.2, 1H), 8.43 (s, 1H), 8.14 (td, J = 7.9, 1.8, 1H), 7.89 (d, J = 1.4, 1H), 7.76 (dt, J = 7.3, 1.6, 1H), 7.71 (d, J = 8.2, 1H), 7.59 (ddd, J = 7.6, 5.3, 0.9, 1H), 7.46 (m, 2H), 7.37 (s, 1H), 6.55 (s, 3H), 4.05 (s, 2H), 3.70 (m, 2H), 3.36 (qd, J = 7.2, 5.7, 2H), 2.96 (d, J = 7.9, 1H), 2.45 (t, J = 10.2, 1H), 2.32 (dd, J = 21.2, 8.7, 3H), 2.11 (d, J = 5.2, 1H), 1.77 (m, 2H), 1.47 (m, 5H), 1.19 (m, 4H), 0.76 (d, J = 13.3, 1H). |
| 254 | [(4-methoxyphenyl)methyl]({2-[(9R)-9-(pyridin-2-yl)-6-oxaspiro[4.5]decan-9-yl]ethyl})amine | 381.1 | δ 9.09 (d, J = 86.1, 2H), 8.69 (d, J = 5.0, 1H), 8.29 (t, J = 7.7, 1H), 8.06 (m, 3H), 7.75 (m, 2H), 7.20 (d, J = 8.6, 2H), 6.81 (d, J = 8.6, 2H), 3.89 (s, 2H), 3.79 (m, 4H), 3.66 (m, 1H), 2.96 (s, 1H), 2.43 (dd, J = 23.4, 11.5, 2H), 2.27 (t, J = 16.0, 3H), 2.01 (m, 1H), 1.83 (dd, J = 19.3, 9.5, 2H), 1.66 (m, 1H), 1.47 (m, 4H), 1.14 (d, J = 7.0, 1H), 0.75 (m, 1H). |
| 255 | 4-[({2-[(9R)-9-(pyridin-2-yl)-6-oxaspiro[4.5]decan-9-yl]ethyl}amino)methyl]phenol | 367 | δ 8.76 (dd, J = 5.5, 1.2, 1H), 8.26 (m, 1H), 7.80 (d, J = 8.2, 1H), 7.72 (ddd, J = 7.6, 5.5, 0.9, 1H), 7.65 (s, 1H), 7.22 (m, 2H), 6.82 (m, 2H), 3.93 (s, 2H), 3.73 (dd, J = 10.7, 7.6, 2H), 2.94 (dd, J = 11.1, 5.9, 1H), 2.36 (m, 4H), 2.13 (m, 1H), 2.01 (m, 1H), 1.80 (d, J = 3.6, 2H), 1.51 (dd, J = 9.7, 5.6, 5H), 1.19 (m, 1H), 0.81 (s, 1H). |
| 256 | [(2,3-difluorophenyl)methyl]({2-[(9R)-9-(pyridin-2-yl)-6-oxaspiro[4.5]decan-9-yl]ethyl})amine | 387 | δ 8.75 (dd, J = 5.4, 1.3, 1H), 8.26 (td, J = 8.0, 1.7, 1H), 7.80 (d, J = 8.2, 1H), 7.71 (ddd, J = 7.5, 5.5, 0.9, 1H), 7.34 (dtd, J = 10.0, 7.9, 1.9, 1H), 7.21 (m, 4H), 4.11 (s, 2H), 3.72 (m, 2H), 3.02 (td, J = 12.0, 5.1, 1H), 2.49 (td, J = 12.1, 4.3, 1H), 2.35 (m, 3H), 2.16 (m, 1H), 2.01 (d, J = 14.1, 1H), 1.79 (ddd, J = 11.2, 9.4, 4.1, 2H), 1.52 (m, 5H), 1.17 (m, 1H), 0.78 (dt, J = 12.9, 8.8, 1H). |
| 257 | [(2,4-difluorophenyl)methyl]({2-[(9R)-9-(pyridin-2-yl)-6-oxaspiro[4.5]decan-9-yl]ethyl})amine | 387 | δ 8.79 (dd, J = 5.5, 1.3, 1H), 8.38 (s, 1H), 8.32 (m, 1H), 7.84 (d, J = 8.2, 1H), 7.76 (ddd, J = 7.6, 5.5, 0.9, 1H), 7.50 (dd, J = 14.8, 8.3, 1H), 7.03 (m, 2H), 4.08 (s, 2H), 3.74 (m, 2H), 3.02 (td, J = 12.0, 5.0, 1H), 2.42 (m, 4H), 2.18 (m, 1H), |

TABLE 1-continued

Compounds with chemical name and characterization data

| Compound. | Name | MS (m/z) [M + H]+ | 1H NMR |
|---|---|---|---|
| | oxaspiro[4.5]decan-9-yl]ethyl})amine | | 2.03 (d, J = 14.2, 1H), 1.82 (ddd, J = 14.2, 9.6, 4.5, 2H), 1.56 (m, 5H), 1.19 (ddd, J = 7.0, 6.2, 2.8, 1H), 0.80 (dt, J = 12.9, 8.8, 1H). |
| 258 | [(2,5-difluorophenyl)methyl]({2-[(9R)-9-(pyridin-2-yl)-6-oxaspiro[4.5]decan-9-yl]ethyl})amine | 387 | δ 8.74 (dd, J = 5.4, 1.2, 1H), 8.26 (td, J = 8.0, 1.7, 1H), 7.72 (m, 2H), 7.21 (dddd, J = 8.4, 7.0, 4.8, 1.8, 3H), 6.45 (s, 3H), 4.07 (s, 2H), 3.73 (ddd, J = 12.2, 11.1, 5.5, 2H), 3.02 (d, J = 5.2, 1H), 2.49 (d, J = 4.3, 1H), 2.36 (dt, J = 11.8, 4.5, 3H), 2.18 (dd, J = 12.3, 5.2, 1H), 2.00 (m, 1H), 1.79 (ddd, J = 13.9, 9.3, 4.4, 2H), 1.49 (m, 5H), 1.18 (m, 1H), 0.78 (d, J = 13.3, 1H). |
| 259 | [(2,6-difluorophenyl)methyl]({2-[(9R)-9-(pyridin-2-yl)-6-oxaspiro[4.5]decan-9-yl]ethyl})amine | 387.1 | δ 8.79 (dd, J = 5.6, 1.3, 1H), 8.36 (m, 1H), 8.20 (s, 4H), 7.86 (d, J = 8.2, 1H), 7.79 (ddd, J = 7.6, 5.6, 1.0, 1H), 7.50 (tt, J = 8.5, 6.6, 1H), 7.04 (m, 2H), 4.13 (s, 2H), 3.72 (m, 2H), 3.05 (td, J = 12.0, 5.1, 1H), 2.52 (td, J = 12.1, 4.2, 1H), 2.37 (m, 3H), 2.19 (m, 1H), 2.04 (d, J = 14.2, 1H), 1.81 (m, 2H), 1.53 (m, 5H), 1.18 (m, 1H), 0.79 (dt, J = 12.8, 8.8, 1H). |
| 260 | [(3,4-difluorophenyl)methyl]({2-[(9R)-9-(pyridin-2-yl)-6-oxaspiro[4.5]decan-9-yl]ethyl})amine | 387.1 | δ 8.84 (s, 1H), 8.79 (dd, J = 5.6, 1.3, 1H), 8.41 (td, J = 8.0, 1.6, 1H), 8.25 (s, 1H), 7.86 (ddd, J = 13.3, 7.6, 7.0, 2H), 7.30 (m, 3H), 3.99 (d, J = 1.7, 2H), 3.73 (m, 2H), 2.96 (dd, J = 12.1, 7.4, 1H), 2.38 (m, 4H), 2.21 (m, 1H), 2.05 (d, J = 14.2, 1H), 1.82 (ddd, J = 12.6, 9.0, 4.2, 2H), 1.53 (m, 5H), 1.21 (m, 1H), 0.81 (dt, J = 12.9, 8.8, 1H). |
| 261 | [(3,5-difluorophenyl)methyl]({2-[(9R)-9-(pyridin-2-yl)-6-oxaspiro[4.5]decan-9-yl]ethyl})amine | 387 | δ 8.77 (d, J = 5.4, 1H), 8.43 (s, 1H), 8.35 (d, J = 7.7, 1H), 7.83 (m, 2H), 7.03 (m, 3H), 4.01 (s, 2H), 3.74 (ddd, J = 27.7, 13.8, 7.4, 2H), 2.96 (m, 1H), 2.39 (m, 4H), 2.23 (dd, J = 13.3, 5.1, 1H), 2.02 (m, 1H), 1.81 (m, 2H), 1.52 (m, 5H), 1.21 (dd, J = 9.4, 5.3, 1H), 0.80 (dt, J = 12.9, 8.9, 1H). |
| 262 | [(2,3-dimethoxyphenyl)methyl]({2-[(9R)-9-(pyridin-2-yl)-6-oxaspiro[4.5]decan-9-yl]ethyl})amine | 411.1 | δ 8.75 (dd, J = 5.4, 1.2, 1H), 8.21 (td, J = 8.0, 1.8, 1H), 7.88 (s, 2H), 7.75 (d, J = 8.2, 1H), 7.66 (ddd, J = 7.6, 5.4, 0.9, 1H), 7.08 (dd, J = 9.0, 5.6, 2H), 6.87 (dd, J = 6.2, 3.0, 1H), 4.05 (s, 2H), 3.86 (d, J = 6.3, 6H), 3.73 (ddd, J = 12.5, 11.1, 5.4, 2H), 2.97 (s, 1H), 2.45 (s, 1H), 2.35 (m, 3H), 2.14 (m, 1H), 1.78 (ddd, J = 14.2, 6.0, 3.9, 2H), 1.49 (m, 5H), 1.16 (m, 1H), 0.77 (d, J = 13.3, 1H). |
| 263 | [(3,4-dimethoxyphenyl)methyl]({2-[(9R)-9-(pyridin-2-yl)-6-oxaspiro[4.5]decan-9-yl]ethyl})amine | 411.1 | δ 8.73 (dd, J = 5.5, 1.2, 1H), 8.24 (td, J = 8.0, 1.7, 1H), 8.00 (s, 1H), 7.78 (d, J = 8.2, 1H), 7.69 (ddd, J = 7.5, 5.5, 0.8, 1H), 6.96 (d, J = 1.0, 1H), 6.88 (d, J = 1.7, 2H), 6.55 (s, 3H), 3.93 (s, 2H), 3.78 (t, J = 7.5, 6H), 3.72 (m, 2H), 2.92 (s, 1H), 2.35 (m, 4H), 2.15 (m, 1H), 1.99 (d, J = 14.2, 1H), 1.79 (m, 2H), 1.49 (m, 5H), 1.18 (s, 1H), 0.79 (dd, J = 15.6, 6.6, 1H). |
| 264 | 2-methoxy-4-[({2-[(9R)-9-(pyridin-2-yl)-6-oxaspiro[4.5]decan-9-yl]ethyl}amino)methyl]phenol | 397.1 | δ 8.62 (dd, J = 5.0, 1.0, 1H), 7.94 (td, J = 7.9, 1.8, 1H), 7.57 (d, J = 8.1, 1H), 7.42 (m, 1H), 7.00 (s, 1H), 6.81 (d, J = 0.8, 2H), 3.93 (s, 2H), 3.84 (s, 3H), 3.70 (m, 3H), 2.93 (s, 1H), 2.36 (s, 3H), 2.17 (m, 1H), 1.90 (d, J = 13.7, 1H), 1.74 (m, 2H), 1.51 (s, 5H), 1.13 (m, 1H), 0.73 (dt, J = 13.2, 8.9, 1H). |
| 265 | [(5-fluoropyridin-3-yl)methyl]({2-[(9R)-9-(pyridin-2-yl)-6-oxaspiro[4.5]decan-9-yl]ethyl})amine | 370 | δ 8.82 (s, 1H), 8.50 (dd, J = 34.5, 26.7, 3H), 7.93 (m, 2H), 7.74 (t, J = 9.7, 1H), 4.12 (d, J = 10.8, 2H), 3.76 (dd, J = 25.7, 11.8, 2H), 3.03 (d, J = 7.9, 1H), 2.39 (m, 5H), 2.09 (t, J = 13.0, 1H), 1.85 (d, J = 9.0, 2H), 1.60 (d, J = 44.8, 5H), 1.24 (s, 1H), 0.86 (d, J = 9.1, 1H). |
| 266 | [(5-bromopyridin-3-yl)methyl]({2-[(9R)-9-(pyridin-2-yl)-6-oxaspiro[4.5]decan-9-yl]ethyl})amine | 430 | δ 8.64 (m, 5H), 8.16 (s, 1H), 8.00 (d, J = 8.2, 1H), 7.95 (m, 1H), 4.10 (m, 2H), 3.76 (m, 2H), 3.02 (td, J = 12.4, 5.0, 1H), 2.49 (m, 2H), 2.29 (m, 3H), 2.12 (t, J = 10.2, 1H), 1.88 (ddd, J = 25.8, 12.8, 8.1, 2H), 1.57 (m, 5H), 1.26 (m, 1H), 0.86 (dt, J = 12.9, 8.9, 1H). |
| 267 | [(5-chloropyridin-3-yl)methyl]({2-[(9R)-9-(pyridin-2-yl)-6-oxaspiro[4.5]decan-9-yl]ethyl})amine | 386 | δ 8.80 (s, 1H), 8.63 (s, 1H), 8.49 (dd, J = 17.4, 10.6, 3H), 7.93 (m, 3H), 4.08 (s, 2H), 3.75 (dd, J = 29.6, 6.9, 2H), 2.99 (d, J = 11.6, 1H), 2.45 (m, 2H), 2.28 (m, 3H), 2.08 (d, J = 14.3, 1H), 1.85 (d, J = 7.5, 2H), 1.60 (m, 5H), 1.23 (s, 1H), 0.84 (d, J = 5.6, 1H). |
| 268 | [(5-methoxypyridin-3-yl)methyl]({2-[(9R)- | 382.1 | δ 8.81 (d, J = 5.5, 1H), 8.48 (m, 3H), 7.95 (m, 3H), 4.22 (d, J = 13.4, 2H), 3.98 (s, 3H), |

TABLE 1-continued

Compounds with chemical name and characterization data

| Compound. | Name | MS (m/z) [M + H]+ | 1H NMR |
|---|---|---|---|
| | 9-(pyridin-2-yl)-6-oxaspiro[4.5]decan-9-yl]ethyl})amine | | 3.75 (ddd, J = 19.2, 12.7, 9.3, 2H), 3.04 (td, J = 11.6, 4.8, 1H), 2.42 (m, 7H), 2.09 (d, J = 14.3, 1H), 1.88 (m, 2H), 1.57 (m, 6H), 1.26 (d, J = 10.9, 1H), 0.85 (dt, J = 12.4, 8.7, 1H). |
| 269 | 5-[({2-[(9R)-9-(pyridin-2-yl)-6-oxaspiro[4.5]decan-9-yl]ethyl}amino)methyl]pyridine-3-carbonitrile | 377.1 | δ 8.96 (d, J = 15.0, 1H), 8.83 (t, J = 10.5, 2H), 8.53 (dt, J = 15.9, 8.0, 2H), 8.23 (d, J = 15.0, 1H), 7.97 (ddd, J = 13.4, 11.9, 7.5, 2H), 4.13 (m, 2H), 3.77 (m, 2H), 3.02 (m, 1H), 2.50 (ddd, J = 26.3, 14.4, 3.7, 2H), 2.31 (m, 3H), 2.13 (dd, J = 19.3, 11.3, 1H), 1.88 (ddd, J = 17.2, 11.0, 7.0, 2H), 1.58 (m, 5H), 1.27 (m, 1H), 0.85 (dt, J = 12.8, 8.7, 1H). |
| 270 | [(5-methylpyridin-3-yl)methyl]({2-[(9R)-9-(pyridin-2-yl)-6-oxaspiro[4.5]decan-9-yl]ethyl})amine | 366 | δ 8.71 (dd, J = 50.6, 19.3, 3H), 8.37 (m, 2H), 7.85 (m, 2H), 4.20 (d, J = 13.3, 2H), 3.74 (ddd, J = 11.9, 11.1, 5.6, 2H), 3.02 (m, 1H), 2.44 (m, 7H), 2.25 (dd, J = 12.5, 5.0, 1H), 1.84 (m, 2H), 1.57 (tdd, J = 24.6, 15.7, 8.5, 5H), 1.22 (d, J = 9.3, 1H), 0.83 (m, 1H). |
| 271 | {2-[(9R)-9-(pyridin-2-yl)-6-oxaspiro[4.5]decan-9-yl]ethyl}({[5-(trifluoromethyl)pyridin-3-yl]methyl})amine | 420.1 | δ 8.96 (s, 1H), 8.81 (m, 2H), 8.45 (td, J = 8.1, 1.6, 2H), 8.21 (s, 1H), 7.90 (m, 2H), 4.16 (m, 2H), 3.77 (dtd, J = 12.7, 9.5, 5.3, 2H), 3.04 (td, J = 12.2, 5.1, 1H), 2.50 (m, 2H), 2.31 (ddd, J = 21.7, 14.1, 7.0, 3H), 2.12 (d, J = 12.6, 1H), 1.87 (ddd, J = 20.7, 12.7, 7.7, 2H), 1.58 (m, 5H), 1.26 (m, 1H), 0.85 (m, 1H). |
| 272 | {[6-chloro-5-(trifluoromethyl)pyridin-3-yl]methyl}({2-[(9R)-9-(pyridin-2-yl)-6-oxaspiro[4.5]decan-9-yl]ethyl})amine | 454.1 | δ 8.70 (m, 1H), 8.60 (d, J = 2.1, 1H), 8.28 (d, J = 2.2, 1H), 8.16 (td, J = 7.9, 1.8, 1H), 7.73 (d, J = 8.2, 1H), 7.62 (ddd, J = 7.6, 5.3, 1.0, 1H), 4.12 (m, 2H), 3.73 (m, 2H), 3.18 (brs, 1H), 2.99 (td, J = 12.0, 5.1, 2H), 2.49 (td, J = 12.0, 4.4, 1H), 2.35 (dd, J = 14.1, 1.9, 3H), 2.13 (ddd, J = 14.2, 12.1, 5.2, 1H), 1.79 (dd, J = 5.6, 3.7, 2H), 1.62 (dd, J = 7.8, 2.8, 1H), 1.51 (dd, J = 7.9, 4.1, 4H), 1.18 (m, 1H), 0.78 (dt, J = 13.2, 8.9, 1H). |
| 273 | {[2-fluoro-5-(trifluoromethyl)pyridin-3-yl]methyl}({2-[(9R)-9-(pyridin-2-yl)-6-oxaspiro[4.5]decan-9-yl]ethyl})amine | 438.1 | δ 8.73 (dd, J = 5.3, 1.2, 1H), 8.62 (s, 1H), 8.35 (dd, J = 8.5, 2.3, 1H), 8.22 (td, J = 8.0, 1.6, 1H), 7.78 (d, J = 8.2, 1H), 7.67 (dd, J = 6.9, 5.8, 1H), 4.25 (brs, 1H), 4.13 (m, 2H), 3.74 (ddd, J = 12.3, 11.0, 5.5, 2H), 3.05 (td, J = 11.9, 5.1, 1H), 2.54 (td, J = 12.0, 4.4, 1H), 2.35 (dt, J = 9.7, 5.3, 3H), 2.16 (ddd, J = 9.9, 8.8, 3.8, 1H), 2.01 (d, J = 14.1, 1H), 1.80 (m, 2H), 1.62 (m, 1H), 1.49 (m, 4H), 1.19 (m, 1H), 0.79 (dt, J = 13.1, 8.8, 1H). |
| 274 | {[6-fluoro-5-(trifluoromethyl)pyridin-3-yl]methyl}({2-[(9R)-9-(pyridin-2-yl)-6-oxaspiro[4.5]decan-9-yl]ethyl})amine | 438.1 | δ 8.58 (d, J = 4.0, 1H), 8.45 (s, 1H), 8.35 (d, J = 9.0, 1H), 7.85 (m, 1H), 7.51 (d, J = 8.1, 1H), 7.33 (dd, J = 7.4, 4.9, 1H), 4.12 (m, 2H), 3.70 (dd, J = 8.8, 2.9, 2H), 2.98 (m, 2H), 2.47 (dd, J = 12.1, 7.4, 2H), 2.38 (t, J = 11.7, 2H), 2.18 (dd, J = 12.9, 4.8, 1H), 1.90 (d, J = 13.7, 1H), 1.70 (m, 2H), 1.60 (m, 1H), 1.50 (dt, J = 39.4, 20.7, 4H), 1.11 (m, 1H), 0.73 (dt, J = 13.5, 9.1, 1H). |
| 275 | {2-[(9R)-9-(pyridin-2-yl)-6-oxaspiro[4.5]decan-9-yl]ethyl}({[3-(trifluoromethyl)pyridin-2-yl]methyl})amine | 420.1 | δ 9.29 (brs, 1H), 8.90 (s, 1H), 8.86 (d, J = 5.1, 1H), 8.80 (dd, J = 5.7, 1.2, 1H), 8.49 (td, J = 8.0, 1.7, 1H), 7.98 (d, J = 8.2, 1H), 7.91 (ddd, J = 7.6, 5.7, 1.0, 1H), 7.74 (d, J = 5.1, 1H), 4.27 (m, 2H), 3.81 (dt, J = 12.8, 4.6, 1H), 3.72 (m, 1H), 3.13 (td, J = 12.1, 5.1, 1H), 2.60 (td, J = 12.3, 4.1, 1H), 2.49 (m, 1H), 2.33 (m, 3H), 2.10 (d, J = 14.3, 1H), 1.85 (m, 2H), 1.65 (m, 1H), 1.52 (m, 4H), 1.25 (m, 1H), 0.84 (dt, J = 12.8, 8.8, 1H). |
| 276 | {2-[(9R)-9-(pyridin-2-yl)-6-oxaspiro[4.5]decan-9-yl]ethyl}({[4-(trifluoromethyl)pyridin-3-yl]methyl})amine | 420.1 | δ 8.81 (dd, J = 5.5, 1.2, 1H), 8.75 (d, J = 4.4, 1H), 8.32 (td, J = 8.0, 1.7, 1H), 8.16 (dd, J = 8.0, 0.7, 1H), 7.86 (d, J = 8.2, 1H), 7.77 (ddd, J = 7.6, 5.5, 1.0, 1H), 7.59 (dd, J = 7.5, 5.0, 1H), 4.40 (m, 2H), 3.75 (m, 2H), 3.13 (td, J = 12.0, 5.3, 1H), 2.66 (td, J = 12.1, 4.5, 1H), 2.49 (ddd, J = 13.7, 11.9, 4.5, 1H), 2.41 (m, 1H), 2.32 (m, 2H), 2.07 (d, J = 14.0, 1H), 1.85 (ddd, J = 9.3, 7.7, 4.5, 2H), 1.64 (m, 1H), 1.51 (m, 4H), 1.22 (m, 1H), 0.82 (dt, J = 13.1, 8.9, 1H). |
| 277 | {2-[(9R)-9-(pyridin-2-yl)-6-oxaspiro[4.5]decan- | 420.1 | δ 8.80 (dd, J = 5.5, 1.3, 1H), 8.75 (d, J = 5.0, 1H), 8.31 (td, J = 8.0, 1.7, 1H), 7.84 (d, J = 8.2, 1H), 7.75 (ddd, J = 7.6, 5.5, 0.9, 1H), 7.65 (M, 2H), |

TABLE 1-continued

Compounds with chemical name and characterization data

| Compound. | Name | MS (m/z) [M + H]+ | 1H NMR |
|---|---|---|---|
| | 9-yl]ethyl}({[4-(trifluoromethyl)pyridin-2-yl]methyl})amine | | 4.31 (m, 2H), 3.74 (m, 2H), 3.09 (td, J = 12.0, 5.2, 1H), 2.60 (td, J = 12.1, 4.4, 1H), 2.36 (m, 4H), 2.05 (d, J = 14.1, 1H), 1.82 (m, 2H), 1.64 (m, 1H), 1.50 (m, 4H), 1.20 (m, 1H), 0.81 (dt, J = 12.8, 8.8, 1H). |
| 500 | [(4-chlorophenyl)methyl]({2-[4-(4-methoxyphenyl)-2,2-dimethyloxan-4-yl]ethyl})amine | | |
| 501 | [(3,4-dimethoxyphenyl)methyl][2-(2,2-dimethyl-4-phenyloxan-4-yl)ethyl]amine | | |
| 502 | 2-[({2-[2-ethyl-2-methyl-4-(4-methylphenyl)oxan-4-yl]ethyl}amino)methyl]phenol | | |
| 503 | [2-(2,2-dimethyl-4-phenyloxan-4-yl)ethyl][(2-fluorophenyl)methyl]amine | | |
| 504 | 4-[({2-[4-(2-methoxyphenyl)-2,2-dimethyloxan-4-yl]ethyl}amino)methyl]-N,N-dimethylaniline | | |
| 505 | 2-[({2-[2-ethyl-4-(4-fluorophenyl)-2-methyloxan-4-yl]ethyl}amino)methyl]phenol | | |

Example 13

Opioid Receptor Ligands

The following compounds in Table 2 can also be prepared according to the procedures described above from appropriate starting materials and appropriate reagents and would be expected to also have similar properties and therapeutic effects as other compounds described herein. In addition to the specific structure shown the other isomers or enantiomers are included with the description herein. Compounds that have been made lists NMR data and prophetic examples do not list NMR data.

TABLE 2

Examples with chemical name and/or characterization data

| Compound | Name | Structure and/or NMR Spectrum |
|---|---|---|
| 506 | {2-[(9R)-9-(pyridin-2-yl)-6-oxaspiro[4.5]decan-9-yl]ethyl}(pyrimidin-5-ylmethyl)amine | 1H NMR (400 MHz, CD3CN) δ 9.16 (s, IH), 8.78 (s, 2H), 8.70 (dd, J = 5.3, 1.1, 1H), 8.16 (td, J = 8.0, 1.8, 1H), 7.74 (d, J 8.2, 1H), 7.62 (ddd, J = 7.6, 5.4, 0.9, 1H), 4.27 (brs, 1H), 4.04 (t, J = 7.7, 2H), 3.73 (m, 2H), 3.01 (td, J = 12.0, 5.1, 1H), 2.50 (td, J = 12.0, 4.4, 1H), 2.33 (m, 3H), 2.12 (ddd, J = 19.0, 11.7, 5.2, 1H), 1.99 (d, J = 10.1, 1H), 1.78 (m, 2H), 1.61 (m, 1H), 1.48 (m, 4H), 1.17 (m, 1H), 0.78 (dt, J = 13.1, 8.9, 1H). |

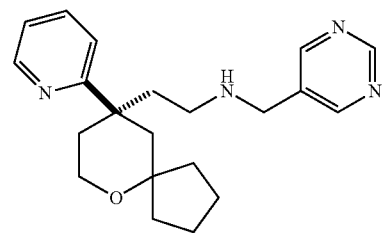 [SMILES: c1ccc([C@]2(CCNCc3cncnc3)CCOC3(CCCC3)C2)nc1]

TABLE 2-continued

Examples with chemical name and/or characterization data

| Compound | Name | Structure and/or NMR Spectrum |
|---|---|---|
| 507. | [(2-methylpyrimidin-5-yl)methyl]({2-[(9R)-(pyridin-2-yl)-6-oxaspiro[4.5]decan-9-yl]ethyl})amine | |
| 508. | {2-[(9R)-9-(pyridin-2-yl)-6-oxaspiro[4.5]decan-9-yl]ethyl}({[2-(trifluoromethyl)pyrimidin-5-yl]methyl})amine | |
| 509. | [(2-methoxypyrimidin-5-yl)methyl]({2-[(9R)-9-(pyridin-2-yl)-6-oxaspiro[4.5]decan-9-yl]ethyl})amine | MS: 383.3<br>$^1$H NMR (400 MHz, CD3CN) δ 8.69 (dd, J = 5.2, 1.1, 1H), 8.54 (s, 2H), 8.10 (td, J = 7.9, 1.7, 1H), 7.69 (d, J = 8.1, 1H), 7.56 (dd, J = 6.7, 5.3, 1H), 3.98 (s, 5H), 3.71 (m, 3H), 3.50 (brs, 1H), 2.98 (td, J = 12.0, 5.0, 1H), 2.47 (td, J = 12.0, 4.3, 1H), 2.37 (m, 2H), 2.27 (m, 1H), 2.10 (m, 1H), 1.77 (m, 2H), 1.62 (m, 1H), 1.47 (dddd, J = 14.1, 12.4, 8.4, 4.9, 4H), 1.17 (m, 1H), 0.77 (dt, J = 13.1, 8.9, 1H). |
| 510. | (pyridazin-4-ylmethyl)({2-[(9R)-9-(pyridin-2-yl)-6-oxaspiro[4.5]decan-9-yl]ethyl})amine | |
| 511. | [(6-methylpyridazin-4-yl)methyl]({2-[(9R)-9-(pyridin-2-yl)-6-oxaspiro[4.5]decan-9-yl]ethyl})amine | |

TABLE 2-continued

Examples with chemical name and/or characterization data

| Compound | Name | Structure and/or NMR Spectrum |
|---|---|---|
| 512. | {2-[(9R)-9-(pyridin-2-yl)-6-oxaspiro[4.5]decan-9-yl]ethyl}({[6-(trifluoromethyl)pyridazin-4-yl]methyl})amine | 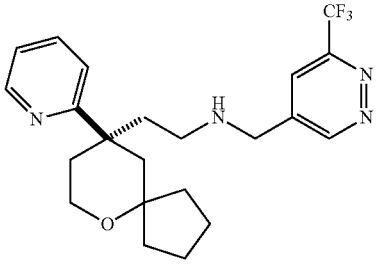 [SMILES: FC(F)(F)c1cc(CNCC[C@@]2(c3ccccn3)CCOC3(CCCC3)C2)cnn1] |
| 513. | [(6-methoxypyridazin-4-yl)methyl]({2-[(9R)-9-(pyridin-2-yl)-6-oxaspiro[4.5]decan-9-yl]ethyl})amine | 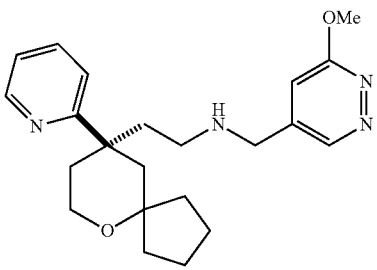 [SMILES: COc1cc(CNCC[C@@]2(c3ccccn3)CCOC3(CCCC3)C2)cnn1] |
| 514. | (pyrazin-2-ylmethyl)({2-[(9R)-9-(pyridin-2-yl)-6-oxaspiro[4.5]decan-9-yl]ethyl})amine | MS: 353.3<br>$^1$H NMR (400 MHz, CD3CN) δ 8.74 (dd, J = 5.3, 1.1, 1H) 8.60 (d J = 1.6, 2H), 8.55 (m, 1H), 8.16 (td, J = 7.9, 1.7, 1H), 7.73 (d, . = 8.2, 1H), 7.61 (ddd, J = 7.5, 5.3, 0.8, 1H), 7.13 (brs, 1H), 4.25 (m, 2H), 3.73 (m, 2H), 3.09 (td, J = 11.8, 5.4, 1H), 2.61 (td, J = 11.9, 4.6, 1H), 2.37 (m, 3H), 2.18 (ddd, J = 13.7, 11.6,5.5, 1H), 1.99 (m, 1H), 1.77 (dd, J = 9.6, 4.4, 2H), 1.62 (m, 1H), 1.48 (m, 4H), 1.18 (m, 1H), 0.79 (dt, J = 13.1, 8.9, 1H).<br>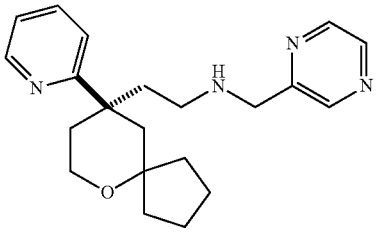 [SMILES: c1ccc([C@]2(CCNCc3cnccn3)CCOC3(CCCC3)C2)nc1] |
| 515. | [(6-methylpyrazin-2-yl)methyl]({2-[(9R)-9-(pyridin-2-yl)-6-oxaspiro[4.5]decan-9-yl]ethyl})amine | 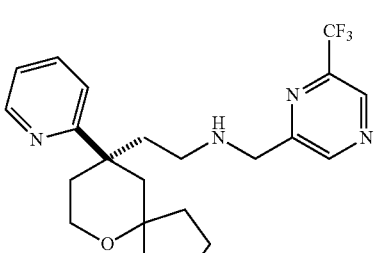 |
| 516. | {2-[(9R)-9-(pyridin-2-yl)-6-oxaspiro[4.5]decan-9-yl]ethyl}({[6-(trifluoromethyl)pyrazin-2-yl]methyl})amine | |

TABLE 2-continued

Examples with chemical name and/or characterization data

| Compound | Name | Structure and/or NMR Spectrum |
|---|---|---|
| 517. | [(6-methoxypyrazin-2-yl)methyl]({2-[(9R)-9-(pyridin-2-yl)-6-oxaspiro[4.5]decan-9-yl]ethyl})amine | |
| 518. | [(5-methylpyrazin-2-yl)methyl]({2-[(9R)-9-(pyridin-2-yl)-6-oxaspiro[4.5]decan-9-yl]ethyl})amine | |
| 519. | {2-[(9R)-9-(pyridin-2-yl)-6-oxaspiro[4.5]decan-9-yl]ethyl}({[5-(trifluoromethyl)pyrazin-2-yl]methyl})amine | |
| 520. | [(5-methoxypyrazin-2-yl)methyl]({2-[(9R)-(pyridin-2-yl)-6-oxaspiro[4.5]decan-9-yl]ethyl})amine | |
| 521. | {2-[(9R)-9-(pyridin-2-yl)-6-oxaspiro[4.5]decan-9-yl]ethyl}(quinolin-3-ylmethyl)amine | MS: 402.3<br>$^1$H NMR (400 MHz, CD3CN) δ 9.90 (brs, 1H), 9.15 (d, J = 1.7 1H) 8.89 (s 1H), 8.77 (dd J = 5.6, 1.3, 1H), 8.40 (td, = 8.0, 1.6, 1H), 8.30 (d, J = 8.6, 1H), 8.16 (d, J = 8.2, 1H), 8.08 (ddd, J = 8.5, 7.0, 1.3, 1H), 7.90 (m, 2H), 7.81 (m, 1H), 4.36 (m, 2H), 3.74 (m, 2H), 3.06 (td, J = 12.0, 5.1, 1H), 2.57 (td, J = 12.2, 4.1, 1H), 2.45 (m, 1H), 2.29 (m, 3H), 2.08 (m, 1H), 1.98 (d, J = 2.5, 1H), 1.83 (m, 2H), 1.64 (ddd, J = 11.6, 8.7, 3.4, 1H), 1.50 (m, 4H), 1.23 (ddd, J = 10.4, 4.4, 2.4, 1H), 0.82 (dt, J = 12.9, 8.8, 1H). |

TABLE 2-continued

Examples with chemical name and/or characterization data

| Compound | Name | Structure and/or NMR Spectrum |
|---|---|---|
| 522. | (1H-pyrazol-3-ylmethyl)({2-[(9R)-9-(pyridin-2-yl)-6-oxaspiro[4.5]decan-9-yl]ethyl})amine | MS: 341.2<br>1H NMR (400 MHz, CD3CN) δ 8.76 (dd, J = 5.5, 1.2 1H) 8.28 (td J = 8.0, 1.7, 1H), 7.80 (d, J = 8.2, 1H), 7.73 (ddd, = 7.6, 5.5, 0.9, 1H), 7.61 (d, J = 2.3, 1H), 6.32 (d, J = 2.3, 1H), 5.78 (brs, 1H), 4.09 (m, 2H), 3.72 (m, 2H), 2.98 (td, J = 12.0, 5.2, 1H), 2.47 (td, J = 12.1, 4.3, 1H), 2.36 (m, 3H), 2.16 (m, 1H), 2.02 (d, J = 14.2, 1H), 1.79 (m, 2H), 1.62 (m, 1H), 1.49 (m, 4H), 1.19 (m, 1H), 0.79 (dt, J = 12.9, 8.8, 1H).<br>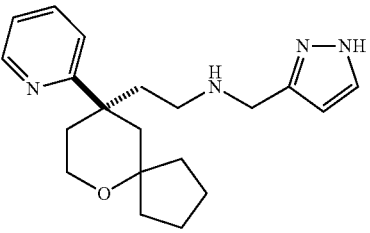 [SMILES: c1ccc([C@]2(CCNCc3cc[nH]n3)CCOC3(CCCC3)C2)nc1] |
| 523. | [(1-methyl-1H-pyrazol-3-yl)methyl]({2-[(9R)-9-(pyridin-2-yl)-6-oxaspiro[4.5]decan-9-yl]ethyl})amine | MS: 355.3<br>1H NMR (400 MHz, CD3CN) δ 8.98 (brs, 1H), 8.73 (dd, J = 5.3, 1.1, 1H), 8.73 (dd, J = 5.3, 1.1, 1H), 8.16 (m, 2H), 7.72 (d, J = 8.2, 1H), 7.72 (d, J = 8.2, 1H), 7.62 (ddd, J = 7.5, 5.4, 0.8, 1H), 7.62 (ddd, J = 7.5, 5.4, 0.8, 1H), 7.47 (d, J = 2.2, 1H), 7.47 (d, J = 2.2, 1H), 6.25 (d, J = 2.2, 1H), 6.25 (d, J = 2.2, 1H), 4.02 (m, 2H), 3.80 (s, 3H), 3.72 (m, 2H), 2.98 (td, J = 11.8, 5.2, 1H), 2.48 (td, J = 11.9, 4.2, 1H), 2.33 (m, 3H), 2.12 (ddd, J = 13.5, 11.9, 5.4, 1H), 1.99 (m, 1H), 1.77 (m, 2H), 1.62 (m, 1H), 1.48 (m, 4H), 1.17 (m, 1H), 0.78 (dt, J = 13.1, 8.9, 1H).<br>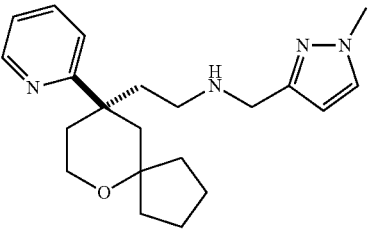 [SMILES: Cn1ccc(CNCC[C@@]2(c3ccccn3)CCOC3(CCCC3)C2)n1] |
| 524. | [(5-methyl-1H-pyrazol-3-yl)methyl]({2-[(9R)-9-(pyridin-2-yl)-6-oxaspiro[4.5]decan-9-yl]ethyl})amine | MS: 355.3<br>1H NMR (400 MHz, CD3CN) δ 8.78 (dd, J = 5.5, 1.2, 1H), 8.34 (td, J = 8.0, 1.7, 1H), 7.79 (m, 2H), 6.07 (s, 1H), 5.95 (brs, 1H), 4.02 (m, 2H), 3.72 (m, 2H), 2.97 (td, J = 12.0, 5.1, 1H), 2.44 (ddd, J = 12.1, 10.0, 4.2, 1H), 2.34 (m, 3H), 2.26 (s, 3H), 2.18 (td, J = 13.1, 5.2, 1H), 2.03 (d, J = 14.2, 1H), 1.81 (ddd, J = 8.7, 7.4, 3.8, 2H), 1.63 (ddd, J = 14.6, 10.4, 4.6, 1H), 1.49 (m, 4H), 1.20 (m, 1H), 0.81 (dt, J = 12.9, 8.9, 1H).<br>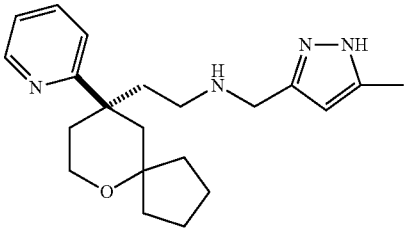 [SMILES: Cc1cc(CNCC[C@@]2(c3ccccn3)CCOC3(CCCC3)C2)n[nH]1] |

TABLE 2-continued

Examples with chemical name and/or characterization data

| Compound | Name | Structure and/or NMR Spectrum |
|---|---|---|
| 525. | [(1,5-dimethyl-1H-pyrazol-3-yl)methyl]({2-[(9R)-9-(pyridin-2-yl)-6-oxaspiro[4.5]decan-9-yl]ethyl})amine | MS: 369.3<br>1H NMR (400 MHz, CD3CN) δ 12.13 (brs, 1H), 8.77 (dd, J = 5.4, 1.2, 1H), 8.28 (td, J = 8.0, 1.7, 1H), 8.00 (brs, 1H), 7.74 (m, 2H), 6.03 (s, 1H), 3.96 (m, 2H), 3.73 (m, 5H), 2.96 (td, J = 12.0, 5.2, 1H), 2.47 (td, J = 12.1, 4.2, 1H), 2.36 (m, 3H), 2.17 (m, 4H), 2.00 (m, 1H), 1.79 (m, 2H), 1.63 (ddd, J 8.4, 7.6, 3.3, 1H), 1.50 (m, 4H), 1.19 (ddd, J = 10.1, 6.6, 1.8, 1H), 0.81 (dt, J = 12.9, 8.9, 1H). |
| 526. | (1H-pyrazol-4-ylmethyl)({2-[(9R)-9-(pyridin-2-yl)-6-oxaspiro[4.5]decan-9-yl]ethyl})amine | MS: 341.2<br>1H NMR (400 MHz, CD3CN) δ 8.73 (dd, J = 5.3, 1.1, 1H), 8.21 (td, J = 8.0, 1.7, 2H), 7.75 (d, J = 8.2, 1H), 7.66 (m, 3H), 7.56 (s, 1H), 3.96 (s, 2H), 3.73 (m, 2H), 2.91 (m, 1H), 2.32 (m, 4H), 2.08 (m, 1H), 1.99 (m, 1H), 1.78 (m, 2H), 1.62 (m, 1H), 1.49 (m, 4H), 1.19 (m, 1H), 0.78 (dt, J = 13.1, 8.8, 1H). |
| 527. | [(1-methyl-1H-pyrazol-4-yl)methyl]({2-[(9R)-9-(pyridin-2-yl)-6-oxaspiro[4.5]decan-9-yl]ethyl})amine | MS: 355.2<br>1H NMR (400 MHz, CD3CN) δ 8.78 (dd, J = 5.5, 1.3, 1H), 8.32 (td, J = 8.0, 1.7, 1H), 7.84 (d, J = 8.2, 1H), 7.77 (ddd, J = 7.6, 5.5, 0.9, 1H), 7.71 (brs, 1H), 7.55 (s, 1H), 7.43 (s, 1H), 3.91 (s, 2H), 3.81 (d, J = 11.7, 3H), 3.73 (m, 2H), 2.90 (dt, J = 11.7, 5.8, 1H), 2.35 (m, 4H), 2.14 (ddd, J = 10.8, 10.2, 5.2, 1H), 2.03 (d, J = 14.2, 1H), 1.80 (m, 2H), 1.62 (tdd, J = 8.7, 6.8, 2.7, 1H), 1.49 (m, 4H), 1.20 (m, 1H), 0.80 (dt, J = 12.9, 8.8, 1H). |
| 528. | [(5-methyl-1H-pyrazol-4-yl)methyl]({2-[(9R)-9-(pyridin-2-yl)-6-oxaspiro[4.5]decan-9-yl]ethyl})amine | |

TABLE 2-continued

Examples with chemical name and/or characterization data

| Compound | Name | Structure and/or NMR Spectrum |
|---|---|---|
| 529. | [(1,5-dimethyl-1H-pyrazol-4-yl)methyl]({2-[(9R)-9-(pyridin-2-yl)-6-oxaspiro[4.5]decan-9-yl]ethyl})amine | |
| 530. | [(5,6-difluoropyridin-3-yl)methyl]({2-[(9R)-9-(pyridin-2-yl)-6-oxaspiro[4.5]decan-9-yl]ethyl})amine | |
| 531. | [(5-chloro-6-fluoropyridin-3-yl)methyl]({2-[(9R)-9-(pyridin-2-yl)-6-oxaspiro[4.5]decan-9-yl]ethyl})amine | |
| 532. | [(5-bromo-6-fluoropyridin-3-yl)methyl]({2-[(9R)9-(pyridin-2-yl)-6-oxaspiro[4.5]decan-9-yl]ethyl})amine | |
| 533. | [(6-fluoro-5-iodopyridin-3-yl)methyl]({2-[(9R)-9-(pyridin-2-yl)-6-oxaspiro[4.5]decan-9-yl]ethyl})amine | |

TABLE 2-continued

Examples with chemical name and/or characterization data

| Compound | Name | Structure and/or NMR Spectrum |
|---|---|---|
| 534. | [(6-fluoro-5-methylpyridin-3-yl)methyl]({2-[(9R)-9-(pyridin-2-yl)-6-oxaspiro[4.5]decan-9-yl]ethyl})amine | MS: 384.3<br>1H NMR (400 MHz, CD3CN) δ 8.73 (d, J = 4.4, 1H), 8.36 (s, 1H), 8.20 (d, J = 7.8 1H) 8.01 (s 1H), 7.77 (t, J = 7.1, 2H), 7.66 (m, 1H), 4.01 (s, 2H), 3.73 (m, 2H), 2.98 (dd, J = 11.6, 6.9, 1H), 2.36 (m, 5H), 2.26 (s, 3H), 2.16 (dd, J = 13.2, 5.1, 2H), 1.80 (m, 2H), 1.51 (m, 6H), 1.20 (dd, J = 8.7, 4.7, 1H), 0.79 (d, J = 13.3, 1H).<br>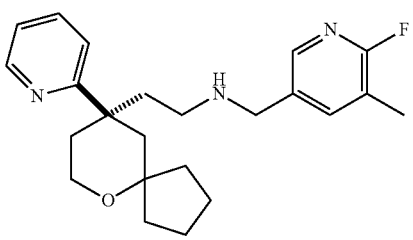 |
| 535. | [(6-fluoro-5-methoxypyridin-3-yl)methyl]({2-[(9R)-9-(pyridin-2-yl)-6-oxaspiro[4.5]decan-9-yl]ethyl})amine | 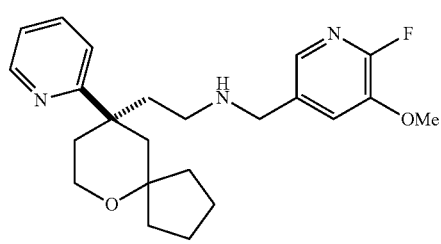 |
| 536. | 2-fluoro-5-[({2-[(9R)-9-(pyridin-2-yl)-6-oxaspiro[4.5]decan-9-yl]ethyl}amino)methyl]pyridine-3-carbonitrile | 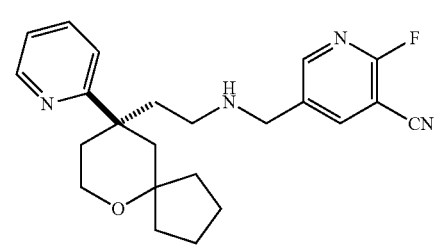 |
| 537. | [(6-chloro-5-fluoropyridin-3-yl)methyl]({2-[(9R)-9-(pyridin-2-yl)-6-oxaspiro[4.5]decan-9-yl]ethyl})amine | MS: 404.2<br>1H NMR (400 MHz, CD3CN) δ 8.68 (dd, J = 5.2, 1.1, 1H), 8.24 (d, J = 1.9, 1H), 8.10 (td, J = 7.9, 1.8, 1H), 7.78 (dd, . = 9.0, 2.0, 1H), 7.69 (d, J = 8.2, 1H), 7.56 (ddd, J = 7.5, 5.3, 0.9, 1H), 4.75 (brs, 1H), 4.07 (m, 2H), 3.72 (m, 2H), 2.99 (td, J = 11.9, 5.2, 1H), 2.48 (td, J = 12.0, 4.5, 1H), 2.32 (m, 3H), 2.11 (m, 1H), 1.77 (m, 2H), 1.62 (m, 1H), 1.49 (m, 4H), 1.17 (m, 1H), 0.77 (dt, J = 13.1, 8.9, 1H).<br>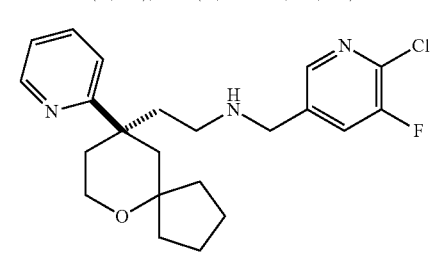 |

TABLE 2-continued

Examples with chemical name and/or characterization data

| Compound | Name | Structure and/or NMR Spectrum |
|---|---|---|
| 538. | [(5,6-dichloropyridin-3-yl)methyl]({2-[(9R)-9-(pyridin-2-yl)-6-oxaspiro[4.5]decan-9-yl]ethyl})amine | MS: 422.2<br>1H NMR (400 MHz, CD3CN) δ 8.51 (m, 1H), 8.33 (d, J =2.1 1H) 8.12(d, J =2.1 1H) 7.76(t, J =7.9 1H), 7.49 (d, J = 8.1, 1H), 7.23 (dd, J = 7.4, 4.9, 1H), 4.26 (d, J = 1.5, 2H), 3.57 (dd, J = 7.7, 3.0, 2H), 3.09 (td, J = 12.2, 4.6, 1H), 2.55 (td, J = 12.1, 4.6, 1H), 2.27 (dddd, J = 25.5, 17.3, 14.3, 3.4, 4H), 1.77 (m, 1H), 1.59 (m, 2H), 1.34 (m, 6H), 0.98 (dd, J = 11.4, 5.0, 1H), 0.60 (dt, J = 13.4, 9.0, 1H).<br>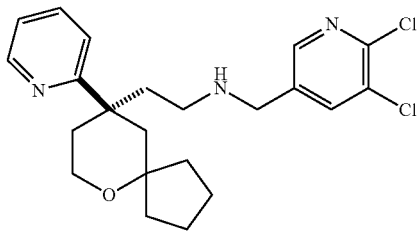 [SMILES: Fc1ncc(CNCC[C@@]2(c3ccccn3)CCOC3(CCCC3)C2)cc1Cl] |
| 539. | [(5-bromo-6-chloropyridin-3-yl)methyl]({2-[(9R)-9-(pyridin-2-yl)-6-oxaspiro[4.5]decan-9-yl]ethyl})amine | MS: 466.1<br>1H NMR (400 MHz, CD3CN) δ 8.64 (d, J = 5.1, 1H), 8.36 (d, J = 2.1, 1H), 8.24 (d, J = 2.1, 1H), 8.02 (m, 1H), 7.69 (d, J = 8.0, 1H), 7.47 (m, 1H), 3.59 (m, 2H), 3.17 (d, J = 4.7, 1H), 2.63 (d, J = 4.5, 1H), 2.34 (m, 4H), 2.12 (d, J = 4.8, 1H), 1.85 (d, J = 13.8, 1H), 1.66 (m, 2H), 1.35 (m, 6H), 1.02 (m, 1H), 0.66 (s, 1H).<br>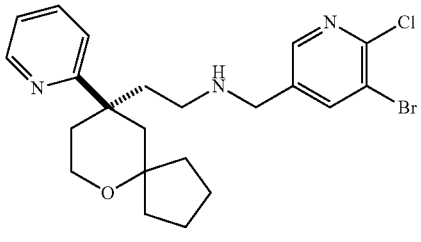 |
| 540. | [(6-chloro-5-iodopyridin-3-yl)methyl]({2-[(9R)-9-(pyridin-2-yl)-6-oxaspiro[4.5]decan-9-yl]ethyl})amine | 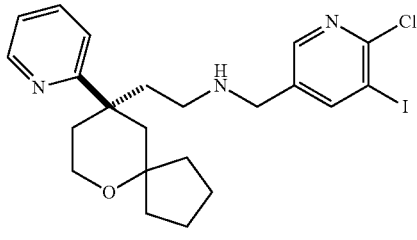 [SMILES: Fc1cc(CNCC[C@@]2(c3ccccn3)CCOC3(CCCC3)C2)cnc1Cl] |
| 541. | [(6-chloro-5-methylpyridin-3-yl)methyl]({2-[(9R)-9-(pyridin-2-yl)-6-oxaspiro[4.5]decan-9-yl]ethyl})amine | MS: 400.2<br>1H NMR (400 MNz, CD3CN) δ 8.70 (dd, J = 5.3, 1.2, 1H), 8.20 (t, J = 2.4, 1H), 8.17 (dd, J = 7.9, 1.7, 1H), 7.74 (t, J = 5.2, 2H), 7.63 (ddd, J = 7.5, 5.3, 0.9, 1H), 5.11 (s, 1H), 4.01 (m, 2H), 3.73 (m, 2H), 2.98 (td, J = 11.9, 5.1, 1H), 2.46 (td, J = 12.0, 4.2, 1H), 2.33 (m, 6H), 2:12 (ddd, J = 14.7, 10.5, 5.3, 1H), 1.99 (d, J = 6.9, 1H), 1.78 (m, 2H), 1.62 (m, 1H), 1.48 (m, 4H), 1.18 (m, 1H. 0.78 (dt. J = 13.1, 8.9, 1H).<br>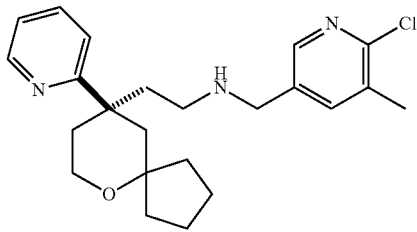 |

TABLE 2-continued

Examples with chemical name and/or characterization data

| Compound | Name | Structure and/or NMR Spectrum |
|---|---|---|
| 542. | [(6-chloro-5-methoxypyridin-3-yl)methyl]({2-[(9R)-9-(pyridin-2-yl)-6-oxaspiro[4.5]decan-9-yl]ethyl})amine | MS: 416.2<br>1H NMR (400 MHz, CD3CN) δ 8.73 (dd, J 5.4, 1.2, 1H), 8.26 (td, J = 7.9, 1.6, 1H), 7.93 (d, J = 1.9, 1H), 7.80 (d, J = 8.2, 1H), 7.70 (dd, J = 7.1, 5.9, 1H), 7.52 (d, J = 1.9, 1H), 5.05 (brs, 1H), 4.04 (m, 2H), 3.90 (s, 3H), 3.74 (m, 2H), 2.98 (td, J = 12.0, 5.1, 1H), 2.40 (dddd, J = 19.5, 12.3, 9.6, 4.7, 3H), 2.16 (m, 1H), 1.99 (m, 1H), 1.80 (m, 2H), 1.63 (ddd, J = 14.5, 7.2, 3.0, 1H), 1.49 (m, 4H), 1.20 (m, 1H), 0.80 (dt, J = 12.9, 8.8, 1H). |
| 543. | 2-chloro-5-[({2-[(9R)-9-(pyridin-2-yl)-6-oxaspiro[4.5]decan-9-yl]ethyl}amino)methyl]pyridine-3-carbonitrile | |
| 544. | 3-fluoro-5-[({2-[(9R)-9-(pyridin-2-yl)-6-oxaspiro[4.5]decan-9-yl]ethyl}amino)methyl]pyridine-2-carbonitrile | |
| 545. | 3-chloro-5-[({2-[(9R)-9-(pyridin-2-yl)-6-oxaspiro[4.5]decan-9-yl]ethyl}amino)methyl]pyridine-2-carbonitrile | |
| 546. | 3-bromo-5-[({2-[(9R)-9-(pyridin-2-yl)-6-oxaspiro[4.5]decan-9-yl]ethyl}amino)methyl]pyridine-2-carbonitrile | |

TABLE 2-continued

Examples with chemical name and/or characterization data

| Compound | Name | Structure and/or NMR Spectrum |
|---|---|---|
| 547. | 3-iodo-5-[({2-[(9R)-9-(pyridin-2-yl)-6-oxaspiro[4.5]decan-9-yl]ethyl}amino)methyl]pyridine-2-carbonitrile | |
| 548. | 3-methyl-5-[({2-[(9R)-9-(pyridin-2-yl)-6-oxaspiro[4.5]decan-9-yl]ethyl}amino)methyl]pyridine-2-carbonitrile | |
| 549. | 3-methyl-5-[({2-[(9R)-9-(pyridin-2-yl)-6-oxaspiro[4.5]decan-9-yl]ethyl}amino)methyl]pyridine-2-carbonitrile | |
| 550. | 5-[({2-[(9R)-9-(pyridin-2-yl)-6-oxaspiro[4.5]decan-9-yl]ethyl}amino)methyl]pyridine-2,3-dicarbonitrile | |
| 551. | 5-[({2-[(9R)-9-(pyridin-2-yl)-6-oxaspiro[4.5]decan-9-yl]ethyl}amino)methyl]-3-(trifluoromethyl)pyridine-2-carbonitrile | |
| 552. | {[5-fluoro-6-(trifluoromethyl)pyridin-3-yl]methyl}({2-[(9R)-9-(pyridin-2-yl)-6-oxaspiro[4.5]decan-9-yl]ethyl})amine | |

TABLE 2-continued

Examples with chemical name and/or characterization data

| Compound | Name | Structure and/or NMR Spectrum |
|---|---|---|
| 553. | {[5-chloro-6-(trifluoromethyl)pyridin-3-yl]methyl}({2-[(9R)-9-(pyridin-2-yl)-6-oxaspiro[4.5]decan-9-yl]ethyl})amine | |
| 554. | {[5-bromo-6-(trifluoromethyl)pyridin-3-yl]methyl}({2-[(9R)-9-(pyridin-2-yl)-6-oxaspiro[4.5]decan-9-yl]ethyl})amine | MS: 498.1<br>1H NMR (400 MHz, CD3CN) δ 8.74 (dd, J = 5.4, 1.2, 1H), 8.64 (d, J = 1.6, 1H), 8.32 (d, J = 1.2, 1H), 8.26 (td, J = 8.0, 1.6, 1H), 7.81 (d, J = 8.2, 1H), 7.71 (dd, J = 7.1, 6.0, 1H), 4.12 (m, 3H), 3.74 (m, 3H), 3.00 (td, J = 12.0, 5.1, 1H), 2.49 (td, J = 12.1, 4.2, 1H), 2.37 (ddd, J = 14.0, 11.9, 5.0, 3H), 2.16 (m, 1H), 2.02 (m, 1H), 1.81 (m, 2H), 1.63 (ddd, J = 14.4, 8.7, 4.7, 1H), 1.49 (m, 4H), 1.21 (m, 1H), 0.80 (dt, J = 13.0, 8.9, 1H). |
| 555. | {[5-iodo-6-(trifluoromethyl)pyridin-3-yl]methyl}({2-[(9R)-9-(pyridin-2-yl)-6-oxaspiro[4.5]decan-9-yl]ethyl})amine | |
| 556. | {[5-methyl-6-(trifluoromethyl)pyridin-3-yl]methyl}({2-[(9R)-9-(pyridin-2-yl)-6-oxaspiro[4.5]decan-9-yl]ethyl})amine | |
| 557. | {[5-methoxy-6-(trifluoromethyl)pyridin-3-yl]methyl}({2-[(9R)-9-(pyridin-2-yl)-6-oxaspiro[4.5]decan-9-yl]ethyl})amine | |

TABLE 2-continued

Examples with chemical name and/or characterization data

| Compound | Name | Structure and/or NMR Spectrum |
|---|---|---|
| 558. | 5-[({2-[(9R)-9-(pyridin-2-yl)-6-oxaspiro[4.5]decan-9-yl]ethyl}amino)methyl]-2-(trifluoromethyl)pyridine-3-carbonitrile | 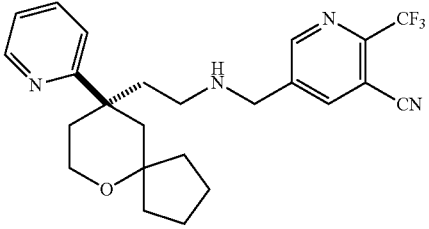 [SMILES: N#Cc1cc(CNCC[C@@]2(c3ccccn3)CCOC3(CCCC3)C2)cnc1C(F)(F)F] |
| 559. | {[5,6-bis(trifluoromethyl)pyridin-3-yl]methyl}({2-[(9R)-9-(pyridin-2-yl)-6-oxaspiro[4.5]decan-9-yl]ethyl})amine | 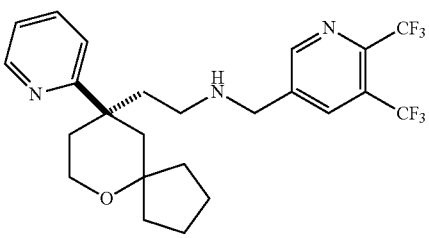 [SMILES: FC(F)(F)c1cc(CNCC[C@@]2(c3ccccn3)CCOC3(CCCC3)C2)cnc1C(F)(F)F] |
| 560. | [(5-fluoro-6-methylpyridin-3-yl)methyl]({2-[(9R)-9-(pyridin-2-yl)-6-oxaspiro[4.5]decan-9-yl]ethyl})amine | 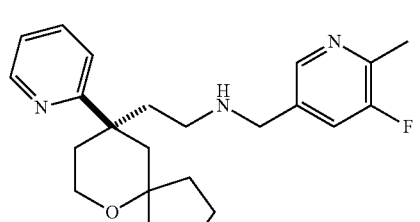 |
| 561. | [(5-chloro-6-methylpyridin-3-yl)methyl]({2-[(9R)-9-(pyridin-2-yl)-6-oxaspiro[4.5]decan-9-yl]ethyl})amine | 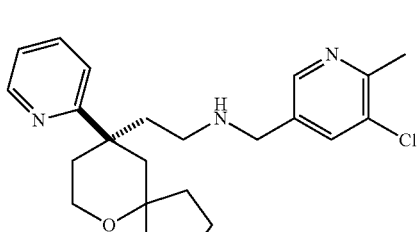 |
| 562. | [(5-bromo-6-methylpyridin-3-yl)methyl]({2-[(9R)-9-(pyridin-2-yl)-6-oxaspiro[4.5]decan-9-yl]ethyl})amine | 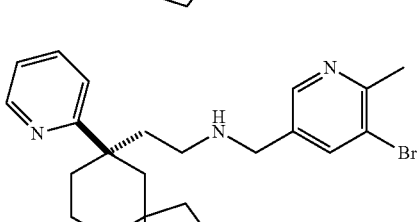 |
| 563. | [(5-iodo-6-methylpyridin-3-yl)methyl]({2-[(9R)-9-(pyridin-2-yl)-6-oxaspiro[4.5]decan-9-yl]ethyl})amine | 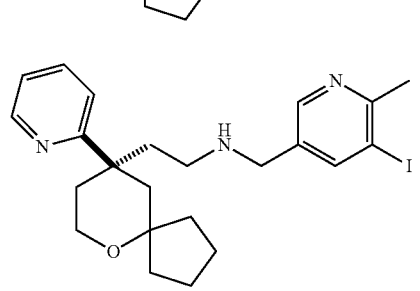 |

TABLE 2-continued

Examples with chemical name and/or characterization data

| Compound | Name | Structure and/or NMR Spectrum |
|---|---|---|
| 564. | [(5,6-dimethylpyridin-3-yl)methyl]({2-[(9R)-9-(pyridin-2-yl)-6-oxaspiro[4.5]decan-9-yl]ethyl})amine | |
| 565. | [(5-methoxy-6-methylpyridin-3-yl)methyl]({2-[(9R)-9-(pyridin-2-yl)-6-oxaspiro[4.5]decan-9-yl]ethyl})amine | |
| 566. | 2-methyl-5-[({2-[(9R)-9-(pyridin-2-yl)-6-oxaspiro[4.5]decan-9-yl]ethyl}amino)methyl]pyridine-3-carbonitrile | |
| 567. | {[6-methyl-5-(trifluoromethyl)pyridin-3-yl]methyl}({2-[(9R)-9-(pyridin-2-yl)-6-oxaspiro[4.5]decan-9-yl]ethyl})amine | |
| 568. | [(5-fluoro-6-methoxypyridin-3-yl)methyl]({2-[(9R)-9-(pyridin-2-yl)-6-oxaspiro[4.5]decan-9-yl]ethyl})amine | MS: 400.3<br>1H NMR (400 MHz, CD3CN) δ 8.63 (dd, J = 5.3, 1.2, 1H), 8.25 (s, 1H), 8.12 (td, J = 8.0, 1.6, 1H), 7.83 (d, J = 1.9, 1H), 7.67 (d, J = 8.2, 1H), 7.57 (dd, J = 6.8, 5.7, 1H), 7.44 (dd, J = 11.1,2.0, 1H), 3.88 (d, J = 6.7, 5H), 3.62 (m, 2H), 2.86 (dd, J = 11.5, 7.1, 1H), 2.26 (m, 4H), 2.05 (dd, J = 12.7, 5.0, 1H), 1.69 (ddd, J = 9.5, 8.0, 4.4, 2H), 1.69 (ddd, J = 9.5, 8.0, 4.4, 2H), 1.39 (m, 5H), 0.68 (d, J = 13.3, 1H). |

TABLE 2-continued

Examples with chemical name and/or characterization data

| Compound | Name | Structure and/or NMR Spectrum |
|---|---|---|
| 569. | [(5-chloro-6-methoxypyridin-3-yl)methyl]({2-[(9R)-9-(pyridin-2-yl)-6-oxaspiro[4.5]decan-9-yl]ethyl})amine | MS: 416.2<br>1H NMR (400 MHz, CD3CN) δ 8.65 (d, J = 5.4, 1H), 8.21 (s, 1H), 8.18 (d, J = 8.0, 1H), 7.96 (d, J = 2.1, 1H), 7.72 (m, 2H), 7.63 (t, J = 6.4, 1H), 3.87 (m, 5H), 3.62 (m, 2H), 2.85 (dd, J = 11.5, 7.2, 1H), 2.27 (m, 4H), 2.07 (d, J = 4.9, 1H), 1.91 (d, J = 14.1, 1H), 1.69 (m, 2H), 1.39 (m, 5H), 1.10 (m, 1H), 0.69 (d, J = 13.2, 1H).<br>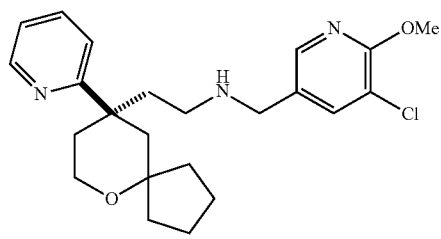 |
| 570. | [(5-bromo-6-methoxypyridin-3-yl)methyl]({2-[(9R)-9-(pyridin-2-yl)-6-oxaspiro[4.5]decan-9-yl]ethyl})amine | MS: 460.2<br>1H NMR (400 MHz, CDCl3) δ 8.79 (dd, J = 5.7, 1.3, 1H), 8.43 (td, J = 8.0, 1.7, 1H), 8.11 (d, J = 2.1, 1H), 7.98 (d, J = 2.1, 1H), 7.92 (d, J = 8.2, 1H), 7.86 (ddd, J = 7.6, 5.7, 1.0, 1H), 5.63 (brs, 1H), 3.97 (m, 5H), 3.75 (m, 2H), 2.96 (m, 1H), 2.42 (dq, J = 12.2, 4.1, 2H), 2.33 (d, J = 14.1, 2H), 2.21 (m, 1H), 2.06 (d, J = 14.2, 1H), 1.83 (m, 2H), 1.64 (ddd, J = 19.4, 10.1, 4.4, 1H), 1.50 (m, 4H), 1.23 (m, 1H), 0.82 (dt, J = 12.9, 8.9, 1H).<br>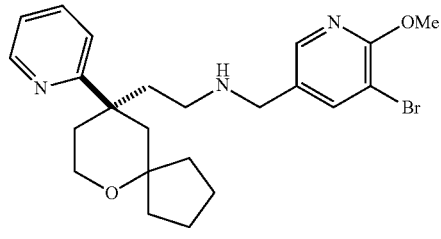 |
| 571. | [(5-iodo-6-methoxypyridin-3-yl)methyl]({2-[(9R)-9-(pyridin-2-yl)-6-oxaspiro[4.5]decan-9-l]ethyl})amine | 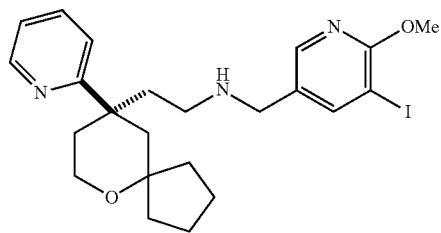 [SMILES: COc1ncc(CNCC[C@@]2(c3ccccn3)CCOC3(CCCC3)C2)cc1F] |

TABLE 2-continued

Examples with chemical name and/or characterization data

| Compound | Name | Structure and/or NMR Spectrum |
|---|---|---|
| 572. | [(6-methoxy-5-methylpyridin-3-yl)methyl]({2-[(9R)-9-(pyridin-2-yl)-6-oxaspiro[4.5]decan-9-yl]ethyl})amine | MS: 396.3<br>1H NMR (400 MHz, CDCl3) δ 8.78 (dd, J = 5.6, 1.3, 1H), 8.38 (td, J = 8.0, 1.7, 1H), 7.96 (d, J = 2.2, 1H), 7.88 (d, J = 8.2, 1H), 7.81 (ddd, J = 7.6, 5.6, 1.0, 1H), 7.49 (d, J = 1.5, 1H), 5.36 (brs, 1H), 3.93 (m, 5H), 3.74 (m, 2H), 2.95 (dd, J = 11.4, 7.7, 1H), 2.39 (m, 4H), 2.21 (dd, J = 13.2, 5.4, 1H), 2.14 (m, 3H), 2.05 (d, J = 14.2, 1H), 1.82 (m, 2H), 1.63 (m, 1H), 1.50 (m, 4H), 1.21 (ddd, J = 10.5, 6.1, 2.5, 1H), 0.81 (dt, J = 12.9, 8.8, 1H). |
| 573. | [(5,6-dimethoxypyridin-3-yl)methyl]({2-[(9R)-9-(pyridin-2-yl)-6-oxaspiro[4.5]decan-9-yl]ethyl})amine | |
| 574. | 2-methoxy-5-[({2-[(9R)-9-(pyridin-2-yl)-6-oxaspiro[4.5]decan-9-yl]ethyl}amino)methyl]pyridine-3-carbonitrile | |
| 575. | {[6-methoxy-5-(trifluoromethyl)pyridin-3-yl]methyl}({2-[(9R)-9-(pyridin-2-yl)-6-oxaspiro[4.5]decan-9-yl]ethyl})amine | |

Example 14

Opioid Receptor Ligands

The following compounds in Table 3 can also be prepared according to the procedures described above from appropriate starting materials and appropriate reagents and would be expected to also have similar properties and therapeutic effects as other compounds described herein. In addition to the specific structure shown the other isomers or enantiomers are included with the description herein. Compounds that have been made lists NMR data and prophetic examples do not list NMR data.

TABLE 3

Opioid Receptor Ligands

| Compound | Name | Structure |
|---|---|---|
| 576 | [(5-chloropyridin-3-yl)methyl]({2-[(9R)-9-phenyl-6-oxaspiro[4.5]decan-9-yl]ethyl})amine | 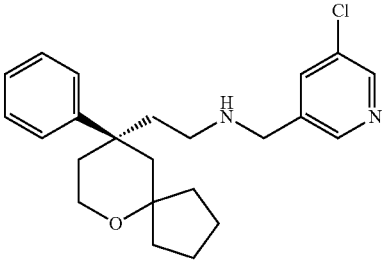 [SMILES: Clc1cncc(CNCC[C@@]2(c3ccccc3)CCOC3(CCCC3)C2)c1] |
| 577 | {2-[(9R)-9-phenyl-6-oxaspiro[4.5]decan-9-yl]ethyl}({[5-(trifluoromethyl)pyridin-3-yl]methyl})amine | 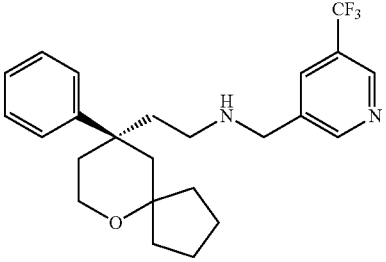 [SMILES: FC(F)(F)c1cncc(CNCC[C@@]2(c3ccccc3)CCOC3(CCCC3)C2)c1] |
| 578 | {2-[(9R)-9-phenyl-6-oxaspiro[4.5]decan-9-yl]ethyl}({[4-(trifluoromethyl)pyridin-3-yl]methyl})amine | 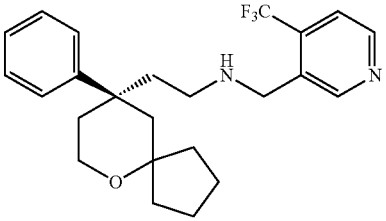 [SMILES: FC(F)(F)c1ccncc1CNCC[C@@]1(c2ccccc2)CCOC2(CCCC2)C1] |
| 579 | [(3,5-difluorophenyl)methyl]({2-[(9R)-9-phenyl-6-oxaspiro[4.5]decan-9-yl]ethyl})amine | 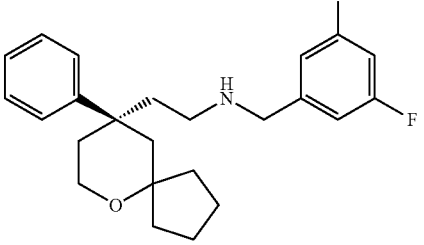 |
| 580 | [(3-methylphenyl)methyl]({2-[(9R)-9-phenyl-6-oxaspiro[4.5]decan-9-yl]ethyl})amine | 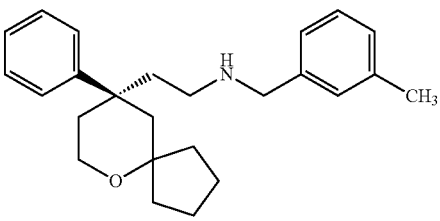 [SMILES: Cc1cccc(CNCC[C@@]2(c3ccccc3)CCOC3(CCCC3)C2)c1] |

TABLE 3-continued

Opioid Receptor Ligands

| Compound | Name | Structure |
|---|---|---|
| 581 | [(5-chloropyridin-3-yl)methyl]({2-[(9R)-9-(4-fluorophenyl)-6-oxaspiro[4.5]decan-9-yl]ethyl})amine | 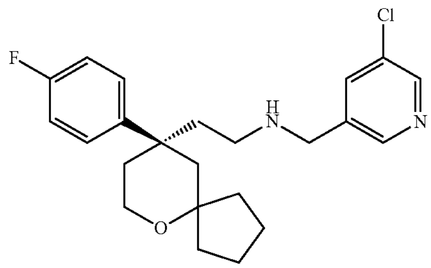 [SMILES: Fc1ccc([C@]2(CCNCc3cncc(Cl)c3)CCOC3(CCCC3)C2)cc1] |
| 582 | {2-[(9R)-9-(4-fluorophenyl)-6-oxaspiro[4.5]decan-9-yl]ethyl}({[5-(trifluoromethyl)pyridin-3-yl]methyl})amin | 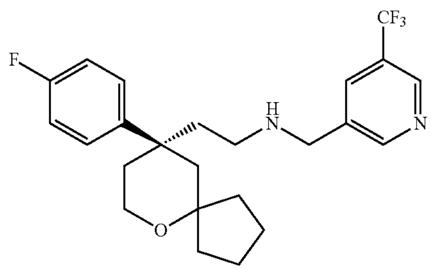 [SMILES: Fc1ccc([C@]2(CCNCc3cncc(C(F)(F)F)c3)CCOC3(CCCC3)C2)cc1] |
| 583 | {2-[(9R)-9-(4-fluorophenyl)-6-oxaspiro[4.5]decan-9-yl]ethyl}({[4-(trifluoromethyl)pyridin-3-yl]methyl})amine | 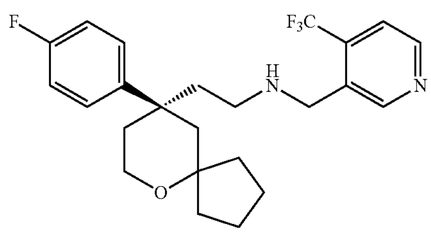 [SMILES: Fc1ccc([C@]2(CCNCc3cnccc3C(F)(F)F)CCOC3(CCCC3)C2)cc1] |
| 584 | [(3,5-difluorophenyl)methyl]({2-[(9R)-9-(4-fluorophenyl)-6-oxaspiro[4.5]decan-9-yl]ethyl})amine | 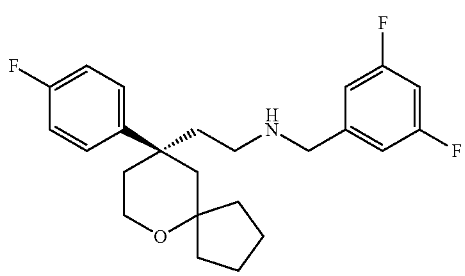 [SMILES: Fc1ccc([C@]2(CCNCc3cc(F)cc(F)c3)CCOC3(CCCC3)C2)cc1] |
| 585 | [(5-chloropyridin-3-yl)methyl]({2-[(9R)-9-[4-(trifluoromethoxy)phenyl]-6-oxaspiro[4.5]decan-9-yl]ethyl})amine | 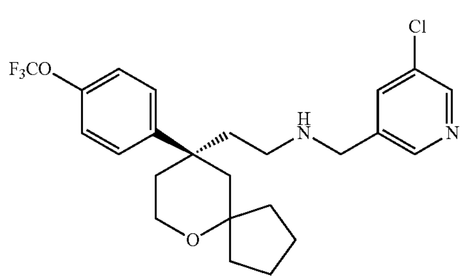 [SMILES: FC(F)(F)Oc1ccc([C@]2(CCNCc3cncc(Cl)c3)CCOC3(CCCC3)C2)cc1] |

TABLE 3-continued

Opioid Receptor Ligands

| Compound | Name | Structure |
|---|---|---|
| 586 | {2-[(9R)-9-[4-(trifluoromethoxy)phenyl]-6-oxaspiro[4.5]decan-9-yl]ethyl}({[5-(trifluoromethyl)pyridin-3-yl]methyl})amine | 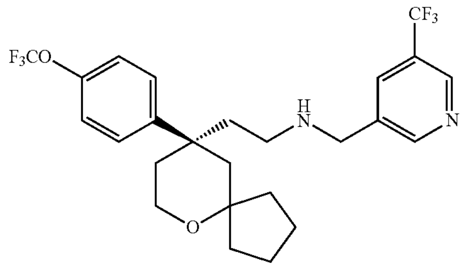 [SMILES: FC(F)(F)Oc1ccc([C@]2(CCNCc3cncc(C(F)(F)F)c3)CCOC3(CCCC3)C2)cc1] |
| 587 | {2-[(9R)-9-[4-(trifluoromethoxy)phenyl]-6-oxaspiro[4.5]decan-9-yl]ethyl}({[4-(trifluoromethyl)pyridin-3-yl]methyl})amine | 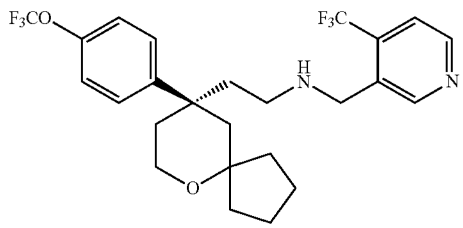 [SMILES: FC(F)(F)Oc1ccc([C@]2(CCNCc3cnccc3C(F)(F)F)CCOC3(CCCC3)C2)cc1] |
| 588 | [(3,5-difluorophenyl)methyl]({2-[(9R)-9-[4-(trifluoromethoxy)phenyl]-6-oxaspiro[4.5]decan-9-yl]ethyl})amine | 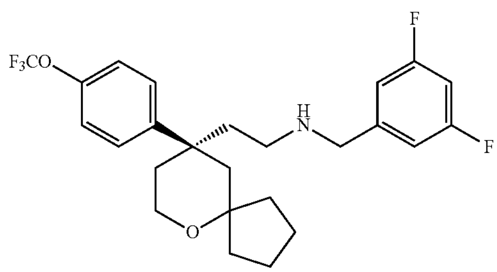 [SMILES: Fc1cc(F)cc(CNCC[C@@]2(c3ccc(OC(F)(F)F)cc3)CCOC3(CCCC3)C2)c1] |
| 589 | [(3-methylphenyl)methyl]({2-[(9R)-9-[4-(trifluoromethoxy)phenyl]-6-oxaspiro[4.5]decan-9-yl]ethyl})amine | 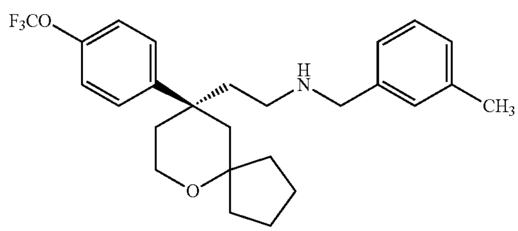 [SMILES: Cc1cccc(CNCC[C@@]2(c3ccc(OC(F)(F)F)cc3)CCOC3(CCCC3)C2)c1] |
| 590 | [(5-chloropyridin-3-yl)methyl]({2-[(9R)-9-(pyridin-3-yl)-6-oxaspiro[4.5]decan-9-yl]ethyl})amine | 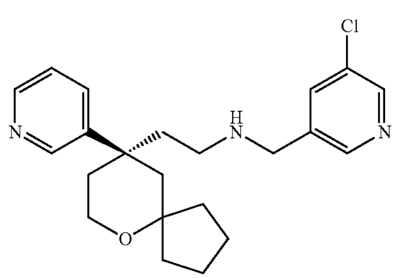 [SMILES: Clc1cncc(CNCC[C@@]2(c3cccnc3)CCOC3(CCCC3)C2)c1] |
| 591 | {2-[(9R)-9-(pyridin-3-yl)-6-oxaspiro[4.5]decan-9-yl]ethyl}({[5-(trifluoromethyl)pyridin-3-yl]methyl})amine | 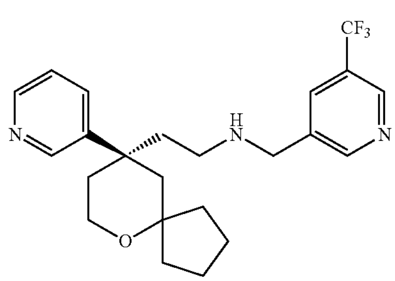 [SMILES: FC(F)(F)c1cncc(CNCC[C@@]2(c3cccnc3)CCOC3(CCCC3)C2)c1] |

TABLE 3-continued

Opioid Receptor Ligands

| Compound | Name | Structure |
|---|---|---|
| 592 | {2-[(9R)-9-(pyridin-3-yl)-6-oxaspiro[4.5]decan-9-yl]ethyl}({[4-(trifluoromethyl)pyridin-3-yl]methyl})amine | 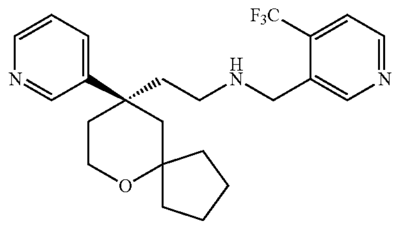 [SMILES: FC(F)(F)c1ccncc1CNCC[C@@]1(c2cccnc2)CCOC2(CCCC2)C1] |
| 593 | [(3,5-difluorophenyl)methyl]({2-[(9R)-9-(pyridin-3-yl)-6-oxaspiro[4.5]decan-9-yl]ethyl})amine | 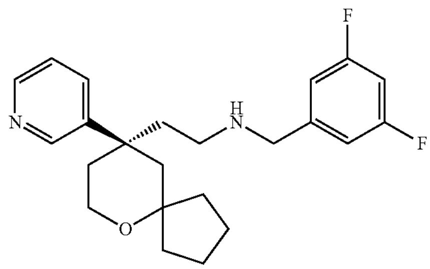 [SMILES: Fc1cc(F)cc(CNCC[C@@]2(c3cccnc3)CCOC3(CCCC3)C2)c1] |
| 594 | [(3-methylphenyl)methyl]({2-[(9R)-9-(pyridin-3-yl)-6-oxaspiro[4.5]decan-9-yl]ethyl})amine | 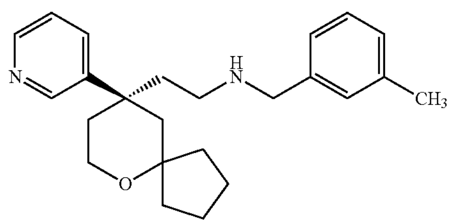 [SMILES: Cc1cccc(CNCC[C@@]2(c3cccnc3)CCOC3(CCCC3)C2)c1] |
| 595 | [(5-chloropyridin-3-yl)methyl]({2-[(9R)-9-(pyridin-4-yl)-6-oxaspiro[4.5]decan-9-yl]ethyl})amine | 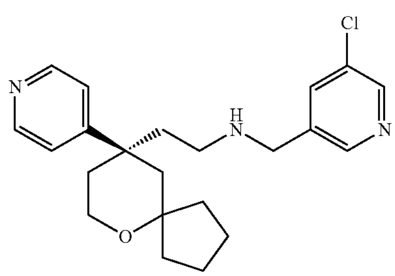 [SMILES: Clc1cncc(CNCC[C@@]2(c3ccncc3)CCOC3(CCCC3)C2)c1] |
| 596 | {2-[(9R)-9-(pyridin-4-yl)-6-oxaspiro[4.5]decan-9-yl]ethyl}({[5-(trifluoromethyl)pyridin-3-yl]methyl})amine | 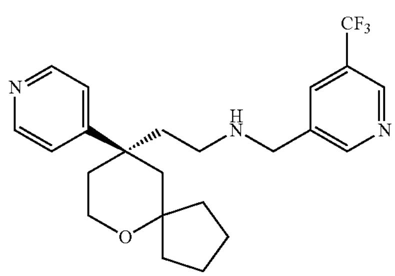 |
| 597 | {2-[(9R)-9-(pyridin-4-yl)-6-oxaspiro[4.5]decan-9-yl]ethyl}({[4-(trifluoromethyl)pyridin-3-yl]methyl})amine | 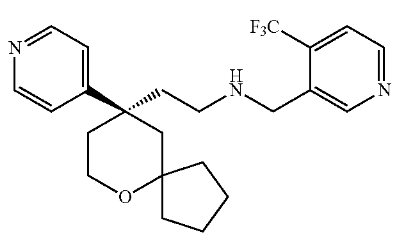 [SMILES: FC(F)(F)c1ccncc1CNCC[C@@]1(c2ccncc2)CCOC2(CCCC2)C1] |

TABLE 3-continued

Opioid Receptor Ligands

| Compound | Name | Structure |
|---|---|---|
| 598 | [(3,5-difluorophenyl)methyl]({2-[(9R)-9-(pyridin-4-yl)-6-oxaspiro[4.5]decan-9-yl]ethyl})amine | 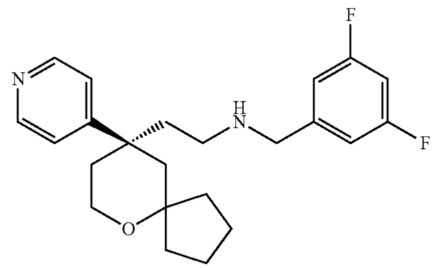 [SMILES: Fc1cc(F)cc(CNCC[C@@]2(c3ccncc3)CCOC3(CCCC3)C2)c1] |
| 599 | [(3-methylphenyl)methyl]({2-[(9R)-9-(pyridin-4-yl)-6-oxaspiro[4.5]decan-9-yl]ethyl})amine | 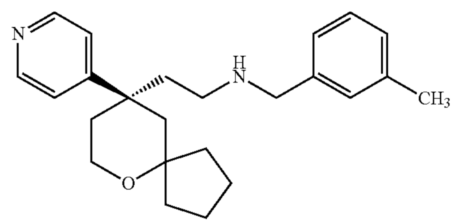 [SMILES: Cc1cccc(CNCC[C@@]2(c3ccncc3)CCOC3(CCCC3)C2)c1] |
| 600 | [(5-chloropyridin-3-yl)methyl]({2-[(9R)-9-(3-methylphenyl)-6-oxaspiro[4.5]decan-9-yl]ethyl})amine | 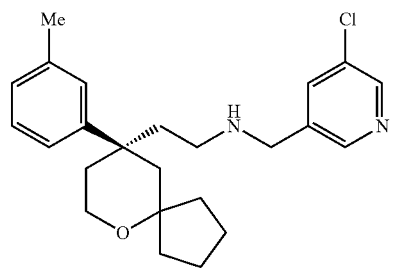 [SMILES: Cc1cccc([C@]2(CCNCc3cncc(Cl)c3)CCOC3(CCCC3)C2)c1] |
| 601 | {2-[(9R)-9-(3-methylphenyl)-6-oxaspiro[4.5]decan-9-yl]ethyl}({[5-(trifluoromethyl)pyridin-3-yl]methyl})amine | 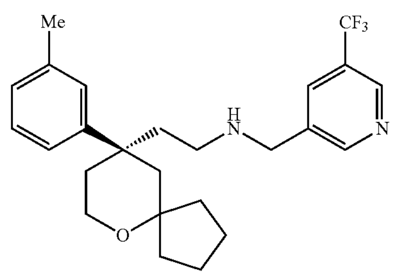 [SMILES: Cc1cccc([C@]2(CCNCc3cncc(C(F)(F)F)c3)CCOC3(CCCC3)C2)c1] |
| 602 | {2-[(9R)-9-(3-methylphenyl)-6-oxaspiro[4.5]decan-9-yl]ethyl}({[4-(trifluoromethyl)pyridin-3-yl]methyl})amine | 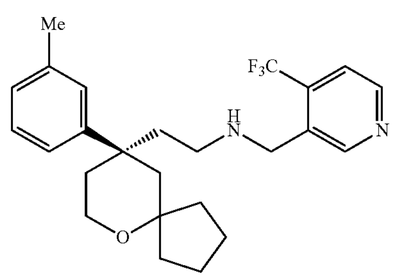 [SMILES: Cc1cccc([C@]2(CCNCc3cnccc3C(F)(F)F)CCOC3(CCCC3)C2)c1] |

TABLE 3-continued

Opioid Receptor Ligands

| Compound | Name | Structure |
|---|---|---|
| 603 | [(3,5-difluorophenyl)methyl]({2-[(9R)-9-(3-methylphenyl)-6-oxaspiro[4.5]decan-9-yl]ethyl})amine | 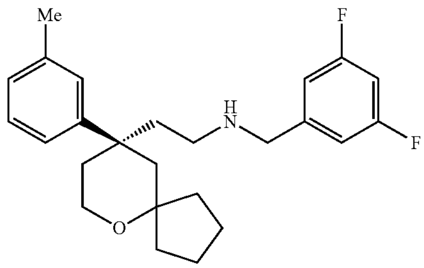 [SMILES: Cc1cccc([C@]2(CCNCc3cc(F)cc(F)c3)CCOC3(CCCC3)C2)c1] |
| 604 | {2-[(9R)-9-(3-methylphenyl)-6-oxaspiro[4.5]decan-9-yl]ethyl}[(3-methylphenyl)methyl]amine | 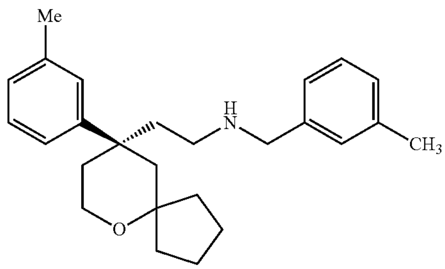 [SMILES: Cc1cccc(CNCC[C@@]2(c3cccc(C)c3)CCOC3(CCCC3)C2)c1] |
| 605 | [(5-chloropyridin-3-yl)methyl]({2-[(9R)-9-[3-(trifluoromethoxy)phenyl]-6-oxaspiro[4.5]decan-9-yl]ethyl})amine | 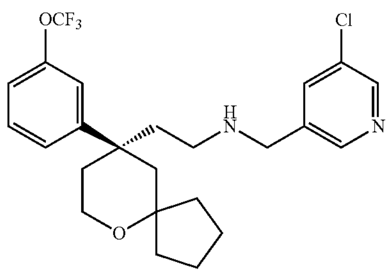 [SMILES: FC(F)(F)Oc1cccc([C@]2(CCNCc3cncc(Cl)c3)CCOC3(CCCC3)C2)c1] |
| 606 | {2-[(9R)-9-[3-(trifluoromethoxy)phenyl]-6-oxaspiro[4.5]decan-9-yl]ethyl}({[5-(trifluoromethyl)pyridin-3-yl]methyl})amine | 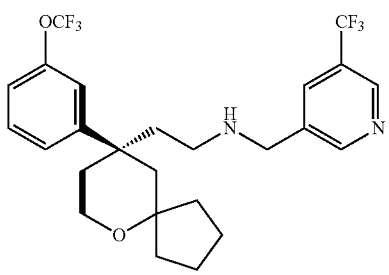 |
| 607 | {2-[(9R)-9-[3-(trifluoromethoxy)phenyl]-6-oxaspiro[4.5]decan-9-yl]ethyl}({[4-(trifluoromethyl)pyridin-3-yl]methyl})amine | 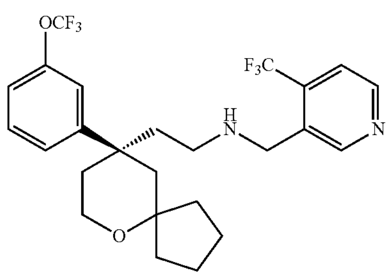 [SMILES: FC(F)(F)Oc1cccc([C@]2(CCNCc3cnccc3C(F)(F)F)CCOC3(CCCC3)C2)c1] |

TABLE 3-continued

Opioid Receptor Ligands

| Compound | Name | Structure |
|---|---|---|
| 608 | [(3,5-difluorophenyl)methyl]({2-[(9R)-9-[3-(trifluoromethoxy)phenyl]-6-oxaspiro[4.5]decan-9-yl]ethyl})amine | 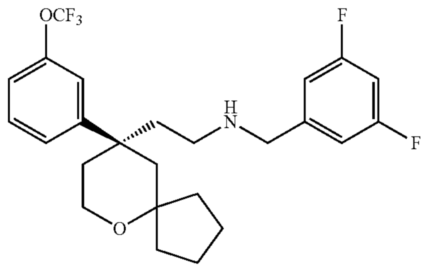 [SMILES: Fc1cc(F)cc(CNCC[C@@]2(c3cccc(OC(F)(F)F)c3)CCOC3(CCCC3)C2)c1] |
| 609 | [(3-methylphenyl)methyl]({2-[(9R)-9-[3-(trifluoromethoxy)phenyl]-6-oxaspiro[4.5]decan-9-yl]ethyl})amine | 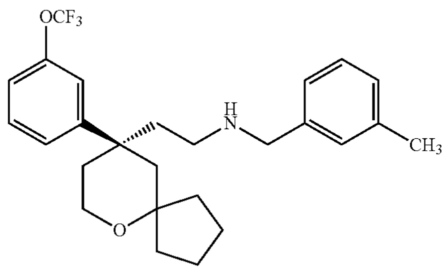 [SMILES: Cc1cccc(CNCC[C@@]2(c3cccc(OC(F)(F)F)c3)CCOC3(CCCC3)C2)c1] |
| 610 | [(5-chloropyridin-3-yl)methyl]({2-[(9R)-9-[4-(trifluoromethyl)phenyl]-6-oxaspiro[4.5]decan-9-yl]ethyl})amine | 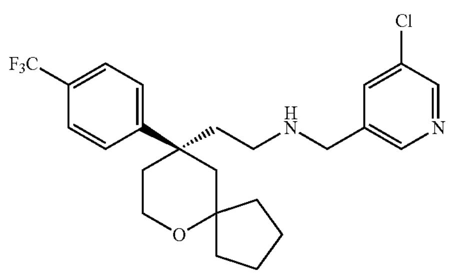 [SMILES: FC(F)(F)c1ccc([C@]2(CCNCc3cncc(Cl)c3)CCOC3(CCCC3)C2)cc1] |
| 611 | {2-[(9R)-9-[4-(trifluoromethyl)phenyl]-6-oxaspiro[4.5]decan-9-yl]ethyl}({[5-(trifluoromethyl)pyridin-3-yl]methyl})amine | 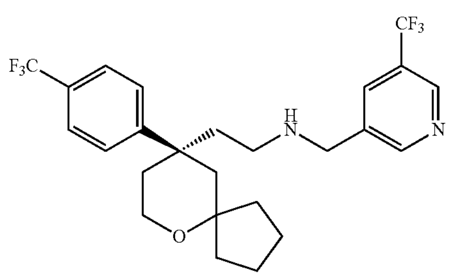 [SMILES: FC(F)(F)c1ccc([C@]2(CCNCc3cncc(C(F)(F)F)c3)CCOC3(CCCC3)C2)cc1] |
| 612 | {2-[(9R)-9-[4-(trifluoromethyl)phenyl]-6-oxaspiro[4.5]decan-9-yl]ethyl}({[4-(trifluoromethyl)pyridin-3-yl]methyl})amine | 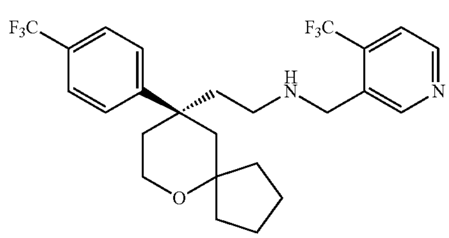 [SMILES: FC(F)(F)c1ccc([C@]2(CCNCc3cnccc3C(F)(F)F)CCOC3(CCCC3)C2)cc1] |

TABLE 3-continued

Opioid Receptor Ligands

| Compound | Name | Structure |
|---|---|---|
| 613 | [(3,5-difluorophenyl)methyl]({2-[(9R)-9-[4-(trifluoromethyl)phenyl]-6-oxaspiro[4.5]decan-9-yl]ethyl})amine | 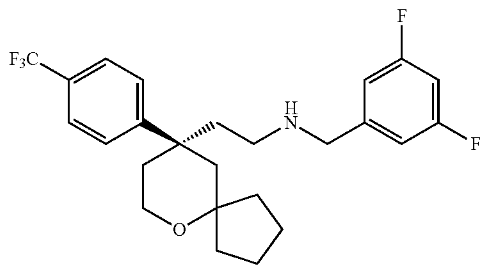 [SMILES: Fc1cc(F)cc(CNCC[C@@]2(c3ccc(C(F)(F)F)cc3)CCOC3(CCCC3)C2)c1] |
| 614 | [(3-methylphenyl]methyl]({2-[(9R)-9-[4-(trifluoromethyl)phenyl]-6-oxaspiro[4.5]decan-9-yl]ethyl})amine | 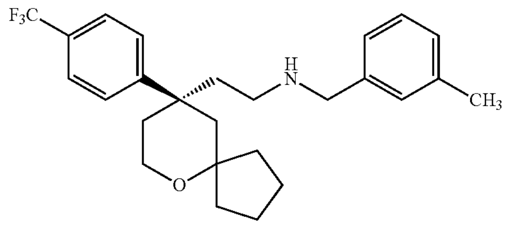 [SMILES: Cc1cccc(CNCC[C@@]2(c3ccc(C(F)(F)F)cc3)CCOC3(CCCC3)C2)c1] |
| 615 | [(5-chloropyridin-3-yl)methyl]({2-[(9R)-9-(3-fluorophenyl)-6-oxaspiro[4.5]decan-9-yl]ethyl})amine | 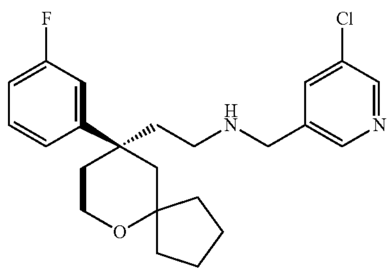 |
| 616 | {2-[(9R)-9-(3-fluorophenyl)-6-oxaspiro[4.5]decan-9-yl]ethyl}({[5-(trifluoromethyl)pyridin-3-yl]methyl})amine | 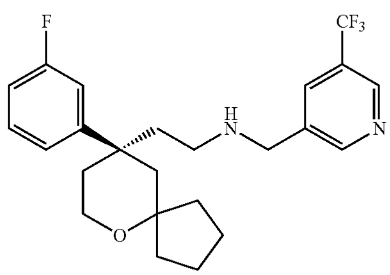 [SMILES: Fc1cccc([C@]2(CCNCc3cncc(C(F)(F)F)c3)CCOC3(CCCC3)C2)c1] |
| 617 | {2-[(9R)-9-(3-fluorophenyl)-6-oxaspiro[4.5]decan-9-yl]ethyl}({[4-(trifluoromethyl)pyridin-3-yl]methyl})amine | 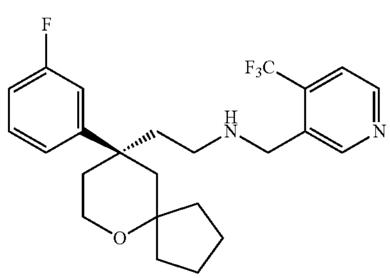 [SMILES: Fc1cccc([C@]2(CCNCc3cnccc3C(F)(F)F)CCOC3(CCCC3)C2)c1] |

TABLE 3-continued

Opioid Receptor Ligands

| Compound | Name | Structure |
|---|---|---|
| 618 | [(3,5-difluorophenyl)methyl]({2-[(9R)-9-(3-fluorophenyl)-6-oxaspiro[4.5]decan-9-yl]ethyl})amine | 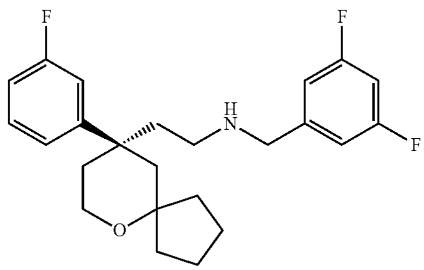 [SMILES: Fc1cc(F)cc(CNCC[C@@]2(c3cccc(F)c3)CCOC3(CCCC3)C2)c1] |
| 619 | {2-[(9R)-9-(3-fluorophenyl)-6-oxaspiro[4.5]decan-9-yl]ethyl}[(3-methylphenyl)methyl]amine | 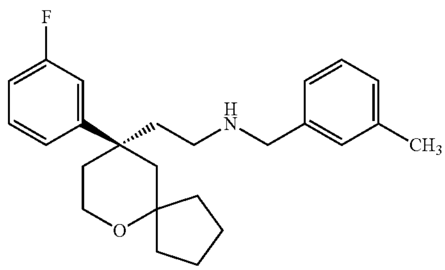 [SMILES: Cc1cccc(CNCC[C@@]2(c3cccc(F)c3)CCOC3(CCCC3)C2)c1] |
| 620 | [(5-chloropyridin-3-yl)methyl]({2-[(9R)-9-[3-(trifluoromethyl)phenyl]-6-oxaspiro[4.5]decan-9-yl]ethyl})amine | 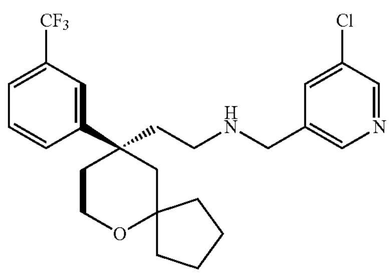 |
| 621 | {2-[(9R)-9-[3-(trifluoromethyl)phenyl]-6-oxaspiro[4.5]decan-9-yl]ethyl}({[5-(trifluoromethyl)pyridin-3-yl]methyl})amine | 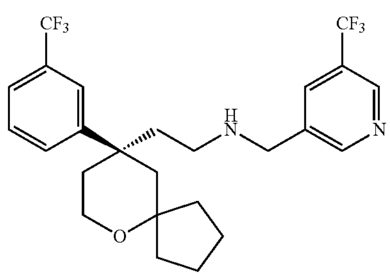 |
| 622 | {2-[(9R)-9-[3-(trifluoromethyl)phenyl]-6-oxaspiro[4.5]decan-9-yl]ethyl}({[4-(trifluoromethyl)pyridin-3-yl]methyl})amine | 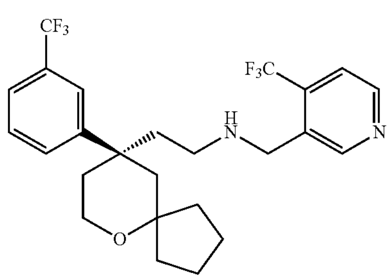 |

TABLE 3-continued

Opioid Receptor Ligands

| Compound | Name | Structure |
|---|---|---|
| 623 | [(3,5-difluorophenyl)methyl]({2-[(9R)-9-[3-(trifluoromethyl)phenyl]-6-oxaspiro[4.5]decan-9-yl]ethyl})amine | 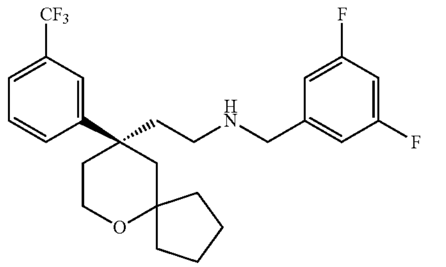 [SMILES: Fc1cc(F)cc(CNCC[C@@]2(c3cccc(C(F)(F)F)c3)CCOC3(CCCC3)C2)c1] |
| 624 | [(3-methylphenyl)methyl]({2-[(9R)-9-[3-(trifluoromethyl)phenyl]-6-oxaspiro[4.5]decan-9-yl]ethyl})amine | 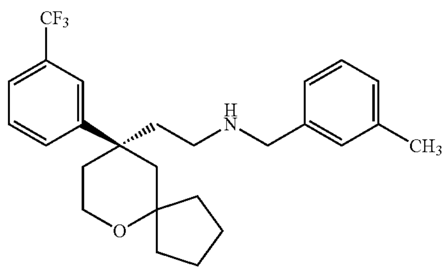 |
| 625 | [(5-chloropyridin-3-yl)methyl](methyl){2-[(9R)-9-(pyridin-2-yl)-6-oxaspiro[4.5]decan-9-yl]ethyl}amine | MS: 400.2<br>1H NMR (400 MHz, CD3CN) δ 8.77 (dd, J = 5.6, 1.3, 1H), 8.67 (d, J = 2.0, 1H), 8.53 (s, 1H), 8.41 (td, J = 8.0, 1.6, 1H), 7.93 (m, 2H), 7.85 (m, 1H), 4.18 (s, 2H), 3.76 (ddd, J = 12.4, 11.3, 5.5, 2H), 3.09 (d, J = 5.1, 1H), 2.65 (s, 3H), 2.55 (m, 2H), 2.33 (m, 3H), 2.08 (d, J = 14.2, 1H), 1.84 (m, 2H), 1.53 (m, 5H), 1.21 (m, 1H), 0.77 (d, J = 13.2, 1H). |
| 626 | methyl({2-[(9R)-9-(pyridin-2-yl)-6-oxaspiro[4.5]decan-9-yl]ethyl}){[5-(trifluoromethyl)pyridin-3-yl]methyl}amine | MS: 434.3<br>1H NMR (400 MHz, CD3CN) δ 8.99 (s, 1H), 8.84 (s, 1H), 8.77 (m, 1H), 8.40 (td, J = 8.0, 1.6, 1H), 8.23 (s, 1H), 7.91 (d, J = 8.2, 1H), 7.84 (dd, J = 6.9, 6.3, 1H), 4.26 (s, 2H), 3.77 (m, 2H), 3.11 (d, J = 4.8, 1H), 2.65 (s, 3H), 2.57 (ddd, J = 17.4, 12.8, 8.9, 2H), 2.34 (dd, J = 19.0, 9.6, 3H), 2.09 (d, J = 14.2, 1H), 1.86 (m, 2H), 1.54 (m, 5H), 1.20 (dd, J = 9.5, 3.8, 1H), 0.77 (dd, J = 9.0, 4.1, 1H). |

TABLE 3-continued

Opioid Receptor Ligands

| Compound | Name | Structure |
|---|---|---|
| 627 | [(5-chloropyridin-3-yl)methyl-(2H2)] {2-[(9R)-9-(pyridin-2-yl)-6-oxaspiro[4.5]decan-9-yl]ethyl}amine | MS: 388.2<br>1H NMR (400 MHz, CD3CN) δ 9.51 (s, 1H), 8.48 (d, J = 1.9, 1H), 8.45 (d, J = 2.3, 1H), 8.42 (ddd, J = 4.8, 1.8, 0.8, 1H), 8.06 (m, 1H), 7.64 (td, J = 7.8, 1.8, 1H), 7.33 (d, J = 8.1, 1H), 7.12 (ddd, J = 7.4, 4.8, 0.7, 1H), 3.57 (m, 2H), 2.74 (td, J = 12.0, 4.7, 1H), 2.21 (m, 4H), 1.96 (dt, J = 12.4, 6.1, 1H), 1.76 (d, J = 13.8, 1H), 1.63 (dd, J = 9.9, 5.9, 1H), 1.40 (m, 6H), 0.95 (m, 1H), 0.59 (m, 1H). |
| 628 | ({2-[(9R)-9-(pyridin-2-yl)-6-oxaspiro[4.5]decan-9-yl]ethyl}){[5-(trifluoromethyl)pyridin-3-yl]methyl-(2H2)}amine | MS: 422.3<br>1H NMR (400 MHz, CD3CN) δ 9.44 (s, 1H), 8.82 (d, J = 1.9, 1H), 8.78 (d, J = 1.2, 1H), 8.40 (ddd, J = 4.8, 1.8, 0.9, 1H), 8.31 (m, 1H), 7.61 (m, 1H), 7.31 (m, 1H), 7.09 (ddd, J = 7.4, 4.8, 1.0, 1H), 3.57 (m, 2H), 2.74 (m, 1H), 2.24 (m, 3H), 2.10 (m, 1H), 1.95 (dd, J = 12.5, 4.7, 1H), 1.75 (d, J = 13.6, 1H), 1.44 (m, 7H), 0.96 (s, 1H), 0.59 (m, 1H). |
| 629 | {2-[(9R)-9-(pyridin-2-yl)-6-oxaspiro[4.5]decan-9-yl]ethyl}({[6-(trifluoromethyl)pyridin-2-yl]methyl})amine | MS: 420.2<br>1H NMR (400 MHz, CD3CN) δ 8.70 (dd, J = 5.2, 1.1, 1H), 8.53 (brs, 1H), 8.11 (td, J = 7.9, 1.7, 1H), 8.05 (t, J = 7.9, 1H), 7.80 (d, J = 7.8, 1H), 7.70 (d, J = 8.2, 1H), 7.57 (ddd, J = 8.3, 7.5, 4.4, 2H), 6.58 (brs, 1H), 4.29 (m, 2H), 3.73 (m, 2H), 3.09 (td, J = 11.8, 5.2, 1H), 2.60 (td, J = 11.9, 4.8, 1H), 2.36 (m, 3H), 2.16 (m, 1H), 1.99 (m, 1H), 1.77 (ddd, J = 14.0, 9.0, 5.1, 2H), 1.62 (m, 1H), 1.48 (m, 4H), 1.16 (ddd, J = 8.5, 7.0, 3.5, 1H), 0.78 (dt, J = 13.1, 8.9, 1H). |

TABLE 3-continued

Opioid Receptor Ligands

| Compound | Name | Structure |
|---|---|---|
| 630 | {2-[(9R)-9-(pyridin-2-yl)-6-oxaspiro[4.5]decan-9-yl]ethyl}({[5-(trifluoromethyl)pyridin-2-yl]methyl})amine | MS: 420.2<br>1H NMR (400 MHz, CD3CN) δ 8.86 (d, J = 0.8, 1H), 8.77 (dd, J = 5.4, 1.2, 1H), 8.20 (m, 1H), 8.11 (dd, J = 8.3, 1.9, 1H), 7.77 (d, J = 8.2, 1H), 7.66 (ddd, J = 7.6, 5.4, 0.9, 1H), 7.53 (d, J = 8.3, 1H), 4.31 (m, 2H), 3.73 (m, 2H), 3.09 (td, J = 11.9, 5.4, 1H), 2.60 (td, J = 11.9, 4.6, 1H), 2.39 (m, 3H), 2.21 (ddd, J = 13.6, 11.8, 5.4, 1H), 2.02 (d, J = 14.0, 1H), 1.80 (ddd, J = 9.5, 8.3, 4.6, 2H), 1.63 (m, 1H), 1.49 (qdd, J = 13.9, 8.5, 3.5, 4H), 1.19 (m, 1H), 0.80 (dt, J = 13.1, 8.8, 1H). |
| 631 | {2-[(9R)-9-(pyridin-2-yl)-6-oxaspiro[4.5]decan-9-yl]ethyl}(pyridin-2-ylmethyl)amine | MS: 352.3<br>1H NMR (400 MHz, CD3CN) δ 10.49 (s, 1H), 8.81 (dd, J = 5.5, 1.2, 1H), 8.55 (dd, J = 3.7, 0.8, 1H), 8.30 (td, J = 8.0, 1.7, 1H), 7.91 (td, J = 7.8, 1.7, 1H), 7.83 (d, J = 8.2, 1H), 7.75 (ddd, J = 7.6, 5.5, 1.0, 1H), 7.45 (dd, J = 11.3, 6.5, 2H), 4.24 (m, 2H), 3.73 (m, 2H), 3.06 (td, J = 12.0, 5.2, 1H), 2.57 (td, J = 12.1, 4.4, 1H), 2.39 (m, 3H), 2.24 (m, 1H), 2.04 (d, J = 14.0, 1H), 1.82 (m, 2H), 1.63 (m, 1H), 1.50 (m, 4H), 1.19 (m, 1H), 0.81 (dt, J = 12.9, 8.8, 1H). |
| 632 | {2-[(9R)-9-(pyridin-2-yl)-6-oxaspiro[4.5]decan-9-yl]ethyl}(pyridin-3-ylmethyl)amine | MS: 352.3<br>1H NMR (400 MHz, CD3CN) δ 8.81 (s, 1H), 8.74 (m, 2H), 8.32 (d, J = 8.1, 1H), 8.26 (td, J = 8.0, 1.7, 1H), 7.80 (m, 2H), 7.70 (m, 1H), 4.18 (m, 2H), 3.73 (m, 2H), 3.02 (td, J = 12.0, 5.1, 1H), 2.51 (td, J = 12.1, 4.3, 1H), 2.36 (m, 3H), 2.15 (m, 1H), 2.01 (d, J = 14.1, 1H), 1.80 (ddd, J = 9.8, 8.2, 4.7, 2H), 1.62 (m, 1H), 1.48 (m, 4H), 1.19 (m, 1H), 0.80 (dt, J = 13.0, 8.8, 1H). |

TABLE 3-continued

Opioid Receptor Ligands

| Compound | Name | Structure |
|---|---|---|
| 633 | {2-[(9R)-9-(pyridin-2-yl)-6-oxaspiro[4.5]decan-9-yl]ethyl}(pyridin-4-ylmethyl)amine | MS: 352.3<br>1H NMR (400 MHz, CD3CN) δ 8.73 (m, 3H), 8.20 (td, J = 8.0, 1.7, 1H), 7.82 (d, J = 6.5, 2H), 7.76 (d, J = 8.2, 1H), 7.65 (m, 1H), 4.22 (m, 2H), 3.73 (m, 2H), 3.03 (td, J = 12.0, 5.1, 1H), 2.53 (td, J = 12.1, 4.4, 1H), 2.37 (m, 3H), 2.16 (m, 1H), 2.00 (d, J = 14.2, 1H), 1.79 (m, 2H), 1.63 (ddd, J = 12.2, 8.8, 4.0, 1H), 1.49 (m, 4H), 1.19 (m, 1H), 0.80 (dt, J = 13.1, 8.9, 1H). |
| 634 | (1H-imidazol-4-ylmethyl)({2-[(9R)-9-(pyridin-2-yl)-6-oxaspiro[4.5]decan-9-yl]ethyl})amine | MS: 341.2<br>1H NMR (400 MHz, CD3CN) δ 8.75 (dd, J = 5.4, 1.2, 1H), 8.54 (d, J = 1.0, 1H), 8.22 (td, J = 8.0, 1.6, 1H), 7.77 (d, J = 8.2, 1H), 7.67 (dd, J = 6.8, 5.6, 1H), 7.47 (s, 1H), 4.18 (s, 2H), 3.72 (m, 2H), 2.92 (td, J = 12.1, 5.0, 1H), 2.38 (m, 4H), 2.13 (m, 1H), 2.00 (m, 1H), 1.79 (m, 2H), 1.63 (m, 1H), 1.48 (m, 4H), 1.19 (m, 1H), 0.82 (dt, J = 13.1, 8.9, 1H). |
| 635 | [(2-methylpyridin-4-yl)methyl]({2-[(9R)-9-(pyridin-2-yl)-6-oxaspiro[4.5]decan-9-yl]ethyl})amine | MS: 366.3<br>1H NMR (400 MHz, CD3CN) δ 8.71 (d, J = 1.9, 1H), 8.65 (dd, J = 5.1, 1.0, 1H), 8.18 (dd, J = 8.2, 2.1, 1H), 8.02 (td, J = 7.9, 1.8, 1H), 7.64 (d, J = 8.1, 2H), 7.49 (dd, J = 6.7, 5.2, 1H), 4.13 (m, 2H), 3.71 (m, 2H), 3.00 (td, J = 11.8, 5.1, 1H), 2.71 (s, 3H), 2.50 (td, J = 11.9, 4.6, 1H), 2.37 (m, 2H), 2.23 (m, 1H), 2.06 (dd, J = 12.0, 5.1, 1H), 1.76 (ddt, J = 14.1, 9.4, 3.8, 3H), 1.61 (dd, J = 16.6, 9.7, 1H), 1.49 (m, 4H), 1.16 (d, J = 11.3, 1H), 0.76 (dt, J = 13.1, 8.9, 1H). |
| 636 | {2-[(9R)-9-(pyridin-2-yl)-6-oxaspiro[4.5]decan-9-yl]ethyl}({[2-(trifluoromethyl)pyridin-4-yl]methyl})amine | MS: 420.2<br>1H NMR (400 MHz, CD3CN) δ 8.75 (d, J = 5.1, 2H), 8.30 (td, J = 8.1, 1.4, 1H), 7.84 (m, 2H), 7.74 (m, 1H), 7.63 (d, J = 4.7, 1H), 4.13 (m, 2H), 3.73 (m, 2H), 3.01 (td, J = 11.9, 5.0, 1H), 2.45 (m, 4H), 2.22 (m, 1H), 2.03 (d, J = 14.1, 1H), 1.81 (m, 2H), 1.63 (m, 1H), 1.49 (m, 4H), 1.21 (dd, J = 9.4, 5.1, 1H), 0.81 (dt, J = 12.8, 8.8,1H). |

TABLE 3-continued

Opioid Receptor Ligands

| Compound | Name | Structure |
|---|---|---|
| 637 | [(6-chloropyridin-3-yl)methyl]({2-[(9R)-9-(pyridin-2-yl)-6-oxaspiro[4.5]decan-9-yl]ethyl})amine | MS: 386.2<br>1H NMR (400 MHz, CD3CN) δ 8.69 (m, 1H), 8.38 (m, 1H), 8.12 (m, 1H), 7.81 (m, 1H), 7.70 (m, 1H), 7.58 (m, 1H), 7.45 (m, 1H), 4.43 (s, 1H), 4.06 (d, J = 13.9, 2H), 3.72 (m, 2H), 2.98 (td, J = 11.9, 5.1, 1H), 2.48 (td, J = 12.0, 4.4, 1H), 2.32 (m, 3H), 2.10 (m, 1H), 1.98 (d, J = 2.4, 1H), 1.77 (m, 2H), 1.61 (ddd, J = 15.0, 8.2, 4.0, 1H), 1.48 (m, 4H), 1.16 (ddd, J = 8.7, 7.1, 4.1, 1H), 0.77 (dt, J = 13.2, 8.9, 1H). |
| 638 | [(1-methyl-1H-imidazol-2-yl)methyl]({2-[(9R)-9-(pyridin-2-yl)-6-oxaspiro[4.5]decan-9-yl]ethyl})amine | MS: 355.3<br>1H NMR (400 MHz, CD3CN) δ 8.71 (ddd, J = 5.3, 1.7, 0.6, 1H), 8.14 (td, J = 8.0, 1.8, 1H), 7.73 (d, J = 8.2, 1H), 7.60 (ddd, J = 7.6, 5.3, 1.0, 1H), 7.43 (d, J = 1.9, 1H), 7.35 (d, J = 1.9, 1H), 4.33 (s, 2H), 3.80 (m, 3H), 3.72 (ddt, J = 15.3, 9.3, 3.1, 2H), 3.03 (td, J = 12.0, 4.9, 1H), 2.59 (td, J = 12.0, 4.6, 1H), 2.36 (m, 3H), 2.15 (m, 1H), 1.99 (m, 1H), 1.80 (m, 2H), 1.63 (ddd, J = 14.4, 9.9, 5.5, 1H), 1.49 (m, 4H), 1.19 (m, 1H), 0.83 (dt, J = 13.1, 8.9, 1H). |
| 639 | (naphthalen-2-ylmethyl)({2-[(9R)-9-(pyridin-2-yl)-6-oxaspiro[4.5]decan-9-yl]ethyl})amine | MS: 401.3<br>1H NMR (400 MHz, CD3CN) δ 8.57 (dd, J = 5.0, 1.0, 1H), 7.90 (m, 5H), 7.59 (m, 2H), 7.54 (d, J = 8.1, 1H), 7.48 (dd, J = 8.5, 1.7, 1H), 7.34 (m, 1H), 4.19 (s, 2H), 3.69 (dt, J = 8.9, 5.1, 3H), 3.48 (brs, 1H), 3.02 (s, 1H), 2.52 (s, 1H), 2.33 (m, 2H), 2.19 (m, 1H), 2.02 (m, 1H), 1.89 (t, J = 9.4, 1H), 1.70 (dq, J = 9.2, 5.1, 2H), 1.59 (m, 1H), 1.44 (m, 4H), 1.10 (m, 1H), 0.69 (dt, J = 13.1, 8.8, 1H). |

TABLE 3-continued

Opioid Receptor Ligands

| Compound | Name | Structure |
|---|---|---|
| 640 | [(6-bromo-5-fluoropyridin-3-yl)methyl]({2-[(9R)-9-(pyridin-2-yl)-6-oxaspiro[4.5]decan-9-yl]ethyl})amine | MS: 448.2<br>1H NMR (400 MHz, CD3CN) δ 8.68 (dd, J = 5.2, 1.2, 1H), 8.24 (d, J = 1.5, 1H), 8.12 (td, J = 7.9, 1.7, 1H), 7.71 (m, 2H), 7.58 (dd, J = 7.1, 5.7, 1H), 4.88 (s, 1H), 4.08 (d, J = 14.0, 2H), 3.72 (m, 2H), 2.98 (td, J = 11.9, 5.1, 1H), 2.48 (td, J = 12.0, 4.4, 1H), 2.32 (m, 3H), 2.11 (m, 1H), 1.98 (d, J = 2.5, 1H), 1.77 (m, 2H), 1.61 (m, 1H), 1.48 (m, 4H), 1.17 (m, 1H), 0.77 (dt, J = 13.1, 8.9, 1H).<br>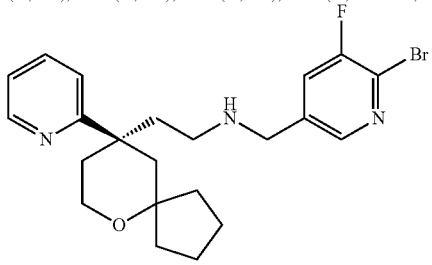 |
| 641 | [(5-methanesulfonylpyridin-3-yl)methyl]({2-[(9R)-9-(pyridin-2-yl)-6-oxaspiro[4.5]decan-9-yl]ethyl})amine | MS: 430.2<br>1H NMR (400 MHz, CD3CN) δ 9.10 (d, J = 2.0, 1H), 8.87 (d, J = 1.8, 1H), 8.71 (dd, J = 5.3, 1.1, 1H), 8.37 (t, J = 2.0, 1H), 8.18 (td, J = 8.0, 1.8, 1H), 7.75 (d, J = 8.2, 1H), 7.63 (ddd, J = 7.6, 5.4, 0.9, 1H), 4.16 (m, 2H), 3.73 (m, 2H), 3.14 (s, 3H), 3.02 (td, J = 12.0, 5.2, 1H), 2.52 (m, 1H), 2.33 (m, 3H), 2.14 (m, 1H), 2.01 (m, 1H), 1.79 (m, 2H), 1.62 (m, 1H), 1.48 (m, 4H), 1.19 (m, 1H), 0.79 (dt, J = 13.1, 8.9, 1H).<br>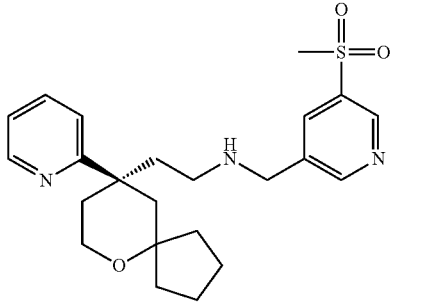 [SMILES: CS(=O)(=O)c1cncc(CNCC[C@@]2(c3ccccn3)CCOC3(CCCC3)C2)c1] |
| 642 | [2-(3-methylphenyl)ethyl]({2-[(9R)-9-(pyridin-2-yl)-6-oxaspiro[4.5]decan-9-yl]ethyl})amine | 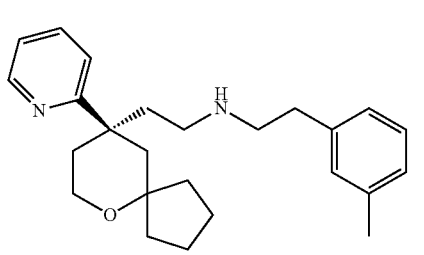 [SMILES: Cc1cccc(CCNCC[C@@]2(c3ccccn3)CCOC3(CCCC3)C2)c1] |
| 643 | [2-(3-chlorophenyl)ethyl]({2-[(9R)-9-(pyridin-2-yl)-6-oxaspiro[4.5]decan-9-yl]ethyl})amine | 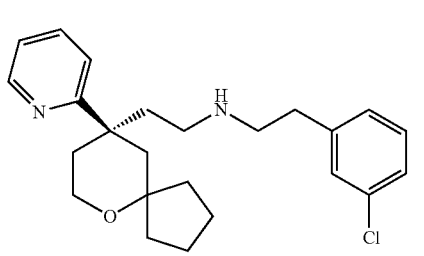 [SMILES: Clc1cccc(CCNCC[C@@]2(c3ccccn3)CCOC3(CCCC3)C2)c1] |

TABLE 3-continued

Opioid Receptor Ligands

| Compound | Name | Structure |
|---|---|---|
| 644 | [2-(3-bromophenyl)ethyl]({2-[(9R)-9-(pyridin-2-yl)-6-oxaspiro[4.5]decan-9-yl]ethyl})amine | 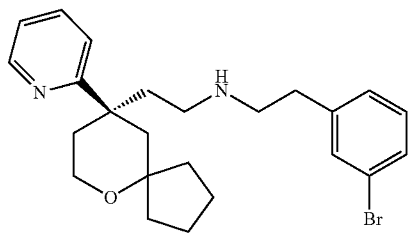 [SMILES: Brc1cccc(CCNCC[C@@]2(c3ccccn3)CCOC3(CCCC3)C2)c1] |
| 645 | [2-(3-fluorophenyl)ethyl]({2-[(9R)-9-(pyridin-2-yl)-6-oxaspiro[4.5]decan-9-yl]ethyl})amine | 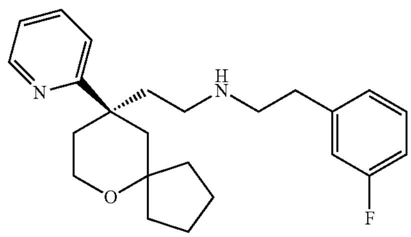 [SMILES: Fc1cccc(CCNCC[C@@]2(c3ccccn3)CCOC3(CCCC3)C2)c1] |
| 646 | {2-[(9R)-9-(pyridin-2-yl)-6-oxaspiro[4.5]decan-9-yl]ethyl}({2-[3-(trifluoromethyl)phenyl]ethyl})amine | 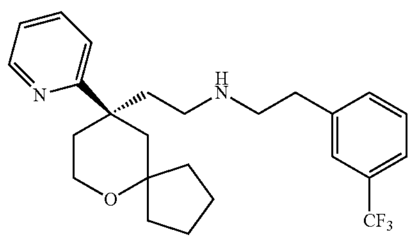 |
| 647 | [2-(3-methoxyphenyl)ethyl]({2-[(9R)-9-(pyridin-2-yl)-6-oxaspiro[4.5]decan-9-yl]ethyl})amine | 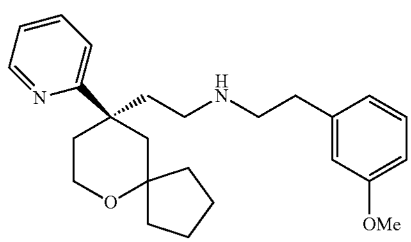 [SMILES: COc1cccc(CCNCC[C@@]2(c3ccccn3)CCOC3(CCCC3)C2)c1] |
| 648 | [2-(4-methylphenyl)ethyl]({2-[(9R)-9-(pyridin-2-yl)-6-oxaspiro[4.5]decan-9-yl]ethyl})amine | 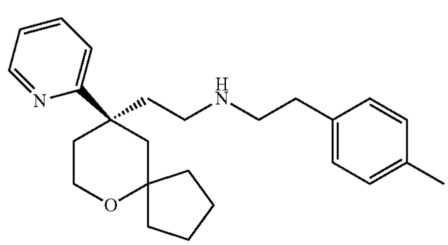 [SMILES: Cc1ccc(CCNCC[C@@]2(c3ccccn3)CCOC3(CCCC3)C2)cc1] |
| 649 | [2-(4-chlorophenyl)ethyl]({2-[(9R)-9-(pyridin-2-yl)-6-oxaspiro[4.5]decan-9-yl]ethyl})amine | 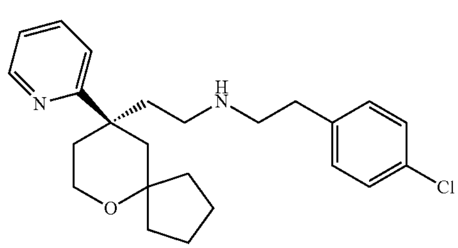 [SMILES: Clc1ccc(CCNCC[C@@]2(c3ccccn3)CCOC3(CCCC3)C2)cc1] |

TABLE 3-continued

Opioid Receptor Ligands

| Compound | Name | Structure |
|---|---|---|
| 650 | [2-(4-bromophenyl)ethyl]({2-[(9R)-9-(pyridin-2-yl)-6-oxaspiro[4.5]decan-9-yl]ethyl})amine | 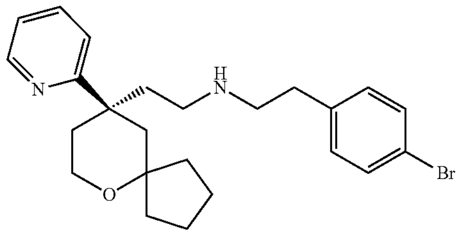 [SMILES: Brc1ccc(CCNCC[C@@]2(c3ccccn3)CCOC3(CCCC3)C2)cc1] |
| 651 | [2-(4-fluorophenyl)ethyl]({2-[(9R)-9-(pyridin-2-yl)-6-oxaspiro[4.5]decan-9-yl]ethyl})amine | 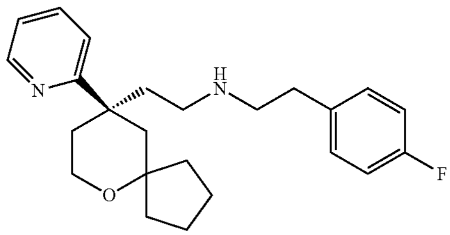 [SMILES: Fc1ccc(CCNCC[C@@]2(c3ccccn3)CCOC3(CCCC3)C2)cc1] |
| 652 | {2-[(9R)-9-(pyridin-2-yl)-6-oxaspiro[4.5]decan-9-yl]ethyl}({2-[4-(trifluoromethyl)phenyl]ethyl})amine | 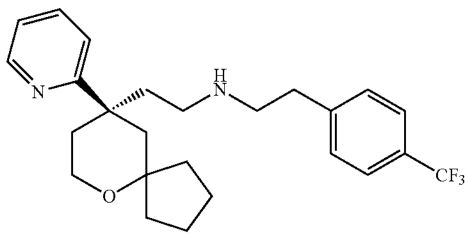 [SMILES: FC(F)(F)c1ccc(CCNCC[C@@]2(c3ccccn3)CCOC3(CCCC3)C2)cc1] |
| 653 | [2-(4-methoxyphenyl)ethyl]({2-[(9R)-9-(pyridin-2-yl)-6-oxaspiro[4.5]decan-9-yl]ethyl})amine | 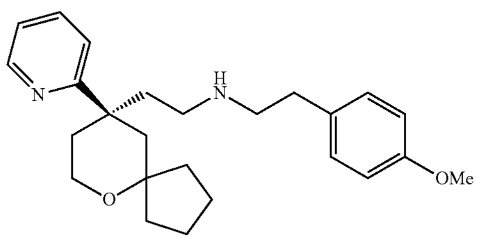 [SMILES: COc1ccc(CCNCC[C@@]2(c3ccccn3)CCOC3(CCCC3)C2)cc1] |
| 654 | [2-(2-methylphenyl)ethyl]({2-[(9R)-9-(pyridin-2-yl)-6-oxaspiro[4.5]decan-9-yl]ethyl})amine | 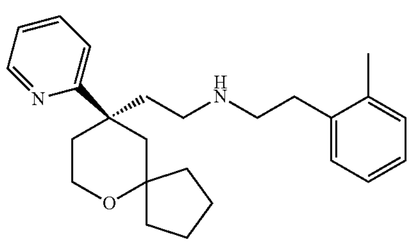 [SMILES: Cc1ccccc1CCNCC[C@@]1(c2ccccn2)CCOC2(CCCC2)C1] |
| 655 | [2-(2-chlorophenyl)ethyl]({2-[(9R)-9-(pyridin-2-yl)-6-oxaspiro[4.5]decan-9-yl]ethyl})amine | 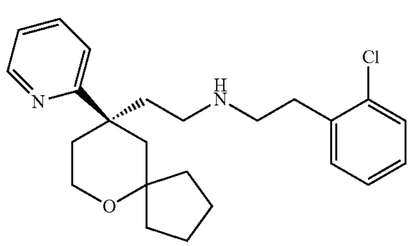 [SMILES: Clc1ccccc1CCNCC[C@@]1(c2ccccn2)CCOC2(CCCC2)C1] |

TABLE 3-continued

Opioid Receptor Ligands

| Compound | Name | Structure |
|---|---|---|
| 656 | [2-(2-bromophenyl)ethyl]({2-[(9R)-9-(pyridin-2-yl)-6-oxaspiro[4.5]decan-9-yl]ethyl})amine | 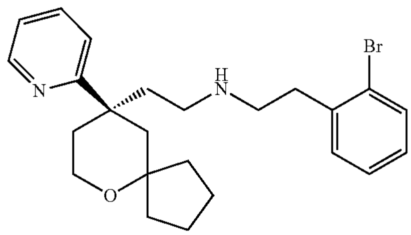 [SMILES: Brc1ccccc1CCNCC[C@@]1(c2ccccn2)CCOC2(CCCC2)C1] |
| 657 | [2-(2-fluorophenyl)ethyl]({2-[(9R)-9-(pyridin-2-yl)-6-oxaspiro[4.5]decan-9-yl]ethyl})amine | 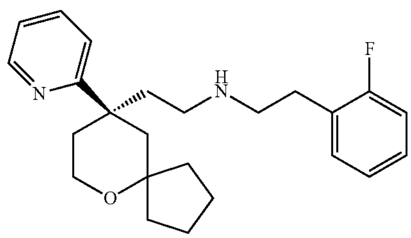 [SMILES: Fc1ccccc1CCNCC[C@@]1(c2ccccn2)CCOC2(CCCC2)C1] |
| 658 | {2-[(9R)-9-(pyridin-2-yl)-6-oxaspiro[4.5]decan-9-yl]ethyl}({2-[2-(trifluoromethyl)phenyl]ethyl})amine | 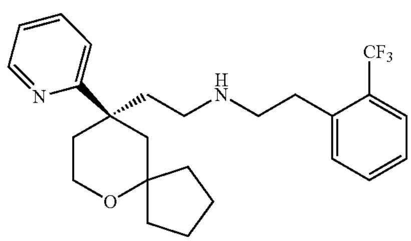 [SMILES: FC(F)(F)c1ccccc1CCNCC[C@@]1(c2ccccn2)CCOC2(CCCC2)C1] |
| 659 | [2-(2-methoxyphenyl)ethyl]({2-[(9R)-9-(pyridin-2-yl)-6-oxaspiro[4.5]decan-9-yl]ethyl})amine | 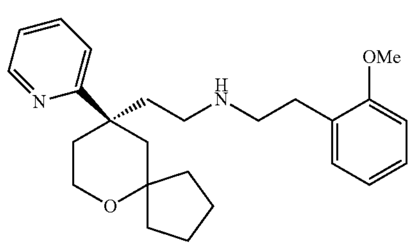 [SMILES: COc1ccccc1CCNCC[C@@]1(c2ccccn2)CCOC2(CCCC2)C1] |

Example 15

Synthesis of [(3-methoxythiophen-2-yl)methyl]({2-[(9R)-9-(pyridin-2-yl)-6-oxaspiro[4.5]decan-9-yl]ethyl})amine (Compound 140)

Methyl 2-cyano-2-[6-oxaspiro[4.5]decan-9-ylidene]acetate (mixture of E and Z isomers)

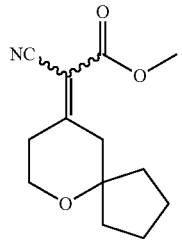

A mixture of 6-oxaspiro[4.5]decan-9-one (13.74 g, 89.1 mmol), methylcyanoacetate (9.4 ml, 106.9 mmol), ammonium acetate (1.79 g, 26.17 mmol) and acetic acid (1.02 ml, 17.8 mmol) in benzene (75 ml) was heated at reflux in a 250 ml round bottom flask equipped with a Dean-Stark and a reflux condenser. After 3 h, TLC (25% EtOAc in hexane, PMA stain) showed the reaction was completed. After cooling, benzene (50 ml) was added and the layer was separated, the organic was washed by water (120 ml) and the aqueous layer was extracted by $CH_2Cl_2$ (3×120 ml). The combined organic was washed with sat'd $NaHCO_3$, brine, dried and concentrated and the residual was purified by flash chromatography (340 g silica gel column, eluted by EtOAc in hexane: 5% EtOAc, 2 CV; 5-25%, 14 CV; 25-40%, 8 CV) gave a mixture of E and Z isomers: methyl 2-cyano-2-[6-oxaspiro[4.5]decan-9-ylidene]acetate (18.37 g, 87.8% yield, m/z 236.0 [M+H]$^+$ observed) as a clear oil.

Methyl 2-cyano-2-[9-(pyridin-2-yl)-6-oxaspiro[4.5]decan-9-yl]acetate

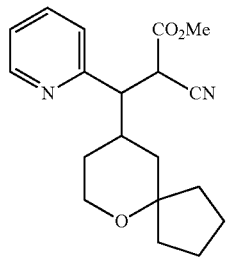 [SMILES: COC(=O)C(C#N)C(c1ccccn1)C1CCOC2(CCCC2)C1]

A solution of 2-bromopyridine (14.4 ml, 150 mmo) in THF (75 ml) was added dropwise to a solution of isopropylmagnesium chloride (75 ml, 2M in THF) at 0° C. under $N_2$, the mixture was then stirred at rt for 3 h, copper Iodide (2.59 g, 13.6 mmol) was added and allowed to stir at rt for another 30 min before a solution of a mixture of E and Z isomers of methyl 2-cyano-2-[6-oxaspiro[4.5]decan-9-ylidene]acetate (16 g, 150 mmol) in THF (60 ml) was added in 30 min. The mixture was then stirred at rt for 18 h. The reaction mixture was poured into a 200 g ice/2 N HCl (100 ml) mixture. The product was extracted with $Et_2O$ (3×300 ml), washed with brine (200 ml), dried ($Na_2SO_4$) and concentrated. The residual was purified by flash chromatography (100 g silica gel column, eluted by EtOAc in hexane: 3% 2 CV; 3-25%, 12 CV; 25-40% 6 CV gave methyl 2-cyano-2-[9-(pyridin-2-yl)-6-oxaspiro[4.5]decan-9-yl]acetate (15.44 g, 72% yield, m/z 315.0 [M+H]+ observed) as an amber oil.

2-[9-(Pyridin-2-yl)-6-oxaspiro[4.5]decan-9-yl]acetonitrile

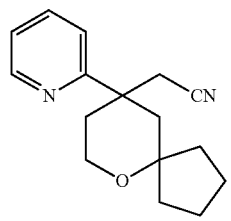 [SMILES: N#CCC1(c2ccccn2)CCOC2(CCCC2)C1]

Ethylene glycol (300 ml) was added to methyl 2-cyano-2-[9-(pyridin-2-yl)-6-oxaspiro[4.5]decan-9-yl]acetate (15.43 g, 49 mmol) followed by potassium hydroxide (5.5 g, 98 mmol), the resulting mix was heated to 120° C., after 3 h, the reaction mix was cooled and water (300 ml) was added, the product was extracted by $Et_2O$ (3×400 ml), washed with water (200 ml), dried (Na2SO4) and concentrated, the residual was purified by flash chromatography (340 g silica gel column, eluted by EtOAc in hexane: 3% 2 CV; 3-25%, 12 CV; 25-40% 6 CV to give 2-[9-(Pyridin-2-yl)-6-oxaspiro[4.5]decan-9-yl]acetonitrile (10.37 g, 82% yield, m/z 257.0 [M+H]+ observed).

2-[(9R)-9-(Pyridin-2-yl)-6-oxaspiro[4.5]decan-9-yl]acetonitrile

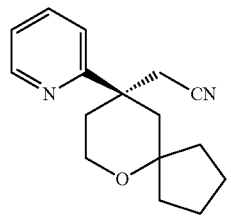 [SMILES: N#CC[C@@]1(c2ccccn2)CCOC2(CCCC2)C1]

The racemic 2-[9-(pyridin-2-yl)-6-oxaspiro[4.5]decan-9-yl]acetonitrile was separated by chiral HPLC column under the following preparative-SFC conditions: Instrument: SFC-80 (Thar, Waters); Column: Chiralpak AD-H (Daicel); column temperature: 40° C.; Mobile phase: Methanol/CO2=40/60; Flow: 70 g/min; Back pressure: 120 Bar; Cycle time of stack injection: 6.0 min; Load per injection: 225 mg; Under these conditions, 2-[9-(pyridin-2-yl)-6-oxaspiro[4.5]decan- 9-yl]acetonitrile (4.0 g) was separated to provide the desired isomer, 2-[(9R)-9-(Pyridin-2-yl)-6-oxaspiro[4.5]decan-9-yl]acetonitrile (2.0 g, >99.5% enantiomeric excess) as a slow-moving fraction. The absolute (R) configuration of the desired isomer was later determined by an X-ray crystal structure analysis of Compound 140.

2-[(9R)-9-(Pyridin-2-yl)-6-oxaspiro[4.5]decan-9-yl]ethan-1-amine

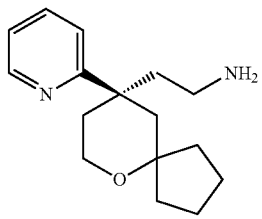 [SMILES: NCC[C@@]1(c2ccccn2)CCOC2(CCCC2)C1]

LAH (1M in Et2O, 20 ml, 20 mmol) was added to a solution of 2-[(9R)-9-(pyridin-2-yl)-6-oxaspiro[4.5]decan-9-yl]acetonitrile (2.56 g, 10 mmol) in Et2O (100 ml, 0.1M) at 0° C. under $N_2$. The resulting mix was stirred and allowed to warm to room temperature. After 2 h, LCMS showed the reaction had completed. The reaction was cooled at 0° C. and quenched with water (1.12 ml), NaOH (10%, 2.24 ml) and another 3.36 ml of water. Solid was filtered and filter pad was washed with ether (3×20 ml). The combined organic was dried and concentrated to give 2-[(9R)-9-(Pyridin-2-yl)-6-oxaspiro[4.5]decan-9-yl]ethan-1-amine (2.44 g, 94% yield, m/z 260.6 [M+H]+ observed) as a light amber oil.

Alternatively, 2-[(9R)-9-(Pyridin-2-yl)-6-oxaspiro[4.5]decan-9-yl]ethan-1-amine was prepared by Raney-Nickel catalyzed hydrogenation.

An autoclave vessel was charged with 2-[(9R)-9-(pyridin-2-yl)-6-oxaspiro[4,5]decan-9-yl]acetonitrile and ammonia (7N solution in methanol). The resulting solution was stirred at ambient conditions for 15 minutes and treated with Raney 2800 Nickel, slurried in water. The vessel was pressurized to 30 psi with nitrogen and agitated briefly. The autoclave was vented and the nitrogen purge repeated additional two times. The vessel was pressurized to 30 psi with hydrogen and agitated briefly. The vessel was vented and purged with hydrogen two additional times. The vessel was pressurized to 85-90 psi with hydrogen and the mixture was warmed to 25-35° C. The internal temperature was increased to 45-50° C. over 30-60 minutes. The reaction mixture was stirred at 45-50° C. for 3 days. The reaction was monitored by HPLC. Once reaction was deemed complete, it was cooled to ambient temperature and filtered through celite. The filter cake was washed with methanol (2×). The combined filtrates were concentrated under reduced pressure at 40-45° C. The resulting residue was co-evaporated with EtOH (3×) and dried to a thick syrupy of 2-[(9R)-9-(pyridin-2-yl)-6-oxaspiro[4.5]decan-9-yl]ethan-1-amine.

[(3-Methoxythiophen-2-yl)methyl]({2-[(9R)-9-(pyridin-2-yl)-6-oxaspiro[4.5]decan-9-yl]ethyl})amine

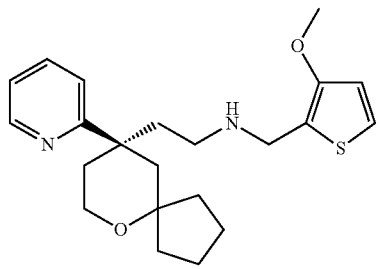 [SMILES: COc1ccsc1CNCC[C@@]1(c2ccccn2)CCOC2(CCCC2)C1]

Into a vial were added 2-[(9R)-9-(Pyridin-2-yl)-6-oxaspiro[4.5]decan-9-yl]ethan-1-amine (500 mg, 1.92 mmole), 18 mL CH2Cl2 and sodium sulfate (1.3 g, 9.6 mmole). The 3-methoxythiophene-2-carboxaldehyde (354 mg, 2.4 mmole) was then added, and the mixture was stirred overnight. NaBH4 (94 mg, 2.4 mmole) was added to the reaction mixture, stirred for 10 minutes, and then MeOH (6.0 mL) was added, stirred 1 h, and finally quenched with water. The organics were separated off and evaporated. The crude residue was purified by a Gilson prep HPLC. The desired fractions collected and concentrated and lyophilized. After lyophilization, residue was partitioned between $CH_2Cl_2$ and 2N NaOH, and the organic layers were collected. After solvent was concentrated to half of the volume, 1.0 eq of 1N HCl in Et2O was added, and majority of solvent evaporated under reduced pressure. The solid obtained was washed several times with Et2O and dried to provide [(3-methoxythiophen-2-yl)methyl]({2-[(9R)-9-(pyridin-2-yl)-6-oxaspiro[4.5]decan-9-yl]ethyl})amine monohydrochloride (336 mg, 41% yield, m/z 387.0 [M+H]+ observed) as a white solid. The NMR for Compound 140 is described herein.

Example 16

Biological Example

Procedure for the Testing for Antinociception

The hot plate assay is adapted from the procedure originally described by O'Callaghan and Holtzman (JPET, 192, 497, 1975) and is commonly used to determine the potential analgesic efficacy of opioid agonists. The antinociceptive effect of the composition(s) described herein in the hot plate is expressed in % MPE (Maximum Possible Effect).

Rats (175-250 g) or mice (20-30 g) acclimated to the vivarium for at least 48 hr prior to behavioral testing. Test drugs were administered by the subcutaneous (SC) route. Animals were placed on the hot plate, which the temperature was set at 50-56° C., depending on the in vitro potency of the compound. A cutoff time of 30-60 seconds was used depending on the temperature of the hot plate so that the paws of the animal displaying analgesia, was not damaged by the heat stimulus. The cutoff time was considered a 100% response to the thermal insult. Prior to drug treatment, each animal was tested to determine the baseline response. Thirty minutes after drug administration, animals were re-tested. Dose response experiments were performed to evaluate the potency of the test compound when various doses were administered at the point when maximal analgesia is observed.

The % MPE was calculated according to the following formula: % MPE=[(Post drug latency−baseline latency)/(60 or 30−baseline latency)]×100

ED$_{50}$ values were calculated from the mean % MPE values for each group using log dose-response curves by least-squares regression analysis.

TABLE 4

| COMPOUND | ED50 or % MPE |
|---|---|
| Morphine | 3.8 mg/kg SC |
| Compound 81 | 100% at 10 mg/kg SC |
| Compound 122 | 1.1 mg/kg SC |
| Compound 28 | 1.2 mg/kg SC |
| Compound 145 | 5.9 mg/kg SC |

Results are shown in Table 4. Naïve or control mice typically exhibit reaction times in the hot plate from 10-15 seconds. The ED50 for morphine in the mouse hot plate was 3.8 mg/kg with full efficacy observed at a dose of 10 mg/kg SC. For comparison, Compound 122 and Compound 28 produced potent efficacy with an ED50 of 1.1 and 1.2 mg/kg SC, respectively. These results demonstrate that Compound 122 and Compound 28 produced a more robust analgesic effect in the mouse hot plate assay compared to morphine.

Example 17

In Vivo Administration to Humans (Prophetic Example)

One or more compounds will be administered in dosage range from 0.15 mg to 4 mg to human subject. The compound(s) will be administered as a continuous infusion over one hour. The dose may be escalated as deemed appropriate to obtain pain relief. Dose escalation will usually not exceed 5-fold as compared to the previous dose. Dosage amounts, however, may be repeated or decreased as deemed appropriate. The subjects will be tested for their ability to withstand or not appreciate pain as compared to a control (placebo) group.

The cold pain test has been shown to be a reproducible and sensitive measure of the effect of opiates and other centrally acting drugs (Van F and Rolan P E. The utility of the cold pain test to measure analgesia from intravenous morphine. Br. J. Clin. Pharmacol. 1996; 42: 663-664; Posner J. Pain Models in Healthy Volunteers. In: Nimmo W S, Tucker G, eds. Clinical Measurement in Drug Evaluation. 1991, Wolfe Publishing Limited, UK.; Wotherspoon H A, Kenny G N C, McArdle C S. Analgesic Efficacy of Controlled-Release DihydroCodeine. Anaesthesia 1991; 46: 915-917.; Lamb R J, Mercer A J, Posner J. The effect of lamotrigine (300 mg) and dipipanone (4 mg and 8 mg), alone and in combination, on the cold-pain test in healthy volunteers. Br. J. Clin. Pharmacol. 1994; 39: 539-588P.). In the test a subject's hand is immersed in cold water chilled to a range of 1 to 3° C. The initial sensation of cold is replaced by a deep burning discomfort in the hand which is mediated by nociceptors in veins. The discomfort gradually builds to a plateau over approximately 90 seconds and then either persists or decreases slightly. The stimulus is easily controlled and the response is reproducible. The technique has been shown to be sensitive to different doses of analgesic drugs.

During the cold pain test, the subject will sit down and place his/her non-dominant hand into a stirred, thermostatically controlled water bath at about 2° C. With the other hand the subject can adjust a visual analogue scale on a computer screen using the arrow keys on the keypad. The scale is labelled "no pain" at one end and "maximum pain" at the other end. The pointer will initially be at the "no pain" end and the subject will move the pointer across the line to rate their feelings continuously over the test period. At the end of 2 minutes the computer will automatically instruct the subject to remove his/her hand which can then be dried. The cold pain test has been used extensively in healthy volunteer studies and is non-invasive.

It is expected that the administration of the compound(s) will enable the human subject to feel no pain or less pain as compared to the control group.

While the compounds described herein have been described with reference to examples, those skilled in the art recognize that various modifications may be made without departing from the spirit and scope thereof.

All of the above U.S. patents, U.S. patent application publications, U.S. patent applications, foreign patents, foreign patent applications and non-patent publications referred to in this specification and/or listed in the Application Data Sheet are incorporated herein by reference, in their entirety.

What is claimed is:

1. A compound having the formula

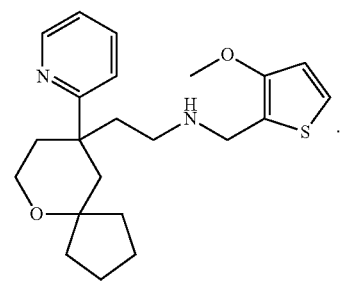 [SMILES: COc1ccsc1CNCCC1(c2ccccn2)CCOC2(CCCC2)C1 ; "."]

2. A pharmaceutical composition comprising a compound of claim 1 and pharmaceutically acceptable carrier.

3. The pharmaceutical composition of claim 2 further comprising at least one additional anti-constipation agent.

4. A compound, having the formula

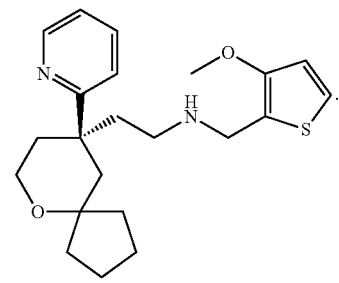 [SMILES: COc1ccsc1CNCC[C@@]1(c2ccccn2)CCOC2(CCCC2)C1]

5. The pharmaceutical composition of claim 2 further comprising at least one additional analgesic or non-opioid analgesic.

6. A pharmaceutical composition comprising a compound of claim 4 and pharmaceutically acceptable carrier.

7. A method of treating pain comprising administering to a subject in need thereof a compound of claim 4.

8. The method of claim 7, wherein the compound is co-administered simultaneously or sequentially with an additional analgesic or non-opioid analgesic.

9. The method of claim 7, wherein the compound is co-administered simultaneously or sequentially with an anti-constipation agent.

10. The pharmaceutical composition of claim 6 further comprising at least one additional analgesic or non-opioid analgesic.

11. The pharmaceutical composition of claim 6 further comprising at least one anti-constipation agent.

12. The pharmaceutical composition of claim 6, wherein the pharmaceutical composition comprises an enantiomeric excess of at least 90% of

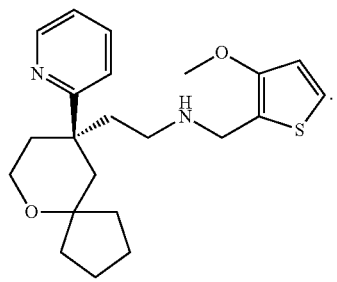 [SMILES: COc1ccsc1CNCC[C@@]1(c2ccccn2)CCOC2(CCCC2)C1]

13. The pharmaceutical composition of claim 6, wherein the pharmaceutical composition comprises an enantiomeric excess of at least 95% of

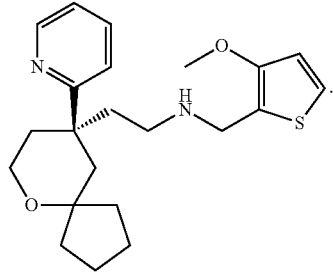 [SMILES: COc1ccsc1CNCC[C@@]1(c2ccccn2)CCOC2(CCCC2)C1]

14. The pharmaceutical composition of claim 6, wherein the pharmaceutical composition comprises an enantiomeric excess of at least 98% of

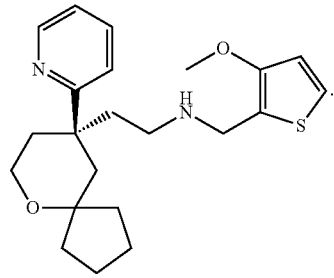 [SMILES: COc1ccsc1CNCC[C@@]1(c2ccccn2)CCOC2(CCCC2)C1]

15. The pharmaceutical composition of claim 6, wherein the pharmaceutical composition comprises an enantiomeric excess of at least 99% of

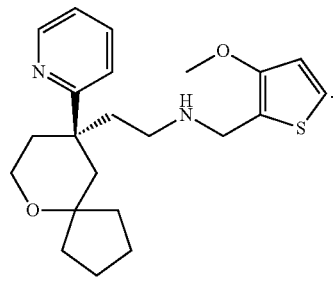 [SMILES: COc1ccsc1CNCC[C@@]1(c2ccccn2)CCOC2(CCCC2)C1]

16. A method of treating pain comprising administering to a subject in need thereof the pharmaceutical composition of claim 6.

17. A method of treating pain comprising administering to a subject in need thereof the pharmaceutical composition of claim 10.

18. A method of treating pain comprising administering to a subject in need thereof the pharmaceutical composition of claim 11.

19. A method of treating pain comprising administering to a subject in need thereof the pharmaceutical composition of claim 12.

20. A method of treating pain comprising administering to a subject in need thereof the pharmaceutical composition of claim 13.

21. A method of treating pain comprising administering to a subject in need thereof the pharmaceutical composition of claim 14.

22. A method of treating pain comprising administering to a subject in need thereof the pharmaceutical composition of claim 15.

* * * * *